(12) United States Patent
Brown et al.

(10) Patent No.: US 11,279,712 B2
(45) Date of Patent: Mar. 22, 2022

(54) MACROCYCLIC COMPOUNDS THAT INHIBIT MCL-1 PROTEIN

(71) Applicant: AMGEN INC., Thousand Oaks, CA (US)

(72) Inventors: Sean P. Brown, San Francisco, CA (US); Yunxiao Li, Thousand Oaks, CA (US); Paul E. Harrington, Thousand Oaks, CA (US); Brian Alan Lanman, Woodland Hills, CA (US); Jonathan D. Low, Reseda, CA (US); Ana Elena Minatti, Los Angeles, CA (US); Vu Van Ma, Oak Park, CA (US); Kexue Li, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/642,441

(22) PCT Filed: Aug. 27, 2018

(86) PCT No.: PCT/US2018/048058
§ 371 (c)(1),
(2) Date: Feb. 27, 2020

(87) PCT Pub. No.: WO2019/046150
PCT Pub. Date: Mar. 7, 2019

(65) Prior Publication Data
US 2020/0247821 A1    Aug. 6, 2020

Related U.S. Application Data

(60) Provisional application No. 62/551,718, filed on Aug. 29, 2017.

(51) Int. Cl.
| | | |
|---|---|---|
| *C07D 513/04* | (2006.01) | |
| *C07D 513/08* | (2006.01) | |
| *C07D 519/00* | (2006.01) | |
| *A61P 35/00* | (2006.01) | |
| *A61K 31/496* | (2006.01) | |
| *A61K 31/5377* | (2006.01) | |
| *A61K 31/7068* | (2006.01) | |

(52) U.S. Cl.
CPC ............ *C07D 513/04* (2013.01); *A61P 35/00* (2018.01); *C07D 519/00* (2013.01); *A61K 31/496* (2013.01); *A61K 31/5377* (2013.01); *A61K 31/7068* (2013.01)

(58) Field of Classification Search
CPC .. C07D 513/04; C07D 519/00; C07D 513/08; A61P 35/00; A61K 31/496; A61K 31/5377; A61K 31/7068
See application file for complete search history.

(56) References Cited

U.S. PATENT DOCUMENTS

| | | |
|---|---|---|
| 4,522,811 A | 6/1985 | Eppstein et al. |
| 6,468,798 B1 | 10/2002 | Deb et al. |
| 6,471,996 B1 | 10/2002 | Sokoll et al. |
| 6,472,375 B1 | 10/2002 | Hoon et al. |
| 9,562,061 B2 | 2/2017 | Brown et al. |
| 10,100,063 B2 | 10/2018 | Brown et al. |
| 10,300,075 B2 | 5/2019 | Brown et al. |
| 10,494,381 B2 | 12/2019 | Brown et al. |
| 10,500,213 B2 | 12/2019 | Brown et al. |
| 10,632,128 B2 | 4/2020 | Harrington et al. |
| 2009/0054402 A1 | 2/2009 | Wang et al. |
| 2014/0051683 A1 | 2/2014 | Wang et al. |

(Continued)

FOREIGN PATENT DOCUMENTS

| | | |
|---|---|---|
| WO | 2008/131000 A2 | 10/2008 |
| WO | 2011/094708 A2 | 8/2011 |

(Continued)

OTHER PUBLICATIONS

Kotschy, A., "The MCL1 inhibitor S63845 is tolerable and effective in diverse cancer models." Nature 538.7626 (2016): 477-482.*

(Continued)

*Primary Examiner* — John M Mauro
(74) *Attorney, Agent, or Firm* — Bernard P. Friedrichsen

(57) ABSTRACT

Provided herein are myeloid cell leukemia 1 protein (Mcl-1) inhibitors, methods of their preparation, related pharmaceutical compositions, and methods of using the same. For example, provided herein are compounds of Formula I, or a stenoisomer thereof; and pharmaceutically acceptable salts thereof and pharmaceutical compositions containing the compounds. The compounds and compositions provided herein may be used, for example, in the treatment of diseases or conditions, such as cancer.

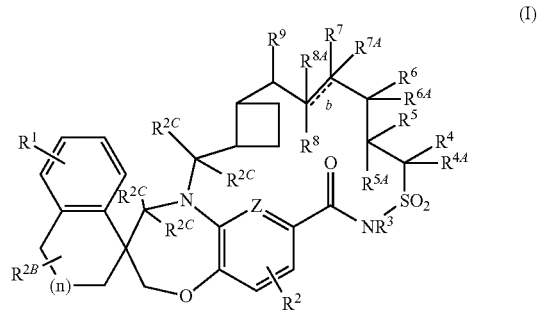

(I)

21 Claims, No Drawings

(56) References Cited

U.S. PATENT DOCUMENTS

| | | |
|---|---|---|
| 2015/0045357 A1 | 2/2015 | Nikolovska-Coleska et al. |
| 2015/0284328 A1 | 10/2015 | Wang et al. |
| 2017/0088560 A1 | 3/2017 | Brown et al. |
| 2019/0023720 A1 | 1/2019 | Brown et al. |
| 2020/0062780 A1 | 2/2020 | Brown et al. |

FOREIGN PATENT DOCUMENTS

| | | |
|---|---|---|
| WO | 2013/052943 A2 | 4/2013 |
| WO | 2013/149124 A1 | 10/2013 |
| WO | 2016/033486 A1 | 3/2016 |
| WO | 2017/147410 A1 | 8/2017 |
| WO | 2018/183418 A1 | 10/2018 |
| WO | 2019/173181 A1 | 9/2019 |
| WO | 2019/036575 A1 | 3/2020 |

OTHER PUBLICATIONS

Verweij, M. F., Preventive medicine between obligation and aspiration. vol. 4. Springer Science & Business Media, 2000; Chapter 3 p. 25-43.*
Skin Cancer Prevention—The Skin Cancer Foundation, 2015 p. 1-3; https://www.skincancer.org/skin-cancer-prevention.*
Beroukhim,R., et al., "The landscape of somatic copy-number alteration across human cancers," Nature 463, 899-905 (2010).
Lessene, G., et al., "BCL-2 family antagonists for cancer therapy," Nat. Rev. Drug. Discov., vol. 7, 989-1000 (2008).
Akgul, C., "Mcl-1 is a potentia l therapeutic target in multiple types of cancer", Cell. Mol. Life Sci. vol, 66 1326-1336 (2009).
Mandelin II, A. M et al., "Myeloid cell leukemia-1 as a therapeutic target," Expert Opin. Ther. Targets, 11(3):363-373 (2007).
Rowe, R. C., et al., Handbook of Pharmaceutical Excipients, $5^{th}$ Edition (2005).
Berge, S. M. et al. "Pharmaceutical Salts", J. Pharm. Sci. 66: 1-19 (1977).
Hamajima, K. et al., Intranasal Administration of HIV-DNA Vaccine Formulated with a Polymer, Carboxymelliylcellulose, Augments Mucosal Antibody Production and Cell-Mediated Immune Response, Clin. Immunol. Immunopathol., 88(2), 205-210 (1998).
Higuchi, T. et al., "Pro-drugs as Novel Delivery Systems," vol. 14 of the A.C.S. Symposium Series (1975).
Roche, E.B., "Bioreversible Carriers in Drug Design", ed. Edward B. Roche, American Pharmaceutical Association and Pergamon Press, (1987).
Brubaker, J. D., et al., "A Practical, Enantioselective Synthetic Route to a Key Precursor to the Tetracycline Antibiotics," Org. Lett., 9, 3523-3525 (2007).
Krasovskiy, A et al., "Convenient Titration Method for Organometallic Zinc, Magnesium, and Lanthanide Reagents," Synthesis, 890-891 (2006).
Sigman, M. S. et al., "Palladium-Catalyzed Allylic Cross-Coupling Reactions of Primary and Secondary Homoallylic Electrophiles," J. Am. Chem. Soc., 134(28), 11408-11411 (2012).
International Search Report for analogous PCT Application No. PCT/US2018/048058, dated Oct. 30, 2018.
Farrell, R. P. "Breaking Symmetry Towards Development and Scale Up of a Complex Drug Candidate," American Chemical Society Meeting Presentation, Philadelphia, PA, Aug. 22, 2016.
Brown, B. "Interdiction at a Protein-Protein Interface: Structure-Based Design of Mcl-1 Inhibitors," American Chemical Society Meeting Presentation, Philadelphia, PA, Aug. 22, 2016.
Brown, S. "Interdiction at a Protein-Protein Interface: Structure-Based Design of Mcl-1 Inhibitors," Presentation at Caltech, Pasadena, CA, Jun. 1, 2016.
Brown, S. "Interdiction at a Protein-Protein Interface: Structure-Based Design of Mcl-1 Inhibitors," American Chemical Society Meeting Presentation, San Francisco, CA, Apr. 5, 2017.
Caenepeel, S. R. et al. "Preclinical Evaluation of AMG 176, A Novel, Potent and Selective Mcl-1 Inhibitor with Robust Anti-tumor Activity in Mcl-1 Dependent Cancer Models," Poster Presentation at American Association for Cancer Research Meeting, Washington DC, Apr. 1-5, 2017.
Hata, A. N. et al., "Combined targeting of MEK and MCL-1 induces apoptosis and tumor regression of KRAS mutant NSCLC," Poster Presentation at American Association for Cancer Research Meeting, Washington DC, Apr. 1-5, 2017.
Hata, A. N. et al., untitled structure slide, Poster Presentation at American Association for Cancer Research Meeting, Washington DC, Apr. 1-5, 2017.
Caenepeel, S. et al. "Preclinical Evaluation of AMG 176, A Novel, Potent and Selective Mcl-1 Inhibitor with Robust Anti-tumor Activity in Mcl-1 Dependent Cancer Models," Poster Presentation at American Association for Cancer Research Meeting, Chicago, IL, Apr. 14-18, 2018.
Caenepeel, S. et al. "Combined Inhibition of MCL1 and BCL-2 With AMG 176 and Venetoclax Induces Anti-tumor Effects in Acute Myeloid Leukemia," Poster Presentation at American Association for Cancer Research Meeting, Chicago, IL, Apr. 14-18, 2018.
Belmontes, B., "The Utilization of a Human MCL1 Knock-In Mouse Suggests that Reductions in B Cells and Monocytes may Serve as Clinically Relevant Pharmacodynamic markers of MCL1 Inhibition," Poster Presentation at American Association for Cancer Research Meeting, Chicago, IL, Apr. 14-18, 2018.
Brown, S. "Interdiction at a Protein-Protein Interface: Structure-Based Design of the Mcl-1 Inhibitor AMG 176," American Chemical Society Meeting Presentation, New Orleans, LA, Mar. 19, 2018.
Hughes, P. "The Discovery and Preclinical Characterization of AMG 176: A First-In-Class MCL-1 Inhibitor in Clinical Development for Multiple Myeloma," Poster Presentation at American Association for Cancer Research Meeting, Chicago, IL, Apr. 14-18, 2018.
Written Opinion for analogous PCT Application No. PCT/US2018/048058, dated Oct. 30, 2018.

* cited by examiner

MACROCYCLIC COMPOUNDS THAT INHIBIT MCL-1 PROTEIN

CROSS REFERENCES TO RELATED APPLICATIONS

This application claims the benefit of U.S. Provisional Application No. 62/551,718, filed on Aug. 29, 2017, which is hereby incorporated by reference in its entirety and for all purposes as if fully set forth herein.

FIELD OF THE INVENTION

The present invention relates to compounds that inhibit myeloid cell leukemia 1 protein (Mcl-1, also abbreviated as MCl-1, MCL-1 or MCL1); methods of treating diseases or conditions, such as cancer, using the compounds; and pharmaceutical compositions containing the compounds.

BACKGROUND OF THE INVENTION

One common characteristic of human cancer is overexpression of Mcl-1. Mcl-1 overexpression prevents cancer cells from undergoing programmed cell death (apoptosis), allowing the cells to survive despite widespread genetic damage.

Mcl-1 is a member of the Bcl-2 family of proteins. The Bcl-2 family includes pro-apoptotic members (such as BAX and BAK) which, upon activation, form a homo-oligomer in the outer mitochondrial membrane that leads to pore formation and the escape of mitochondrial contents, a step in triggering apoptosis. Antiapoptotic members of the Bcl-2 family (such as Bcl-2, Bcl-XL, and Mcl-1) block the activity of BAX and BAK. Other proteins (such as BID, BIM, BIK, and BAD) exhibit additional regulatory functions.

Research has shown that Mcl-1 inhibitors can be useful for the treatment of cancers. MCl-1 is overexpressed in numerous cancers. See Beroukhim et al. (2010) Nature 463, 899-90. Cancer cells containing amplifications surrounding the Mcl-1 and Bcl-2-1-1 anti-apoptotic genes depend on the expression of these genes for survival. Beroukhim et al. Mcl-1 is a relevant target for the re-iniation of apoptosis in numerous cancer cells. See G. Lessene, P. Czabotar and P. Colman, Nat. Rev. Drug. Discov., 2008, 7, 989-1000; C. Akgul Cell. Mol. Life Sci. Vol. 66, 2009; and Arthur M. Mandelin II, Richard M. Pope, Expert Opin. Ther. Targets (2007) 11(3):363-373.

New compositions and methods for preparing and formulating Mcl-1 inhibitors would be useful.

SUMMARY OF THE INVENTION

1. An embodiment of the present invention comprises a compound of Formula I:

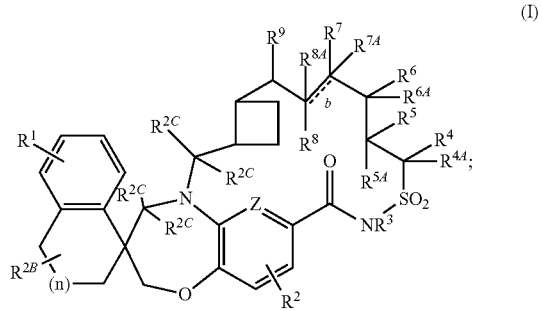

(I)

a stereoisomer thereof, a pharmaceutically acceptable salt thereof, or a pharmaceutically acceptable salt of the stereoisomer thereof,
wherein:
Z is C or N;
b, represented by the symbol ====, is a single or double chemical bond which may be cis or trans;
$R^1$ is independently selected from H, halo, $C_{1-6}$alkylhalo, $C_{1-6}$alkyl, $C_{2-6}$alkenyl, $-(CH_2CH_2O)_nR^a$, $-SO_2R^a$, $-C(=O)R^a$, $-C(=O)OR^a$, or $-C(=O)NR^aR^b$;
$R^2$ is selected from H, halo, $-C_{1-6}$haloalkyl, $-C_{1-6}$alkyl, $-O-C_{1-6}$alkyl, $-C_{2-6}$alkenyl, $-C_{2-6}$alkynyl, $-C_{1-6}$alkyl-O$-C_{1-6}$alkyl, $-(CH_2CH_2O)_nR^a$, $-SO_2R^a$, $-C(=O)R^a$, $-C(=O)OR^a$, $-OC(=O)R^a$, $-C(=O)NR^aR^b$, a 6- to 12-membered aryl or heteroaryl, a 5- to 12-membered spirocycloalkyl or spiroheterocycloalkyl, or a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl or heterocycloalkyl group have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl, and heterocycloalkyl groups may include a S=O or $SO_2$;
$R^3$ is selected from H, $-C_{1-6}$alkylhalo, $-C_{1-6}$alkyl, $-C_{2-6}$alkenyl, $-(CH_2CH_2O)_nR^a$, $-C(=O)R^a$, $-C(=O)OR^a$, or $-C(=O)NR^aR^b$;
each of $R^{2B}$, $R^{2C}$, $R^4$, $R^5$, $R^6$, $R^7$, and $R^8$ is independently selected from H, halo, $-C_{1-6}$haloalkyl, $-C_{1-6}$alkyl, $-O-C_{1-6}$alkyl, $-C_{2-6}$alkenyl, $-C_{2-6}$alkynyl, $-C_{1-6}$alkyl-O$-C_{1-6}$alkyl, $-(CH_2CH_2O)_nR^a$, $-SO_2R^a$, $-C(=O)R^a$, $-C(=O)OR^a$, $-OC(=O)R^a$, $-C(=O)NR^aR^b$, a 6- to 12-membered aryl or heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may include a C=O group, and further wherein the spiroheterocycloalkyl and heterocycloalkyl groups may include a S=O or $SO_2$;
alternatively $R^3$ and $R^4$ together with the atoms to which they are bonded may form a 5- to 12-membered ring, optionally containing a heteroatom selected from a N, O or S atom, in addition to the S and N atoms present in the ring, wherein the ring may optionally contain at least one double bond; and the ring may be substituted with 0, 1, 2, or 3 $R^{3A}$ substituents;
wherein $R^{3A}$ is selected from H, halo, $-OH$, $C_{1-6}$haloalkyl, $C_{1-6}$alkyl, $O-C_{1-6}$alkyl, $C_{2-6}$alkenyl, $-C_{1-6}$alkyl-O$-C_{1-6}$alkyl, $-(CH_2CH_2O)_nR^a$, $-SO_2R^a$, $-C(=O)R^a$, $-C(=O)OR^a$, $-OC(=O)R^a$, or $-C(=O)NR^aR^b$;
each of $R^{4A}$, $R^{5A}$, $R^{6A}$, $R^{7A}$, and $R^{8A}$ is independently selected from H, OH, halo, or $-C_{1-6}$alkyl;
$R^{7A}$ and $R^{8A}$ are absent when b is a double chemical bond;
alternatively $R^7$ and $R^8$ together with the atoms to which they are bonded may form a 3- to 12-membered ring, wherein the ring may optionally contain at least one double bond;
$R^9$ is $-C_{1-6}$alkyl, unsubstituted or substituted with 1, 2, or 3 $R^{10}$ substituents independently selected from halo, $-C_{1-6}$haloalkyl, $-OH$, $-NR^aR^b$; $-(=O)$, $-OC_{1-6}$alkyl, $-SO_2R^a$, cyano, $-C_2-C_6$ alkenyl, $-C_2-C_6$ alkynyl, $-(CH_2CH_2O)_nR^a$, $-SR^a$, $-S(=O)R^a$, $-OSO_2R^a$, $-(O)$ R$^a$, —(=O)OR$^a$, —O—C$_{1-6}$alkyl-O—C$_{1-6}$alkyl, phenyl, a 6- to 12-membered monocyclic or bicyclic aryl, a 6- to 12-membered monocyclic or bicyclic heteroaryl, a 5- to 12-membered spirocycloalkyl or spiroheterocycloalkyl, a 3- to 12-membered cycloalkenyl, a 3- to 12-membered monocyclic or bicyclic cycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S, wherein the cycloalkyl, spirocycloalkyl, spiroheterocycloalkyl, and heterocycloalkyl groups may contain a double bond and may contain one or two C=O group, and further wherein the spiroheterocycloalkyl, and heterocycloalkyl groups may include a S=O or SO$_2$; and still further wherein two adjacent carbon atoms or an adjacent carbon atom and N atom on a R$^{10}$ heterocycloalkyl group may join together to form a 6-membered aromatic ring that is unsubstituted or is substituted with 1, 2, or 3, R$^{11}$ group;

R$^{11}$ is independently selected from —OH, halo, cyano, —C$_{1-6}$haloalkyl, —C$_{1-6}$alkyl, —C$_{1-6}$alkyl-OH, —C$_2$-C$_6$ alkenyl, —C$_2$-C$_6$ alkynyl, —(CH$_2$CH$_2$O)$_n$R$^a$, —CSR$^a$, —CS(=O)R$^a$, —SR$^a$, —SOR$^a$, —OSO$_2$R$^a$, —SO$_2$R$^a$, —(CH$_2$CH$_2$O)$_n$CH$_3$, —(=O), —C(=O), —C(=O)R$^a$, —C(=O)OR$^a$, —C(=O)NR$^a$R$^b$, —(CH$_2$)$_n$—NR$^a$R$^b$, and —NR$^a$R$^b$;

wherein the aryl, heteroaryl, cycloalkyl, heterocycloalkyl, spirocycloalkyl and spiroheterocycloalkyl groups of any of the R$^{10}$ substituents can be unsubstituted or substituted with 1, 2, 3 or 4 R$^{12}$ substituents independently selected from, OH, halo, —NR$^a$R$^b$, —C$_{1-6}$alkyl, —C$_2$-C$_6$ alkenyl, —C$_2$-C$_6$alkynyl, —(=O), —OC$_{1-6}$alkyl, —C$_{1-6}$alkyl-OH, —C$_{1-6}$alkyl-O—C$_{1-6}$alkyl, C$_{1-6}$haloalkyl, —O-haloC$_{1-6}$alkyl, —SO$_2$R$^a$, —CN, —C(=O)NR$^a$R$^b$, —C(=O)R$^a$, —OC(=O)R$^a$, and —C(=O)OR$^a$;

wherein the C$_{1-6}$alkyl, C$_{2-6}$ alkenyl, C$_{2-6}$ alkynyl and the —OC$_{1-6}$alkyl of any of the R$^1$, R$^2$, R$^3$, R$^4$, R$^5$, R$^6$, R$^7$, R$^8$, R$^{10}$, R$^{4A}$, R$^{5A}$, R$^{6A}$, R$^{7A}$, and R$^{8A}$ substituents is unsubstituted or substituted by 1, 2 or 3 R$^{13}$ substituents independently selected from OH, —OC$_{1-6}$alkyl, —C$_{1-6}$alkyl-O—C$_{1-6}$alkyl, halo, —O-haloC$_{1-6}$-alkyl, —CN, —NR$^a$R$^b$, —(NR$^a$R$^b$R$^c$)$_n$, —OSO$_2$R$^a$, —SO$_2$R$^a$, —(CH$_2$CH$_2$O)$_n$CH$_3$, —(=O), —C(=O), —C(=O)R$^a$, —OC(=O)R$^a$, —C(=O)OR$^a$, —C(=O)NR$^a$R$^b$, —O—SiR$^a$R$^b$R$^c$, and —SiR$^a$R$^b$R$^c$;

wherein the aryl, heteroaryl, cycloalkyl, heterocycloalkyl, spirocycloalkyl and spiroheterocycloalkyl group of any of the R$^2$, R$^4$, R$^5$, R$^6$, R$^7$, and R$^8$ substituents can be unsubstituted or substituted with 1, 2, 3 or 4 R$^{14}$ substituents independently selected from OH, halo, —NR$^a$R$^b$, —C$_{1-6}$alkyl, —OC$_{1-6}$alkyl, —C$_{1-6}$alkyl-OH, —C$_{1-6}$alkyl-O—C$_{1-6}$alkyl, C$_{1-6}$haloalkyl, —O-haloC$_{1-6}$alkyl, —SO$_2$R$^a$, —CN, —C(=O)NR$^a$R$^b$, —C(=O)R$^a$, —OC(=O)R$^a$, and —C(=O)OR$^a$;

wherein each R$^a$, R$^b$ and R$^c$ is independently H, OH, —C$_{1-6}$alkyl, —C$_{2-6}$alkenyl, —C$_{2-6}$alkynyl, —C$_{1-6}$alkyl-NR$^{15}$R$^{15}$, —NR$^{15}$R$^{15}$, —SO$_2$R$^{15}$, —(CH$_2$CH$_2$O)$_n$CH$_3$, —(=O), —C(=O)R$^{15}$, —OC(=O)R$^{15}$, —C(=O)OR$^{15}$, —C(=O)NR$^{15}$R$^{15}$, —C$_{1-6}$haloalkyl, —O-haloC$_{1-6}$alkyl, —C$_{1-6}$alkyl-O—C$_{1-6}$alkyl, benzyl, phenyl, —C$_{1-6}$alkyl-C(=O)OH, —C$_{1-6}$alkyl-C(=O)—O—C$_{1-6}$alkyl, —C$_{1-6}$alkyl-cycloalkyl, C$_{3-6}$cycloalkyl, and —C$_{1-6}$alkyl-heterocycloalkyl;

R$^{15}$ is independently selected from H, OH, —C$_{1-6}$alkyl, halo, —C$_{1-6}$alkyl-O—C$_{1-6}$alkyl, —OC$_{1-6}$alkyl, —O-haloC$_{1-6}$-alkyl, —CN, —NR$^a$R$^b$, (CH$_2$CH$_2$O)$_n$CH$_3$, —(O=), —C(=O), —C(=O)—C$_{1-6}$alkyl, —OC(=O), and —C(=O)O—C$_{1-6}$alkyl, and wherein n is independently in each instance an integer of 1, 2, 3 or 4.

In some embodiments, the compound of Formula I is a compound other than a compound having one of the following structures or a salt thereof, or a stereoisomer thereof, or a salt of the stereoisomer:

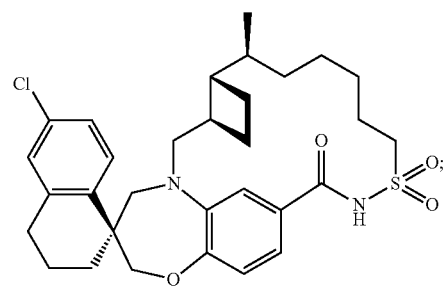

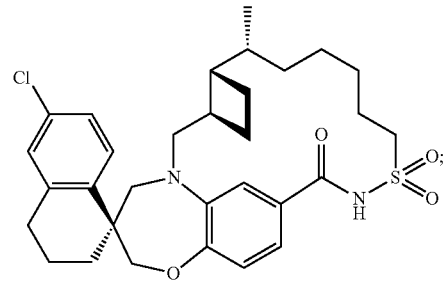

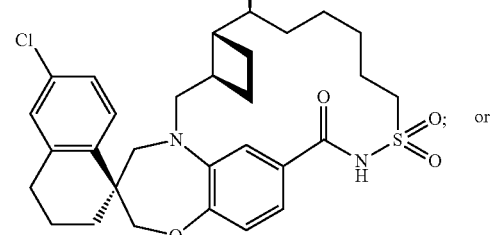

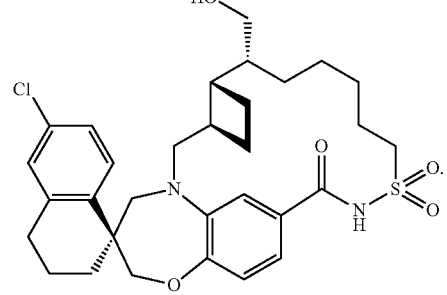

In some embodiments where b is a single bond and R$^9$ is a —CH$_3$ or —CH$_2$OH, at least one of R$^4$, R$^{4A}$, R$^5$, R$^{5A}$, R$^6$, R$^{6A}$, R$^7$, R$^{7A}$R, or R$^{8A}$ is other than —H.

2. Another embodiment of the present invention comprises compound of Formula IA:

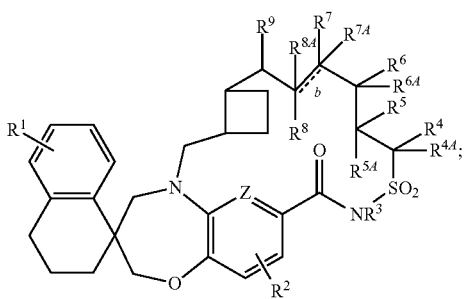

(IA)

a stereoisomer thereof, a pharmaceutically acceptable salt thereof, or a pharmaceutically acceptable salt of the stereoisomer thereof, wherein:

Z is C or N;

b, represented by the symbol ------, is a single or double chemical bond which may be cis or trans;

$R^1$ is selected from H, halo, or $C_{1-6}$alkyl;

$R^2$ is selected from H, halo, or $C_{1-6}$alkyl;

$R^3$ is selected from H or —$C_{1-6}$alkyl;

each of $R^4$, $R^5$, $R^6$, $R^7$, and $R^8$ is independently selected from H, —$C_{1-6}$alkyl, or —$C_{1-6}$alkyl-O—$C_{1-6}$alkyl;

each of $R^{4A}$, $R^{5A}$, $R^{6A}$, $R^{7A}$, and $R^{8A}$ is independently selected from H, or —$C_{1-6}$alkyl;

$R^{7A}$ and $R^{8A}$ are absent when b is a double chemical bond;

$R^9$ is —$C_{1-6}$alkyl, unsubstituted or substituted with 1, 2, 3 or 4 $R^{10}$ substituents independently selected from halo, —OH, —$NR^aR^b$; —(=O), —$OC_{1-6}$alkyl, —$SO_2R^a$, a 5- to 12-membered spirocycloalkyl or spiroheterocycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatomns independently selected from O, N or S, wherein the aryl, heteroaryl, cycloalkyl, heterocycloalkyl, spirocycloalkyl and spiroheterocycloalkyl groups of any of the $R^{10}$ substituents can be unsubstituted or substituted with 1, 2, 3 or 4 $R^{12}$ substituents independently selected from halo, —$NR^aR^b$, —$C_{1-6}$alkyl, —(=O), —$C_{1-6}$alkyl-O —$C_{1-6}$alkyl, —$SO_2R^a$, —C(=O)$R^a$, and —C(=O)O$R^a$;

wherein each $R^a$, $R^b$ and $R^c$ is independently H, —$C_{1-6}$alkyl, and —$(CH_2CH_2O)_nCH_3$, and wherein n is independently in each instance an integer of 1.

3. Another embodiment of the present invention comprises a compound of embodiment 1, wherein the compound has the Formula II:

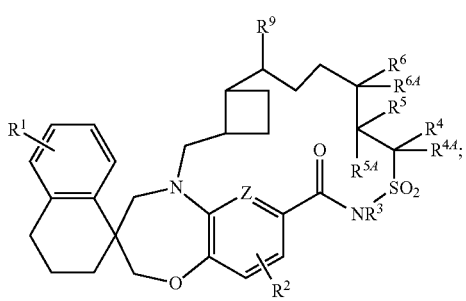

(II)

4. Another embodiment of the present invention comprises a compound of any of embodiments 1, 2 or 3, wherein the compound has the Formula IIa:

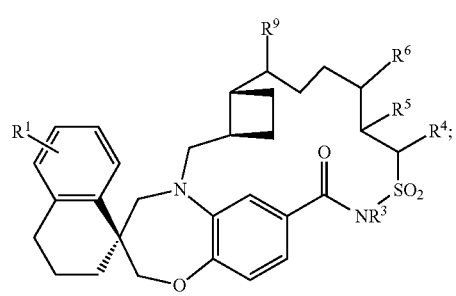

(IIa)

a stereoisomer thereof, a pharmaceutically acceptable salt thereof, or a pharmaceutically acceptable salt of the stereoisomer thereof.

5. The compound of any one of embodiments 1-4, wherein $R^1$ is halo.

6. The compound of embodiment 5, wherein $R^1$ is —Cl.

7. The compound of any one of embodiments 1-6, wherein $R^1$ is H.

8. The compound of any one of embodiments 1-7, wherein $R^4$ is independently selected from H, —$C_{1-6}$alkyl, or —$C_{1-6}$alkyl-O—$C_{1-6}$alkyl.

9. The compound of embodiment 9, wherein $R^4$ is —$CH_3$.

10. The compound of any one of embodiments 1-10, wherein $R^5$ is selected from H or —$C_{1-6}$alkyl.

11. The compound of embodiment 11, wherein $R^5$ is —$CH_3$.

12. The compound of any one of embodiments 1-12, wherein $R^6$ is selected from H or —$C_{1-6}$alkyl.

13. The compound of embodiment 13, wherein $R^6$ is —$CH_3$.

14. The compound of embodiment 13, wherein $R^6$ is H.

15. The compound of any one of embodiments 1-15, wherein $R^9$ is —$C_{1-6}$alkyl unsubstituted or substituted with 1, 2, or 3 $R^{10}$ substituents.

16. The compound of any one of embodiments 1-15, wherein $R^9$ is unsubstituted —$C_{1-6}$alkyl.

17. The compound of any one of embodiments 1-15, wherein $R^9$ is —$C_{1-6}$alkyl substituted with 1, 2, or 3 $R^{10}$ substituents.

18. The compound of any one of embodiments 1-15 or 17, wherein $R^{10}$ is independently selected from halo, —OH, —$NR^aR^b$; —(=O), —$OC_{1-6}$alkyl, —$SO_2R^a$, phenyl, a 5- to 12-membered spirocycloalkyl or spiroheterocycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S.

19. The compound of embodiment 18, wherein $R^{10}$ is —OH, halo, or —$NR^aR^b$.

20. The compound of embodiment 19, wherein $R^{10}$ is —OH.

21. The compound of embodiment 19, wherein $R^{10}$ is halo.

22. The compound of any one of embodiments 20 or 21, wherein $R^{10}$ is F.

23. The compound of embodiment 19, wherein $R^{10}$ is —$NR^aR^b$.

24. The compound of embodiment 18, wherein $R^{10}$ is —(=O).

25. The compound of embodiment 18, wherein $R^{10}$ is a 3- to 12-membered monocyclic or bicyclic heterocycloalkyl group, wherein the heterocycloalkyl group has 1, 2, 3 or 4 heteroatomns independently selected from O, S, or N.

26. The compound of any one of embodiments 1-17, wherein $R^9$ is independently selected from —$CH_3$, —$CH_2OH$, $CH(OH)CF_3$, —$C(=O)$, —$C(=O)OH$, —$CHCH_2(OH)$, —$CH(OH)CH_3$, —$CH_2(O)CH_3$, —$C(=O)CH_3$, —$CH_2S(O)_2CH_3$, —$C(=O)NH(CH_2)_2OCH_3$,

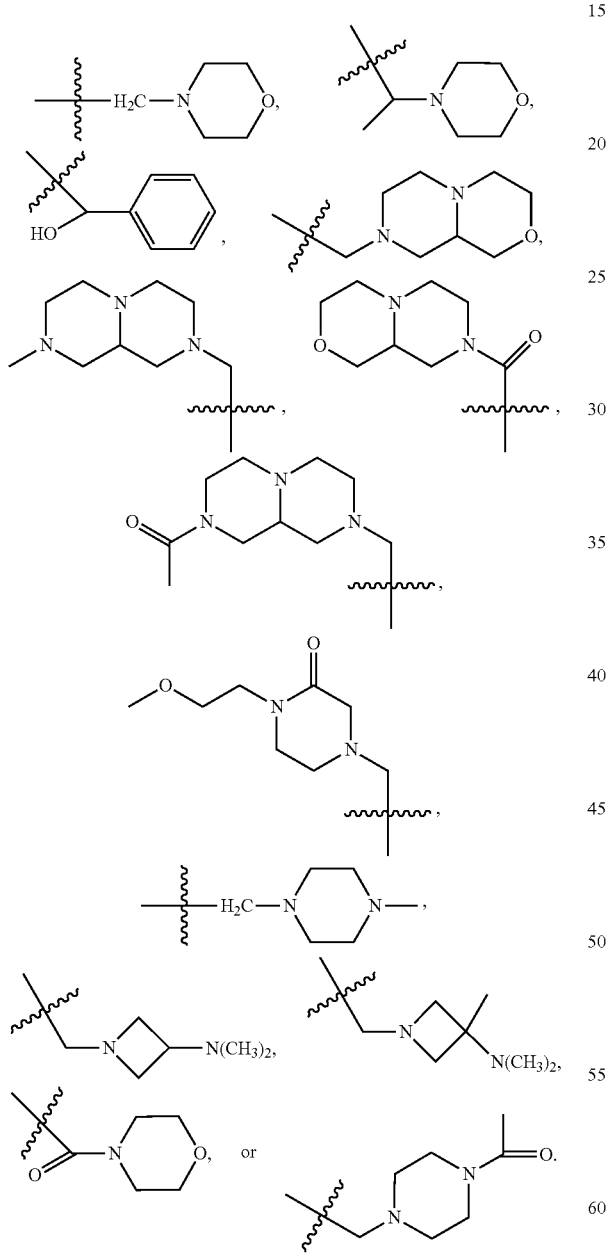

27. The compound of embodiment 26, wherein $R^9$ is —$CH_3$.

28. The compound of embodiment 26, wherein $R^9$ is —$CH_2OH$.

29. The compound of embodiment 26, wherein $R^9$ is —$CH(OH)CH_3$.

30. The compound of embodiment 26, wherein $R^9$ is

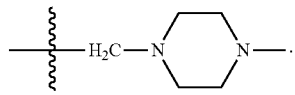

31. The compound of embodiment 26, wherein $R^9$ is

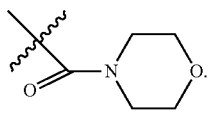 [SMILES: *C(=O)N1CCOCC1]

32. The compound of embodiment 26, wherein $R^9$ is

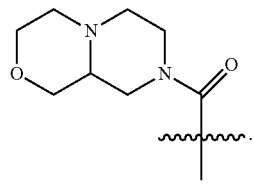

33. The compound of embodiment 26, wherein $R^9$ is

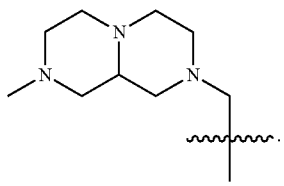 [SMILES: *CN1CCN2CCN(C)CC2C1]

34. The compound of embodiment 26, wherein $R^9$ is

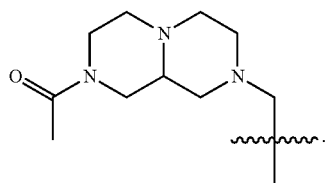 [SMILES: *CN1CCN2CCN(C(C)=O)CC2C1]

35. The compound of embodiment 26, wherein $R^9$ is

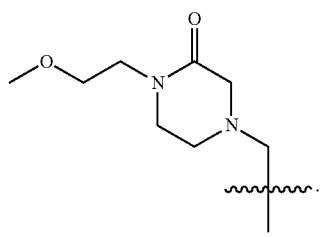 [SMILES: *CN1CCN(CCOC)C(=O)C1]

36. Another embodiment of the present invention comprises a compound of embodiment 1, wherein the compound has the Formula III:

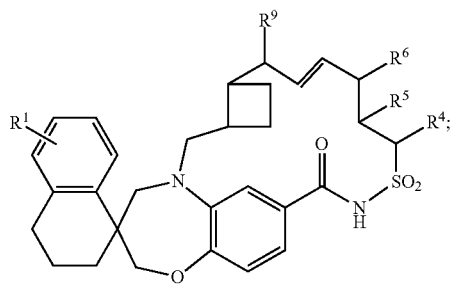

(III)

or a stereoisomer thereof, a pharmaceutically acceptable salt thereof, or a pharmaceutically acceptable salt of the stereoisomer thereof.

37. Another embodiment of the present invention comprises a compound of any one of embodiments 1 or 36, wherein the compound has the Formula IIIa:

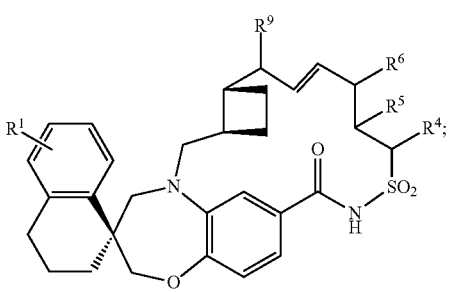

(IIIa)

or a stereoisomer thereof, a pharmaceutically acceptable salt thereof, or a pharmaceutically acceptable salt of the stereoisomer thereof.

38. The compound of any one of embodiments 1 or 36-37, wherein $R^1$ is halo.

39. The compound of embodiment 38, wherein $R^1$ is Cl.

40. The compound of any one of embodiments 1 or 36-39, wherein $R^4$ is —$C_{1-6}$alkyl.

41. The compound of embodiment 40, wherein $R^4$ is —$CH_3$.

42. The compound of any one of embodiments 1 or 36-41, wherein $R^5$ is —$C_{1-6}$alkyl.

43. The compound of embodiment 42, wherein $R^5$ is —$CH_3$.

44. The compound of any one of embodiments 1 or 36-43, wherein $R^6$ is H.

45. The compound of any one of embodiments 1 or 36-44, wherein $R^9$ is —$CH_2OH$, —$CH(OH)CH_2CH_3$, or

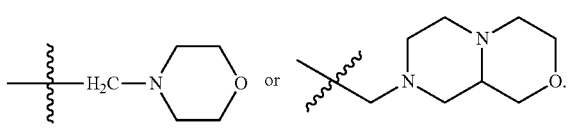 [SMILES: *CN1CCOCC1 ; "or" ; *CN1CCN2CCOCC2C1]

46. The compound of any one of embodiments 1, 44-53, wherein $R^9$ is —$CH_2OH$.

47. Another embodiment of the present invention comprises a compound, wherein the compound has a structure selected from:

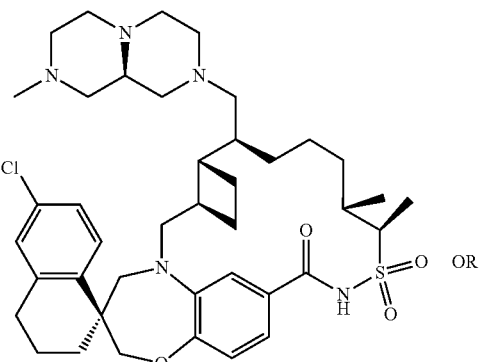

OR

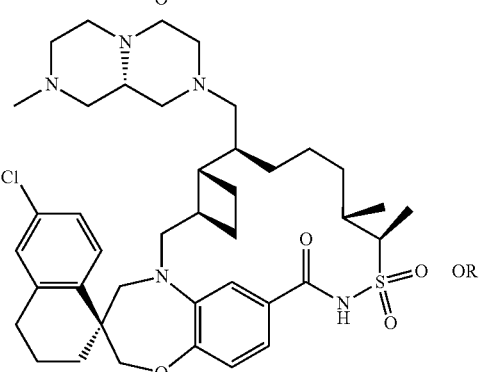

OR

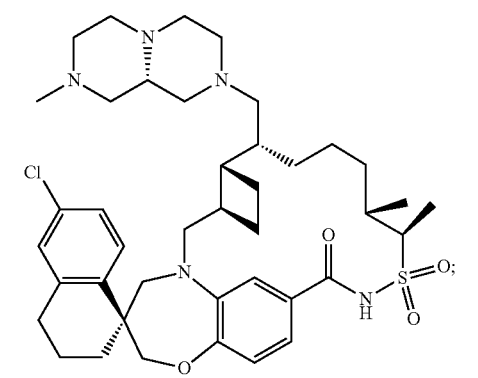

OR

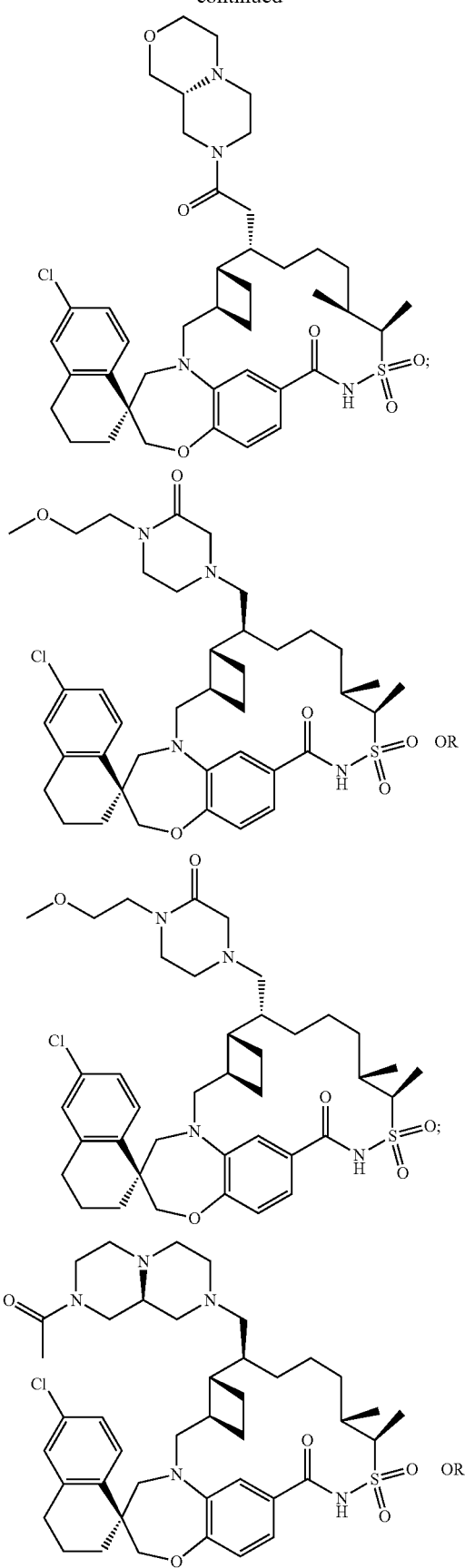
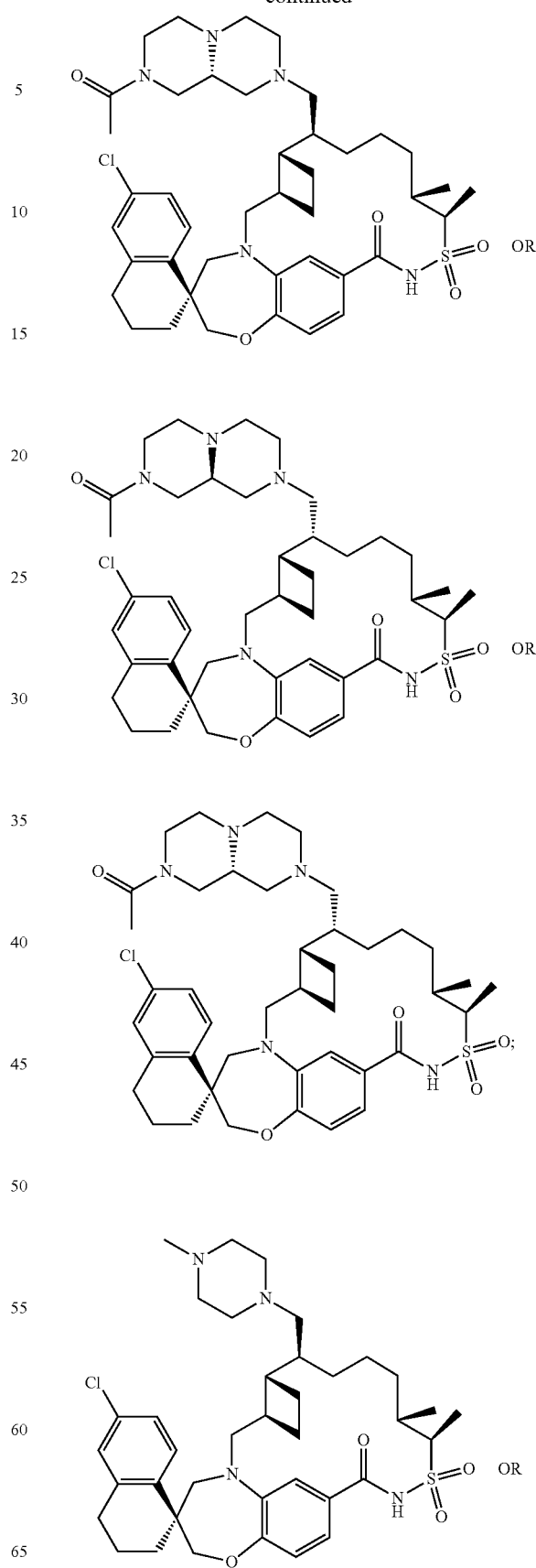

13
-continued
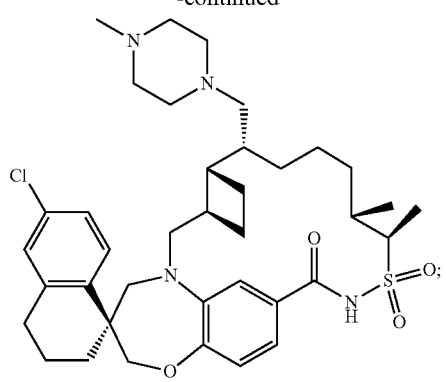
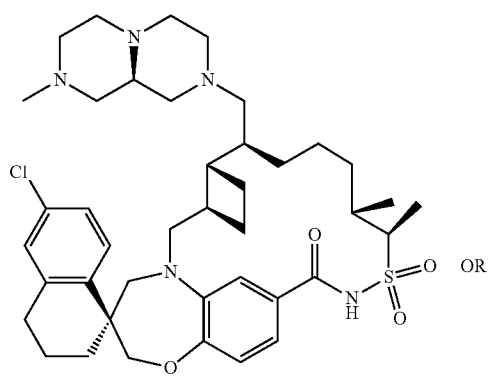
OR
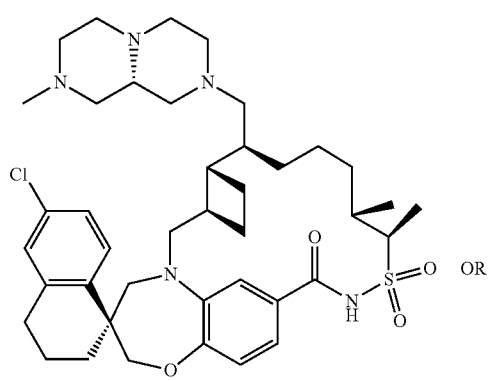
OR
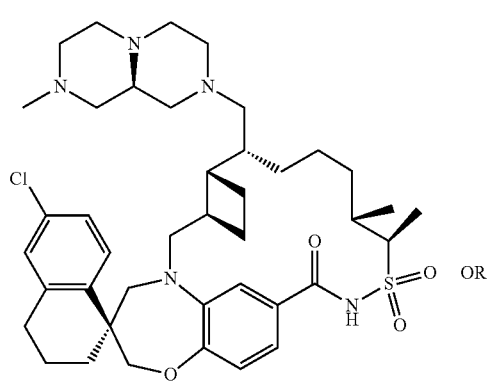
OR
14
-continued
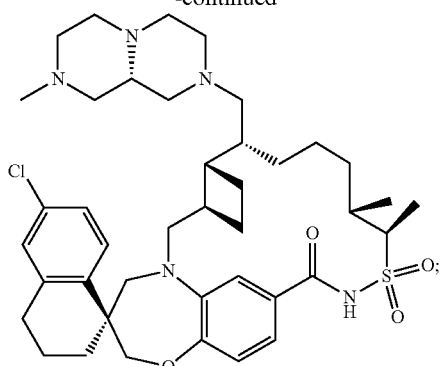
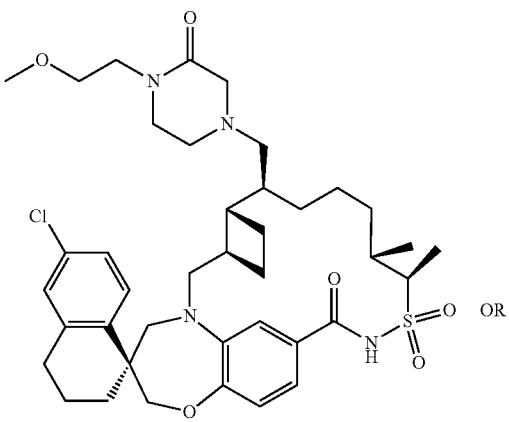
OR
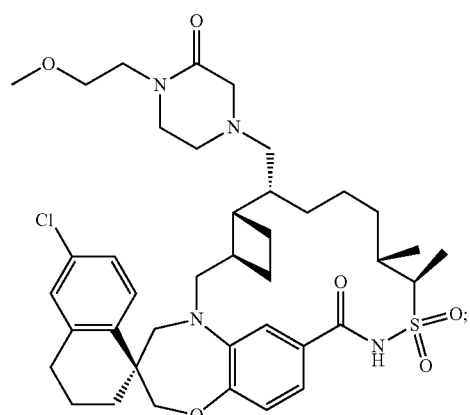
OR
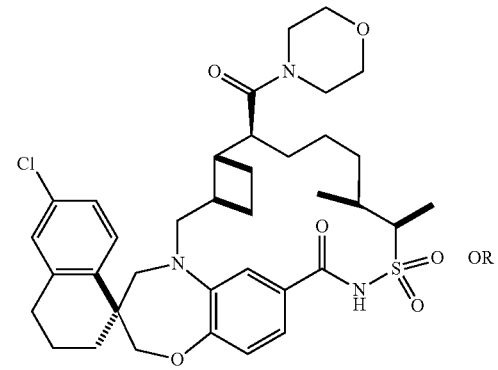
OR 15
-continued
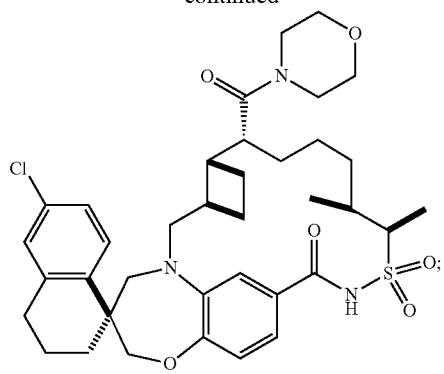
16
-continued
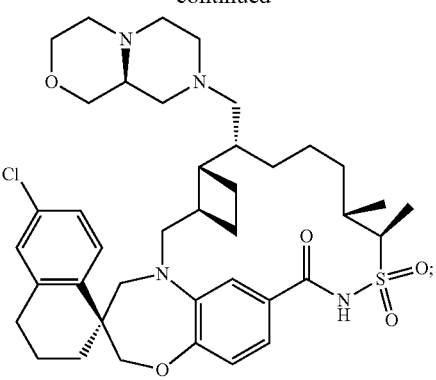
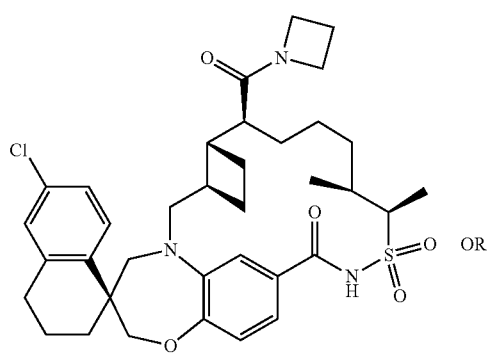
OR
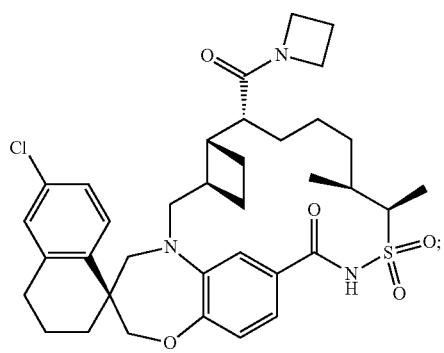
OR
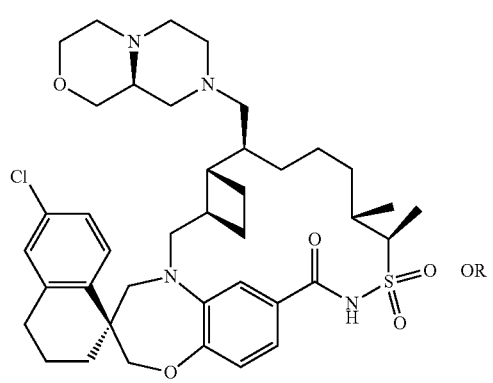
OR -continued
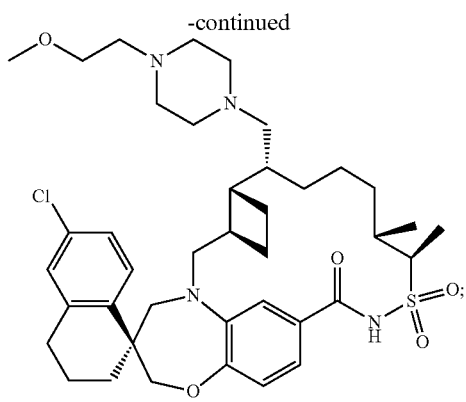
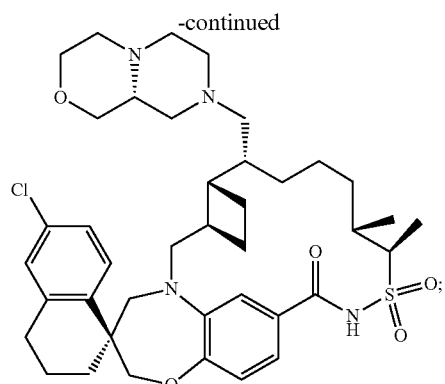
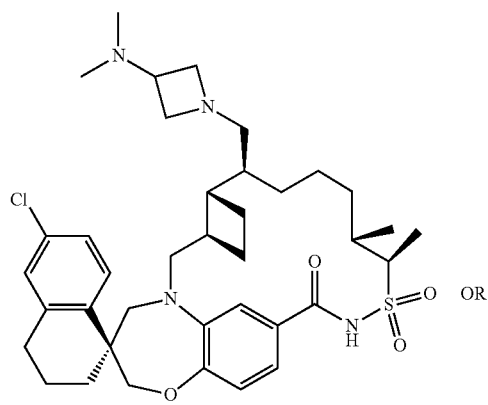
OR
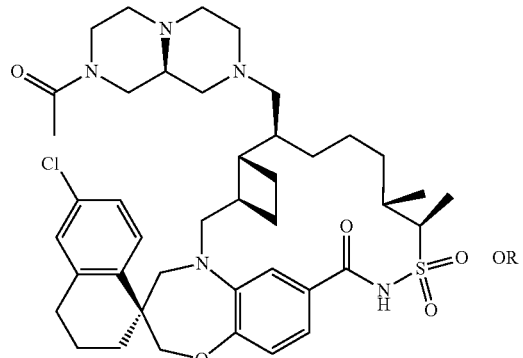
OR
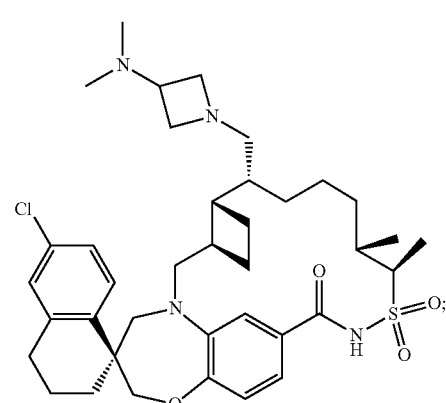
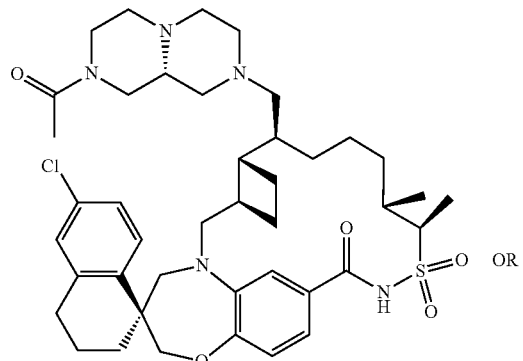
OR
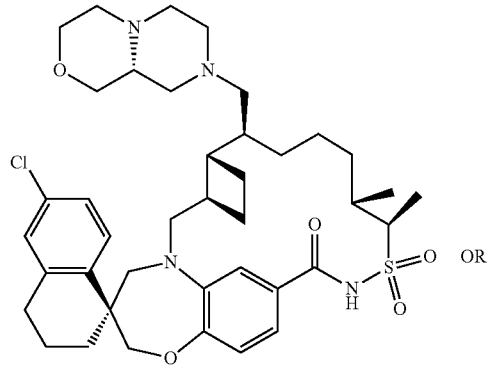
OR
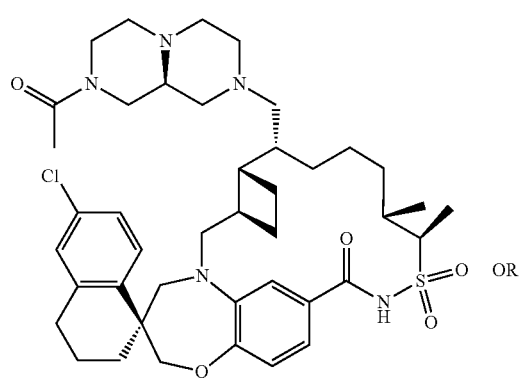
OR 19
-continued
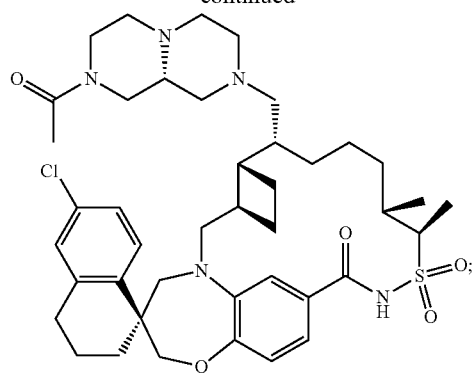
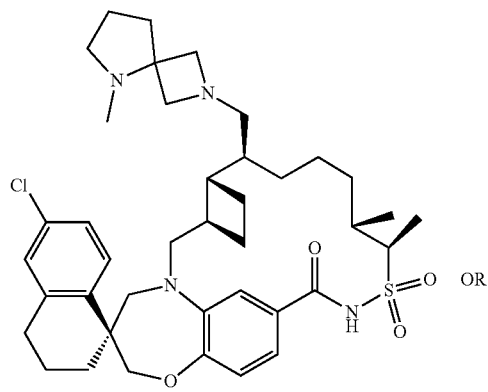
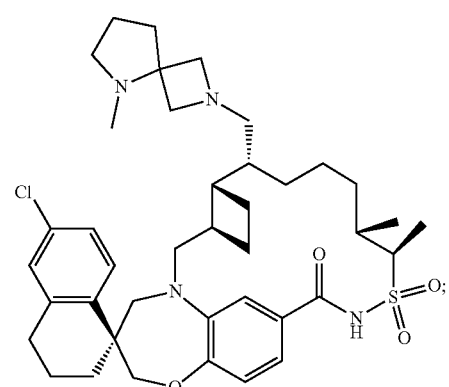
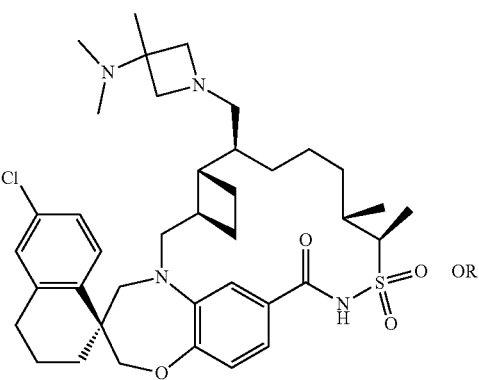
20
-continued
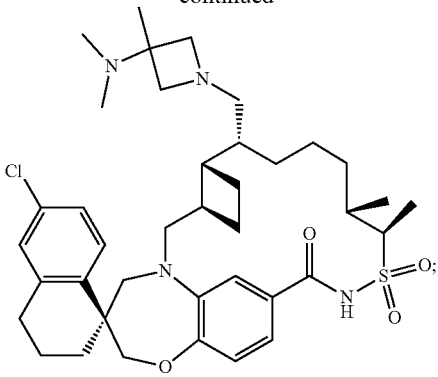
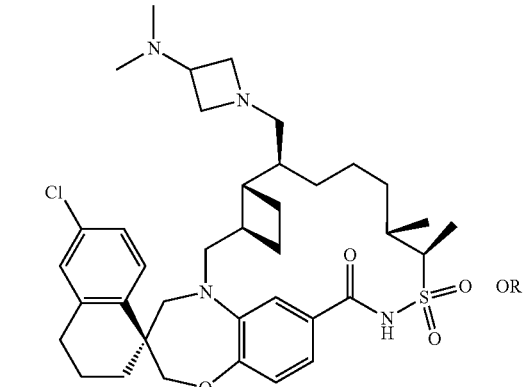
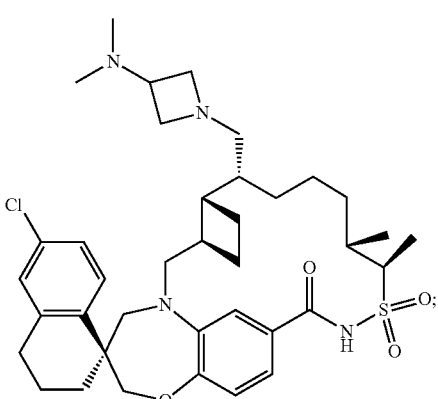
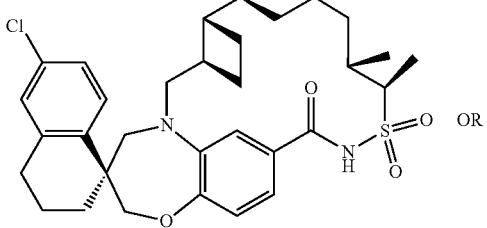

21
-continued
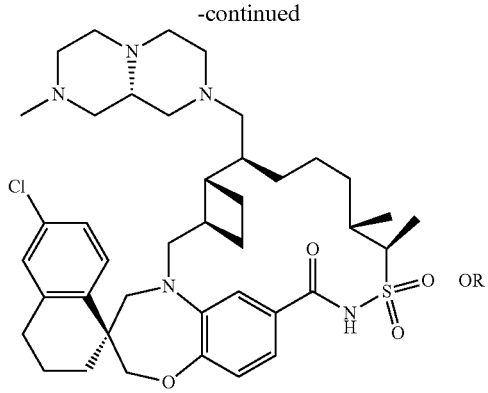
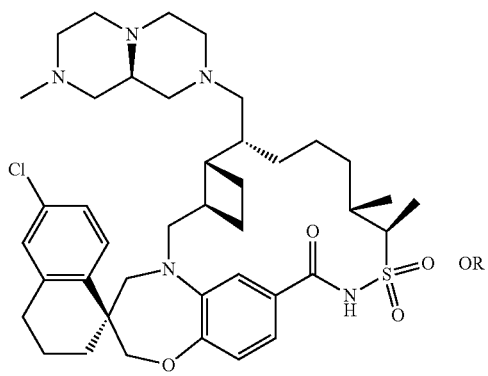
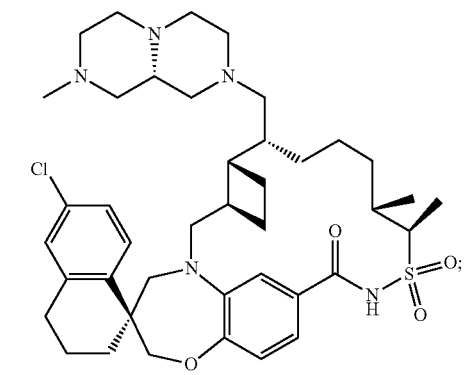
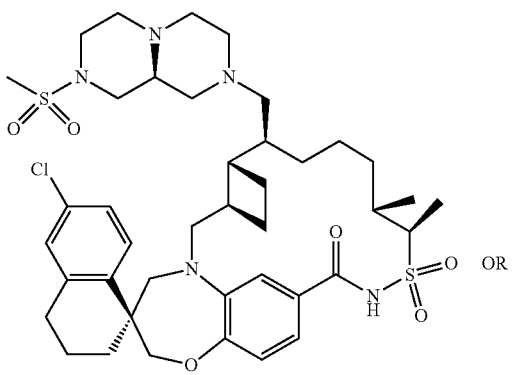
22
-continued
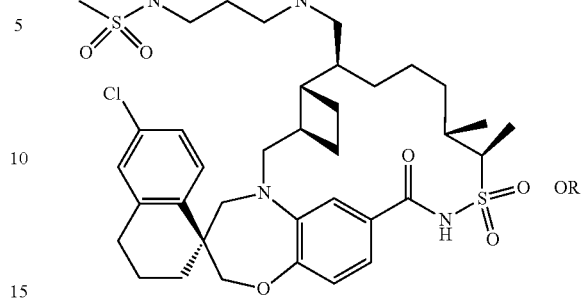
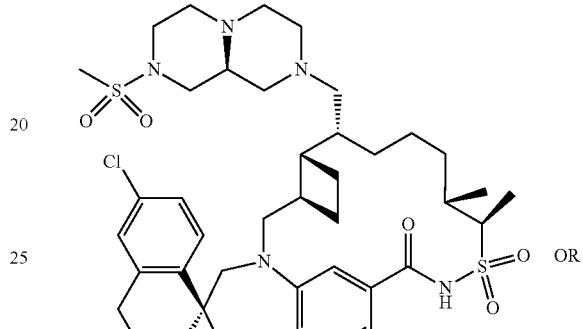
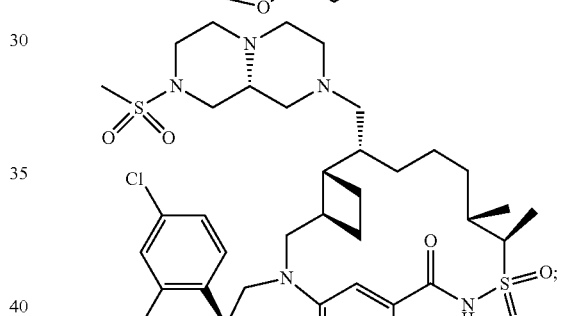
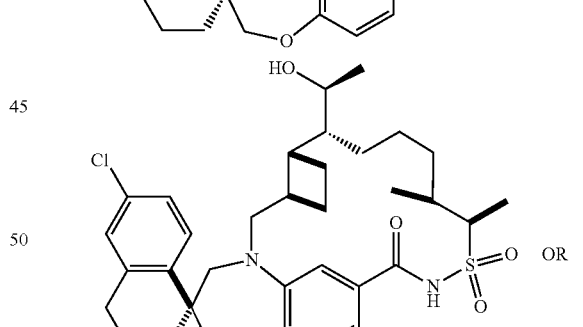
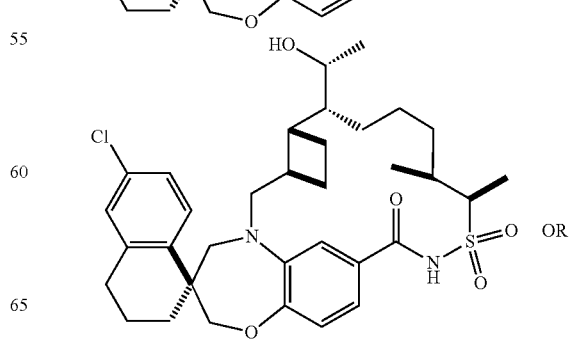

-continued
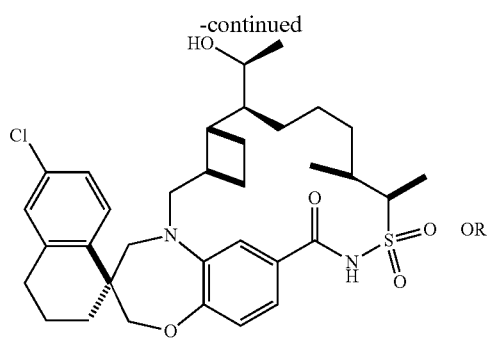
OR
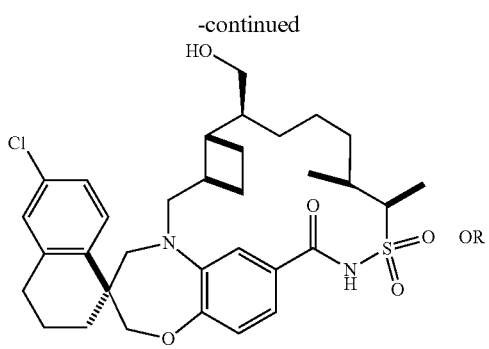
OR
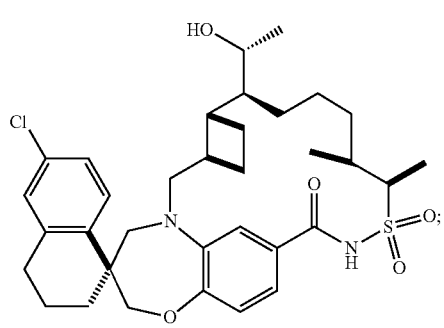
;
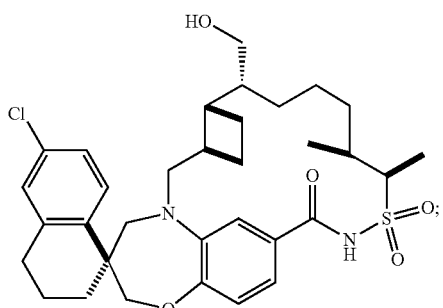
;
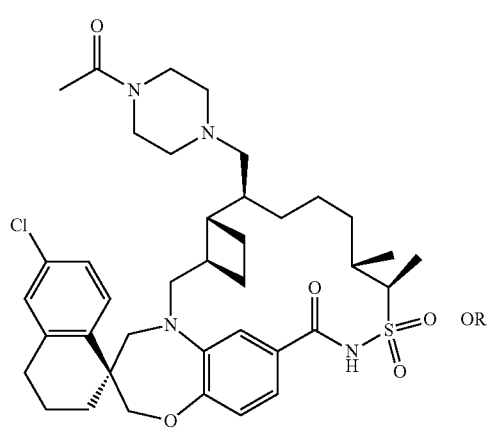
OR
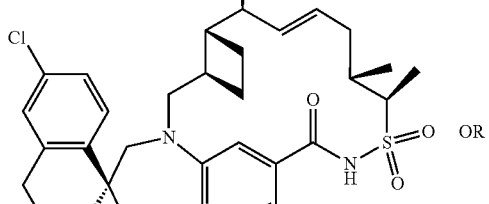
OR
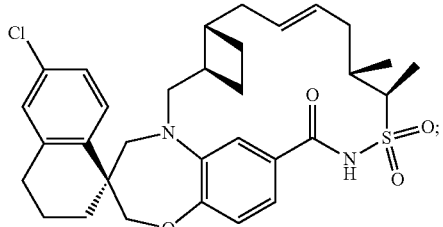
;
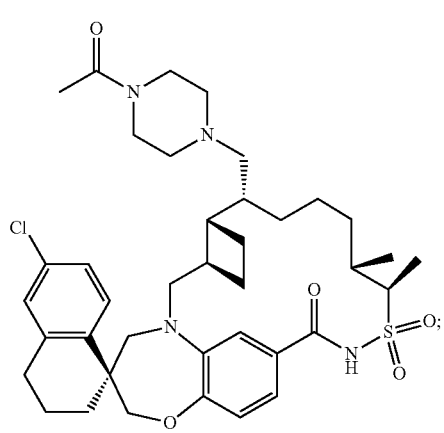
;
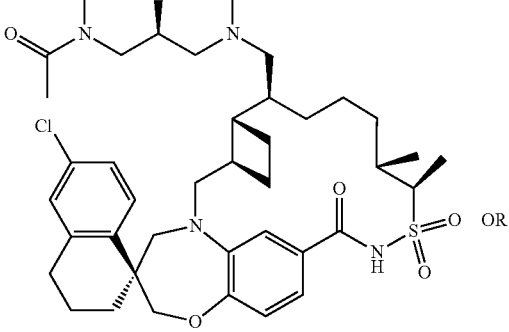
OR

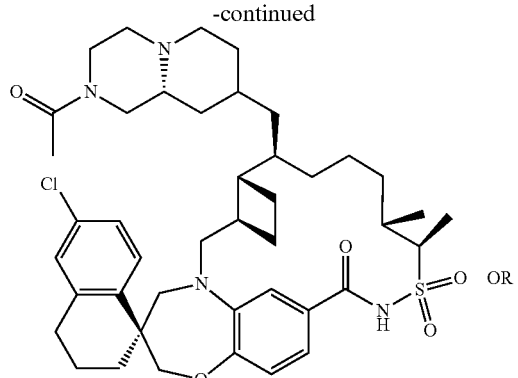
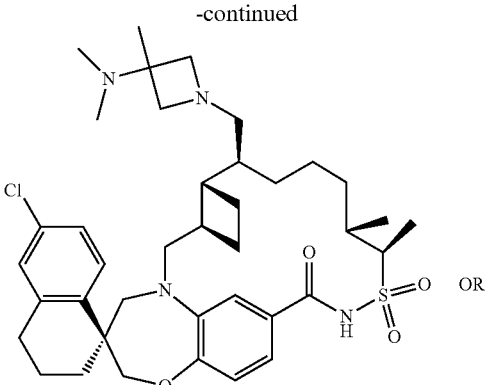
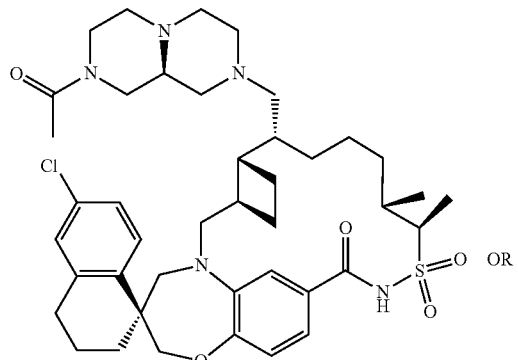
OR
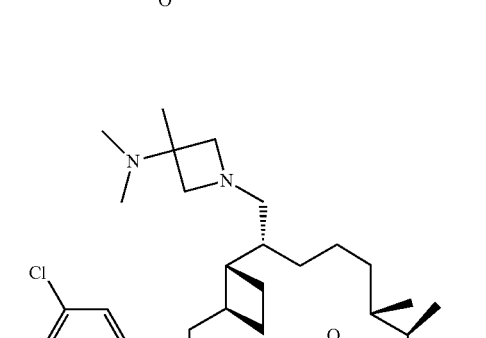
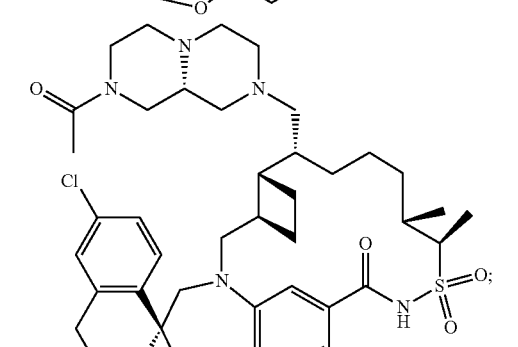
;
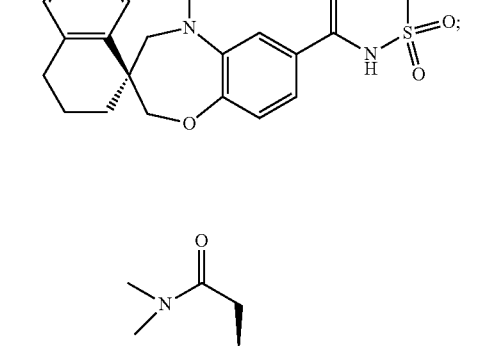
;
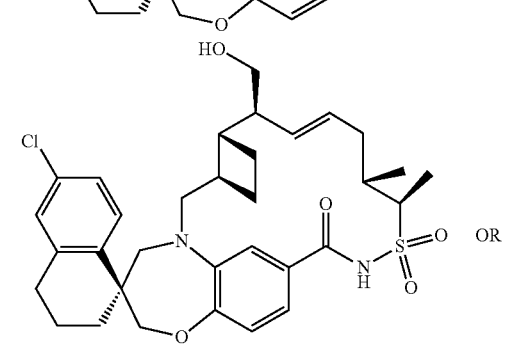
OR
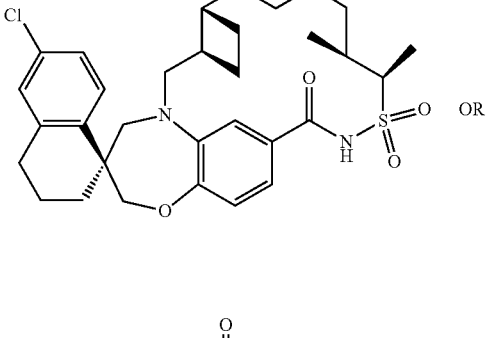
OR
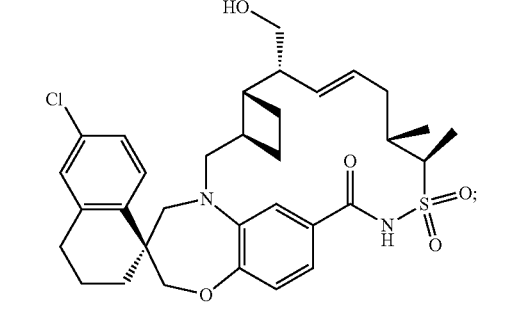
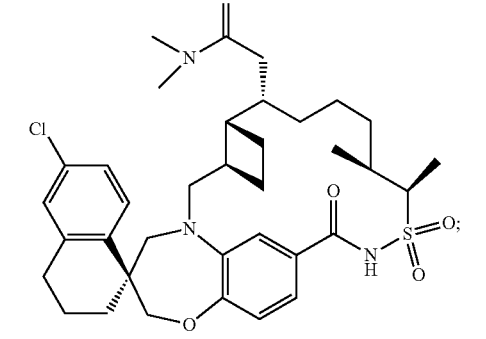
;

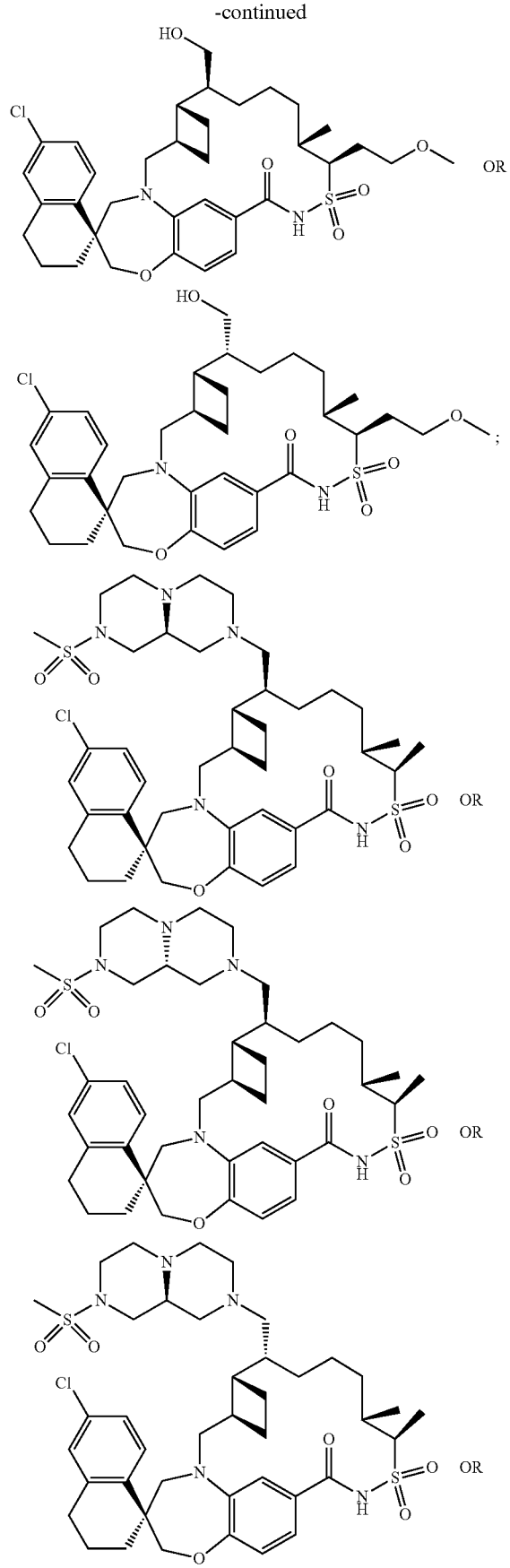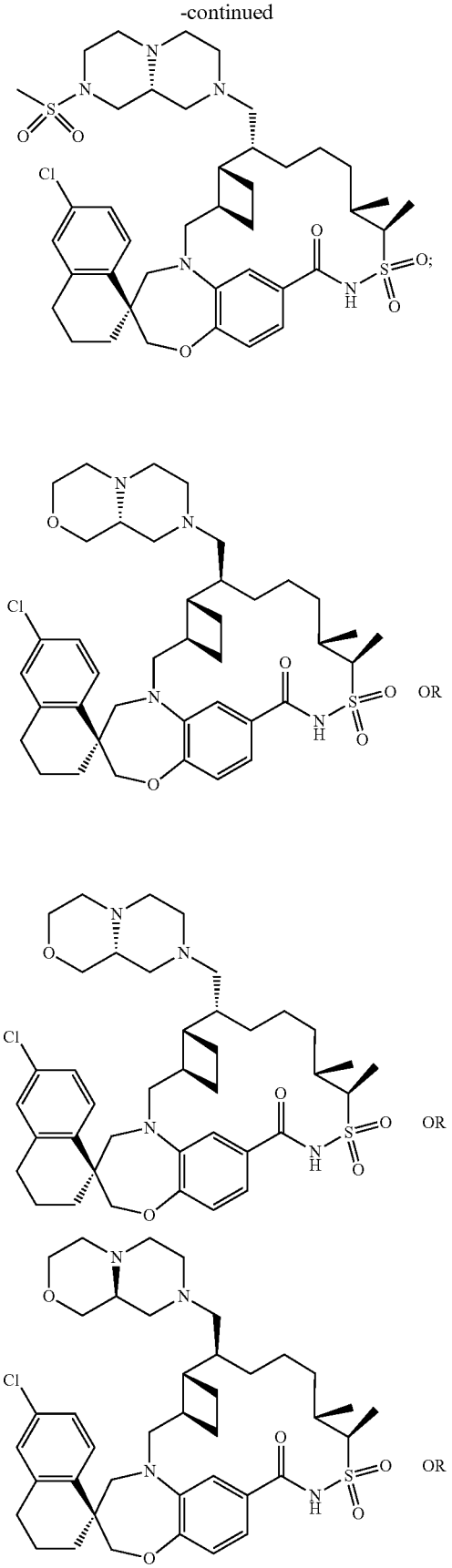

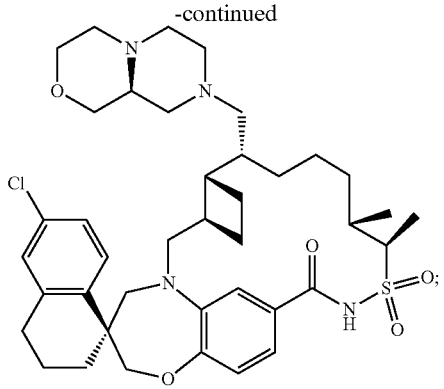
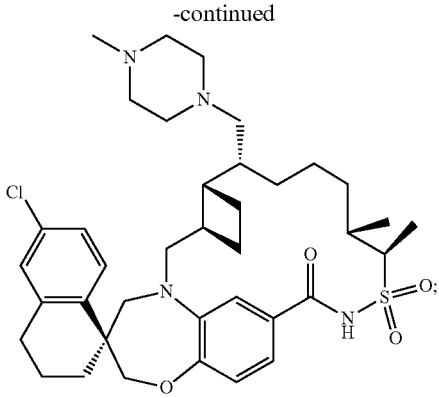
or
or
or
or
or

31
-continued
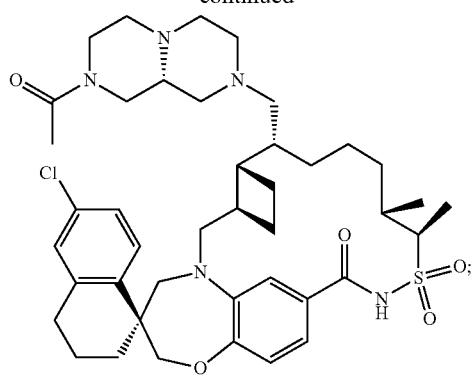
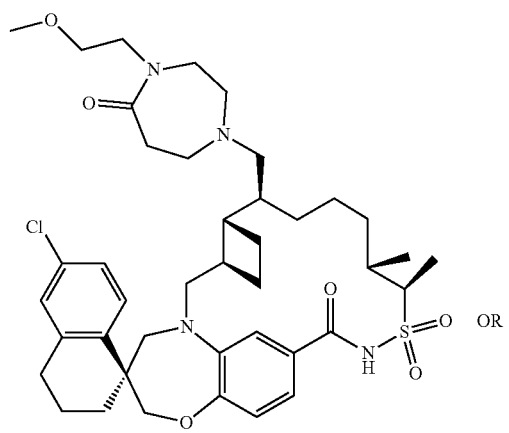
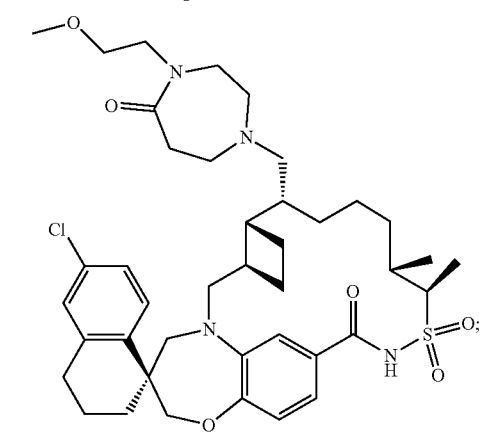
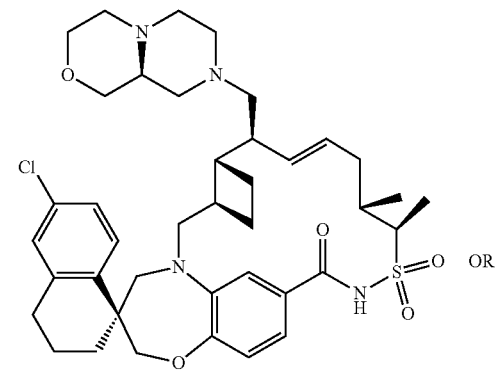
32
-continued
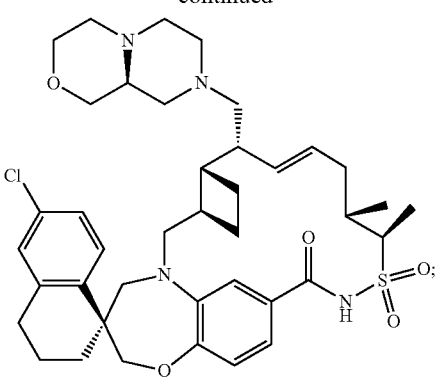
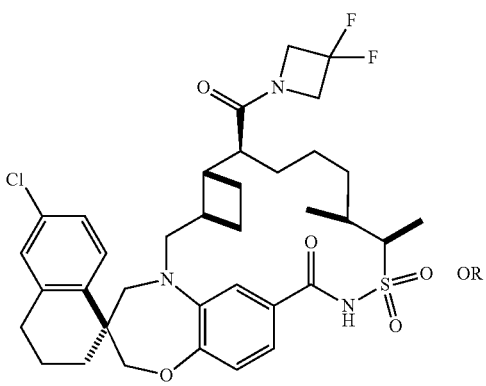
OR
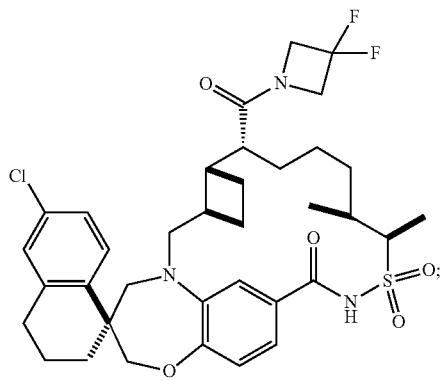
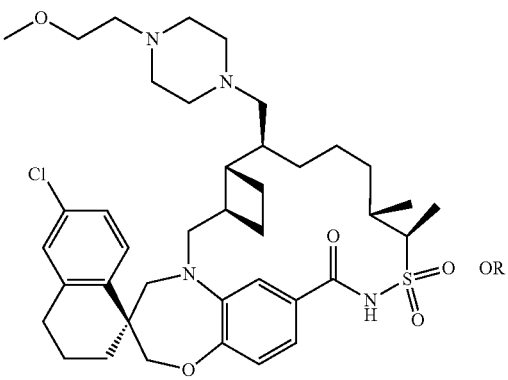
OR 33
-continued
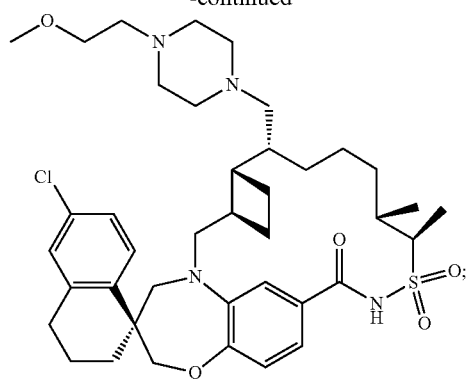
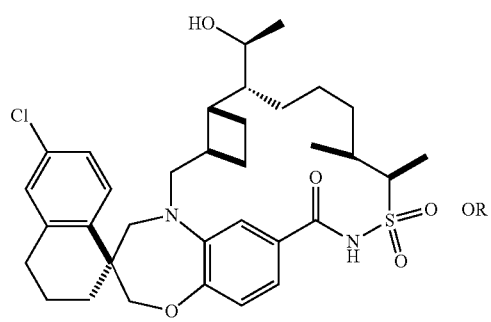
OR
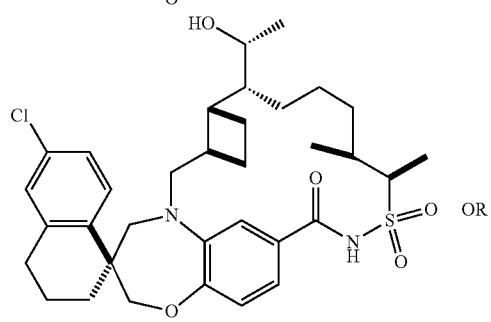
OR
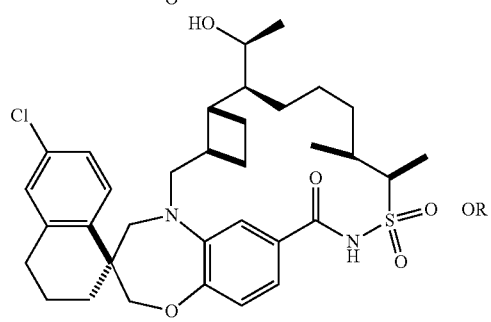
OR
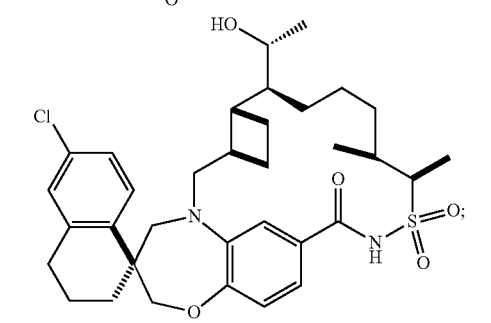
34
-continued
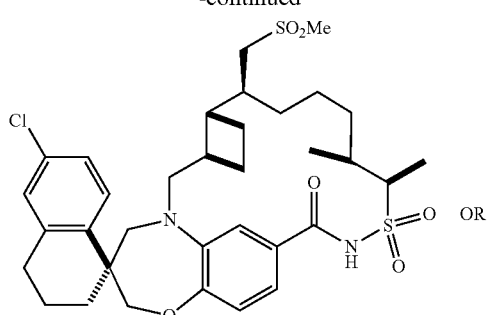
OR
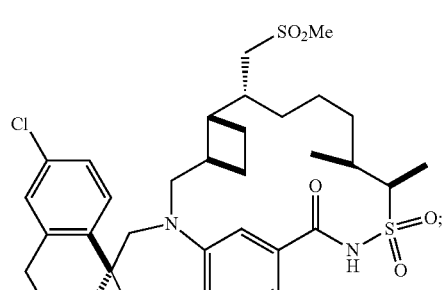
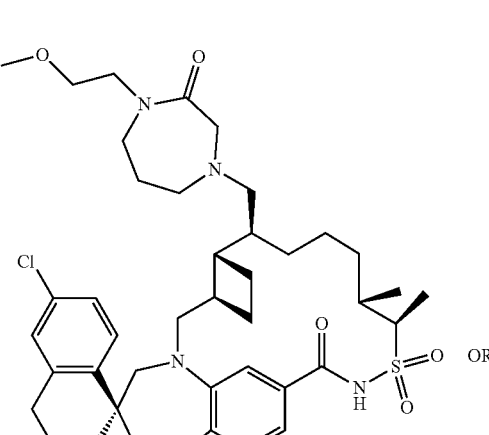
OR
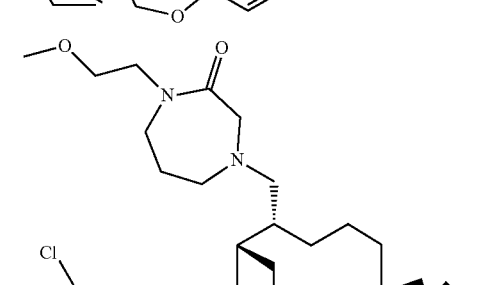
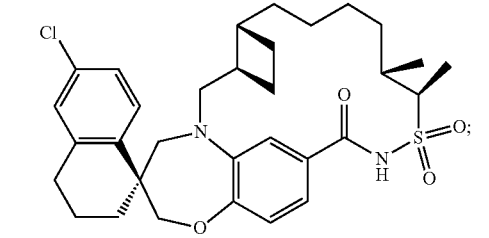

-continued
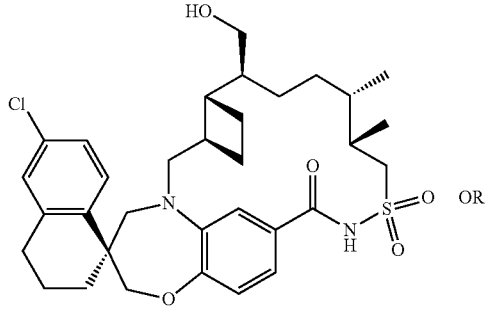
or
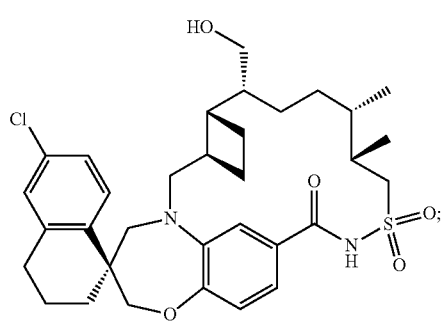
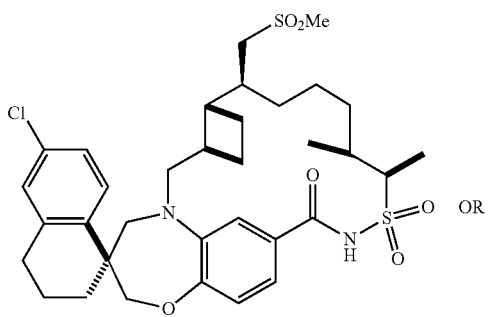
or
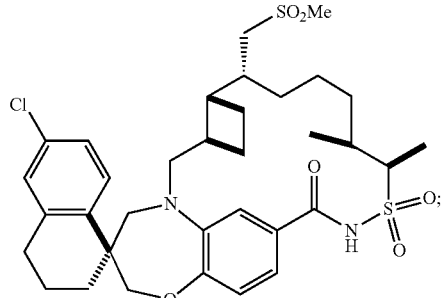
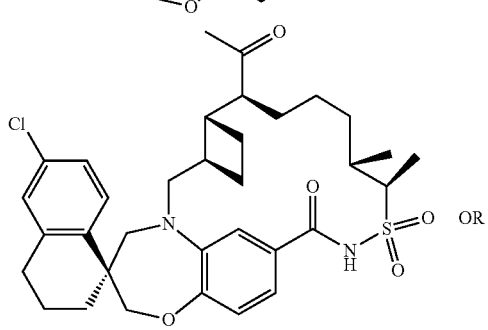
or
-continued
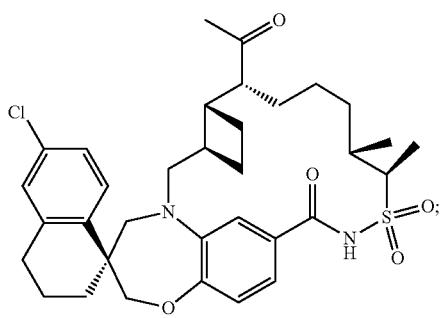
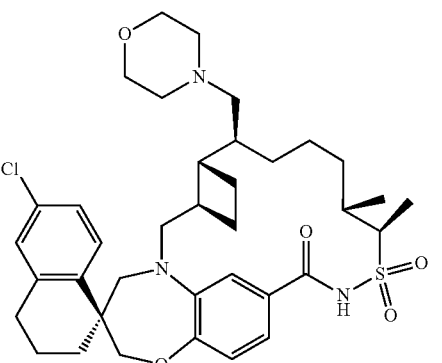
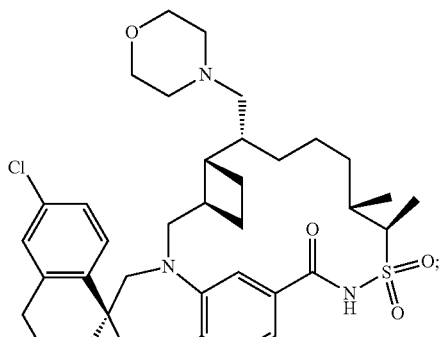
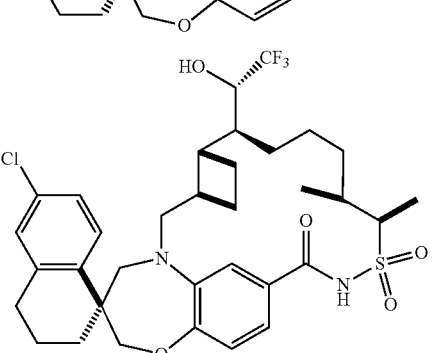
or
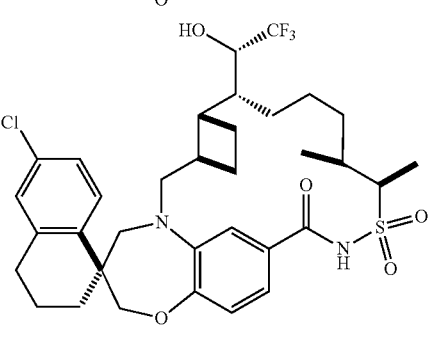
or

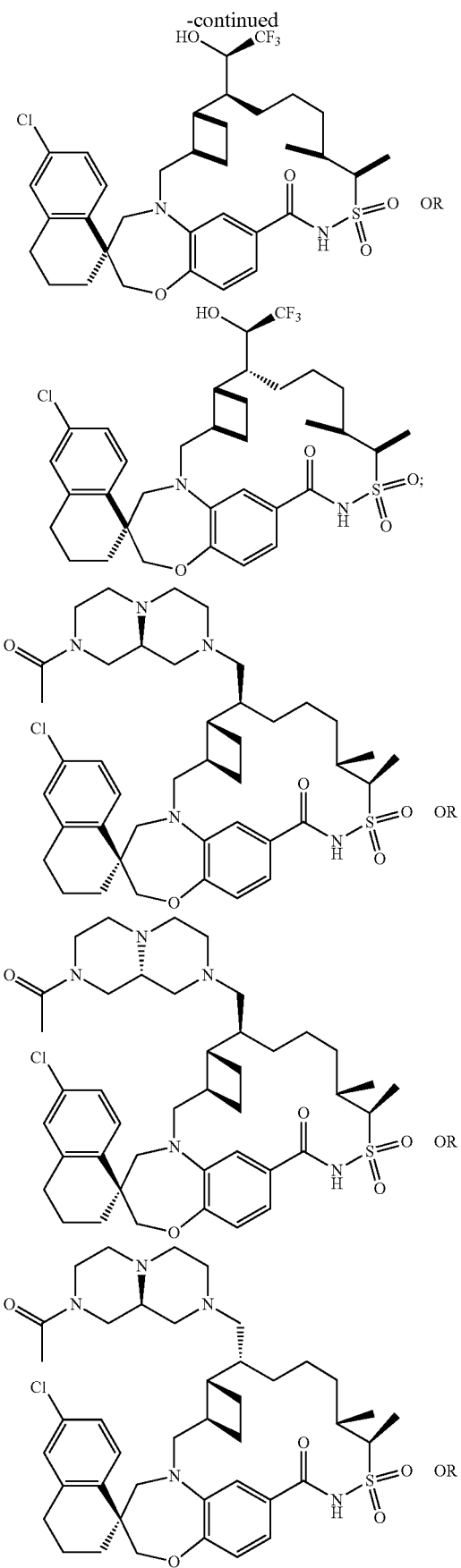
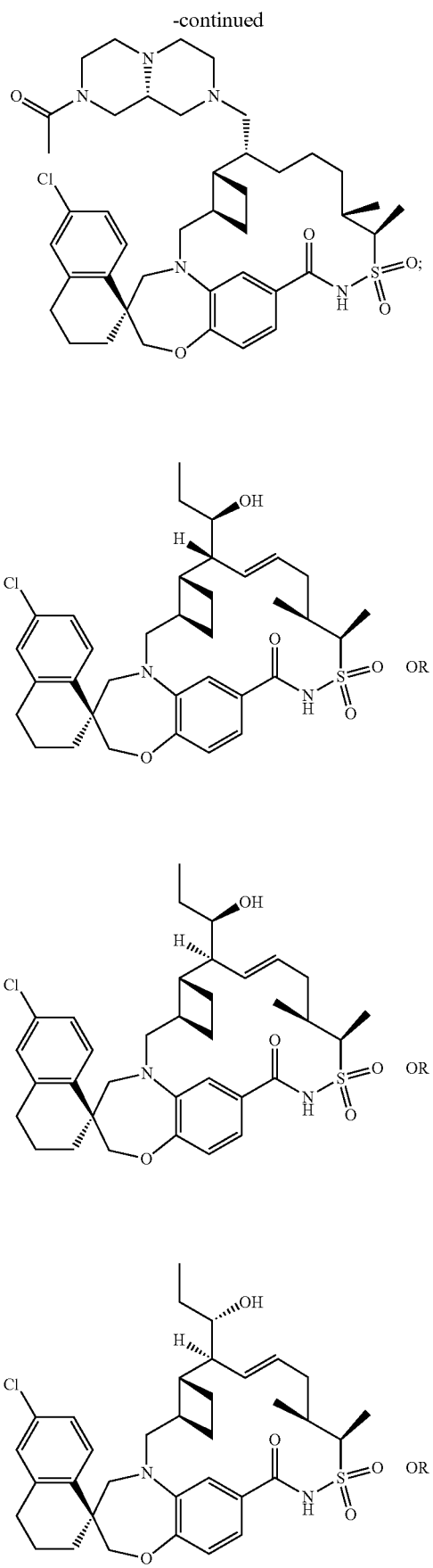

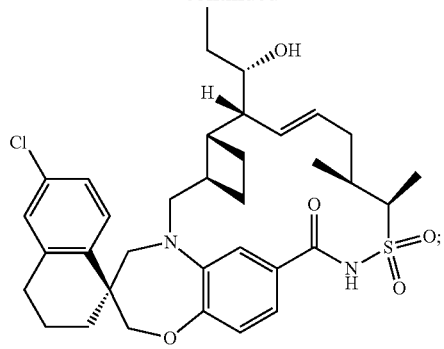
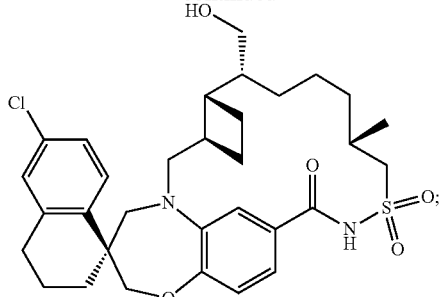
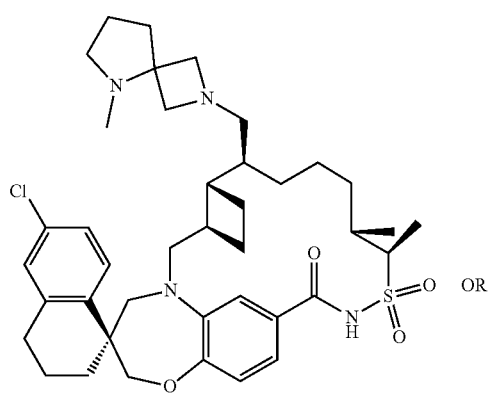
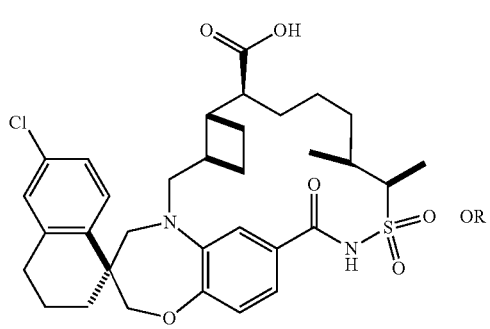
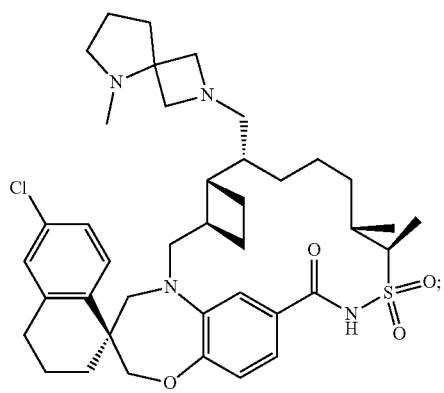
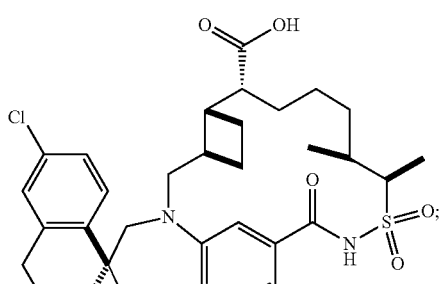
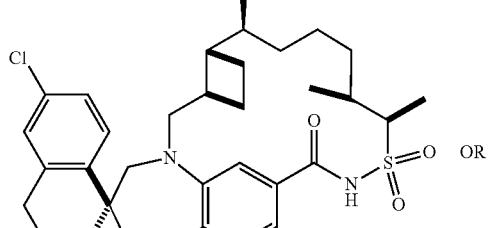
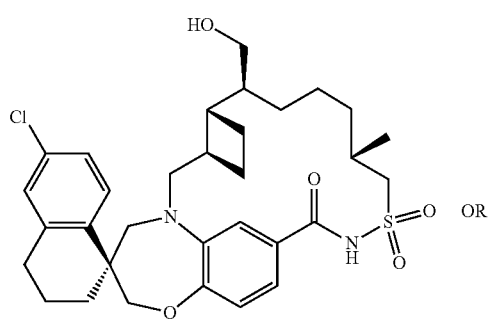
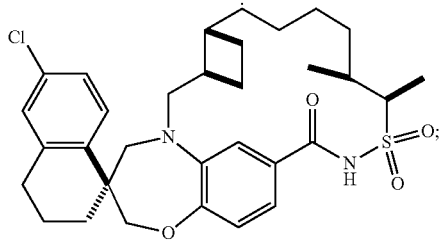

-continued
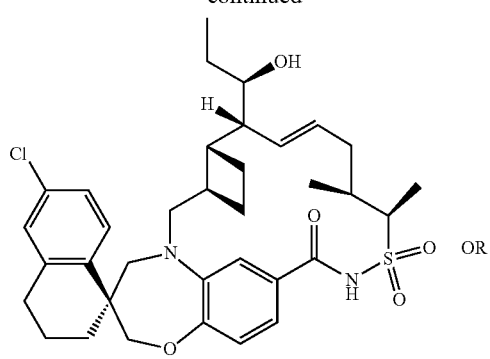
OR
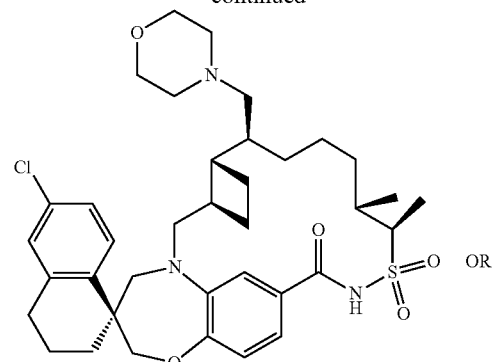
OR
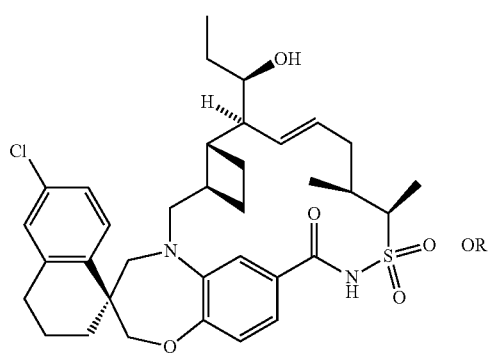
OR
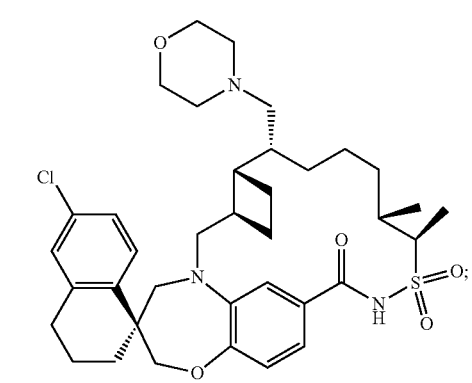
;
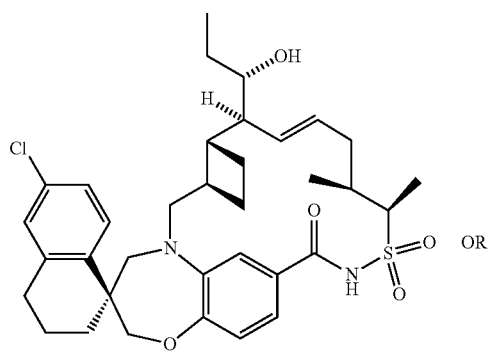
OR
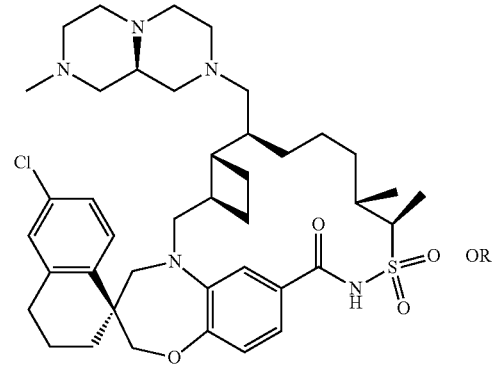
OR
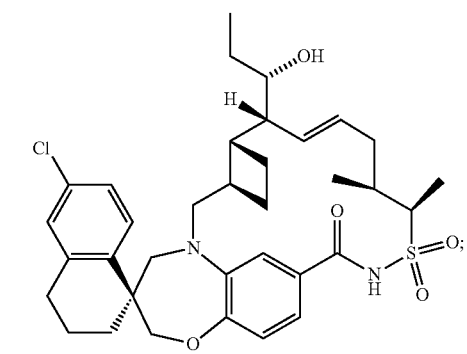
;
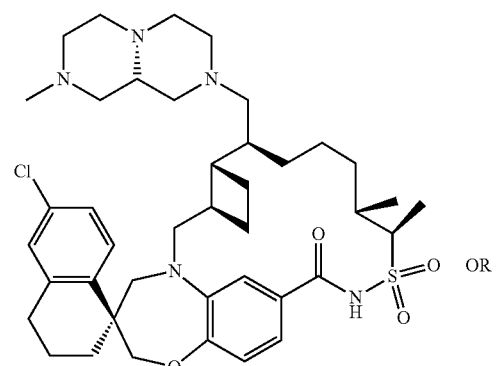
OR

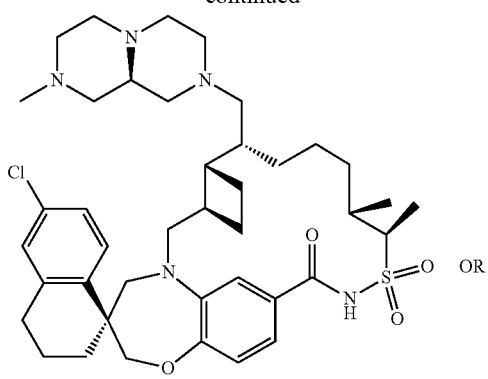
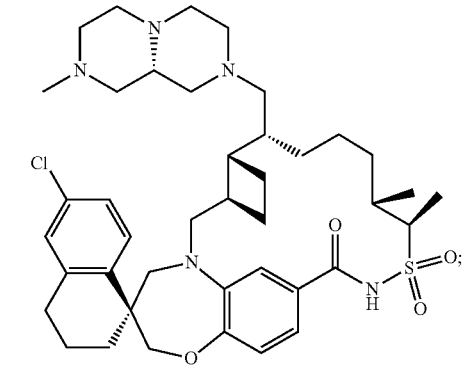
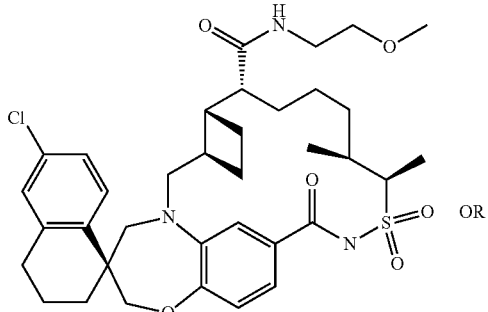
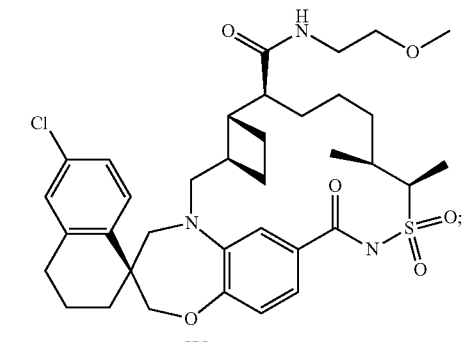
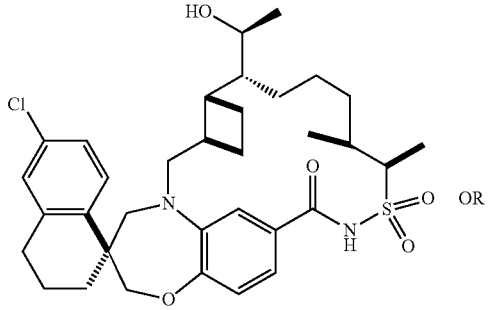
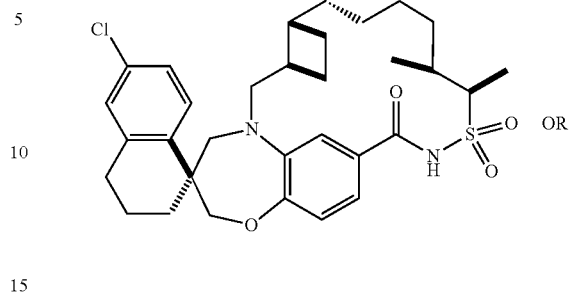
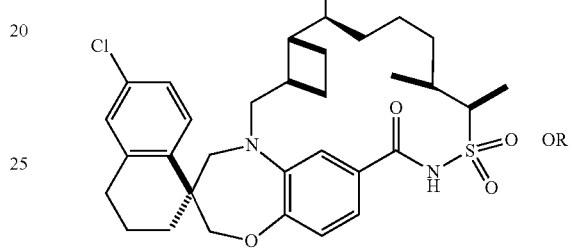
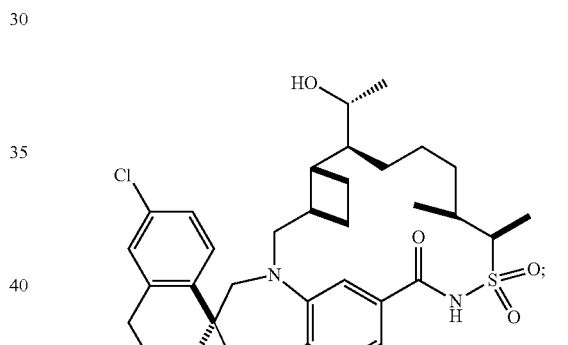
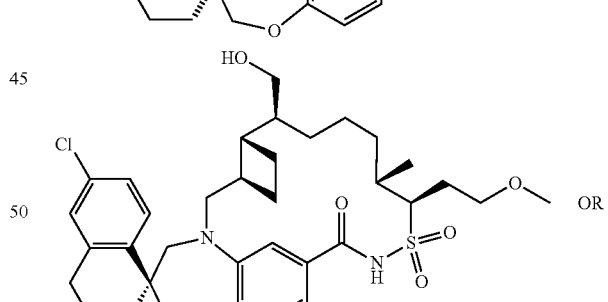
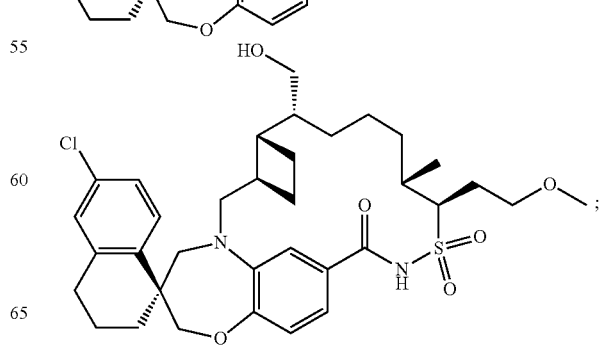

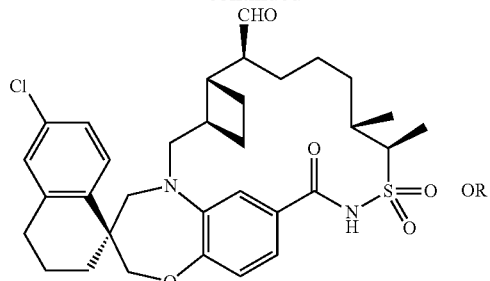
or
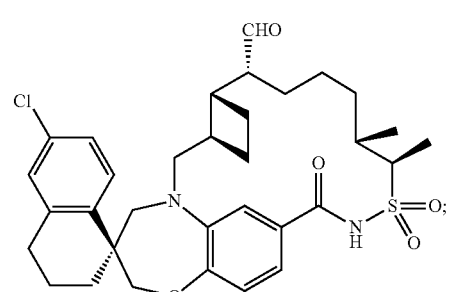
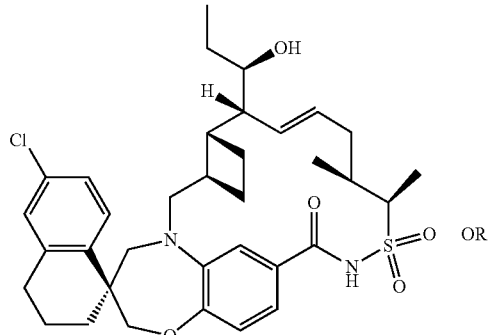
or
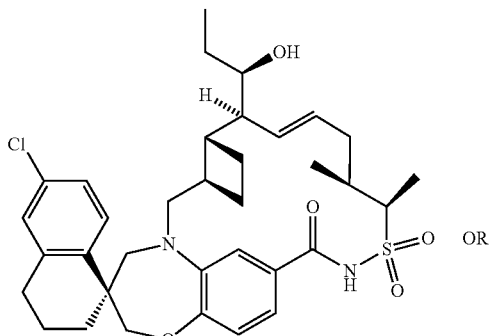
or
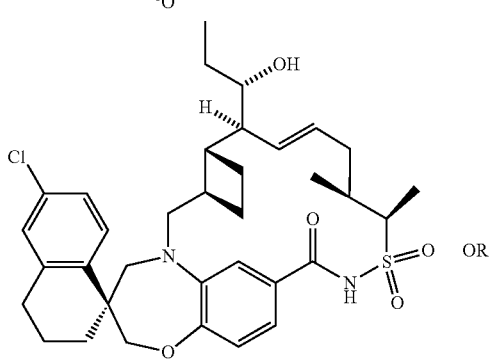
or
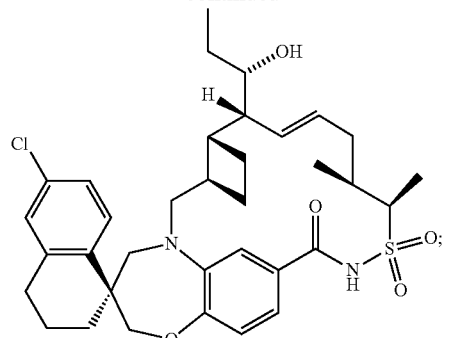
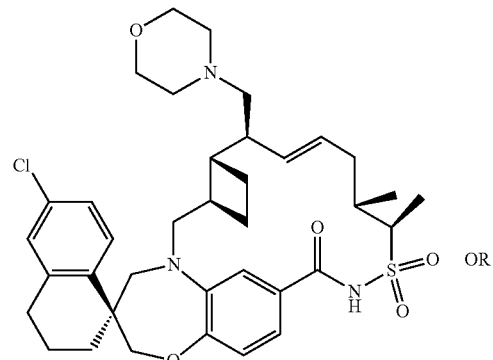
or
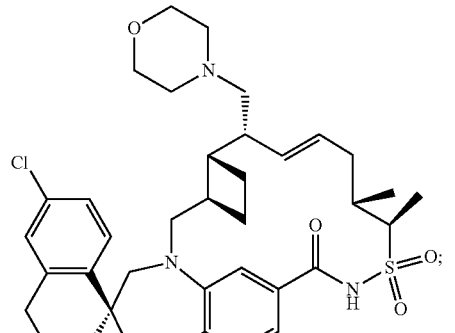
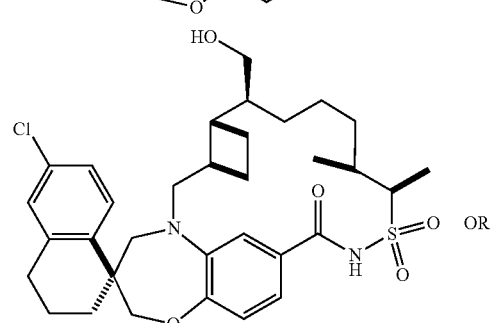
or
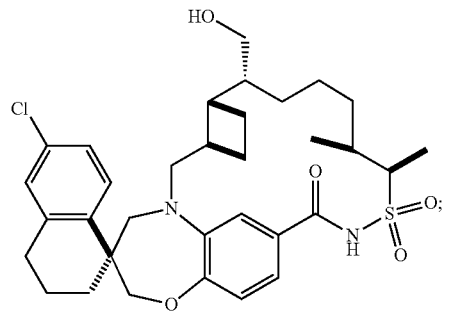

-continued
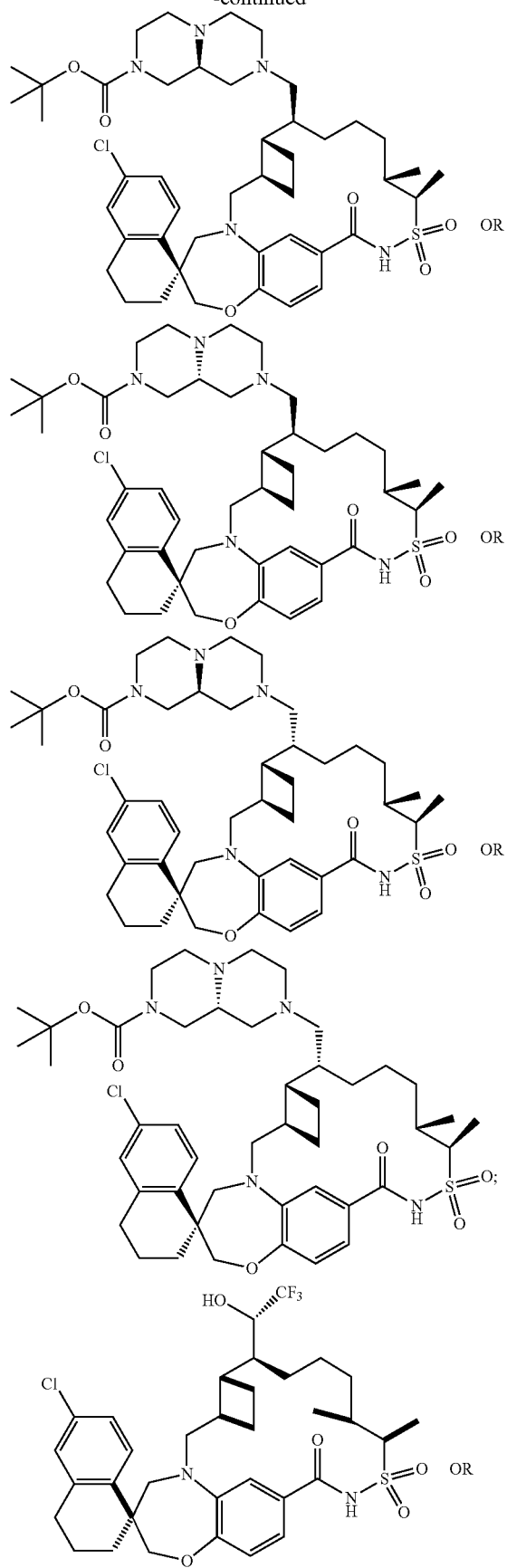
-continued
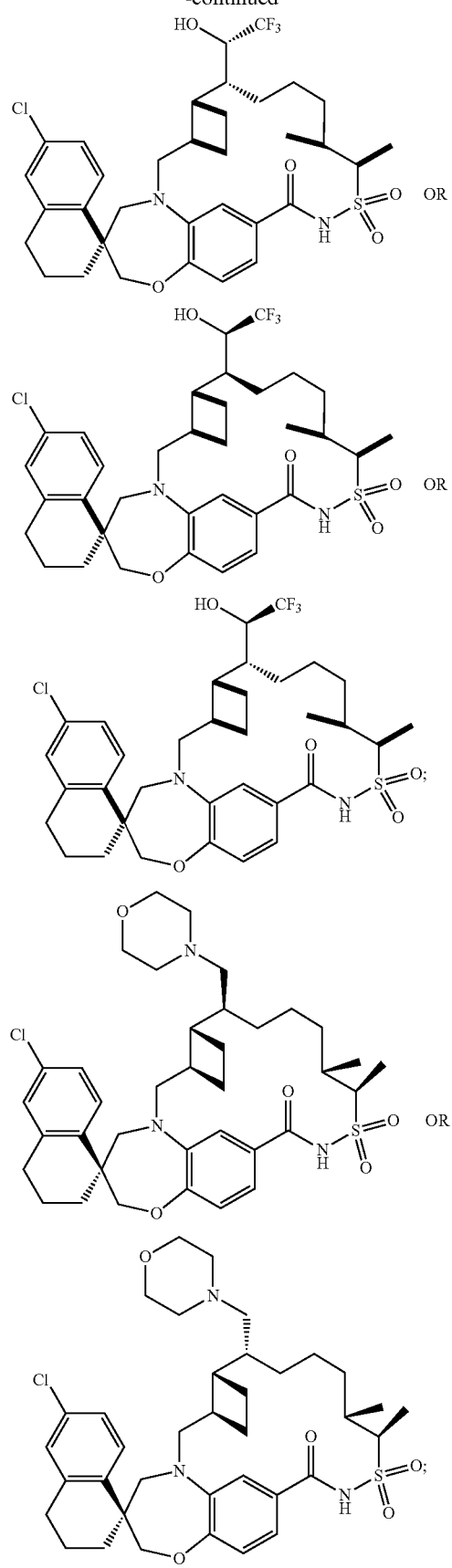

49
-continued
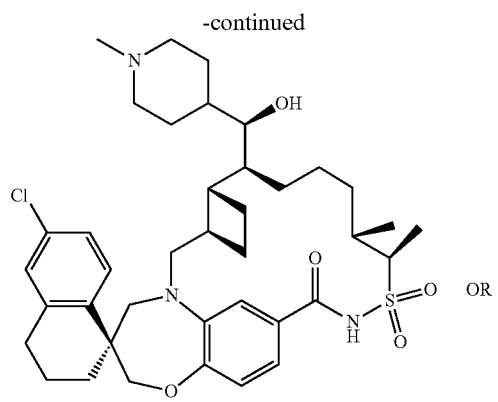
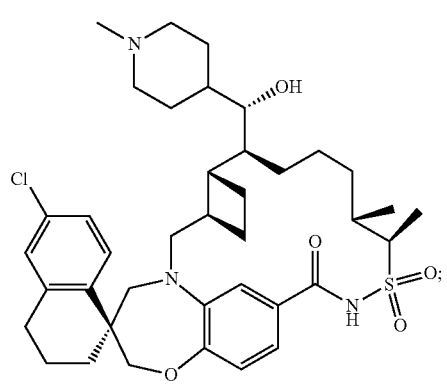
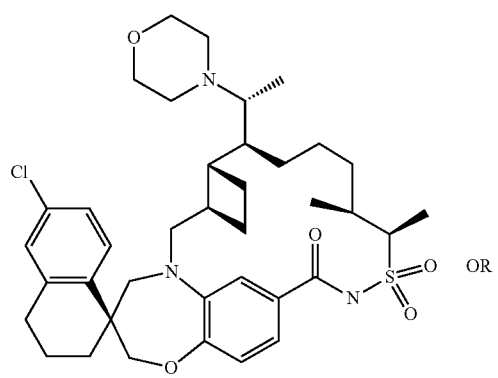
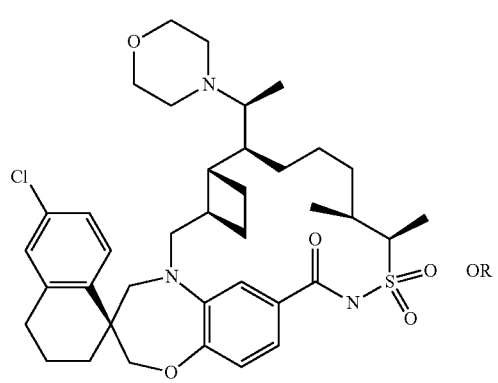
50
-continued
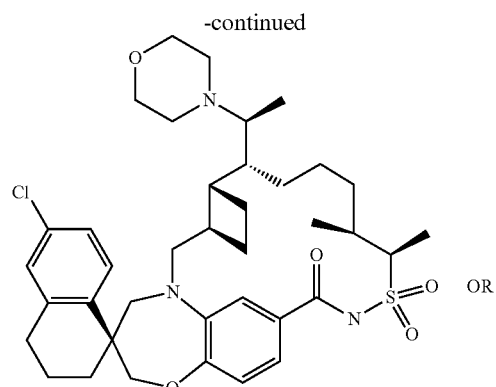
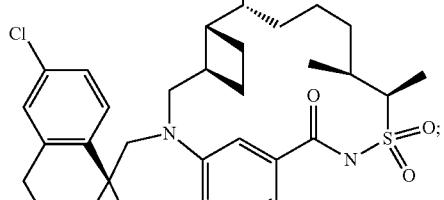
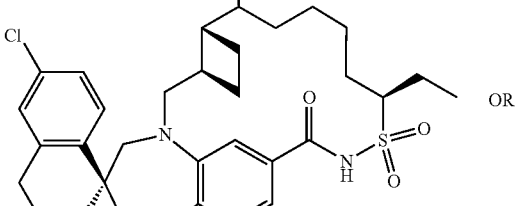
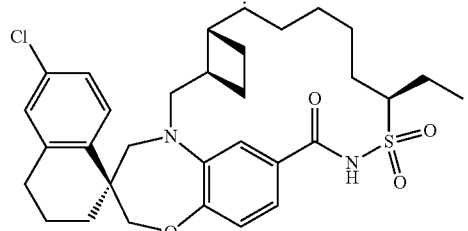
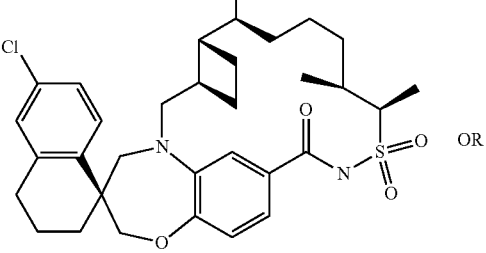

51
-continued
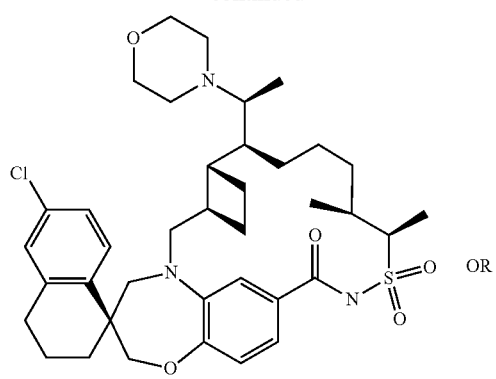
OR
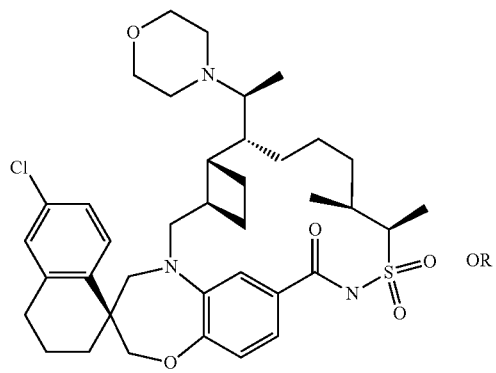
OR
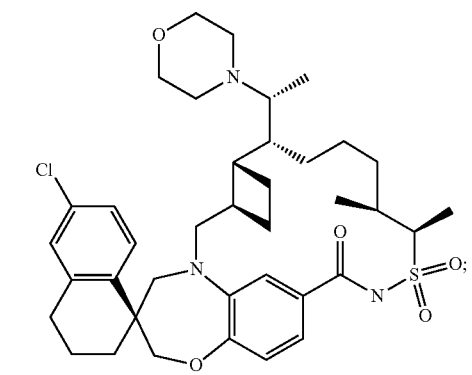
;
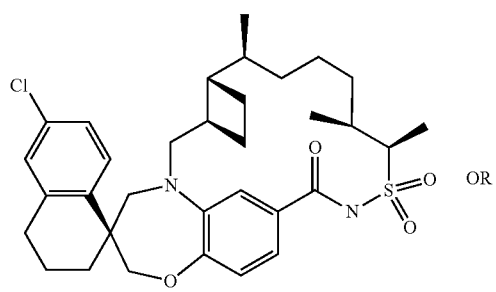
OR
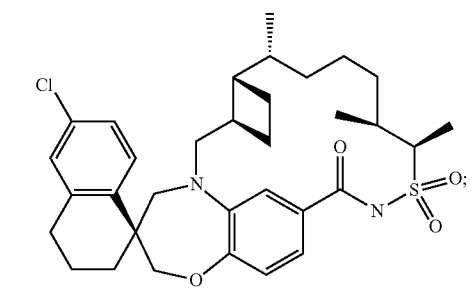
;
52
-continued
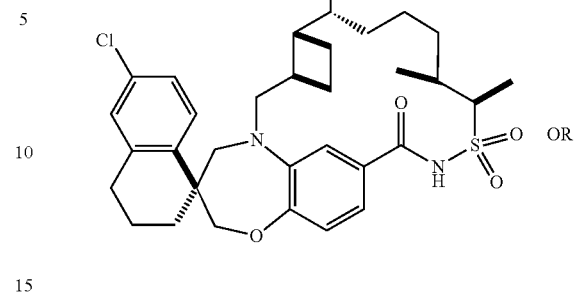
OR
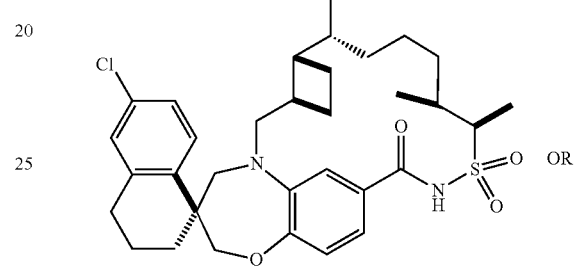
OR
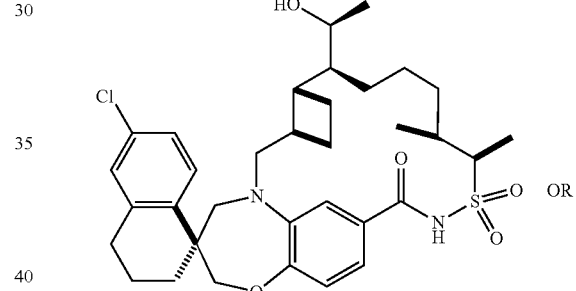
OR
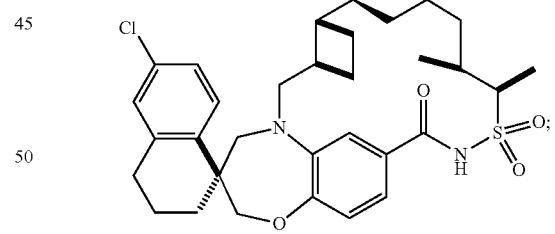
;
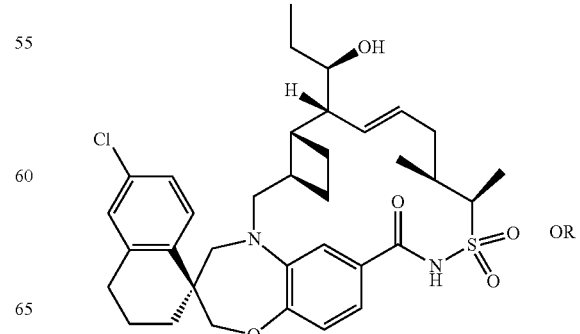
OR

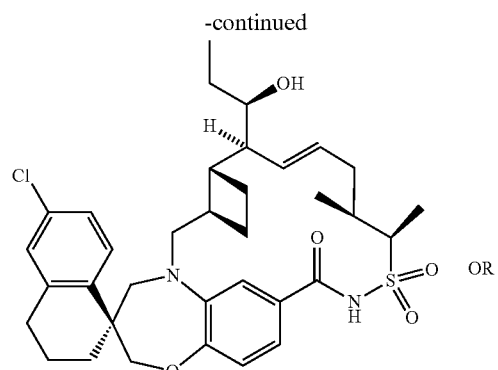
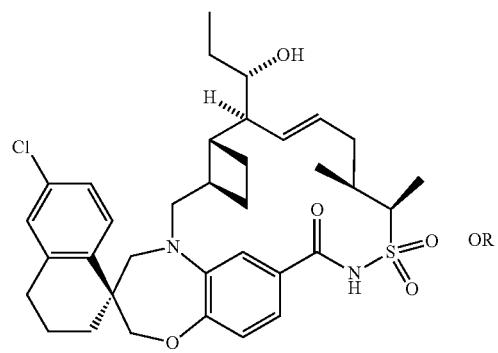
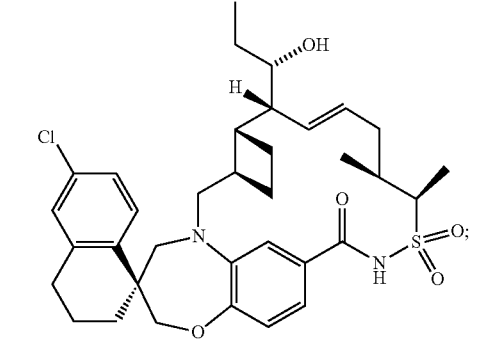
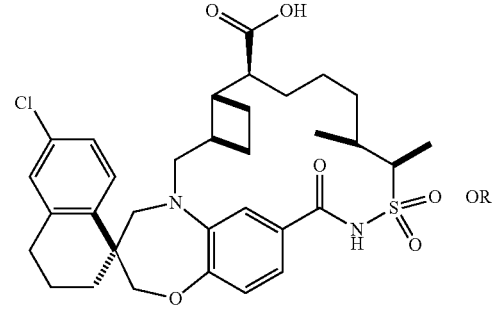
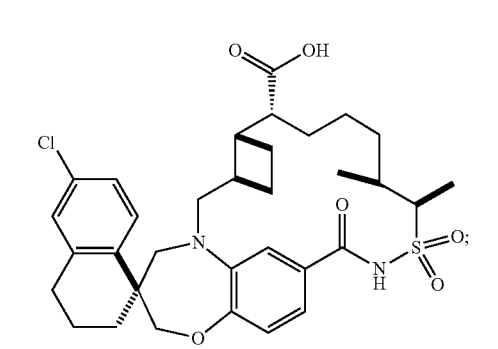
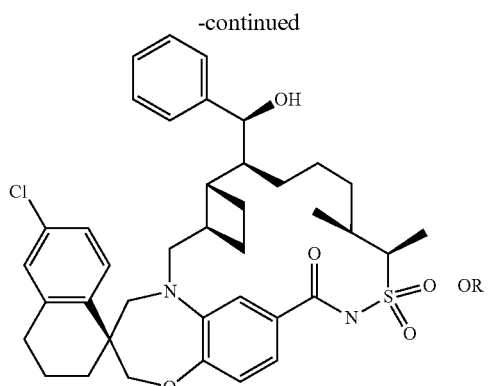
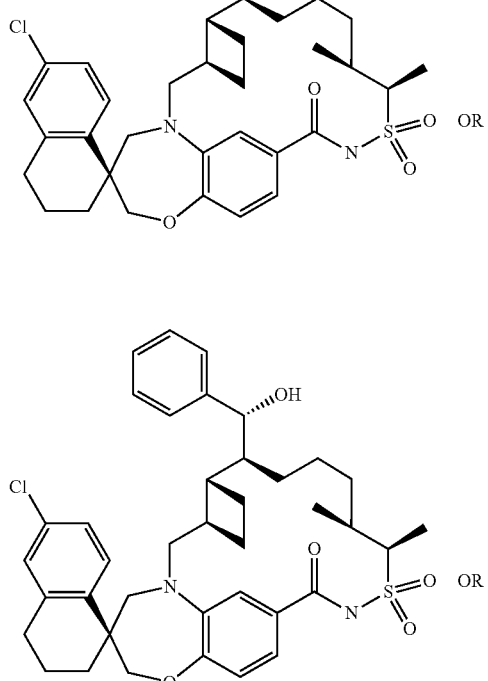
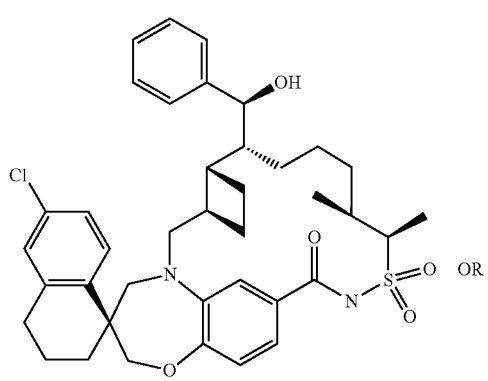
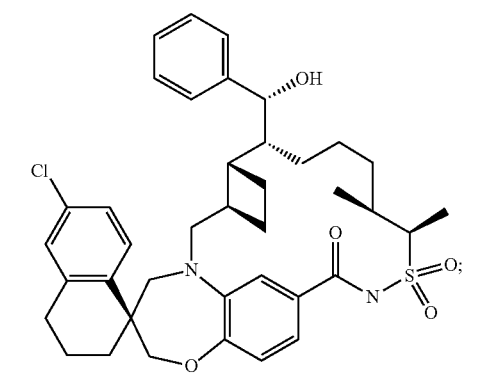

| 55 | 56 |
|---|---|
| -continued | -continued |
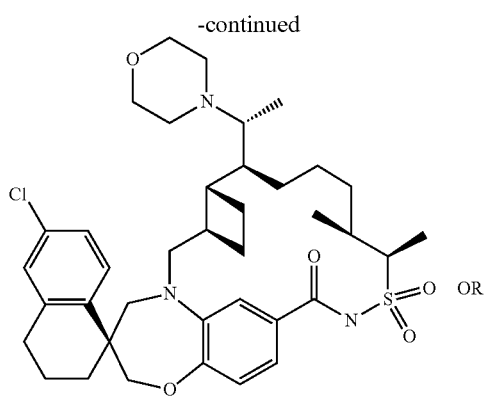
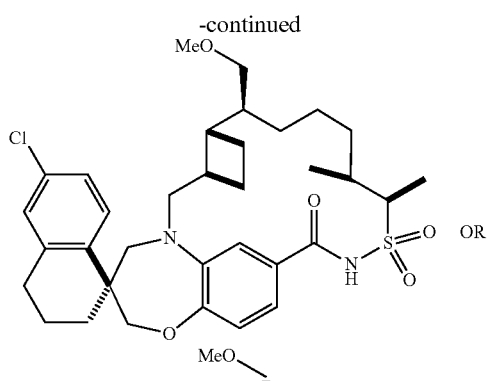
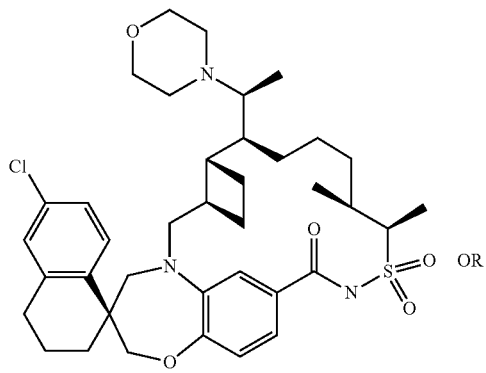
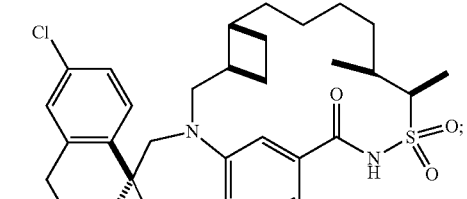
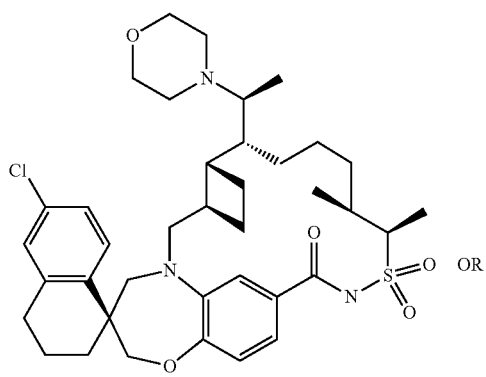
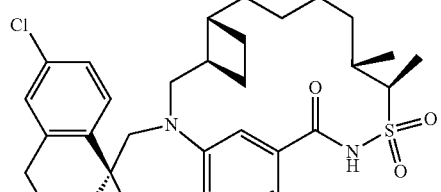
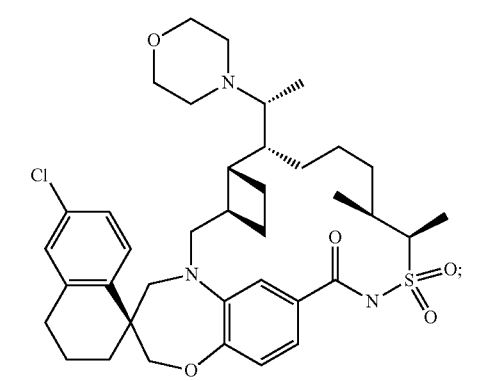
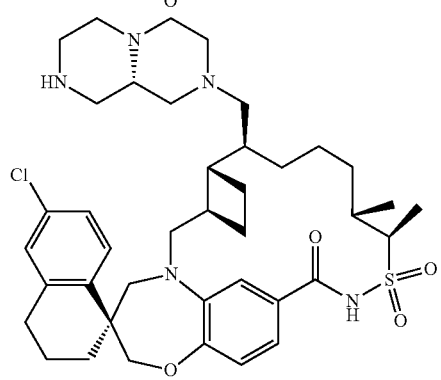
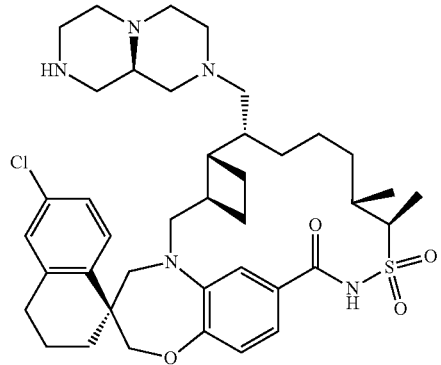

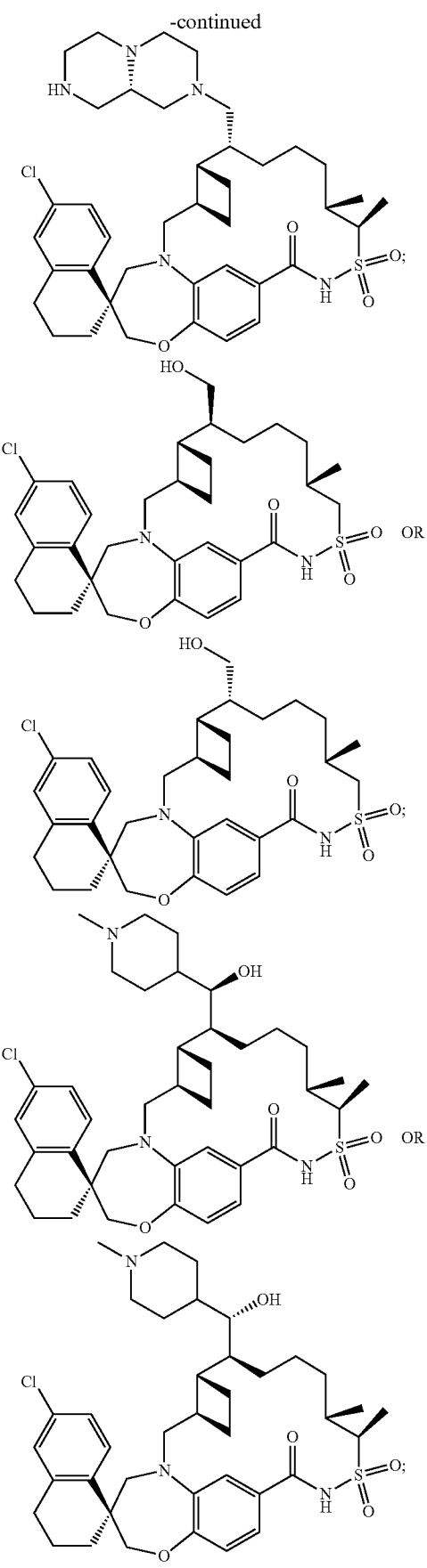
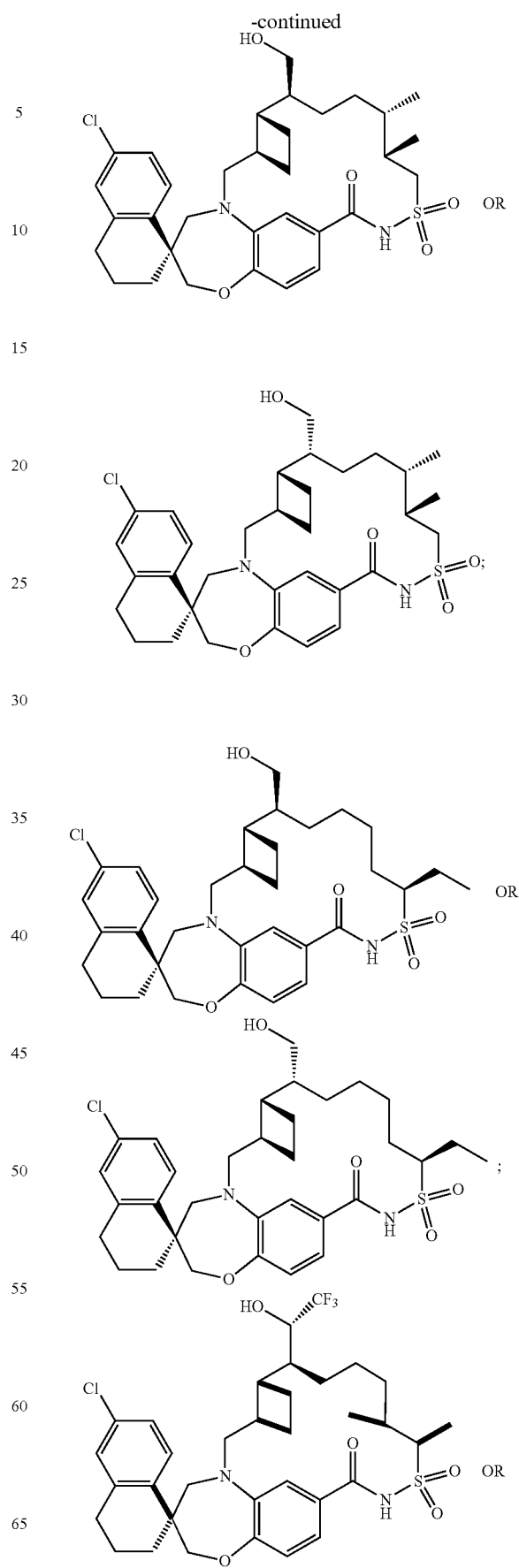

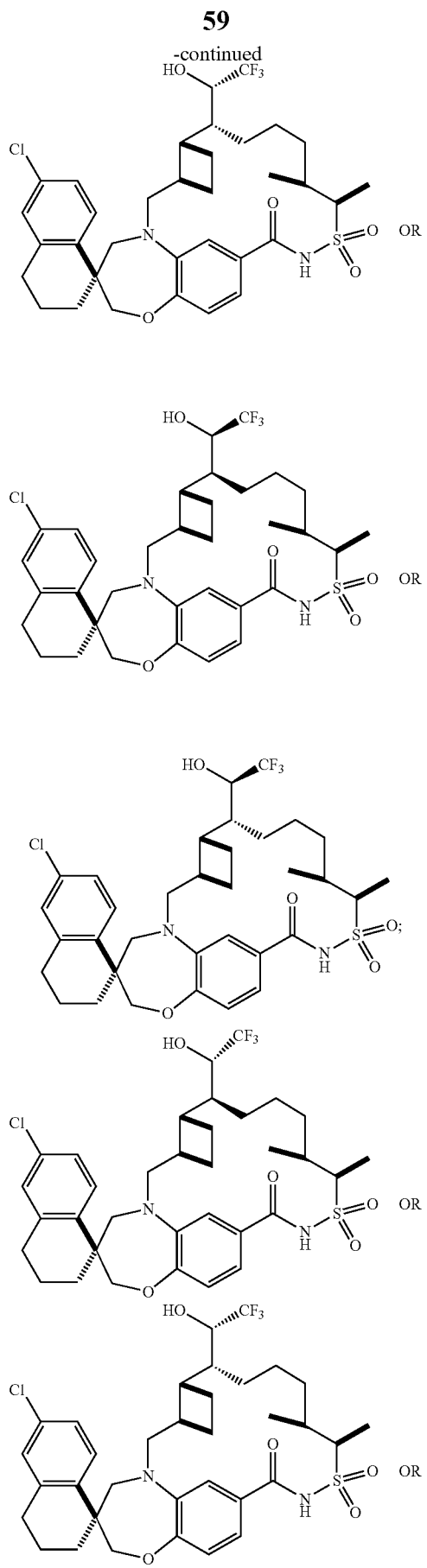
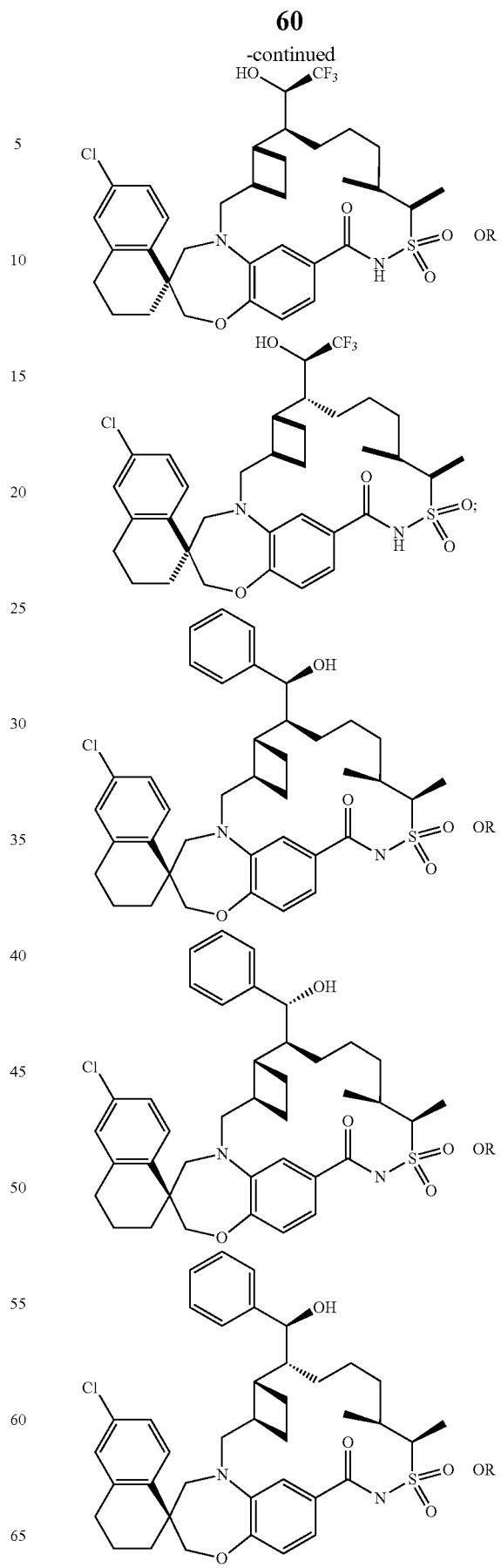

61
-continued
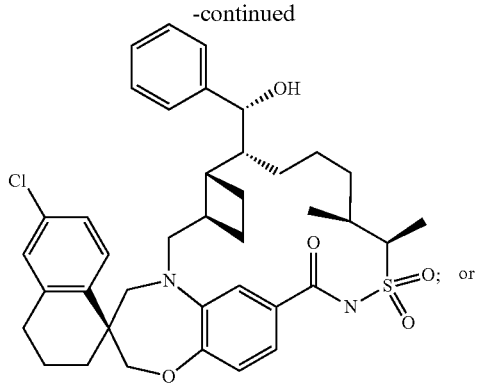
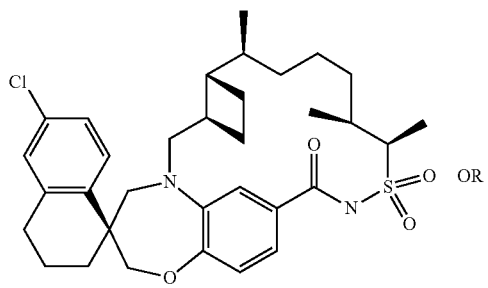
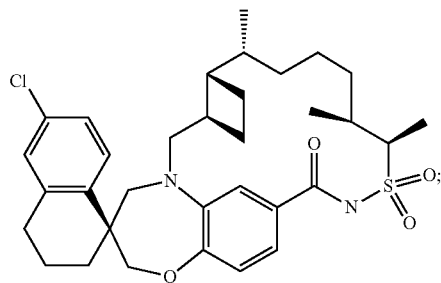
or a stereoisomer thereof; a pharmaceutically acceptable salt thereof, a pharmaceutically acceptable salt of the stereoisomer thereof.
48. Another embodiment of the present invention comprises a compound, wherein the compound has a structure selected from:
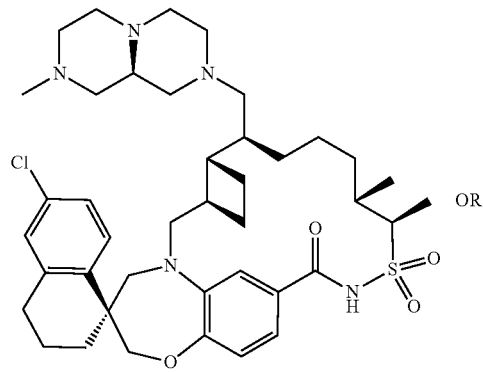
62
-continued
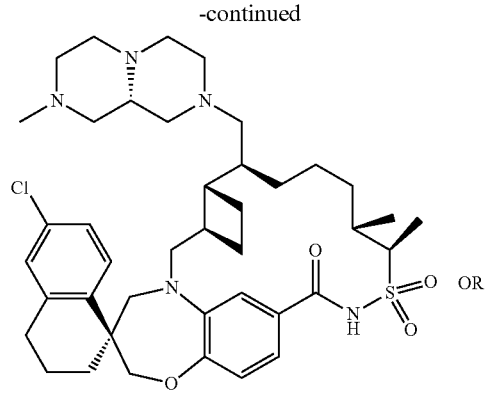
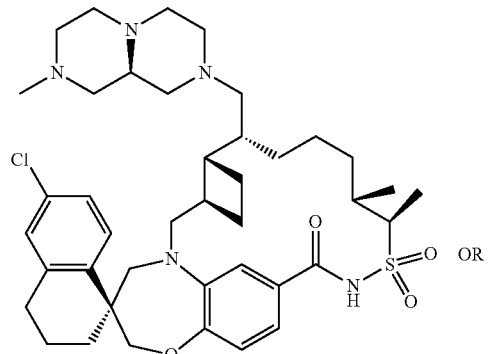
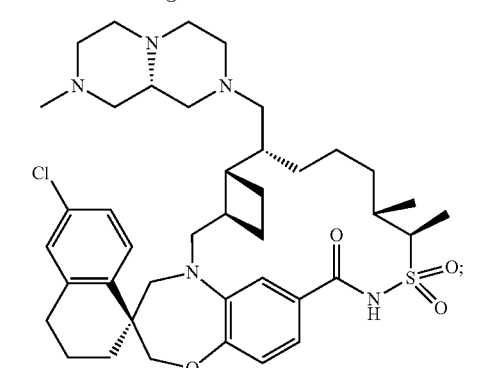
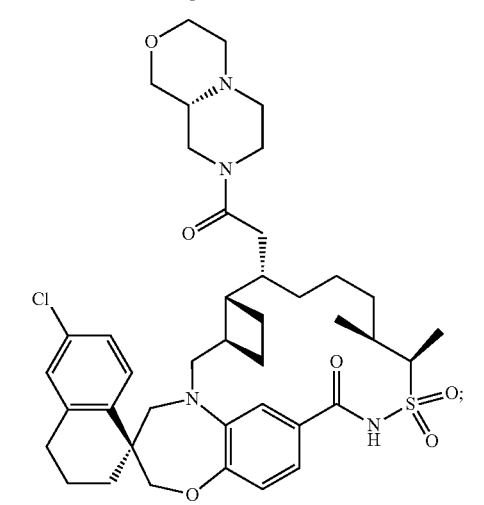

63
-continued
64
-continued
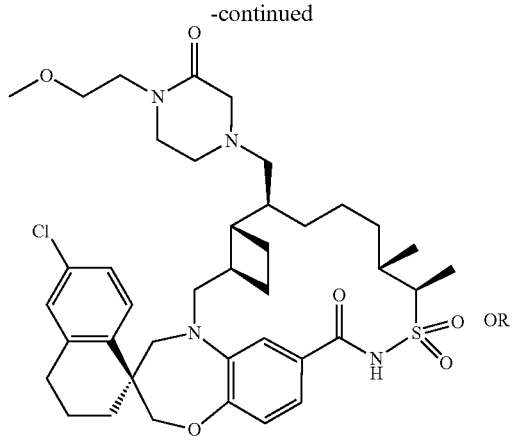
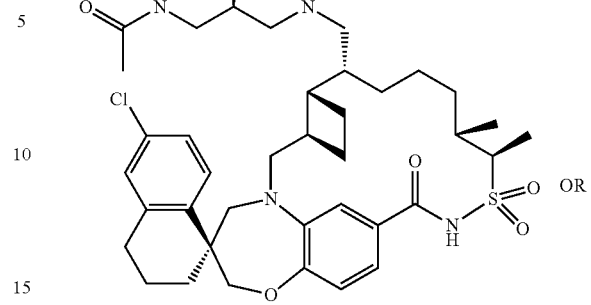
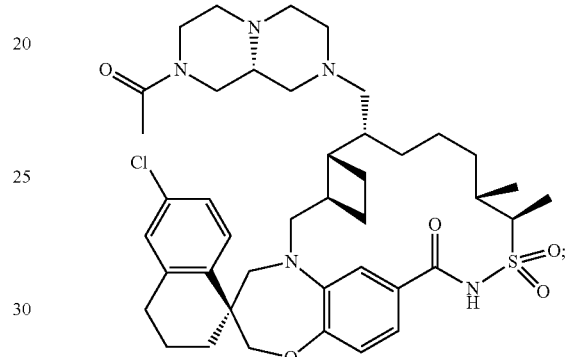
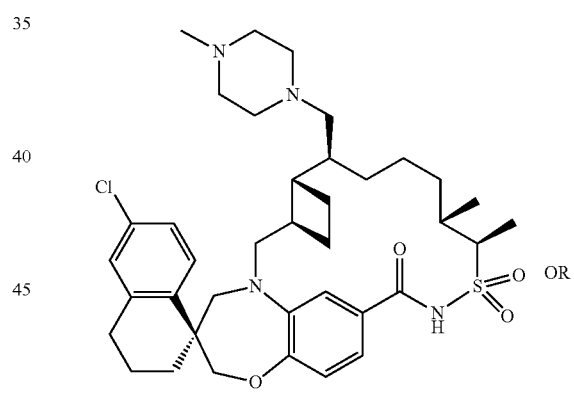
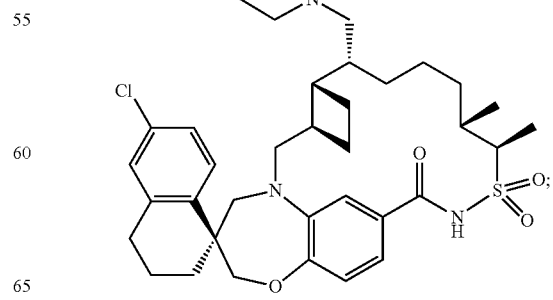

65
-continued
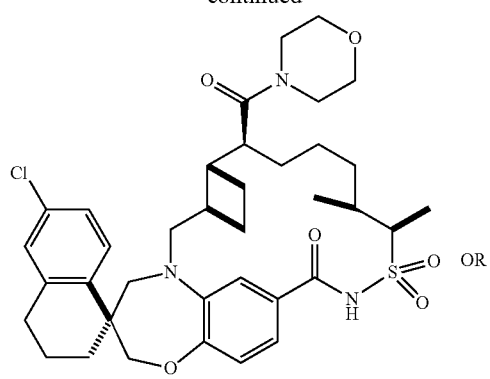
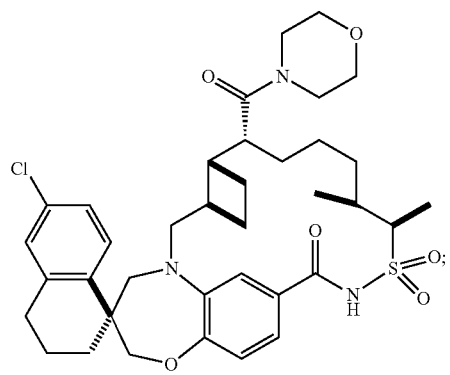
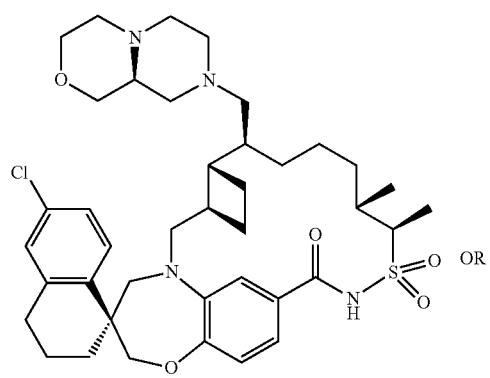
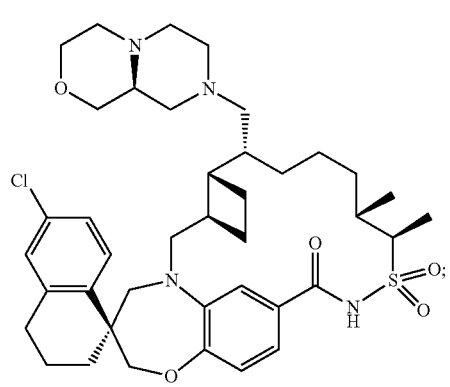
66
-continued
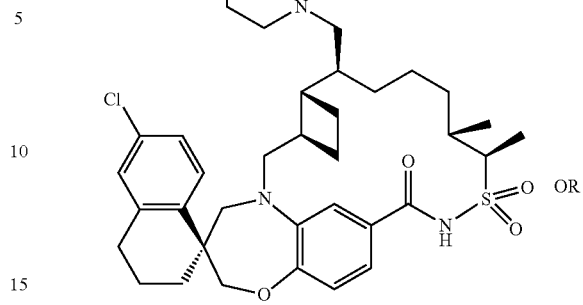
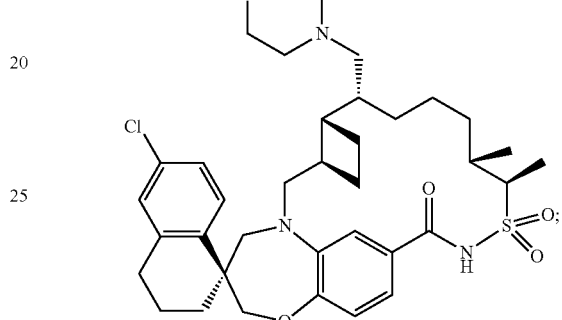
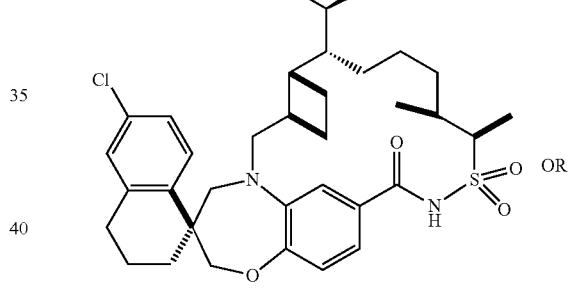
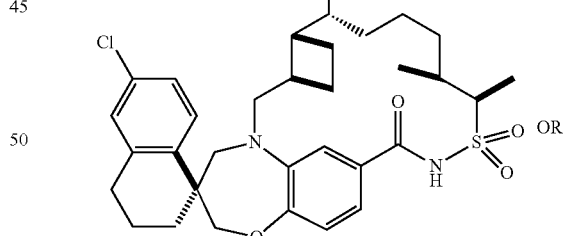
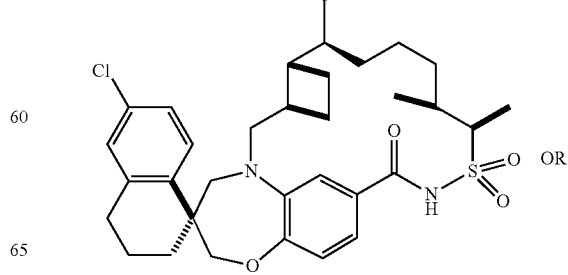

-continued

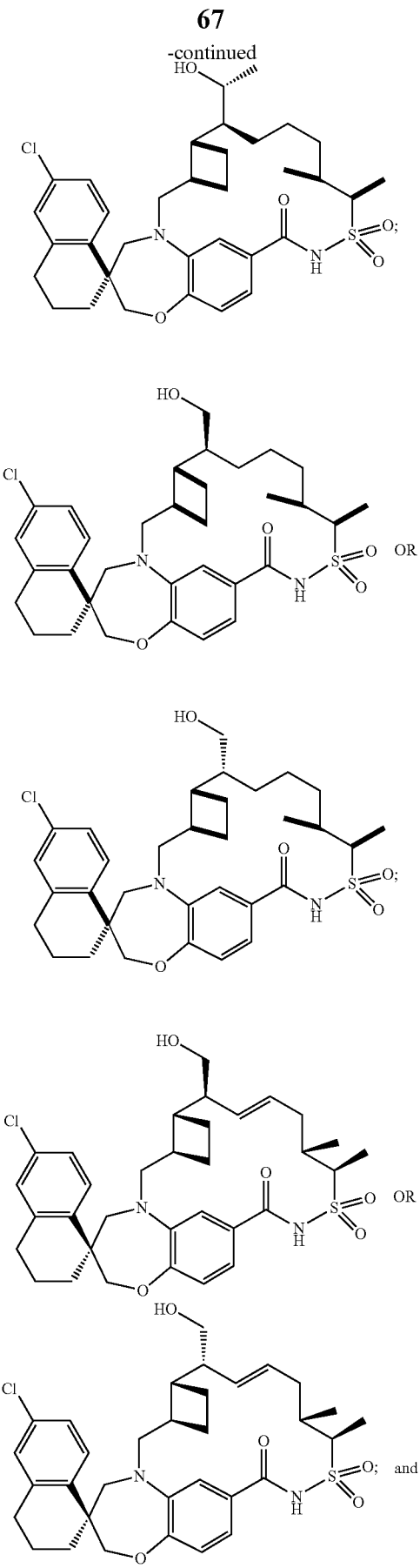

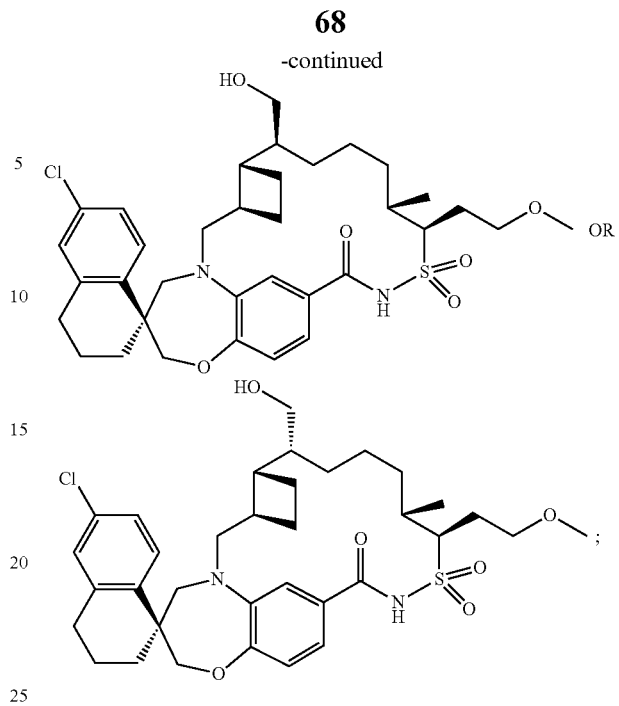

or a pharmaceutically acceptable salt thereof.

49. The compound of embodiment 48 or the pharmaceutically acceptable salt thereof.

50. Another embodiment of the present invention comprises a pharmaceutical composition comprising the compound of any one of embodiments 1-49 or the pharmaceutically acceptable salt thereof, and a pharmaceutically acceptable carrier or diluent.

51. Another embodiment of the present invention comprises a method of treating cancer, the method comprising: administering to a patient in need thereof a therapeutically effective amount of the compound of any of embodiments 1-50 or a pharmaceutically acceptable salt thereof.

52. The method of embodiment 51, wherein the cancer is a hematologic malignancy.

53. The method of embodiment 51, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

54. The method of embodiment 53, wherein the cancer is multiple myeloma.

55. The method of embodiment 51, further comprising administering to the patient in need thereof a therapeutically effective amount of an additional pharmaceutically active compound.

56. The method of embodiment 55, wherein the additional pharmaceutically active compound is carfilzomib.

57. The method of embodiment 55, wherein the additional pharmaceutically active compound is venetoclax.

58. The method of embodiment 55, wherein the additional pharmaceutically active compound is cytarabine.

59. Another embodiment of the present invention comprises a use of a compound according to any one of Embodiments 1-58 for treating cancer in a subject.

60. Another embodiment of the present invention comprises a compound according to any one of Embodiments 1-50 in the preparation of a medicament for treating cancer.

61. The compound according to embodiment 60, wherein the cancer is a hematologic malignancy.

62. The compound according to embodiment 60, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

63. The compound according to embodiment 62, wherein the cancer is multiple myeloma.

64. The compound according to embodiment 62, wherein the cancer is acute myelogenous leukemia.

65. The compound according to embodiment 62, wherein the cancer is non-Hodgkin's lymphoma.

Another embodiment of the present invention is directed to a method of inhibiting myeloid cell leukemia 1 protein (Mcl-1) of a cell comprising contacting the cell with the compound of Formula I in an effective amount to inhibit the Mcl-1, in conjunction with any of the above or below embodiments. In one embodiment, the contacting is in vitro. In another embodiment, the contacting is in vivo. In one embodiment, the contacting comprises administering the compound to a subject. In one embodiment, the administering is oral, parenteral, via injection, via inhalation, transdermal, or transmucosal. In one embodiment, the subject suffers from cancer.

One embodiment of the present invention is directed to a method of the treatment of cancer, comprising administering to a patient in need thereof a therapeutically effective amount of the compound of Formula I or a pharmaceutical composition comprising the compound of Formula I, or pharmaceutically acceptable salt thereof, and a pharmaceutically acceptable excipient, in conjunction with any of the above or below embodiments. In one embodiment, the cancer is a hematologic malignancy. In one embodiment, the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia. In one embodiment, the cancer is multiple myeloma. In another embodiment, the method further comprises the step of administering to the patient in need thereof a therapeutically effective amount of at least one additional pharmaceutically active compound. In one embodiment, the additional pharmaceutically active compound is carfilzomib, in conjunction with any of the above embodiments.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

DETAILED DESCRIPTION

The symbol "-" represents a covalent bond and can also be used in a radical group to indicate the point of attachment to another group. In chemical structures, the symbol — is commonly used to represent a methyl group in a molecule.

As used herein, chemical structures which contain one or more stereocenters depicted with dashed and bold bonds (i.e., ⋯⋯ and ➖) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$ alkyl.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "cycloalkyl" means a cyclic, nonaromatic hydrocarbon. Representative examples of cycloalkyl groups include cyclopropyl, cyclobutyl, cyclopentyl, cyclohexyl and cycloheptyl. A cycloalkyl group can contain one or more double bonds. Representative examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "excipient", as used herein, means any pharmaceutically acceptable additive, carrier, diluent, adjuvant or other ingredient, other than the active pharmaceutical ingredient (API), which is typically included for formulation and/or administration to a patient. Handbook of Pharmaceutical Excipients, 5$^{th}$ Edition, R. C. Rowe, P. J. Sheskey, and S. C. Owen, editors, Pharmaceutical Press, 2005, Hardback, 928, 0853696187.

For the terms "for example" and "such as" and grammatical equivalences thereof, the phrase "and without limitation" is understood to follow unless explicitly stated otherwise.

The term "halogen" or "halo" means F, Cl, Br or I.

The term "patient" means subjects including animals, such as dogs, cats, cows, horses, sheep and humans. Particular patients are mammals. The term patient includes males and females.

The term "patient in need" means a patient having, or at risk of having, one or more diseases or conditions where the Mcl-1 protein is involved, such as cancers. Identifying a patient in need can be in the judgment of a subject or a health care professional and can be subjective (e.g., opinion) or objective (e.g., measurable by a test or diagnostic method).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection, and infusion.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The term "pharmaceutically acceptable" is employed herein to refer to those ligands, materials, compositions, and/or dosage forms which are, within the scope of sound medical judgment, suitable for administration to a patient, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

The phrases "systemic administration", "administered systemically", "peripheral administration", and "administered peripherally" as used herein mean the administration of a ligand, drug, or other material via route other than directly into the central nervous system, such that it enters the patient's system and thus, is subject to metabolism and other like processes, for example, subcutaneous administration.

The term "therapeutically effective amount" means an amount of a compound that ameliorates, attenuates or eliminates one or more symptom of a particular disease or condition, or prevents or delays the onset of one of more symptom of a particular disease or condition.

The terms "treating", "treat" or "treatment" and the like include preventative (e.g., prophylactic) and palliative treatment.

The methods provided herein include the manufacture and use of pharmaceutical compositions, which include one or more of the compounds provided herein. Also included are the pharmaceutical compositions themselves.

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxida Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. The dose of the compound or composition can be varied over time. All combinations, delivery methods and administration sequences are contemplated.

The compounds of the present invention and in some embodiments, other additional pharmaceutically active compounds, can be administered to a patient either orally, rectally, parenterally, (for example, intravenously, intramuscularly, or subcutaneously) intracistemally, intravaginally, intraperitoneally, intravesically, locally (for example, powders, ointments or drops), or as a buccal or nasal spray. All methods that are used by those skilled in the art to administer a pharmaceutically active agent are contemplated.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Formulations suitable for oral administration may be in the form of capsules (e.g., gelatin capsules), cachets, pills, tablets, lozenges (using a flavored basis, usually sucrose and acacia or tragacanth), powders, troches, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound provided herein as an active ingredient. A composition may also be administered as a bolus, electuary, or paste. Oral compositions generally include an inert diluent or an edible carrier.

Pharmaceutically compatible binding agents, and/or adjuvant materials can be included as part of an oral composition. In solid dosage forms for oral administration (capsules, tablets, pills, dragees, powders, granules, and the like), the active ingredient can be mixed with one or more pharmaceutically acceptable carriers, such as sodium citrate or dicalcium phosphate, and/or any of the following: (1) fillers or extenders, such as starches, cyclodextrins, lactose, sucrose, saccharin, glucose, mannitol, and/or silicic acid; (2) binders, such as, for example, carboxymethylcellulose, microcrystalline cellulose, gum tragacanth, alginates, gelatin, polyvinyl pyrrolidone, sucrose, and/or acacia; (3) humectants, such as glycerol; (4) disintegrating agents, such as agar-agar, calcium carbonate, potato, corn, or tapioca starch, alginic acid, Primogel, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, Sterotes, solid polyethylene glycols, sodium lauryl sulfate, and mixtures thereof; (10) a glidant, such as colloidal silicon dioxide; (11) coloring agents; and (12) a flavoring agent such as peppermint, methyl salicylate, or orange flavoring. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of a powdered compound moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, microspheres, and/or nanoparticles. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in microencapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions suitable for parenteral administration can include one or more compounds provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In one embodiment, the IV formulation consists of a composition containing hydroxypropyl beta cyclodextrin within a pH range between 8-10 as a buffered or unbuffered solution. The IV formulation can be formulated as a sterile solution ready for injection, a sterile solution ready for dilution into an IV admixture or a sterile solid for reconstitution. The API in the IV formulation may exist as a free acid/base or an in situ salt.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, N.J.). In all cases, the composition must be sterile and should be fluid to the extent that easy syringability exists. Proper fluidity can be maintained, for example, by the use of coating materials, such as lecithin, by the maintenance of the required particle size in the case of dispersions, and by the use of surfactants.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

For administration by inhalation, the compounds can be delivered in the form of an aerosol spray from a pressured container or dispenser that contains a suitable propellant (e.g., a gas such as carbon dioxide) or a nebulizer. Such methods include those described in U.S. Pat. No. 6,468,798. Additionally, intranasal delivery can be accomplished, as described in, inter alia, Hamajima et al., *Clin. Immunol. Immunopathol.*, 88(2), 205-10 (1998). Liposomes (e.g., as described in U.S. Pat. No. 6,472,375, which is incorporated herein by reference in its entirety), microencapsulation and nanoencapsulation can also be used. Biodegradable targetable microparticle delivery systems or biodegradable targetable nanoparticle delivery systems can also be used (e.g., as described in U.S. Pat. No. 6,471,996, which is incorporated herein by reference in its entirety).

Systemic administration of a therapeutic compound as described herein can also be by transmucosal or transdermal means. Dosage forms for the topical or transdermal administration of a compound provided herein include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The ointments, pastes, creams, and gels may contain, in addition to one or more compounds provided herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound provided herein, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound provided herein can be administered by aerosol. This is accomplished by preparing an aqueous aerosol, liposomal preparation, or solid particles containing a compound or composition provided herein. A non-aqueous (e.g., fluorocarbon propellant) suspension could be used. In some embodiments, sonic nebulizers are used because they minimize exposing the agent to shear, which can result in degradation of the compound.

Ordinarily, an aqueous aerosol can be made by formulating an aqueous solution or suspension of the agent together with conventional pharmaceutically acceptable carriers and stabilizers. The carriers and stabilizers vary with the requirements of the particular composition, but typically include nonionic surfactants (TWEEN® (polysorbates), PLURONIC® (poloxamers), sorbitan esters, lecithin, CREMOPHOR® (polyethoxylates)), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a compound provided herein to the body. Such dosage forms can be made by dissolving or dispersing the agent in the proper medium. Absorption enhancers can also be used to increase the flux of the compound across the skin. The rate of such flux can be controlled by either providing a rate controlling membrane or dispersing the compound in a polymer matrix or gel.

The pharmaceutical compositions can also be prepared in the form of suppositories or retention enemas for rectal and/or vaginal delivery. Formulations presented as a suppository can be prepared by mixing one or more compounds provided herein with one or more suitable nonirritating excipients or carriers comprising, for example, cocoa butter, glycerides, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially (e.g., from Alza Corporation and Nova Pharmaceuticals, Inc.). Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety for all purposes.

The compounds of the present invention are used in the treatment of diseases, disorders or symptoms mediated by Mcl-1 inhibition. Examples of diseases, disorders or symptoms mediated by Mcl-1 inhibition include, but are not limited to, cancers. Non-limiting examples of cancers include breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

The cancers can include carcinomas (originating in the outer layer of cells of the skin and internal membranes, e.g., breasts, kidneys, lungs, skin); sarcomas (arising from connective tissue such as bone, muscle, cartilage, and blood vessels), and hematologic malignancies (e.g., lymphomas and leukemias, which arise in the blood or blood-forming organs such as the spleen, lymph nodes, and bone marrow). Cancer cells can include, for example, tumor cells, neoplastic cells, malignant cells, metastatic cells, and hyperplastic cells.

In an embodiment, the disease, disorder or symptom is a hyperproliferative disorder, e.g., a lymphoma, leukemia, carcinoma (e.g., renal, breast, lung, skin), multiple myeloma, or a sarcoma. In one embodiment, the leukemia is acute myeloid leukemia. In one embodiment, the hyperproliferative disorder is a relapsed or refractory cancer.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The specific dosage and dosage range depends on a number of factors, including the requirements of the patient, the severity of the condition or disease being treated, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain about 0.001%-100% active ingredient, in one embodiment from about 0.1 to about 95%, in another embodiment from about 75 to about 85%. Although the dosage will vary depending on the symptoms, age and body weight of the patient, the nature and severity of the disorder to be treated or prevented, the route of administration and the form of the drug, in general, a daily dosage of from about 0.01 to about 3,000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing The compounds of the present invention can be administered alone, in combination with other compounds of the present invention, or with other pharmaceutically active compounds or agents. The other pharmaceutically active compounds/agents can be intended to treat the same disease or condition as the compounds of the present invention or a different disease or condition. If the patient is to receive or is receiving multiple pharmaceutically active compounds or agents, the compounds can be administered simultaneously, or sequentially.

The compounds of the present invention, or pharmaceutically acceptable salts thereof, may be used in combination with one or more additional pharmaceutically active compounds/agents.

One or more additional pharmaceutically active compounds or agents may be administered separately, as part of a multiple dose regimen, from the compound of Formula I (e.g., sequentially, e.g., on different overlapping schedules with the administration of one or more compounds of Formula I (including any subgenera or specific compounds thereof). In other embodiments, the one or more additional compounds/agents may be part of a single dosage form, mixed together with the compound of Formula I in a single composition. In still another embodiment, the one or more additional compounds/agents can be given as a separate dose that is administered at about the same time that one or more compounds of Formula I are administered (e.g., simultaneously with the administration of one or more compounds of Formula I (including any subgenera or specific compounds thereof). Both the compound of Formula I and the one or more additional compounds/agents can be present at dosage levels of between about 1 to 100%, and more preferably between about 5 to 95% of the dosage normally administered in a monotherapy regimen.

In a particular embodiment, the additional pharmaceutically active compound/agent is a compound or agent that can be used to treat a cancer. For example, the additional pharmaceutically active compound/agent can be selected from antineoplastic agents, anti-angiogenic agents, chemotherapeutic agents, and peptidal cancer therapy agents. In another embodiment, the antineoplastic agents are selected from antibiotic-type agents, alkylating agents, antimetabolite agents, hormonal agents, immunological agents, interferon-type agents, kinase inhibitors, proteasome inhibitors, and combinations thereof. It is noted that the additional pharmaceutically active compound/agent may be a traditional small organic chemical molecule or can be a macromolecule such as a protein, antibody, peptibody, DNA, RNA or a fragment of such macromolecules.

Examples of additional pharmaceutically active compounds/agents that can be used in the treatment of cancers and that can be used in combination with one or more compounds of the present invention include: acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; cytarabine; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflomithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracilloteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; 65rimethyl polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; trametinib; tumor necrosis factor alpha natural; ubenimex; bladder cancer vaccine; Maruyama vaccine; melanoma lysate vaccine; valrubicin; venetoclax; verteporfin; virulizin; zinostatin stimalamer; abarelix; AE 941 (Aetema); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (Mab) (Biomira); cancer Mab (Japan Pharmaceutical Development); HER-2 and Fc Mab (Medarex); idiotypic 105AD7 Mab (CRC Technology); idiotypic CEA Mab (Trilex); LYM-1-iodine 131 Mab (Techniclone); polymorphic epithelial mucin-yttrium 90 Mab (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine; melanoma oncolysate vaccine; viral melanoma cell lysates vaccine; valspodarl; fluorouracil; 5-fluorouracil; 66rimethyla; imatinib; altretamine; cladibrine; cyclophosphamine; decarazine; irinotecan; mitosmycin; mitoxane; topotecan; vinorelbine; 66rimethyla; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temnsirolimus; bortezomib; 66rimethylam; oprozomib; vorinostat; capecitabine; zoledronic acid; anastrozole; sunitinib; aprepitant and nelarabine, or a pharmaceutically acceptable salt thereof.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNTO328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., elotuzumab), inhibitors of KRAS including covalent inhibiors of KRAS G12C, MEK inhibitor, including trametinib, HSP90 inhibitors (e.g., 17 AAG and KOS 953), P13K/Akt inhibitors (e.g., perifosine), Akt inhibitor (e.g., GSK-2141795), PKC inhibitors (e.g., enzastaurin), FTIs (e.g., Zamestra™), anti-CD138 (e.g., BT062), Torcl/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, 69rimethylamine, ethylamine, and the like. See, for example, S. M. Berge, et al., "Pharmaceutical Salts," J Pharm Sci, 66: 1-19 (1977).

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$—$Cl_2$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers.

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The compounds of the present invention may exist in various solid states including crystalline states and as an amorphous state. The different crystalline states, also called polymorphs, and the amorphous states of the present compounds are contemplated as part of this invention.

EXAMPLES

The examples presented below illustrate specific embodiments of the present invention. These examples are meant to be representative and are not intended to limit the scope of the claims in any manner.

The following abbreviations may be used herein:
~ About
Ac acetate
Ac$_2$O acetic anhydride
AcOH or HOAc acetic acid
Br broad
Boc tert-butyloxycarbonyl
Calcd calculated
CO$_2$ carbon dioxide
CSA 10-camphorsulfonic acid
d day or doublet
DBU 1,8-diazabicyclo[5.4.0]undec-7-ene
DCE Dichloroethane
DCM Dichloromethane
DEA Diethylamine
Dess-Martin 1,1,1-triacetoxy-1,1-dihydro-1,2-benziodoxol-3-periodinane; (1H)-one
DIEA or DIPEA Diisopropylethylamine
DMA N,N-dimethylacetamide
DMAP 4-dimethylaminopyridine DMF N,N-dimethylformamide
DMSO dimethyl sulfoxide
EDC N-ethyl-N'-(3-dimethylaminopropyl)carbodiimide
ee or e.e. enantiomeric excess
ELISA enzyme-linked immunosorbent assay
eq Equivalent
ESI or ES electrospray ionization
Et Ethyl
$Et_2O$ diethyl ether
EtOAc ethyl acetate
$Et_3N$ triethylamine
EtOH ethyl alcohol
g gram(s)
GC gas chromatography
h hour(s)
$^1H$ NMR proton nuclear magnetic resonance spectroscopy
$H_2$ hydrogen gas
$H_2O$ Water
$H_2SO_4$ sulfuric acid
HATU 1-[Bis(dimethylamino)methylene]-1H-1,2,3-triazolo[4,5-b]pyridinium 3-oxid hexafluorophosphate
HCl hydrochloric acid
HWE rxn Homer-Wadsworth-Emmons reaction
Hex hexane(s)
HPLC high performance liquid chromatography
Hz Hertz
IP intraperitoneal
IPA isopropyl alcohol
IPAc isopropyl acetate
$K_2CO_3$ potassium carbonate
$K_3PO_4$ potassium phosphate
KF Karl Fischer titration
KHMDS potassium hexamethyldisilazide
KOAc potassium acetate
KOH potassium hydroxide
KOtBu Potassium tert-butoxide
L liter(s)
LAH lithium aluminium hydride
LCMS, LC-MS or
liquid chromatography mass spectrometry
LC/MS
LiHMDS lithium hexamethyldisilazide
LiOH lithium hydroxide
m multiplet
M molar (mol $L^{-1}$)
Me methyl
MeCN acetonitrile
MHz megahertz
MeI iodomethane
MeOH methyl alcohol
MeTHF methyltetrahydrofuran
mg milligram(s)
$MgSO_4$ magnesium sulphate
min minute(s)
μm micrometer
μL microliter
mL milliliter(s)
mm millimeter
mol mole
MS mass spectrometry
MSA methanesulfonic acid
MsCl methanesulfonyl chloride
m/z mass-to-charge ratio
N Normality (Eq/L)
$N_2$ nitrogen gas
NaCl sodium chloride
$Na_2CO_3$ sodium carbonate
$NaHCO_3$ sodium bicarbonate
NaOH sodium hydroxide
NaOtBu sodium tert-butoxide
$Na_2SO_4$ sodium sulfate
$Na_2S_2O_3$ sodium thiosulfate
$NH_3$ ammonia, azane
$NH_4Cl$ ammonium chloride
$NH_4OH$ ammonium hydroxide
NMR nuclear magnetic resonance spectroscopy
OMe methoxy
PO per oral
+ve positive
Ph phenyl
PhMe toluene
PMB p-methoxybenzyl
Ppm parts per million
prep preparative
psi pounds per square inch
q quartet
QD once daily
QNMR quantitative NMR
RBF round-bottomed flask
RT or rt or r.t. room temperature
s singlet
sat. or sat'd or satd Saturated
SFC supercritical fluid chromatography
$SiO_2$ silicon dioxide, silica
T triplet
tBu tert-butyl
t-BuOH tert-butanol
TFA triflouroacetic acid
THF Tetrahydrofuran
TLC thin layer chromatography
TsOH toluene sulfonic acid
UV Ultraviolet
v/v Volume per volume
wt % Weight percent It is noted that when a percent (%) is used with regard to a liquid, it is a percent by volume with respect to the solution. When used with a solid, it is the percent with regard to the solid composition.

The following synthetic schemes show generally how to make intermediates and compounds of the present invention.

General Synthetic Schemes

Unless otherwise stated, starting materials and reagents used in preparing these compounds are either available from commercial suppliers such as Aldrich Chemical Co., (Milwaukee, Wis.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry (John Wiley and Sons, 4th Edition) and Larock's Comprehensive Organic Transformations (VCH Publishers Inc., 1989).

The starting materials for the following synthetic methods can be found in the General Methods and General Synthesis for Intermediates. The synthesis of some of the starting materials and the intermediates are disclosed in U.S. Pat. No. 9,562,061 and PCT/US 17/19336, respectively, herein incorporated by reference in their entireties for all purposes. These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 22° C.

IUPAC names were generated using either ACD/Name v2015 or ChemBioDraw Ultra 12.

General Method 1: Synthesis of Amine Derivatives from Carbaldehyde

General Method 2: Synthesis of 1° Alcohol Derivatives from Carbaldehyde

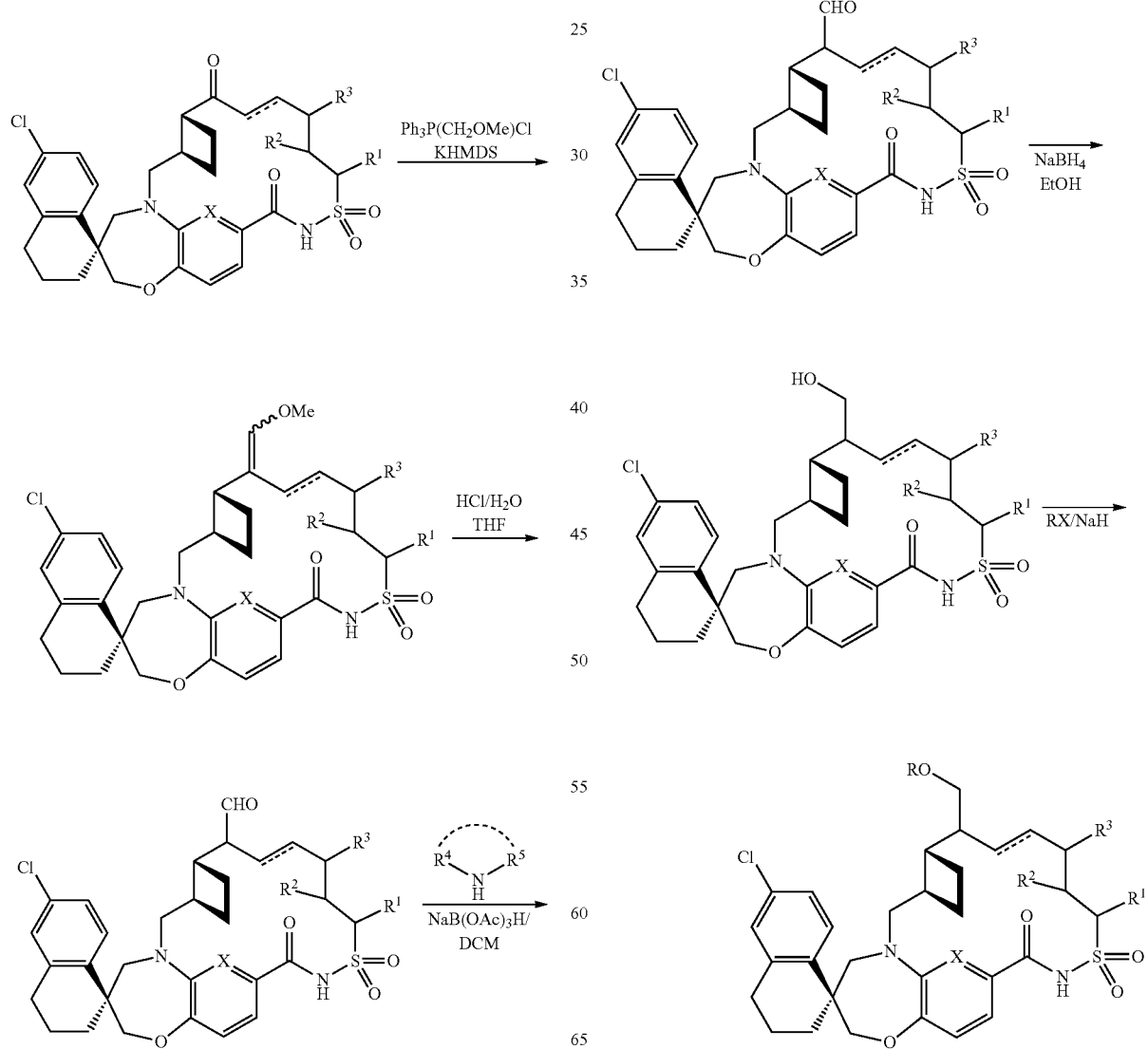

General Method 3: Synthesis of 2° Alcohol Derivatives from Carbaldehyde
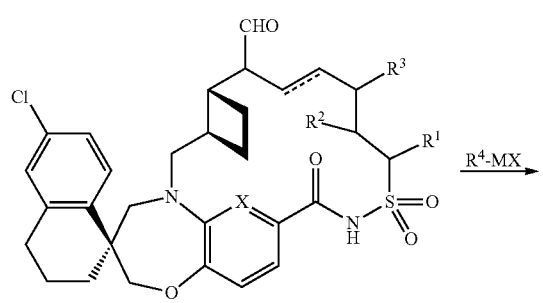
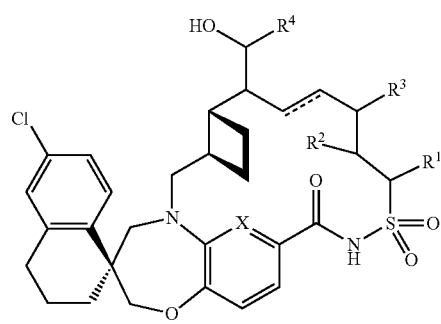
General Method 4: Synthesis of Caboxamides from Carbaldehyde
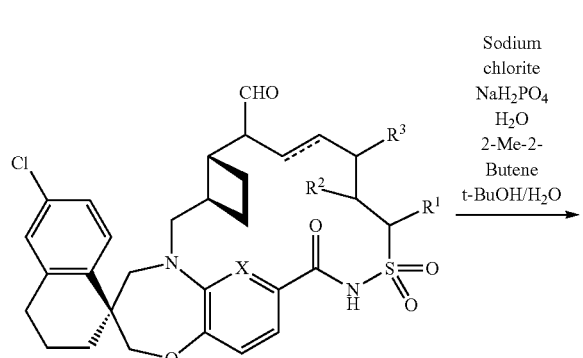
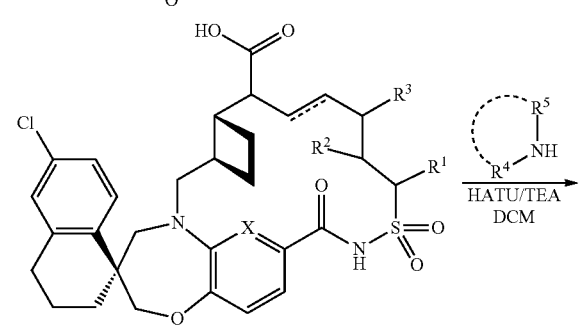
-continued
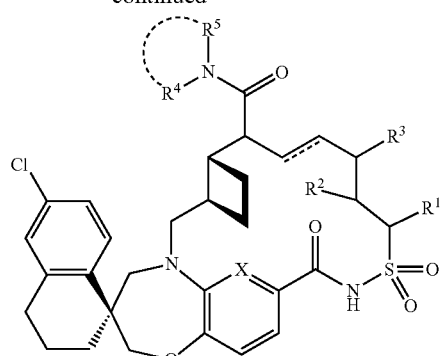
General Method 5: Synthesis of Homologous Caboxamides from Ketone
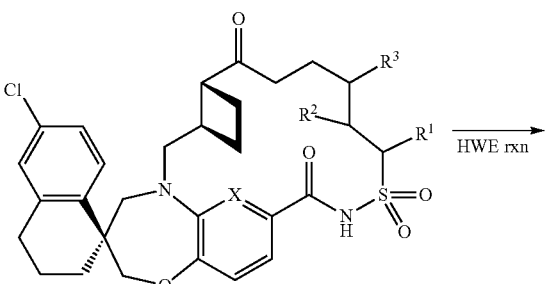
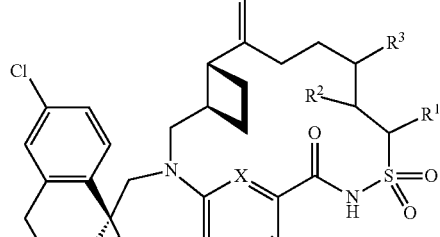
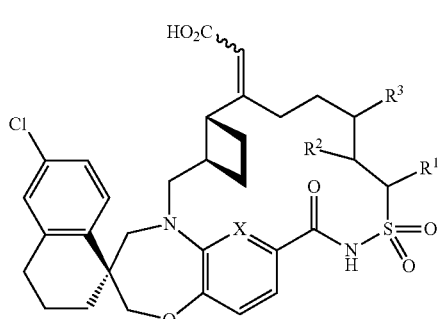

-continued

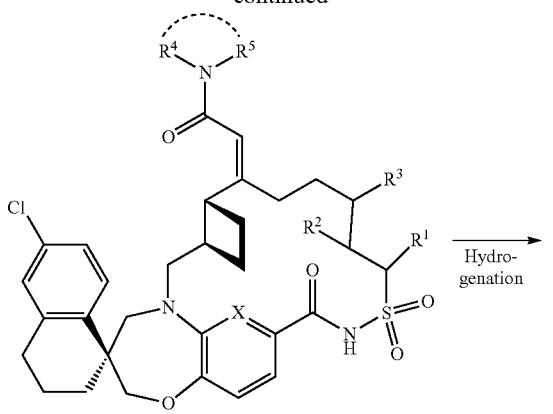
↓ Hydrogenation

Examples 1, 6, 19, 56, and 60

(1s,3'r,6'r,7's,11's,12'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~.0.0~19,24~]pent acosa[16,18,24]triene]-7'-carbaldehyde 13',13'-dioxide and (1s,3'r,6'r,7'r,11's,12'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~.0.0~19,24~]pent acosa[16,18,24]triene]-7'-carbaldehyde 13',13'-dioxide (example 60)

(1s,3'r,6's,7's,11's,12'r)-6-chloro-11',12'-dimethyl-7'-(((9ar)-8-methyloctahydro-2h-pyrazino[1,2-a]pyrazin-2-yl)methyl)-3,4-dihydro-2h,15'h-spiro[naphthalene-1,22'-[20]oxa[13]thia[1,14]diazatetracyclo[14.7.2.0~3,6~.0.0~19,24~]pent acosa[16,18,24]trien]-15'-one 13',13'-dioxide or (1s,3'r,6's,7's,11's,12'r)-6-chloro-11',12'-dimethyl-7'-(((9as)-8-methyloctahydro-2h-pyrazino[1,2-a]pyrazin-2-yl)methyl)-3,4-dihydro-2h,15'h-spiro[naphthalene-1,22'-[20]oxa[13]thia[1,14]diazatetracyclo[14.7.2.0~3,6~.0.0~19,24~]pent acosa[16,18,24]trien]-15'-one 13',13'-dioxide or (1s,3'r,6's,7'r,11's,12'r)-6-chloro-11',12'-dimethyl-7'-(((9ar)-8-methyloctahydro-2h-pyrazino[1,2-a]pyrazin-2-yl)methyl)-3,4-dihydro-2h,15'h-spiro[naphthalene-1,22'-[20]oxa[13]thia[1,14]diazatetracyclo[14.7.2.0~3,6~.0.0~19,24~]pent acosa[16,18,24]trien]-15'-one 13',13'-dioxide or (1s,3'r,6's,7'r,11's,12'r)-6-chloro-11',12'-dimethyl-7'-(((9as)-8-methyloctahydro-2h-pyrazino[1,2-a]pyrazin-2-yl)methyl)-3,4-dihydro-2h,15'h-spiro[naphthalene-1,22'-[20]oxa[13]thia[1,14]diazatetracyclo[14.7.2.0~3,6~.0.0~19,24~]pent acosa[16,18,24]trien]-15'-one 13',13'-dioxide (examples 1, 6, 19 and 56)

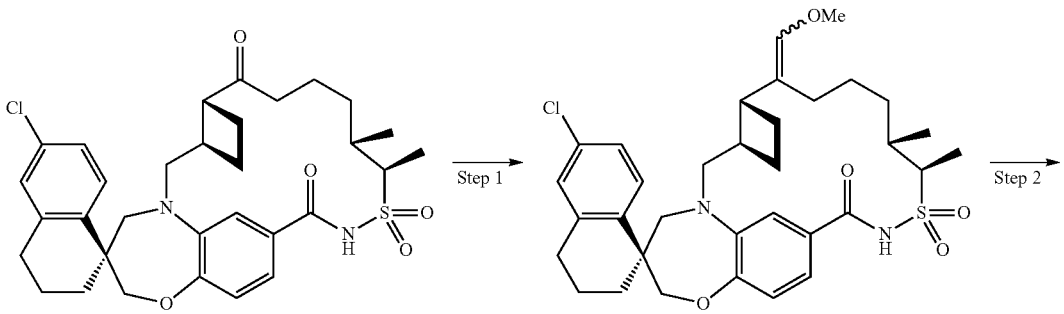

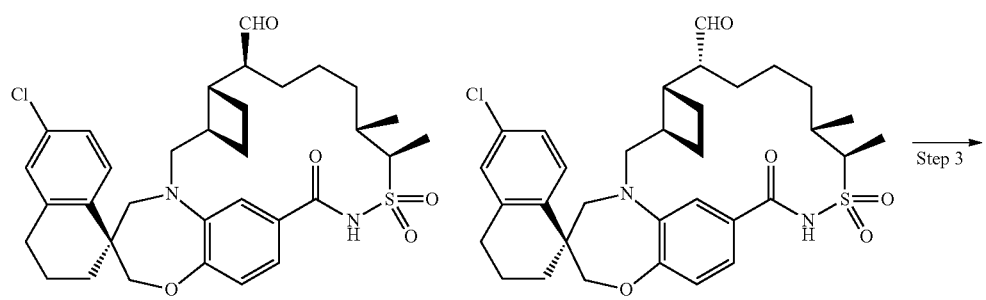

Example 60

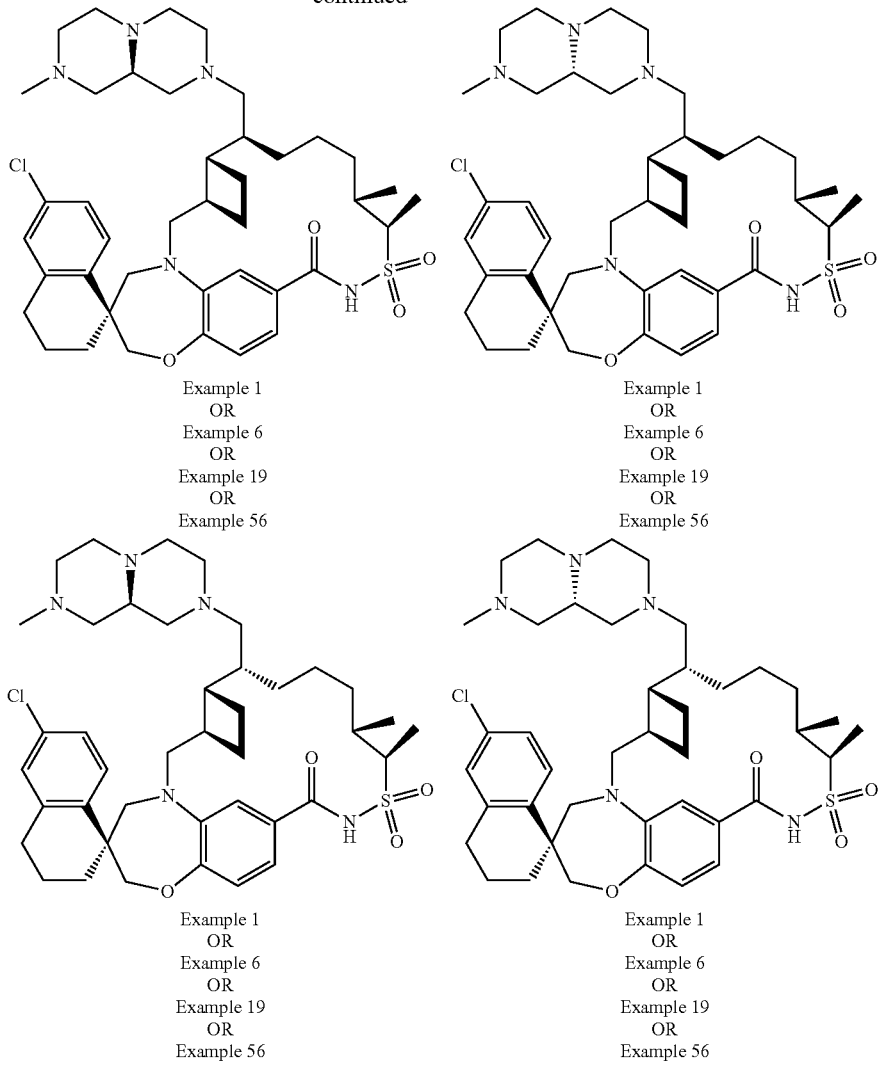

Example 1
OR
Example 6
OR
Example 19
OR
Example 56

Step 1: 1 s,3'r,6'r,7'z, 11's,12'r)-6-chloro-7'-(methoxymethylidene)-11',12'-dimethyl-3,4-dihydro-2h,15'h-spiro[naphthalene-1,22'-[20]oxa[13]thia[1,14]diazatetracyclo[14.7.2.0~3,6~.0.0~19,24~]pent acosa[16,18,24]trien]-15'-one 13',13'-dioxide and (1s,3'r,6'r,7'e, 1's, 12'r)-6-chloro-7'-(methoxymethylidene)-11',12'-dimethyl-3,4-dihydro-2h,15'h-spiro[naphthalene-1,22'-[20]oxa[13]thia[1,14]diazatetracyclo[14.7.2.0~3,6~.0.0~19,24~]pent acosa[16,18,24]trien]-15'-one 13',13'-dioxide To a stirred ice-cooled solution of (methoxymethyl)triphenylphosphonium chloride (2.288 g, 6.68 mmol) in THF (10 mL) was dropwise added potassium bis(trimethylsilyl)amide, 1M solution in tetrahydrofuran (6.68 mL, 6.68 mmol) over 10 min. The resulting mixture was stirred at 0° C. for a period of 35 min. A solution of (1S,3'R,6'R,11'S,12'R)-6-chloro-11',12'-dimethyl-3,4-dihydro-2H,7'H, 15'H-spiro[naphthalene-1,22'-[20]oxa[13]thia[1,14]diazatetracyclo[14.7.2.0~3,6~.0.0~19,24~]pentacosa[16,18,24]triene]-7',15'-dione 13',13'-dioxide (0.50 g, 0.834 mmol) in THF (6 mL) was slowly added at 0° C. via a syringe. The resulting mixture was stirred at 0° C. for 1 h, and allowed to slowly warm up to rt and stirred at rt for a period of 4 h. Upon workup, the reaction mixture was poured into ice and a saturated aqueous solution of ammonium chloride and extracted with EtOAc (2×). The combined organics were dried over anhydrous sodium sulfate and concentrated in vacuo. The residue was loaded onto a silica gel precolumn (25 g) and subjected to combi-flash column chromatography on a 40-g ISCO GOLD, eluting with EtOAc/Hexanes (35 min from 0 to 40%), to give a geoisomeric mixture of (1S,3'R,6'R,7'Z,11'S,12'R)-6-chloro-7'-(methoxymethylidene)-11',12'-dimethyl-3,4-dihydro-2H,15'H-spiro[naphthalene-1,22'-[20]oxa[13]thia[1,14]diazatetracyclo[14.7.2.0~3,6~.0.0~19,24~]pentacosa[16,18,24]trien]-15'-one 13',13'-dioxide and (1S,3'R,6'R,7'E,11'S,12'R)-6-chloro-7'-(methoxymethylidene)-11',12'-dimethyl-3,4-dihydro-2H,15'H-spiro[naphthalene-1,22'-[20]oxa[13]thia[1,14]diazatetracyclo[14.7.2.0~3,6~.0.0~19,24~]pentacosa[16,18,24]trien]-15'-one 13',13'-dioxide (0.34 g, 0.542 mmol, 65.0% yield) as a colorless film. The geoisomeric ratio was determined to be 2 (the first eluting isomer on reverse-phase HPLC) to 3. This mixture was directly used in the next step without separation. MS (ESI, +ve) m/z 627.2 [M+H]$^+$.

Step 2: (1s,3'r,6'r,7's,11's,12'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~0.0~19,24~]pent acosa[16,18,24]triene]-7'-carbaldehyde 13',13'-dioxide and (1s,3'r,6'r,7'r,7'r,11's,12'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~0.0~19,24~]pent acosa[16,18,24]triene]-7'-carbaldehyde 13',13'-dioxide example 60

To a stirred solution of a geoisomeric mixture of (1S,3'R,6'R,7'Z,11'S,12'R)-6-chloro-7'-(methoxymethylidene)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide and (1S,3'R,6'R,7'E,11'S,12'R)-6-chloro-7'-(methoxymethylidene)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide (1.93 g, 3.08 mmol) in THF (50 mL) was added at rt hydrochloric acid 1 N standard aqueous solution (30 mL, 360 mmol) followed by commercial concentrated HCl (37% aq. commercial) (6.0 mL). The resulting mixture was stirred at rt for 66 h. Upon workup, the white precipitate was collected by vacuum filtration to give, in the first batch, an epimeric mixture of (1S,3'R,6'R,7'S,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~0.0~19,24~]pentacosa[16,18,24]triene]-7'-carbaldehyde 13',13'-dioxide and (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~0.0~19,24~]pentacosa[16,18,24]triene]-7'-carbaldehyde 13',13'-dioxide (1.62 g, 2.64 mmol, 86% yield) (Example 60). The epimeric ratio was determined to be about 65 to 35 favoring the more polar epimer (of a shorter retention time on LC-MS). The filtrate was diluted with water and extracted with EtOAc (2×). The combined organics were dried over anhydrous sodium sulfate and concentrated in vacuo to give, in the second batch, 66 mg of a nearly 1-to-1 epimeric mixture of the same two compounds. MS (ESI, +ve) m/z 613.2 [M+H]⁺.

Step 3: (1s,3'r,6's,7's,11's,12'r)-6-chloro-11',12'-dimethyl-7'-(((9ar)-8-methyloctahydro-2h-pyrazino[1,2-a]pyrazin-2-yl)methyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6',7's, 11s,12'r)-6-chloro-1',12'-dimethyl-7'-(((9as)-8-methyloctahydro-2h-pyrazino[1,2-a]pyrazin-2-yl)methyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6's,7'r,11's,12'r)-6-chloro-11',12'-dimethyl-7'-(((9ar)-8-methyloctahydro-2h-pyrazino[1,2-a]pyrazin-2-yl)methyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6's,7'r,11's,12'r)-6-chloro-11',12'-dimethyl-7'-(((9as)-8-methyloctahydro-2h-pyrazino[1,2-a]pyrazin-2-yl)methyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide (examples 1, 6, 19 and 56)

A mixture of an epimeric mixture of (1S,3'R,6'R,7'S,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~0.0~19,24~]pentacosa[16,18,24]triene]-7'-carbaldehyde 13',13'-dioxide and (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~0.0~19,24~]pentacosa[16,18,24]triene]-7'-carbaldehyde 13',13'-dioxide (60 mg, 0.098 mmol) and 2-methyloctahydro-2h-pyrazino[1,2-a]pyrazine (99 mg, 0.636 mmol, ChemBridge Corporation) in DCM (2.5 mL) was stirred at rt for 25 min before sodium triacetoxyhydroborate (51.8 mg, 0.245 mmol) was added in one portion as a solid. The resulting mixture was stirred at rt for 1 h. The crude mixture was directly loaded onto a silica gel precolumn, previously covered with a layer of sodium bicarbonate, and subjected to combi-flash column chromatography on a 4-g ISCO GOLD column eluting with MeOH/DCM to give an impure mixture of all four title compounds of stereoisomers (80 mg) as a white solid. This was separated by SFC (Princeton Pa. (21×250 mm, 5 um), Organic modifier: 13% Methanol with 20 mM NH₃. 87% Carbon Dioxide, F=70 ml/min, T=40 C, BPR=100 bar, 220 nm. P=165 bar, all samples dissolved in 5 ml MeOH, 0.8 ml injection) to give all four single stereoisomers:
(1S,3'R,6'S,7'S,11'S,12'R)-6-chloro-11',12'-dimethyl-7'-(((9aR)-8-methyloctahydro-2H-pyrazino[1,2-a]pyrazin-2-yl)methyl)-3,4-dihydro-2H,15H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'S,11'S,12'R)-6-chloro-11',12'-dimethyl-7'-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'R,11'S,12'R)-6-chloro-11',12'-dimethyl-7'-(((9aR)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'R,11'S,12'R)-6-chloro-11',12'-dimethyl-7'-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide (Example 1) as off-white solids. It was the third eluting peak off of the SFC column. ¹H NMR (400 MHz, CHLOROFORM-d) δ 7.72 (d, J=8.41 Hz, 1H), 7.19 (dd, J=2.15, 8.41 Hz, 1H), 7.09 (d, J=2.15 Hz, 1H), 7.05 (s, 1H), 6.90-6.99 (m, 2H), 4.01-4.14 (m, 3H), 3.80 (br d, J=15.06 Hz, 1H), 3.72 (br d, J=14.08 Hz, 1H), 3.25 (d, J=14.08 Hz, 1H), 2.96 (br dd, J=9.19, 15.26 Hz, 1H), 2.87 (br d, J=10.76 Hz, 1H), 2.78 (br t, J=7.73 Hz, 6H), 2.27-2.58 (m, 10H), 1.84-2.14 (m, 9H), 1.09-1.71 (m, 15H), 1.01 (d, J=6.85 Hz, 3H). MS (ESI, +ve) m/z: 752.5 (M+1)⁺;
(1S,3'R,6'S,7'S,11'S,12'R)-6-chloro-11',12'-dimethyl-7'-(((9aR)-8-methyloctahydro-2H-pyrazino[1,2-a]pyrazin-2-yl)methyl)-3,4-dihydro-2H,15H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'S,11'S,12'R)-6-chloro-11',12'-dimethyl-7'-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'R,11'S,12'R)-6-chloro-11',12'-dimethyl-7'-(((9aR)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~9, 24~]pentacosa[16,18,24]trien]-15'-one 13',13'-dioxide OR (1S,3'R,6'S,7'R,11'S,12'R)-6-chloro-11',12'-dimethyl-7'-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (Example 6) as off-white solids. It was the second eluting peak off of the SFC column. $^1$H NMR (400 MHz, CHLOROFORM-d) δ 7.72 (d, J=8.61 Hz, 1H), 7.19 (dd, J=2.35, 8.41 Hz, 1H), 7.09 (d, J=2.15 Hz, 1H), 7.04 (s, 1H), 6.89-6.99 (m, 2H), 4.04-4.14 (m, 3H), 3.68-3.81 (m, 2H), 3.24 (d, J=14.28 Hz, 1H), 2.74-2.99 (m, 8H), 2.67 (br d, J=10.95 Hz, 2H), 2.23-2.51 (m, 10H), 1.89-2.11 (m, 7H), 1.34-1.86 (m, 12H), 1.10-1.30 (m, 3H), 1.01 (d, J=6.85 Hz, 3H). MS (ESI, +ve) m/z: 752.5 (M+1)$^+$; (1S,3'R,6'S,7'S,11'S,12'R)-6-chloro-11',12'-dimethyl-7'-(((9aR)-8-methyloctahydro-2H-pyrazino[1,2-a]pyrazin-2-yl)methyl)-3,4-dihydro-2H,15H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'S,11'S,12'R)-6-chloro-11',12'-dimethyl-7'-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'R,11'S,12'R)-6-chloro-11',12'-dimethyl-7'-(((9aR)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'R,11'S,12'R)-6-chloro-11',12'-dimethyl-7'-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (Example 19) as off-white solids. It was the first eluting peak off of the SFC column. $^1$H NMR (400 MHz, CHLOROFORM-d) δ 7.71 (d, J=8.41 Hz, 1H), 7.14-7.20 (m, 2H), 7.09 (d, J=1.96 Hz, 1H), 6.95-7.00 (m, 1H), 6.90-6.94 (m, 1H), 4.03-4.13 (m, 3H), 3.77 (br d, J=15.45 Hz, 1H), 3.68 (br d, J=14.28 Hz, 1H), 3.21 (br d, J=14.28 Hz, 1H), 2.69-3.01 (m, 9H), 2.61 (br d, J=10.56 Hz, 1H), 1.22-2.55 (m, 32H), 1.02 (d, J=6.85 Hz, 3H), MS (ESI, +ve) m/z: 752.5 (M+1)$^+$; and (1S,3'R,6'S,7'S,11'S,12'R)-6-chloro-11',12'-dimethyl-7'-(((9aR)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'S,7'S,11'S,12'R)-6-chloro-11',12'-dimethyl-7'-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'S,7'R,11'S,12'R)-6-chloro-11',12'-dimethyl-7'-(((9aR)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'S,7'R,11'S,12'R)-6-chloro-11',12'-dimethyl-7'-(((9aS)-8-methyloctahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (Example 56) as off-white solids. It was the fourth and last eluting peak off of the SFC column. $^1$H NMR (400 MHz, CHLOROFORM-d) δ 7.72 (d, J=8.61 Hz, 1H), 7.15-7.20 (m, 2H), 7.08 (d, J=2.15 Hz, 2H), 6.90 (d, J=8.02 Hz, 1H), 4.02-4.12 (m, 2H), 3.94 (br s, 1H), 3.64-3.81 (m, 2H), 3.23 (br d, J=14.28 Hz, 1H), 2.68-3.10 (m, 11H), 2.20-2.61 (m, 12H), 1.18-2.09 (m, 19H), 1.03 (d, J=6.85 Hz, 3H). MS (ESI, +ve) m/z: 752.5 (M+1)+.

Example 2

(1s,3'r,6's,7's,11's,12'r)-6-chloro-7'-(2-((9ar)-hexahydropyrazino[2,1-c][1,4]oxazin-8(1h)-yl)-2-oxoethyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide trifluoroacetic acid

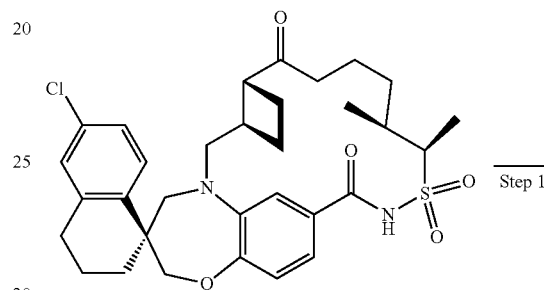

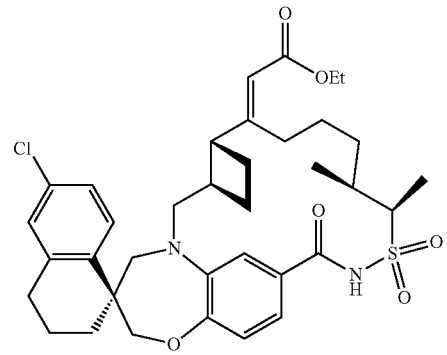

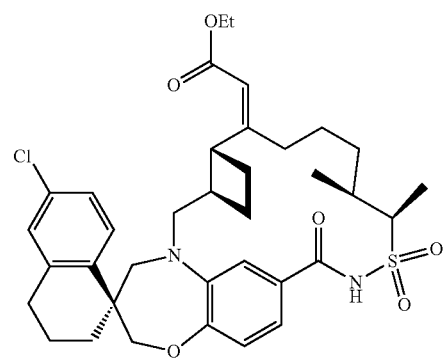

99

-continued

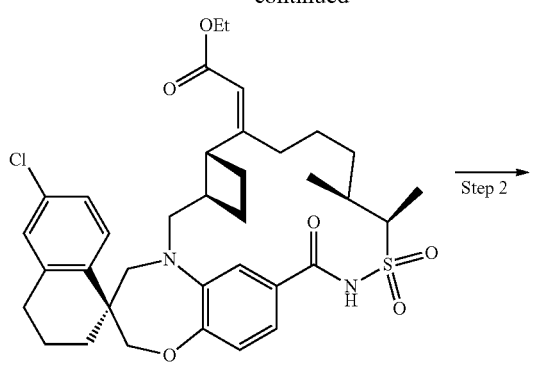

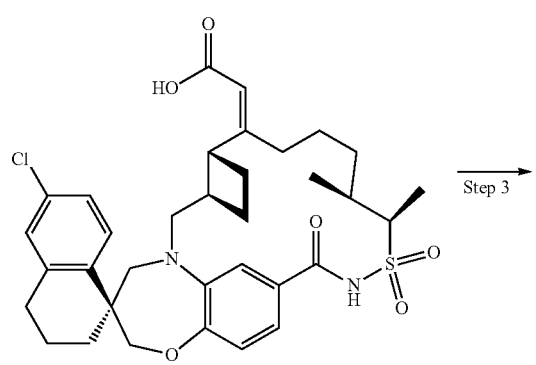

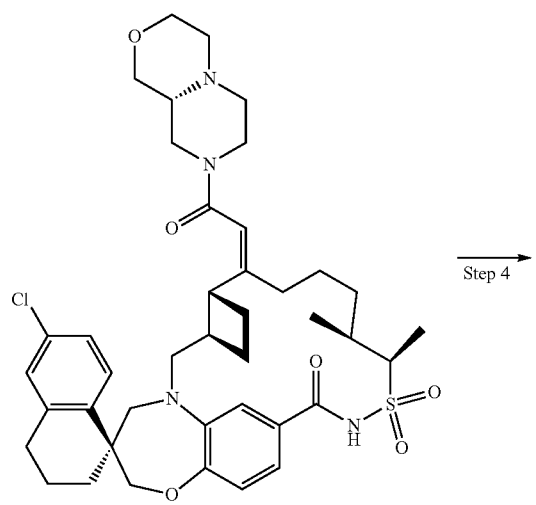

100

-continued

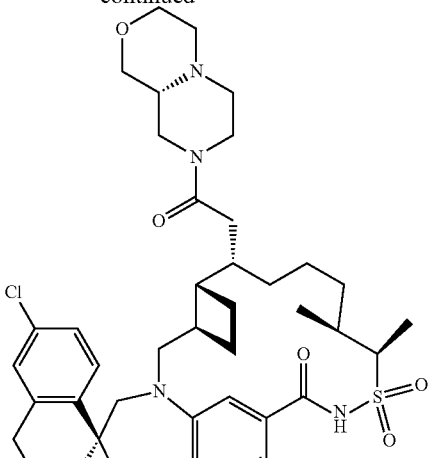

Example 2 step 1: ethyl (2z)-[(4s,7ar,9r,9ar,14s,15r)-6'-chloro-14,15-dimethyl-16,16-dioxido-18-oxo-3',4',7a,8,9,9a,12,13,14,15,17,18-dodecahydro-2'h,7h-spiro[1,19-ethenocyclobuta[i][1,4]oxazepino[3,4-f][1,2,7]thiadiazacyclohexadecine-4,1'-naphthalen]-10(11h)-ylidene]acetate To a solution of potassium tert-butoxide, 98% (655 mg, 5.84 mmol, aldrich) in THF (3 mL) at 0° C. under $N_2$ was added triethyl phosphonoacetate (1.310 mL, 5.84 mmol, Oakwood Products, Inc.) dropwise. After addition, the mixture was stirred at 0° C. for 30 min, then a solution of (4S,7aR,9aR,14S,15R)-6'-chloro-14,15-dimethyl-3',4',7a,8,9,9a,12,13,14,15-decahydro-2'H,7H-spiro[1,19-ethenocyclobuta[i][1,4]oxazepino[3,4-f][1,2,7]thiadiazacyclohexadecine-4,1'-naphthalene]-10,18(11H,17H)-dione 16,16-dioxide (700 mg, 1.168 mmol) in THF (3 mL) was added. The resulting mixture was then stirred at reflux for 64 hours. Then, the mixture was quenched with a saturated aqueous solution of $NH_4Cl$ (5 mL) and extracted with EtOAc (2×20 mL). The combined organic extracts were then dried over MgSO4 and concentrated. Chromatographic purification of the residue (silica gel, 0%-100% EtOAc/heptane) provided a desired product as mixture of ethyl (2E)-[(4S,7aR,9aR,14S,15R)-6'-chloro-14,15-dimethyl-16,16-dioxido-18-oxo-3',4',7a,8,9,9a,12,13,14,15,17,18-dodecahydro-2'H,7H-spiro[1,19-ethenocyclobuta[i][1,4]oxazepino[3,4-f][1,2,7]thiadiazacyclohexadecine-4,1'-naphthalen]-10(11H)-ylidene]acetate) and ethyl (2Z)-[(4S,7aR,9aR,14S,15R)-6'-chloro-14,15-dimethyl-16,16-dioxido-18-oxo-3',4',7a,8,9,9a,12,13,14,15,17,18-dodecahydro-2'H,7H-spiro[1,19-ethenocyclobuta[i][1,4]oxazepino[3,4-f][1,2,7]thiadiazacyclohexadecine-4,1'-naphthalen]-10(11H)-ylidene]acetate as a white solid (675 mg, 1.009 mmol, 86% yield). MS (ESI, positive) m/z: 669.2 $(M+H)^+$.

The mixture (E,Z isomers) was then purified via preparative SFC (Column: Princeton Pa. (250×21 mm, 5 μm); Mobile Phase: 80:20 (A:B); A: Liquid $CO_2$; B: Methanol (20 mM $NH_3$); Flow Rate: 70 mL/min; Column/Oven temp.: 40° C.; 240 nm; 22.3 mg/injection; Cycle time=4 min; End of run=7.2 min; 186-193 bar inlet pressure; BPR=100 bar; SN: 06-6707) provided ethyl (2E)-[(4S,7aR,9aR,14S,15R)-6'-chloro-14,15-dimethyl-16,16-dioxido-18-oxo-3',4',7a,8,9, 9a,12,13,14,15,17,18-dodecahydro-2'H,7H-spiro[1,19-ethenocyclobuta[i][1,4]oxazepino[3,4-f][1,2,7]thiadiazacyclohexadecine-4,1'-naphthalen]-10(11H)-ylidene]acetate (209 mg, 0.312 mmol) as a white solid. $^1$H NMR (400 MHz, CHLOROFORM-d) δ ppm 7.97 (1H, s) 7.72 (1H, d, J=8.41 Hz) 7.19 (1H, dd, J=8.51, 2.25 Hz) 7.09 (2H, dd, J=4.11, 2.15 Hz) 6.84-6.91 (1H, m) 6.74-6.83 (1H, m) 5.47 (1H, s) 3.99-4.15 (5H, m) 3.80-3.89 (2H, m) 3.30 (1H, d, J=14.28 Hz) 3.04 (1H, dd, J=15.65, 6.46 Hz) 2.94 (1H, q, J=9.13 Hz) 2.74-2.86 (2H, m) 2.54-2.73 (2H, m) 2.20 (1H, td, J=12.37, 4.01 Hz) 2.00-2.11 (2H, m) 1.95 (3H, d, J=8.61 Hz) 1.53-1.88 (8H, m) 1.45 (3H, d, J=7.43 Hz) 1.26 (3H, t, J=7.14 Hz) 1.04 (3H, d, J=7.04 Hz). MS (ESI, positive) m/z: 669.2 (M+H)$^+$.

and ethyl (2Z)-[(4S,7aR,9aR,14S,15R)-6'-chloro-14,15-dimethyl-16,16-dioxido-18-oxo-3',4',7a,8,9,9a, 12,13,14,15, 17,18-dodecahydro-2'H,7H-spiro[1,19-ethenocyclobuta[i][1,4]oxazepino[3,4-f][1,2,7]thiadiazacyclohexadecine-4,1'-naphthalen]-10(11H)-ylidene]acetate (251 mg, 0.375 mmol) as a white solid. $^1$H NMR (400 MHz, CHLOROFORM-d) δ ppm 7.70 (1H, d, J=8.41 Hz) 7.18 (1H, dd, J=8.61, 2.15 Hz) 7.09 (1H, d, J=2.15 Hz) 6.87-6.94 (2H, m) 6.83 (1H, s) 5.79 (1H, s) 4.43-4.57 (1H, m) 4.11-4.25 (3H, m) 4.07 (2H, s) 3.84 (1H, d, J=15.65 Hz) 3.69 (1H, d, J=14.28 Hz) 3.04-3.23 (2H, m) 2.70-2.86 (2H, m) 2.54-2.66 (1H, m) 2.25-2.38 (1H, m) 1.82-2.11 (8H, m) 1.66-1.73 (1H, m) 1.58 (5H, br. s.) 1.46 (3H, d, J=7.24 Hz) 1.29-1.33 (3H, m) 1.04 (3H, d, J=6.85 Hz). MS (ESI, positive) m/z: 669.2 (M+H)$^+$.

Step 2: (2z)-[(4s,7ar,9ar,14s,15r)-6'-chloro-14,15-dimethyl-16,16-dioxido-18-oxo-3',4',7a,8,9,9a,12,13, 14,15,17,18-dodecahydro-2'h,7h-spiro[1,19-ethenocyclobuta[i][1,4]oxazepino[3,4-f][1,2,7]thiadiazacyclohexadecine-4,1'-naphthalen]-10(11h)-ylidene]acetic acid A solution of ethyl (2Z)-[(4S,7aR,9aR,14S,15R)-6'-chloro-14,15-dimethyl-16,16-dioxido-18-oxo-3',4',7a,8,9, 9a, 12,13,14,15,17,18-dodecahydro-2'H,7H-spiro[1,19-ethenocyclobuta[i][1,4]oxazepino[3,4-f][1,2,7]thiadiazacyclohexadecine-4,1'-naphthalen]-10(11H)-ylidene]acetate (200 mg, 0.299 mmol), lithium hydroxide hydrated (0.083 mL, 2.99 mmol, Fluka Chemie GmbH) in ethanol (2 mL) and water (0.400 mL) was stirred at room temperature for 64 hours. Then, the mixture was concentrated and diluted with H$_2$O (0.5 mL). The mixture was adjusted to pH=4-6 by aqueous HCl solution (5 N). The mixture was then extracted with EtOAc (2×3 mL). The combined organic extracts were then dried over MgSO$_4$, concentrated, and dried in vacuo provided (2Z)-[(4S,7aR,9aR,14S,15R)-6'-chloro-14,15-dimethyl-16,16-dioxido-18-oxo-3',4',7a,8,9,9a,12,13,14,15,17,18-dodecahydro-2'H,7H-spiro[1,19-ethenocyclobuta[i][1,4]oxazepino[3,4-f][1,2,7]thiadiazacyclohexadecine-4,1'-naphthalen]-10(11H)-ylidene]acetic acid (192 mg, 0.299 mmol, 100% yield) as a white solid, which was used in the next step without purification. $^1$H NMR (400 MHz, CHLOROFORM-d) δ ppm 7.94 (1H, s) 7.91-7.97 (1H, m) 7.70 (1H, d, J=8.41 Hz) 7.18 (1H, dd, J=8.41, 2.15 Hz) 7.09 (1H, d, J=1.96 Hz) 6.92 (2H, s) 6.82 (1H, s) 5.80-5.86 (1H, m) 4.42-4.54 (1H, m) 4.17-4.26 (1H, m) 4.07 (2H, s) 3.81 (1H, d, J=15.45 Hz) 3.69 (1H, d, J=13.89 Hz) 3.19 (1H, d, J=14.08 Hz) 3.07 (1H, s) 2.70-2.84 (2H, m) 2.54-2.66 (1H, m) 2.28-2.40 (1H, m) 1.64-2.13 (14H, m) 1.47 (3H, d, J=7.24 Hz) 1.04 (3H, d, J=6.65 Hz). MS (ESI, positive) m/z: 641.2 (M+H)$^+$.

Step 3: (4s,7ar,9ar,10z,14s,15r)-6'-chloro-10-(2-[(9ar)-hexahydropyrazino[2,1-c][1,4]oxazin-8(1h)-yl]-2-oxoethylidene)-14,15-dimethyl-3',4',7a,8,9,9a, 10,11,12,13,14,15-dodecahydro-2'h,7h-spiro[1,19-ethenocyclobuta[i][1,4]oxazepino[3,4-f][11,2,7]thiadiazacyclohexadecine-4,1'-naphthalen]-18(17h)-one 16,16-dioxide trifluoroacetic acid To a solution of (2Z)-[(4S,7aR,9aR,14S,15R)-6'-chloro-14,15-dimethyl-16,16-dioxido-18-oxo-3',4',7a,8,9,9a,12,13, 14,15,17,18-dodecahydro-2'H,7H-spiro[1,19-ethenocyclobuta[i][1,4]oxazepino[3,4-f][1,2,7]thiadiazacyclohexadecine-4,1'-naphthalen]-10(11H)-ylidene]acetic acid (95 mg, 0.148 mmol) and (R)-octahydropyrazino[2,1-c][1,4]oxazine (105 mg, 0.741 mmol, Synthonix) in dichloromethane (3.0 mL) at 0° C. was added propylphosphonic anhydride solution, 50 wt. % in ethyl acetate (0.471 mL, 0.741 mmol, aldrich) dropwise followed by addition of triethylamine (0.206 mL, 1.482 mmol, aldrich). The resulting mixture was then stirred at room temperature overnight. Then, the mixture was quenched with a saturated aqueous solution of NaHCO$_3$ until no bubbles were observed. The mixture was diluted with MeOH/DMSO (1 mL, 1:1) and was filtered. The filtrate was purified via preparative HPLC (Phenomenex Gemini C18 column, 150×30 mm, 10 u, 110 A, 10-100%, 0.1% TFA in MeCN/H$_2$O) provided (4S,7aR,9aR,10Z,14S,15R)-6'-chloro-10-{2-[(9aR)-hexahydropyrazino[2,1-c][1,4]oxazin-8(1H)-yl]-2-oxoethylidene}-14,15-dimethyl-3',4',7a,8,9,9a, 10,11,12,13,14,15-dodecahydro-2'H,7H-spiro[1,19-ethenocyclobuta[i][1,4]oxazepino[3,4-f][1,2,7]thiadiazacyclohexadecine-4,1'-naphthalen]-18(17H)-one 16,16-dioxide trifluoroacetic acid (100 mg, 0.131 mmol, 88% yield) as white solid. $^1$H NMR (400 MHz, CHLOROFORM-d) δ ppm 8.05 (1H, br. s.) 7.68 (1H, d, J=8.61 Hz) 7.17 (1H, d, J=8.22 Hz) 7.09 (1H, s) 6.90-6.99 (2H, m) 6.70 (1H, br. s.) 5.92 (1H, d, J=10.76 Hz) 4.25-4.91 (2H, m) 3.75-4.19 (9H, m) 3.45-3.71 (5H, m) 3.31-3.43 (1H, m) 2.99-3.24 (4H, m) 2.72-2.85 (3H, m) 2.45-2.56 (1H, m) 2.19 (1H, d, J=11.15 Hz) 1.84-2.11 (8H, m) 1.50-1.80 (5H, m) 1.46 (3H, d, J=6.06 Hz) 1.03 (3H, d, J=6.85 Hz). 19F NMR (377 MHz, CHLOROFORM-d) δ ppm −75.80 (3F, s). MS (ESI, positive) m/z: 765.3 (M+H)$^+$.

Step 4: (4s,7ar,9as,10s,14s,15r)-6'-chloro-10-(2-[(9ar)-hexahydropyrazino[2,1-c][1,4]oxazin-8(1h)-yl]-2-oxoethyl)-14,15-dimethyl-3',4',7a,8,9,9a,10,11, 12,13,14,15-dodecahydro-2'h,7h-spiro[1,19-ethenocyclobuta[i][1,4]oxazepino[3,4-f][1,2,7]thiadiazacyclohexadecine-4,1'-naphthalen]-18(17h)-one 16,16-dioxide A solution of (4S,7aR,9aR,10Z,14S,15R)-6'-chloro-10-(2-[(9aR)-hexahydropyrazino[2,1-c][1,4]oxazin-8(1H)-yl]-2-oxoethylidene)-14,15-dimethyl-3',4',7a,8,9,9a,10,11,12, 13,14,15-dodecahydro-2'H,7H-spiro[1,19-ethenocyclobuta[i][1,4]oxazepino[3,4-f][1,2,7]thiadiazacyclohexadecine-4, 1'-naphthalen]-18(17H)-one 16,16-dioxide (15 mg, 0.020 mmol) and platinum (iv) oxide (1.780 mg, 7.84 μmol, aldrich) in ethyl acetate (0.5 mL) was stirred at room temperature under H$_2$ (40 psi) for 3 hours. LC-MS showed traces of desired product (M+H=767). Then, more platinum (iv) oxide (1.780 mg, 7.84 μmol, aldrich) was added and the mixture was stirred at room temperature under H$_2$ (50 psi) for 3 hours. LCMS showed 5% conversion. Then, even more platinum (iv) oxide (1.780 mg, 7.84 μmol, aldrich) and acetic acid, >99.7% (1.132 μl, 0.020 mmol, aldrich) were added and the mixture was stirred under $H_2$ (45 psi) overnight. The mixture was then filtered through celite and the celite was washed with EtOAc (2×1 mL). The combined filtrates were concentrated. The residue was taken up in DMSO (1 mL) and purified via preparative HPLC (Phenomenex Gemini C18 column, 150×30 mm, 10 u, 110 A, 10-100% 0.1% TFA in MeCN/$H_2O$) provided (4S,7aR,9aS, 10S,14S,15R)-6'-chloro-10-{2-[(9aR)-hexahydropyrazino[2,1-c][1,4]oxazin-8(1H)-yl]-2-oxoethyl}-14,15-dimethyl-3',4',7a,8,9,9a, 10,11,12,13,14,15-dodecahydro-2'H,7H-spiro[1,19-ethenocyclobuta[i][1,4]oxazepino[3,4-f][1,2,7]thiadiazacyclohexadecine-4,1'-naphthalen]-18(17H)-one 16,16-dioxide trifluoroacetic acid (5 mg, 6.52 µmol, 33.2% yield) as a light yellow solid. $^1$H NMR (400 MHz, CHLOROFORM-d) δ ppm 8.10 (1H, br. s.) 7.69 (1H, d, J=8.61 Hz) 7.18 (1H, dd, J=8.51, 2.05 Hz) 7.09 (1H, d, J=1.96 Hz) 7.05 (1H, s) 6.91-7.01 (2H, m) 4.69 (1H, d, J=11.35 Hz) 4.40 (1H, br. s.) 4.13 (3H, s) 3.92-4.07 (4H, m) 3.83 (1H, br. s.) 3.68 (2H, d, J=14.48 Hz) 3.35-3.49 (2H, m) 2.93-3.24 (6H, m) 2.73-2.82 (2H, m) 2.40-2.51 (2H, m) 2.15-2.31 (6H, m) 1.92-2.09 (7H, m) 1.57-1.84 (5H, m) 1.42 (3H, d, J=7.04 Hz) 0.99 (3H, d, J=6.65 Hz). 19F NMR (377 MHz, CHLOROFORM-d) δ ppm −75.74 (3F, s). MS (ESI, positive) m/z: 767.3 $(M+H)^+$.

Examples 8, 52 and 77

(1s,3'r,6'r,7'r,11's,12'r)-6-chloro-11',12'-dimethyl-7'-(4-morpholinylcarbonyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6'r,7's,1s,12'r)-6-chloro-11',12'-dimethyl-7'-(4-morpholinylcarbonyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide (example 8)

(1s,3'r,6'r,7's,11's,12'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~0.0~19,24~]pent acosa[16,18,24]triene]-7'-carboxylic acid 13',13'-dioxide or (1s,36'r,6'r,7'r,11's,12'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~0.0~19,24~]pent acosa[16,18,24]triene]-7'-carboxylic acid 13',13'-dioxide (examples 52 and 77)

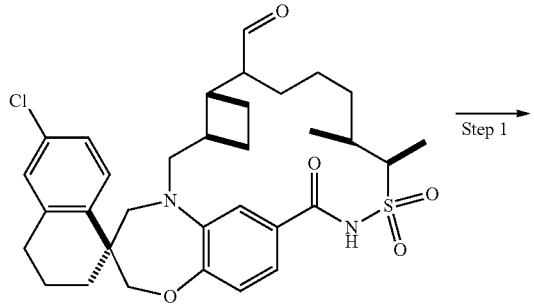

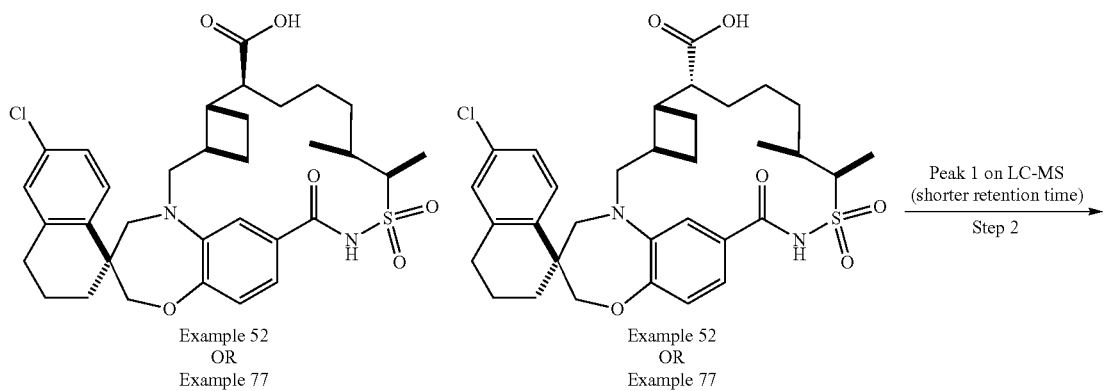

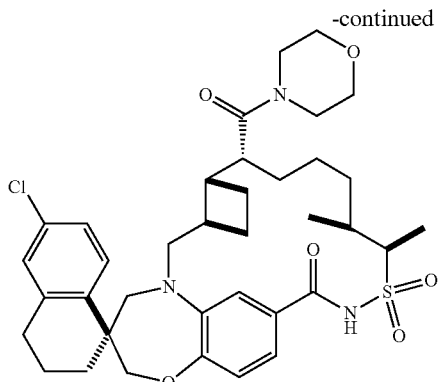
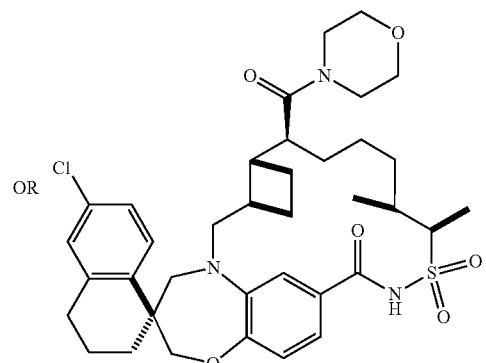

Example 8

Step 1: (1s,3'r,6'r,7's,11's,12'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~.0.0~19,24~]pentacosa[16,18,24]triene]-7'-carboxylic acid 13',13'-dioxide or (1s,3'r,6'r,7'r,11's,12'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~.0.0~19,24~]pentacosa[16,18,24]triene]-7'-carboxylic acid 13',13'-dioxide (examples 52 and 77)

To a mixture of (1S,3'R,6'R,7'S,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[16,18,24]triene]-7'-carbaldehyde 13',13'-dioxide and (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~19,24~]pentacosa[16,18,24]triene]-7'-carbaldehyde 13',13'-dioxide (123 mg, 0.201 mmol), tert-BuOH (2.5 mL), and 2-methyl-2-butene (0.149 mL, 1.404 mmol) was added at rt a solution of sodium phosphate, monobasic, monohydrate (60.2 mg, 0.501 mmol) and sodium chlorite (34.0 mg, 0.301 mmol) in water (0.4 mL). The resulting mixture was then stirred at room temperature for 1.5 hours. Then, the mixture was quenched with a saturated aqueous solution of NH4Cl and a few drops of HOAc/H2O. The crude isomeric product mixture was purified and separated to provide two single isomers: (1S,3'R,6'R,7'S,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[16,18,24]triene]-7'-carboxylic acid 13',13'-dioxide or (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[16,18,24]triene]-7'-carboxylic acid 13',13'-dioxide (Example 52) as an off-white solid. This was the first peak (of a shorter retention time) on LC-MS and was taken onto the next step. $^1$H NMR (500 MHz, CHLOROFORM-d) δ 7.71 (br d, J=8.44 Hz, 1H), 7.18 (br d, J=7.95 Hz, 1H), 7.09 (s, 1H), 6.78-7.05 (m, 3H), 3.99-4.17 (m, 3H), 3.85 (br d, J=15.04 Hz, 1H), 3.68 (br d, J=14.06 Hz, 1H), 3.19 (br d, J=14.18 Hz, 1H), 2.98 (br dd, J=9.41, 15.04 Hz, 1H), 2.60-2.84 (m, 3H), 2.35-2.58 (m, 2H), 1.25-2.17 (m, 15H), 1.22 (d, J=6.11 Hz, 3H), 1.00 (br d, J=5.99 Hz, 3H). MS (ESI, positive) m/z: 629.2 (M+H)$^+$;

and (1S,3'R,6'R,7'S,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[16,18,24]triene]-7'-carboxylic acid 13',13'-dioxide or (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[16,18,24]triene]-7'-carboxylic acid 13',13'-dioxide (Example 77) as an off-white solid. This was the second peak (of a longer retention time) on LC-MS. $^1$H NMR (500 MHz, CHLOROFORM-d) δ 8.26-8.72 (m, 1H), 7.69 (d, J=8.56 Hz, 1H), 7.14-7.22 (m, 2H), 7.08 (d, J=2.08 Hz, 1H), 6.99 (br d, J=7.95 Hz, 1H), 6.87 (d, J=8.19 Hz, 1H), 3.90-4.07 (m, 3H), 3.85 (q, J=6.36 Hz, 1H), 3.67 (br d, J=14.18 Hz, 1H), 3.15 (br d, J=14.31 Hz, 1H), 2.89 (br dd, J=9.48, 15.22 Hz, 1H), 2.67-2.82 (m, 2H), 2.42-2.61 (m, 2H), 2.28 (br d, J=11.00 Hz, 2H), 1.91-2.05 (m, 3H), 1.59-1.88 (m, 5H), 1.32-1.54 (m, 9H), 1.07 (d, J=6.60 Hz, 3H). MS (ESI, positive) m/z: 629.2 (M+H)$^+$.

Step 2: (1s,3'r,6'r,7'r,11's,12'r)-6-chloro-11',12'-dimethyl-7'-(4-morpholinylcarbonyl)-3,4-dihydro-2h,15'h-spiro[naphthalene-1,22'-[20]oxa[13]thia[1,14]diazatetracyclo[14.7.2.0~3,6~.0.0~19,24~]pentacosa[16,18,24]trien]-15'-one 13',13'-dioxide or (1s,3'r,6'r,7's,11's,12'r)-6-chloro-11',12'-dimethyl-7'-(4-morpholinylcarbonyl)-3,4-dihydro-2h,15'h-spiro[naphthalene-1,22'-[20]oxa[13]thia[1,14]diazatetracyclo[14.7.2.0~3,6~.0.0~19,24~]pentacosa[16,18,24]trien]-15'-one 13',13'-dioxide (example 8)

To a solution of (1S,3'R,6'R,7'S,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~19,24~]pentacosa[16,18,24]triene]-7'-carboxylic acid 13',13'-dioxide or (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~19,24~]pentacosa[16,18,24]triene]-7'-carboxylic acid 13',13'-dioxide (16 mg, 0.025 mmol) (the first peak of the shorter retention time on LC-MS) in dichloromethane (1 mL) were added morpholine (8.9 uL, 0.1 mmol), HATU (29 mg, 0.076 mmol), and triethylamine (28 uL, 0.2 mmol). The resulting mixture was then stirred at room temperature for 1.5 hrs. The LC-MS indicated completion of the reaction.

The reaction mixture was diluted with ethyl acetate, washed with 1 N HCl, water, brine, dried over MgSO4, and concentrated in vacuo. Chromatographic purification of the residue (silica gel, 35%-100% EtOAc/hexanes) provided (1S,3'R,6'R,7'R,11'S,12'R)-6-chloro-11',12'-dimethyl-7'-(4-morpholinylcarbonyl)-3,4-dihydro-2H,15H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide or (1S,3'R,6'R,7'S,11'S,12'R)-6-chloro-11',12'-dimethyl-7'-(4-morpholinylcarbonyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide as a white solid (18 mg, 100% yield). 1H NMR (500 MHz, Solvent) δ ppm 0.98-1.06 (m, 3H) 1.16-1.32 (m, 5H) 1.32-1.40 (m, 4H) 1.41-1.50 (m, 1H) 1.51-1.69 (m, 5H) 1.80-1.98 (m, 4H) 1.99-2.11 (m, 2H) 2.12-2.23 (m, 1H) 2.52 (quin, J=8.80 Hz, 1H) 2.70-2.86 (m, 2H) 3.00-3.10 (m, 2H) 3.19-3.27 (m, 1H) 3.45-3.56 (m, 1H) 3.59-3.81 (m, 9H) 3.84 (d, J=15.16 Hz, 1H) 3.97-4.07 (m, 1H) 4.07-4.13 (m, 2H) 6.91-6.99 (m, 1H) 7.02 (d, J=1.96 Hz, 1H) 7.08-7.20 (m, 3H) 7.73 (d, J=8.56 Hz, 1H). MS (ESI, positive) m/z: 698.2 (M+H)+.

Examples 23, 53, and 63

(1s,3'r,6'r,7'r,11's,12'r)-6-chloro-7'-(methoxymethyl)-11',12'-dimethyl-3,4-dihydro-2h,15h-spiro[naphthalene-1,22'-[20]oxa[13]thia[1,14]diazatetracyclo[14.7.2.0~3,6~-0.0~19,24~]pentacosa[16,18,24]trien]-15'-one 13',13'-dioxide or (1s,3'r,6'r,7's,11's,12'r)-6-chloro-7'-(methoxymethyl)-11',12'-dimethyl-3,4-dihydro-2h,15h-spiro[naphthalene-1,22'-[20]oxa[13]thia[1,14]diazatetracyclo[14.7.2.0~3,6~-0.0~19,24~]pentacosa[16,18,24]trien]-15'-one 13',13'-dioxide (example 53)

(1s,3'r,6'r,7's,11's,12'r)-6-chloro-7'-(hydroxymethyl)-11',12'-dimethyl-3,4-dihydro-2h,15h-spiro[naphthalene-1,22'-[20]oxa[13]thia[1,14]diazatetracyclo[14.7.2.0~3,6~-0.0~19,24~-]pentacosa[16,18,24]trien]-15'-one 13',13'-dioxide or (1s,3'r,6'r,7'r,11's,12'r)-6-chloro-7'-(hydroxymethyl)-11',12'-dimethyl-3,4-dihydro-2h,15'h-spiro[naphthalene-1,22'-[20]oxa[13]thia[1,14]diazatetracyclo[14.7.2.0~3,6~-0.0~19,24~-]pentacosa[16,18,24]trien]-15'-one 13',13'-dioxide (examples 23 and 63)

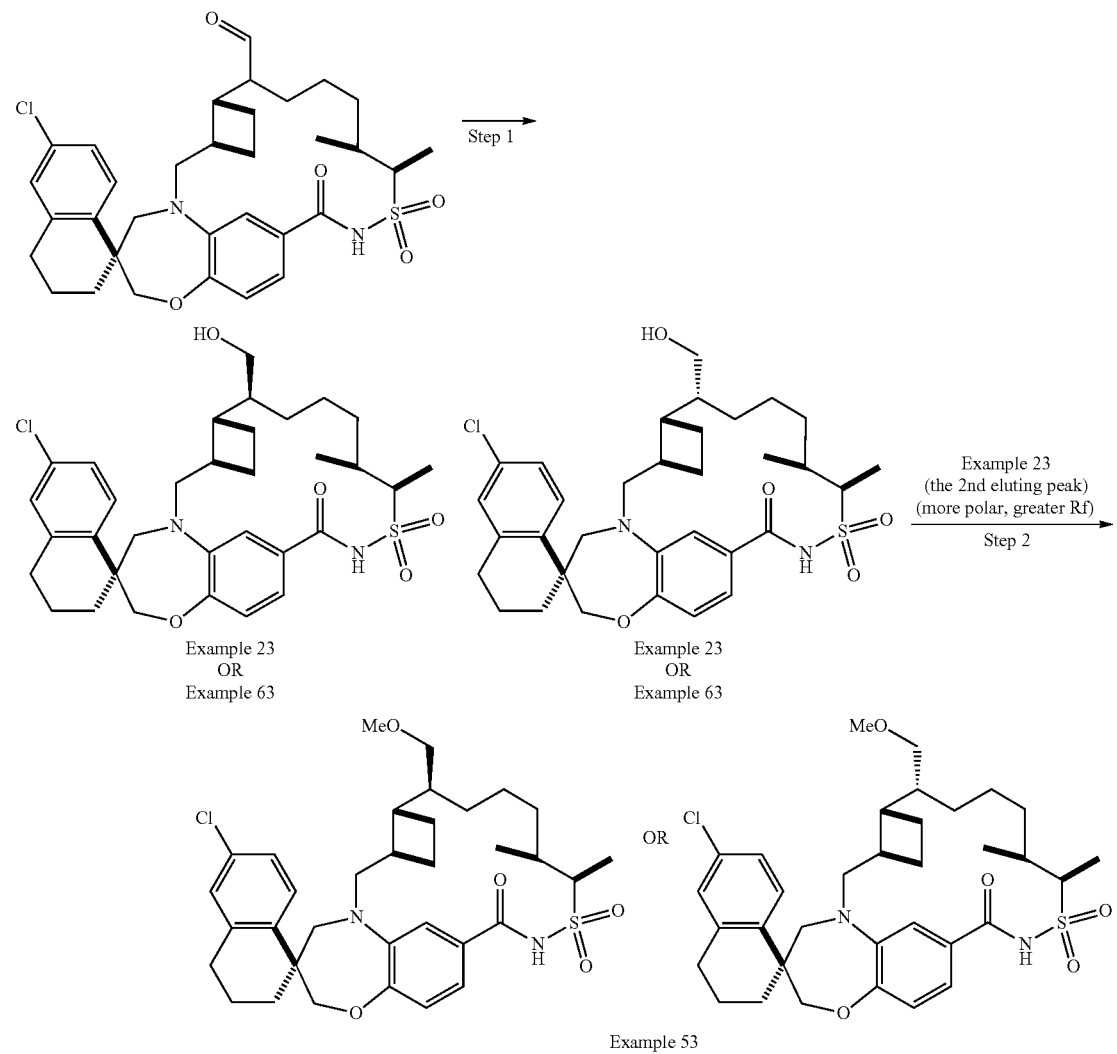

step 1: (1s,3'r,6'r,7's,11's,12'r)-6-chloro-7'-5 (hydroxymethyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16, 18,24]trien]-15'-one 13',13'-dioxide or (1s,3'r,6'r,7'r, 11's,12'r)-6-chloro-7'-(hydroxymethyl)-11',12-dimethyl-3,4-dihydro-2h,15h-spiro[naphthalene-1, 22'-[20]oxa[13]thia[1,14]diazatetracyclo[14.7.2.0~3, 6~0.0~19,24~]pent acosa[16,18,24]trien]-15'-one 13',13'-dioxide (examples 23 and 63)

To a solution of (1S,3'R,6'R,7'R,11'S,12'R)-6-chloro-11', 2'-dimethyl-15'-oxo-3,4-dihydro-2H-spiro[naphthalene-1, 22'-[20]oxa[13]thia[1,14]diazatetracyclo[14.7.2.0~3, 6~0.0~19,24·]pentacosa[16,18,24]triene]-7'-carbaldehyde 13',13'-dioxide and (1S,3'R,6'R,7'S,11'S,12'R)-6-chloro-11', 12'-dimethyl-15'-oxo-3,4-dihydro-2H-spiro[naphthalene-1, 22'-[20]oxa[13]thia[1,14]diazatetracyclo[14.7.2.0~3, 6~0.0~9,24~]pentacosa[16,18,24]triene]-7'-carbaldehyde 13',13'-dioxide (257 mg, 0.419 mmol) in MeOH (5 ml) was added NaBH$_4$ (63.4 mg, 1.676 mmol). The resulting mixture was then stirred at room temperature for 1 hour. Then, the mixture was quenched with a saturated aqueous solution of NH$_4$Cl and extracted with EtOAc. The organic layer was collected, dried over MgSO$_4$, and concentrated in vacuo. Chromatographic purification of the residue (0%-45% (hexanes with 0.3% HOAc)/EtOAc provided two products: (1S,3'R,6'R,7'S,11'S,12'R)-6-chloro-7'-(hydroxymethyl)-11',12'-dimethyl-3,4-dihydro-2H,15'H-spiro[naphthalene-1, 22'-[20]oxa[13]thia[1,14]diazatetracyclo[14.7.2.0~3, 6~0.0~9,24~]pentacosa[16,18,24]trien]-15'-one 13',13'-dioxide or (1S,3'R,6'R,7'R,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18, 24]trien]-15'-one 13',13'-dioxide (170 mg) (Example 23) as a white solid. It was the second eluting (more polar) isomer off of the silica gel column. $^1$H NMR (400 MHz, DICHLOROMETHANE-d$_2$) δ 8.05 (s, 1H), 7.63 (d, J=8.41 Hz, 1H), 7.08 (dd, J=2.25, 8.51 Hz, 1H), 7.00 (d, J=2.15 Hz, 1H), 6.90 (s, 1H), 6.84 (s, 2H), 3.95-4.05 (m, 3H), 3.73 (d, J=15.26 Hz, 1H), 3.62 (d, J=14.28 Hz, 1H), 3.43 (dd, J=4.99, 10.66 Hz, 1H), 3.28 (dd, J=7.24, 10.56 Hz, 1H), 3.15 (d, J=14.08 Hz, 1H), 2.90 (dd, J=9.49, 15.36 Hz, 1H), 2.63-2.72 (m, 2H), 2.36-2.47 (m, 1H), 2.24-2.34 (m, 1H), 1.81-2.00 (m, 4H), 1.69-1.78 (m, 1H), 0.94-1.66 (m, 15H), 0.90 (d, J=6.85 Hz, 3H). MS (ESI, positive) m/z: 615.4 (M+H)$^+$;
and (1S,3'R,6'R,7'S,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide or (1S,3'R,6'R,7'R,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (69 mg) (Example 63) as a white solid. It was the first eluting (less polar) isomer off of the silica gel column. $^1$H NMR (400 MHz, DICHLOROMETHANE-d$_2$) δ 8.24 (s, 1H), 7.71 (d, J=8.61 Hz, 1H), 7.57 (d, J=1.96 Hz, 1H), 7.17 (dd, J=2.25, 8.51 Hz, 1H), 7.09 (d, J=2.15 Hz, 1H), 6.94-6.99 (m, 1H), 6.86-6.93 (m, 1H), 4.04-4.22 (m, 4H), 3.95 (dd, J=2.84, 12.03 Hz, 1H), 3.67 (d, J=14.08 Hz, 1H), 3.51 (dd, J=2.15, 11.93 Hz, 1H), 3.20 (d, J=14.08 Hz, 1H), 2.91 (dd, J=9.39, 15.26 Hz, 1H), 2.70-2.81 (m, 2H), 1.12-2.50 (m, 22H), 1.00 (d, J=6.65 Hz, 3H). MS (ESI, positive) m/z: 615.4 (M+H)$^+$.

Step 2: (1s,3'r,6'r,7'r,11's,12'r)-6-chloro-7'-(methoxymethyl)-11',12'-dimethyl-3,4-dihydro-2h, 15'h-spiro[naphthalene-1,22'-[20]oxa[13]thia[1,14] diazatetracyclo[14.7.2.0~3,6~0.0~9,24~]pent acosa [16,18,24]trien]-15'-one 13',13'-dioxide or (1s,3'r,6'r, 7's,11's,12'r)-6-chloro-7'-(methoxymethyl)-11',12'-dimethyl-3,4-dihydro-2h,151'h-spiro[naphthalene-1, 22'-[20]oxa[13]thia[1,14]diazatetracyclo[14.7.2.0~3, 6~0.0~9,24~]pent acosa[16,18,24]trien]-15'-one 13',13'-dioxide To a solution of (1S,3'R,6'R,7'S,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide or (1S,3'R,6'R,7'R,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18, 24]trien]-15'-one 13',13'-dioxide (Example 23, the more polar isomer) (30.5 mg, 0.050 mmol) in DMF (0.8 mL) was added sodium hydride (10.51 mg, 0.263 mmol) at 0° C. The resulting mixture was then stirred at the same temperature for 5 min and at room temperature for 15 min. Then, methyliodide (0.016 mL, 0.263 mmol) was added. The resulting mixture was then stirred at room temperature for 5 hours. The mixture was then quenched with a saturated aqueous solution of NH$_4$Cl and was extracted with EtOAc. The organic layer was collected, washed with brine, dried over MgSO$_4$, and concentrated in vacuo. The crude residue was purified on a Redi-Sep gold column with EtOAc/(0.3% HOAc in hexanes) (0%-30%) to provide (1S,3'R,6'R,7'R, 11'S,12'R)-6-chloro-7'-(methoxymethyl)-11',12'-dimethyl-3,4-dihydro-2H,15'H-spiro[naphthalene-1,22'-[20]oxa[13] thia[1,14]diazatetracyclo[14.7.2.0~3,6~0.0~9,24~] pentacosa[16,18,24]trien]-15'-one 13',13'-dioxide or (1S, 3'R,6'R,7'S,11'S,12'R)-6-chloro-7'-(methoxymethyl)-11', 12'-dimethyl-3,4-dihydro-2H,15'H-spiro[naphthalene-1,22'-[20]oxa[13]thia[1,14]diazatetracyclo[14.7.2.0~3,6~0.0~9, 24~]pentacosa[16,18,24]trien]-15'-one 13',13'-dioxide (9.5 mg) (Example 53) as a white solid. $^1$H NMR (500 MHz, CHLOROFORM-d) δ 8.12 (s, 1H), 7.71 (br d, J=8.56 Hz, 1H), 7.19 (br d, J=8.31 Hz, 1H), 7.09 (s, 1H), 7.02 (s, 1H), 6.94 (s, 2H), 4.14-4.21 (m, 1H), 4.06-4.13 (m, 2H), 3.82 (br d, J=15.16 Hz, 1H), 3.71 (br d, J=14.18 Hz, 1H), 3.30 (s, 3H), 3.17-3.24 (m, 2H), 3.06-3.15 (m, 1H), 2.89-2.99 (m, 1H), 2.69-2.84 (m, 2H), 2.42-2.54 (m, 1H), 2.32-2.40 (m, 1H), 1.90-2.07 (m, 4H), 1.81 (br s, 2H), 1.05-1.73 (m, 13H), 1.01 (br d, J=6.72 Hz, 3H). MS (ESI, positive) m/z: 629.2 (M+H)$^+$.

Examples 24 and 26

(1s,3'r,6'r,7's,8'e,11's,12'r)-6-chloro-7'-(hydroxymethyl)-11',12'-dimethyl-3,4-dihydro-2h,15'h-spiro[naphthalene-1,22'-[20]oxa[13]thia[1,14]diazatetracyclo[14.7.2.0~3,6~.0.0~19,24~]pent acosa[8,16,18,24]tetraen]-15'-one 13',13'-dioxide or (1s,3'r,6'r,7'r,8'e,11's,12'r)-6-chloro-7'-(hydroxymethyl)-11',12'-dimethyl-3,4-dihydro-2h,15'h-spiro[naphthalene-1,22'-[20]oxa[13]thia[1,14]diazatetracyclo[14.7.2.0~3,6~.0.0~19,24~]pent acosa[8,16,18,24]tetraen]-15'-one 13',13'-dioxide

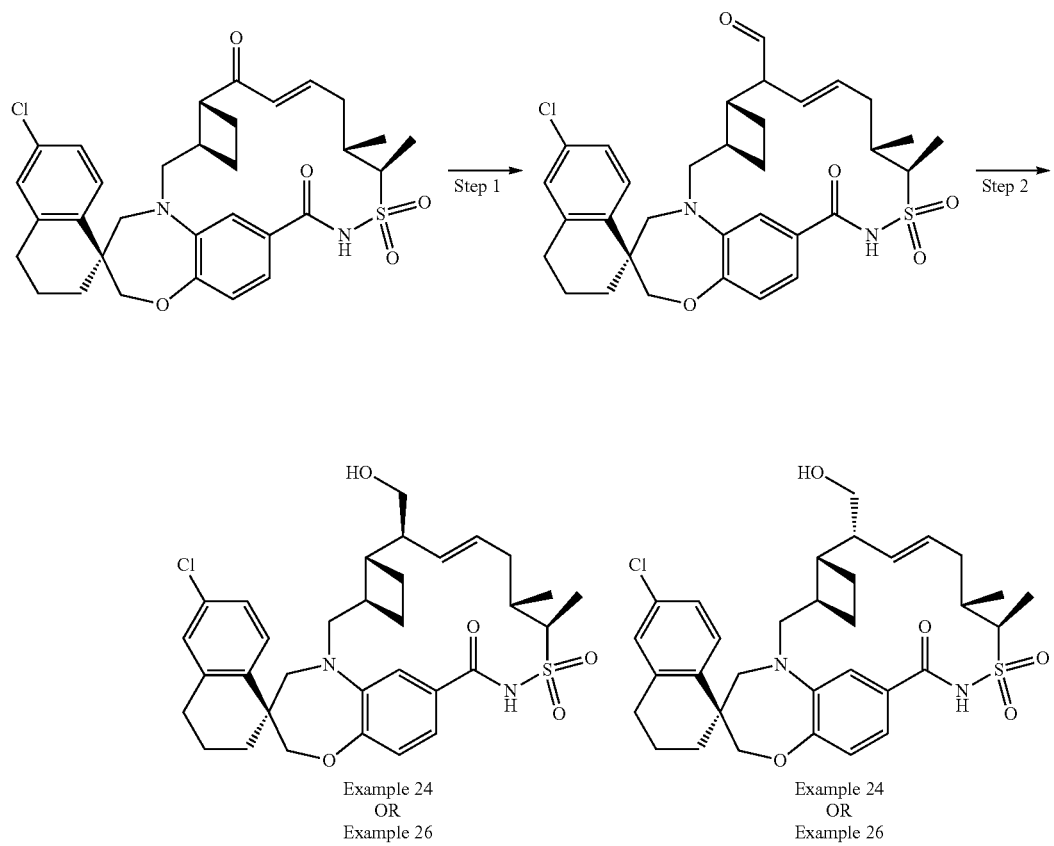

Example 24 OR Example 26

Example 24 OR Example 26

STEP 1: (1s,3'r,6'r,7's,8'e,11's,112'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~.0.0~19,24~]pent acosa[8,16,18,24]tetraene]-7'-carbaldehyde 13',13'-dioxide and (1s,3'r,6'r,7'r,8'e,11's,12'r)-6-chloro-11',12'-dimethyl-15'-oxo-3,4-dihydro-2h-spiro[naphthalene-1,22'-[20]oxa[13]thia[1,14]diazatetracyclo[14.7.2.0~3,6~.0.0~19,24~]pent acosa[8,16,18,24]tetraene]-7'-carbaldehyde 13',13'-dioxide To a stirred solution of (1S,3'R,6'R,8'E,11'S,12'R)-6-chloro-11',12'-dimethyl-3,4-dihydro-2H,7'H, 15'H-spiro[naphthalene-1,22'-[20]oxa[13]thia[1,14]diazatetracyclo[14.7.2.0~3,6~.0.0~19,24~]pentacosa[8,16,18,2 4]tetraene]-7',15'-dione 13',13'-dioxide (200 mg, 0.335 mmol) and trimethylsulfonium iodide (71.8 mg, 0.352 mmol) in dimethyl sulfoxide (2.0 mL) was dropwise added potassium tert-butoxide, 1.0 m solution in tetrahydrofuran (0.837 mL, 0.837 mmol) under argon over 5 min. The resulting mixture was stirred at ambient temperature for 15 min. The crude reaction mixture was directly loaded onto a silica gel pre-column (25 g) previously covered with a layer of ammonium chloride and subjected to combi-flash column chromatography on a 12-g ISCO Gold eluting with EtOAc/Hexanes (15 min from 20 to 100% and 10 min at 100%) to give, as minor products, an impure epimeric mixture of (1S,3'R,6'R,7'S,8'E,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~19,24~]pentacosa[8,16,18,24]tetraene]-7'-carbaldehyde 13',13'-dioxide and (1S,3'R,6'R,7'R,8'E,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[8,16,18,24]tetraene]-7'-carbaldehyde 13',13'-dioxide (50 mg) as a white solid. It was directly taken onto the next step without further purification. MS (ESI, +ve) m/z 611.4 [M+H]$^+$.

Step 2: (1s,3'r,6'r,7's,8'e,11's,12'r)-6-chloro-7'-(hydroxymethyl)-11',12'-dimethyl-3,4-dihydro-2h,15'h-spiro[naphthalene-1,22'-[20]oxa[13]thia[1,14]diazatetracyclo[14.7.2.0~3,6~.0.0~19,24~]pent acosa[8,16,18,24]tetraen]-15'-one 13',13'-dioxide or (1s,3'r,6'r,7'r,8'e,11's,12'r)-6-chloro-7'-(hydroxymethyl)-11',12'-dimethyl-3,4-dihydro-2h,15'h-spiro[naphthalene-1,22'-[20]oxa[13]thia[1,14]diazatetracyclo[14.7.2.0~3,6~.0.0~19,24~]pent acosa[8,16,18,24]tetraen]-15'-one 13',13'-dioxide (examples 24 and 26)

To a stirred ice-cooled solution of an impure epimeric mixture of (1S,3'R,6'R,7'S,8'E,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[8,16,18,24]tetraene]-7'-carbaldehyde 13',13'-dioxide and (1S,3'R,6'R,7'R,8'E,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[8,16,18,24]tetraene]-7'-carbaldehyde 13',13'-dioxide (40 mg, 0.065 mmol) in EtOH (2.0 mL) was added sodium borohydride (24.76 mg, 0.654 mmol) under argon. The resulting mixture was stirred at 0° C. for 5 min and at ambient temperature for 40 min. The crude mixture was diluted with aqueous MeOH and subjected to combi-flash column chromatography on a 12-g ISCO Gold column eluting with MeOH/DCM to give a still impure product mixture. This was dissolved in MeOH/DMSO and subjected to preparative reverse-phase HPLC (Gemini™ Prep C18 10 μm column; Phenomenex, Torrance, Calif.; gradient elution of 40 to 90% MeCN in water, where both solvents contain 0.1% TFA, 21 min in a 30-min method) to give, after lyophilization, (1S,3'R,6'R,7'S,8'E,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0.0~9,24~]pentacosa[8,16,18,24]tetraen]-15'-one 13',13'-dioxide or (1S,3'R,6'R,7'R,8'E,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0.0~19,24~]pentacosa[8,16,18,24]tetraen]-15'-one 13',13'-dioxide (3.0 mg) (Example 24) as a white solid. It's the first eluting epimeric product. $^1$H NMR (400 MHz, CHLOROFORM-d) δ 7.90 (s, 1H), 7.71 (d, J=8.41 Hz, 1H), 7.19 (dd, J=2.15, 8.41 Hz, 1H), 7.09 (d, J=2.15 Hz, 1H), 6.87-6.96 (m, 3H), 5.74-5.85 (m, 1H), 5.51 (dd, J=9.39, 15.06 Hz, 1H), 4.34 (q, J=7.17 Hz, 1H), 4.09 (s, 2H), 3.82 (br d, J=15.26 Hz, 1H), 3.71 (d, J=14.48 Hz, 1H), 3.39-3.47 (m, 1H), 3.29-3.37 (m, 1H), 3.23 (d, J=14.08 Hz, 1H), 2.97 (dd, J=10.07, 15.16 Hz, 1H), 2.72-2.84 (m, 2H), 2.39-2.55 (m, 2H), 2.20-2.30 (m, 1H), 1.92-2.15 (m, 6H), 1.60-1.86 (m, 5H), 1.49 (d, J=7.04 Hz, 3H), 1.34-1.43 (m, 1H), 1.05 (d, J=6.65 Hz, 3H). MS (ESI, +ve) m/z 613.4 [M+H]$^+$; and (1S,3'R,6'R,7'S,8'E,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0.0~19,24~]pentacosa[8,16,18,24]tetraen]-15'-one 13',13'-dioxide or (1S,3'R,6'R,7'R,8'E,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~.0.0~19,24~]pentacosa[8,16,18,24]tetraen]-15'-one 13',13'-dioxide (9 mg) (Example 26) as a white solid. It's the second eluting epimeric product. 1H NMR (400 MHz, CHLOROFORM-d) δ 7.99 (s, 1H), 7.71 (d, J=8.61 Hz, 1H), 7.42 (d, J=1.56 Hz, 1H), 7.19 (dd, J=2.25, 8.51 Hz, 1H), 7.09 (d, J=2.15 Hz, 1H), 6.83-6.95 (m, 2H), 5.62-5.71 (m, 1H), 5.53-5.62 (m, 1H), 4.27 (q, J=6.78 Hz, 1H), 4.06-4.17 (m, 3H), 4.01 (dd, J=3.52, 11.54 Hz, 1H), 3.66-3.77 (m, 2H), 3.25 (d, J=14.08 Hz, 1H), 2.96 (dd, J=9.39, 15.26 Hz, 1H), 2.71-2.81 (m, 2H), 2.45-2.55 (m, 1H), 2.28-2.41 (m, 1H), 1.55-2.16 (m, 12H), 1.48 (d, J=7.24 Hz, 3H), 1.34-1.42 (m, 1H), 1.07 (d, J=6.06 Hz, 3H). MS (ESI, +ve) m/z 613.4 [M+H]$^+$.

Example 45

(1s,3'r,6'r,7'r,11's,12'r)-7'-acetyl-6-chloro-11',12'-dimethyl-3,4-dihydro-2h,15'h-spiro [naphthalene-1,22'-[20]oxa[13]thia[1,14]diazatetracyclo[14.7.2.0~3,6~.0.0~19,24~]pent acosa[16,18,24]trien]-15'-one 13',13'-dioxide or (1s,3'r,6'r,7's,11's,12'r)-7'- acetyl-6-chloro-11',12'-dimethyl-3,4 dihydro-2h,15-h-spiro [naphthalene-1,22'-20]oxa[13]thia[1,14]diazatetracyclo[14.7.2.0~3,6~.0.0~19,24~]pent acosa[16,18,24]trien]-15'-one 13',13'-dioxide

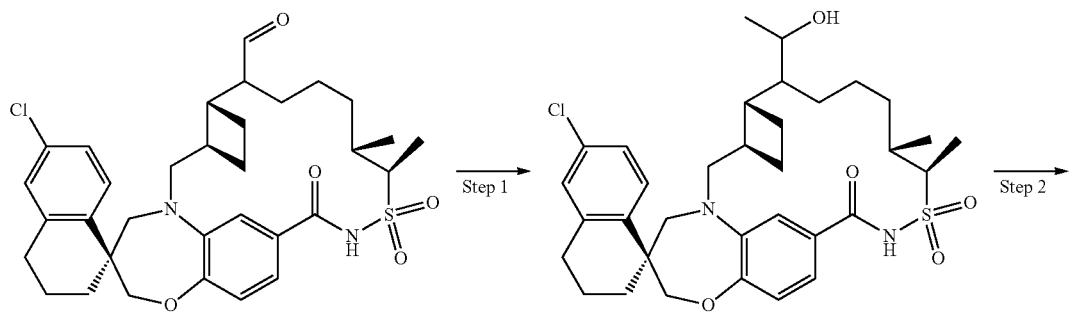

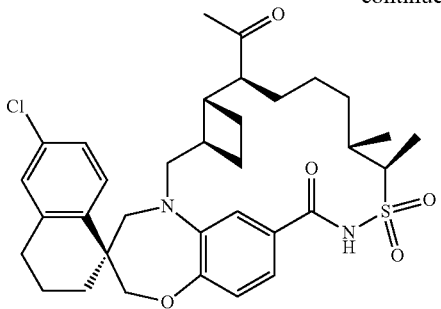 OR 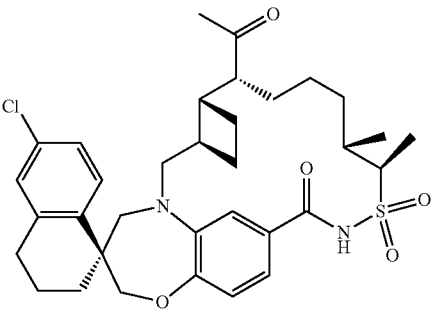

Example 45

Step 1: (1s,3'r,6'r,7's,11's,12'r)-6-chloro-7'-((1r)-1-hydroxyethyl)-11',12'-dimethyl-3,4-dihydro-2h,15h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3r,6'r,7'r,11's,12'r)-6-chloro-7'-((1r)-1-hydroxyethyl)-1',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3'r,6'r,7's,11's,12'r)-6-chloro-7'-((1s)-1-hydroxyethyl)-1',12'-dimethyl-3,4-dihydro-2h,15-h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3'r,6'r,7'r,11's,12'r)-6-chloro-7'-((1s)-1-hydroxyethyl)-11',12'-dimethyl-3,4-dihydro-2h,15-h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide To a stirred ice-cooled solution of (1S,3'R,6'R,7'S, 1'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~0.0~9,24~]pentacosa[16,18,24]triene]-7'-carbaldehyde 13',13'-dioxide and (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~0.0~19,24~]pentacosa[16,18,24]triene]-7'-carbaldehyde 13',13'-dioxide (130 mg, 0.212 mmol) in DCM (5.0 mL) was added under argon gas methylmagnesium bromide 3.0 M in diethyl ether (0.707 mL, 2.120 mmol) via a syringe. The resulting mixture was stirred at 0° C. for a period of 1.5 h before carefully quenched with methanol. The mixture was loaded onto a silica gel precolumn (25 g) and subjected to combi-flash column chromatography on a 24-g ISCO Gold column eluting with EtOAc/Hexanes to give an stereoisomeric mixture of (1S,3'R,6'R,7'S,11'S,12'R)-6-chloro-7'-((1R)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide and (1S,3'R,6'R,7'R,11'S,12'R)-6-chloro-7'-((1R)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide and (1S,3'R,6'R,7'S,11'S,12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide and (1S,3'R,6'R,7'R,11'S,12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide (135 mg) as a white film. It was taken on the next step directly. MS (ESI, +ve) m/z 629.2 [M+H]+.

Step 2: (1s,3'r,6'r,7'r,11's,12'r)-7'-acetyl-6-chloro-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6'r,7's,11's,12'r)-7'-acetyl-6-chloro-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide To a stirred ice-cooled solution of an stereoisomeric mixture of (1S,3'R,6'R,7'S,11'S,12'R)-6-chloro-7'-((1R)-1-hydroxyethyl)-1',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide and (1S,3'R,6'R,7'R,11'S,12'R)-6-chloro-7'-((1R)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide and (1S,3'R,6'R,7'S, 1S, 12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide and (1S,3'R,6'R,7'R,11'S,12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-dioxide (130 mg, 0.207 mmol) in DCM (5.0 mL) was added dess-martin periodinane (88 mg, 0.207 mmol) in one portion as a solid. The resulting mixture was stirred at 0° C. for a period of 35 min and at ambient temperature for 25 min. More DMP (23 mg) was added at rt and stirring continued for 10 min. The mixture was directly loaded onto a silica gel precolumn and subjected to combi-flash column chromatography (EtOAc/Hexanes, 15 min from 0 to 100%, 12 g silica gel) to give (1S,3'R,6'R,7'R,11'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide or (1S, 3'R,6'R,7'S,11'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~19,24~]

pentacosa[16,18,24]trien]-15'-one 13',13'-dioxide (Example 45) (100 mg) as a white solid. It was the predominant product and a single stereoisomer. ¹H NMR (400 MHz, DICHLOROMETHANE-d₂) δ 8.05 (s, 1H), 7.72 (d, J=8.41 Hz, 1H), 7.18 (dd, J=2.35, 8.61 Hz, 1H), 7.09 (d, J=2.15 Hz, 1H), 6.91-7.01 (m, 3H), 4.04-4.14 (m, 3H), 3.85 (d, J=15.45 Hz, 1H), 3.70 (d, J=14.67 Hz, 1H), 3.21 (d, J=14.28 Hz, 1H), 3.01 (dd, J=9.78, 15.26 Hz, 1H), 2.70-2.81 (m, 3H), 2.45-2.58 (m, 1H), 2.22-2.35 (m, 1H), 2.12 (s, 3H), 1.89-2.07 (m, 4H), 1.74-1.82 (m, 1H), 1.43-1.63 (m, 7H), 1.38 (d, J=7.24 Hz, 3H), 1.21-1.30 (m, 3H), 0.98 (d, J=6.85 Hz, 3H). MS (ESI, +ve) m/z 627.3 [M+H]⁺.

Examples 21, 40, 58, and 74

(1s,3'r,6'r,7's, 1s, 12'r)-6-chloro-7'-((1r)-1-hydroxyethyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6'r,7's,11's,12'r)-6-chloro-7'-((1r)-1-hydroxyethyl)-11',12'-dimethyl-3,4-dihydro-2h,151h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6'r,7's,11's,12'r)-6-chloro-7'-((1s)-1-hydroxyethyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~] pent acosa[16,18,24]trien]-15'-one 13',13'-dioxide or (1s,3'r,6'r,7's,11's,12'r)-6-chloro-7'-((1s)-1-hydroxyethyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide

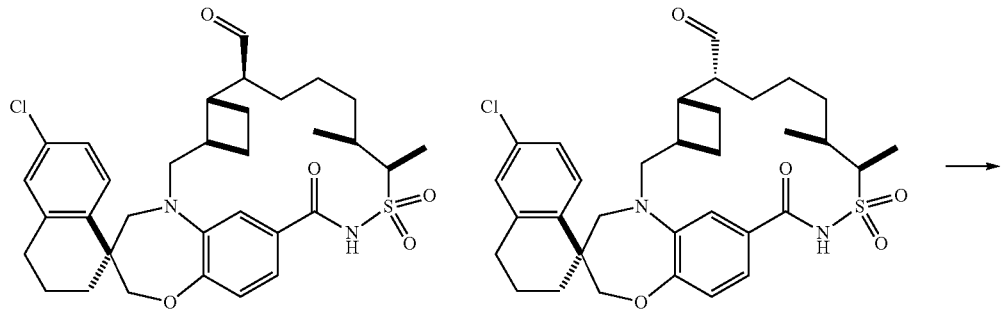

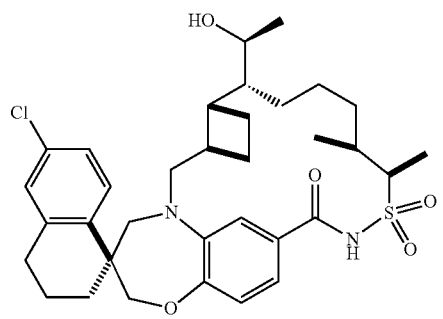

Example 21
OR
Example 40
OR
Example 58
OR
Example 74

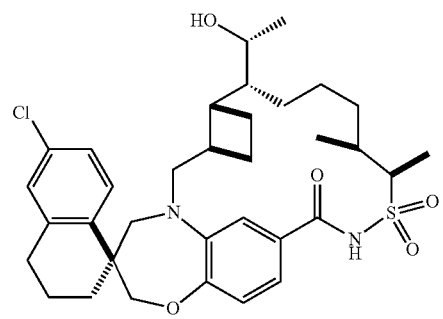

Example 21
OR
Example 40
OR
Example 58
OR
Example 74

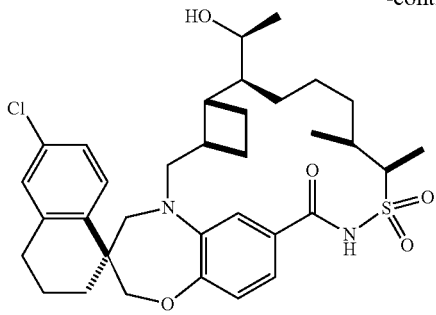

Example 21
OR
Example 40
OR
Example 58
OR
Example 74

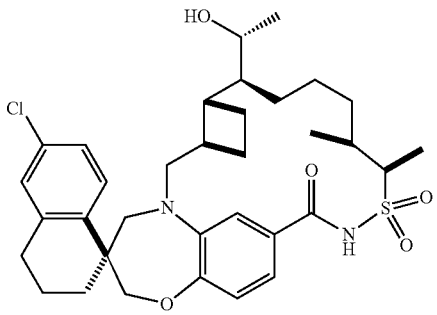

Example 21
OR
Example 40
OR
Example 58
OR
Example 74

An epimeric mixture of (1S,3'R,6'R,7'S,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~0.0~9,24~]pentacosa[16,18,24]triene]-7'-carbaldehyde 13',13'-dioxide and (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~0.0~19,24~]pentacosa[16,18,24]triene]-7'-carbaldehyde 13',13'-dioxide (36 mg, 0.059 mmol) were azeotroped with toluene before THF (1 mL) was added. To this solution cooled at −78° C. was added dropwise methylmagnesium bromide (0.235 mL, 0.704 mmol). The resulting mixture was stirred for 2.5 h at −78° C. before quenched with a sat'd aqueous solution of NH$_4$Cl and extracted with EtOAc. The organic extract was dried over anhydrous sodium sulfate and concentrated in vacuo. The crude residue was purified by silica gel chromatography on a 4-g Redi-Sep gold column with a gradient 0-45% EtOAc in Hexanes+0.3% HOAc to give: (1S,3'R,6'R,7'S,11'S,12'R)-6-chloro-7'-((1R)-1-hydroxyethyl)-1',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien-15'-one 13',13'-dioxide OR (1S,3'R,6'R,7'R,11'S,12'R)-6-chloro-7'-((1R)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien-15'-one 13',13'-dioxide OR (1S,3'R,6'R,7'S,11'S,12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien-15'-one 13',13'-dioxide OR (1S,3'R,6'R,7'R,11'S,12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien-15'-one 13',13'-dioxide (Example 74) as a white solid. It was the first eluting stereoisomer off of silic gel column. $^1$H NMR (500 MHz, DICHLOROMETHANE-d$_2$) δ 8.33 (s, 1H), 7.71 (d, J=8.56 Hz, 1H), 7.61 (br s, 1H), 7.17 (dd, J=2.32, 8.44 Hz, 1H), 7.08 (d, J=2.20 Hz, 1H), 6.84-7.02 (m, 2H), 4.24 (br d, J=13.69 Hz, 1H), 4.02-4.19 (m, 4H), 3.66 (br d, J=11.86 Hz, 1H), 3.19 (br d, J=12.47 Hz, 1H), 2.68-2.95 (m, 3H), 2.48 (q, J=9.05 Hz, 1H), 2.33-2.43 (m, 1H), 2.10-2.18 (m, 1H), 2.04-2.08 (m, 1H), 1.89-1.97 (m, 2H), 1.77-1.87 (m, 1H), 1.52-1.72 (m, 6H), 1.48 (br dd, J=4.77, 12.35 Hz, 1H), 1.32-1.42 (m, 5H), 1.23-1.29 (m, 1H), 1.21 (d, J=6.48 Hz, 3H), 1.08-1.17 (m, 2H), 0.99 (d, J=6.72 Hz, 3H). MS (ESI, +ve) m/z 628.8 [M+H]$^+$;

and (1S,3'R,6'R,7'S,11'S,12'R)-6-chloro-7'-((1R)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'R,11'S,12'R)-6-chloro-7'-((1R)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'S, 11'S,12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'R,11'S,12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (Example 58) as a white solid. It was the second eluting stereoisomer off of silic gel column. $^1$H NMR (500 MHz, DICHLOROMETHANE-d$_2$) δ 8.22 (br s, 1H), 7.71 (d, J=8.44 Hz, 1H), 7.41 (d, J=1.96 Hz, 1H), 7.17 (dd, J=2.26, 8.50 Hz, 1H), 7.09 (d, J=2.32 Hz, 1H), 6.93-6.99 (m, 1H), 6.87-6.93 (m, 1H), 4.03-4.13 (m, 4H), 3.88 (br dd, J=4.10, 6.17 Hz, 1H), 3.67 (d, J=14.18 Hz, 1H), 3.20 (d, J=14.18 Hz, 1H), 2.92 (dd, J=9.23, 15.22 Hz, 1H), 2.58-2.82 (m, 3H), 2.45 (quin, J=8.71 Hz, 1H), 2.24 (q, J=8.88 Hz, 1H), 1.16-2.15 (m, 22H), 0.99 (d, J=6.85 Hz, 3H). MS (ESI, +ve) m/z 628.8 [M+H]$^+$;

and a stereoisomeric mixture the two remaining isomers as they coeluted on silica gel as the third product peak. This was subsequently separated by SFC to give:

(1S,3'R,6'R,7'S,11'S,12'R)-6-chloro-7'-((1R)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0.0~9,24~]pentacosa[16,18,24]trien]-15'-one 13',13'-dioxide OR (1S,3'R,6'R,7'R,11'S,12'R)-6-chloro-7'-((1R)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0.0~9,24~]pentacosa[16,18,24]trien]-15'-one 13',13'-dioxide OR (1S,3'R,6'R,7'S, 11'S, 12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0.0~9,24~]pentacosa[16,18,24]trien]-15'-one 13',13'-dioxide OR (1S,3'R,6'R,7'R,11'S,12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0.0~9,24~]pentacosa[16,18,24]trien]-15'-one 13',13'-dioxide (Example 40) as a white solid. It was the first eluting stereoisomer off of SFC column. $^1$H NMR (500 MHz, DICHLOROMETHANE-d$_2$) δ 7.72 (d, J=8.56 Hz, 1H), 7.17 (dd, J=2.32, 8.44 Hz, 1H), 7.09 (d, J=2.32 Hz, 1H), 6.95 (s, 1H), 6.92 (d, J=0.98 Hz, 2H), 4.04-4.15 (m, 3H), 3.78-3.87 (m, 2H), 3.71 (d, J=14.18 Hz, 1H), 3.24 (d, J=14.31 Hz, 1H), 2.98 (br dd, J-=9.60, 15.34 Hz, 1H), 2.69-2.84 (m, 2H), 2.40-2.51 (m, 2H), 2.06 (br d, J=13.69 Hz, 1H), 1.89-1.99 (m, 3H), 1.77-1.87 (m, 2H), 1.06-1.73 (m, 14H), 0.99 (d, J=6.72 Hz, 6H). MS (ESI, +ve) m/z 628.8 [M+H]$^+$; and (1S,3'R,6'R,7'S, 11'S,12'R)-6-chloro-7'-((1R)-1-hydroxyethyl)-11',12'-dimethyl-3,4-dihydro-2H,15'H-spiro[naphthalene-1,22'-[20]Oxa[3]thia[114]diazatetracyclo[14.7.2.0~3,6~.0.0~9,24~]pentacosa[16,18,24]trien]-15'-one 13',13'-dioxide OR (1S,3'R,6'R,7'R,11'S,12'R)-6-chloro-7'-((1R)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0.0~9,24~]pentacosa[16,18,24]trien]-15'-one 13',13'-dioxide OR (1S,3'R,6'R,7'S, 11'S, 12'R)-6-chloro-7'-((1S)-1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~.0.0~19,24~]pentacosa[16,18,24]trien]-15'-one 13',13'-dioxide OR (1S,3'R,6'R,7'R,11'S,12'R)-6-chloro-7'-((1S)-1-hydroxyethyl)-1',12'-dimethyl-3,4-dihydro-2H,15'H-spiro[naphthalene-1,22'-[20]oxa[13]thia[1,14]diazatetracyclo[14.7.2.0~3,6~.0.0~19,24~]pentacosa[16,18,24]trien]-15'-one 13',13'-dioxide (Example 21) as a white solid. It was the second eluting stereoisomer off of SFC column. $^1$H NMR (500 MHz, DICHLOROMETHANE-d$_2$) δ 7.76 (d, J=8.56 Hz, 1H), 7.21 (dd, J=1.77, 8.50 Hz, 1H), 7.13 (d, J=2.08 Hz, 1H), 6.97 (br d, J=13.20 Hz, 3H), 4.12 (s, 3H), 3.80-3.92 (m, 2H), 3.75 (br d, J=14.31 Hz, 1H), 3.29 (d, J=14.31 Hz, 1H), 3.01 (dd, J=10.15, 15.41 Hz, 1H), 2.73-2.88 (m, 2H), 2.53 (quin, J=8.89 Hz, 1H), 2.28-2.39 (m, 1H), 2.10 (br d, J=13.69 Hz, 1H), 1.94-2.05 (m, 3H), 1.79-1.92 (m, 2H), 1.21-1.77 (m, 14H), 1.15 (d, J=6.48 Hz, 3H), 1.03 (d, J=6.85 Hz, 3H). MS (ESI, +ve) m/z 628.8 [M+H]$^+$.

Examples 47, 66, 86, and 87

(1s,3'r,6'r,7'r,11's,12'r)-6-chloro-11',12'-dimethyl-7'-((1s)-2,2,2-trifluoro-1-hydroxyethyl)-3,4-dihydro-2h,15'h-spiro[naphthalene-1,22' [20]oxa[13]thia[1,14]diazatetracyclo[14.7.2.0~3,6~.0.0~19,24~]pent acosa[16,18,24]trien]-15'-one 13',13'-dioxide or (1s,3'r,6'r,7's,11's,12'r)-6-chloro-11',12'-dimethyl-7'-((1s)-2,2,2-trifluoro-1-hydroxyethyl)-3,4-dihydro-2h,15'h-spiro[naphthalene-1,22'-[20]oxa[13]thia[1,14]diazatetracyclo[14.7.2.0~3,6~.0.0~19,24~]pent acosa[16,18,24]trien]-15'-one 13',13'-dioxide or (1s,3'r,6'r,7'r,11's,12'r)-6-chloro-11',12'-dimethyl-7'-((1r)-2,2,2-trifluoro-1-hydroxyethyl)-3,4-dihydro-2h,15'h-spiro[naphthalene-1,22'-[20]oxa[13]thia[1,14]diazatetracyclo[14.7.2.0~3,6~.0.0~19,24~]pent acosa[16,18,24]trien]-15'-one 13',13'-dioxide or (1s,3'r,6'r,7's,11's,12'r)-6-chloro-11',12'-dimethyl-7'-((1r)-2,2,2-trifluoro-1-hydroxyethyl)-3,4-dihydro-2h,15'h-spiro[naphthalene-1,22'-[20]oxa[13]thia[1,14]diazatetracyclo[14.7.2.0~3,6~.0.0~19,24~]pent acosa[16,18,24]trien]-15'-one 13',13'-dioxide

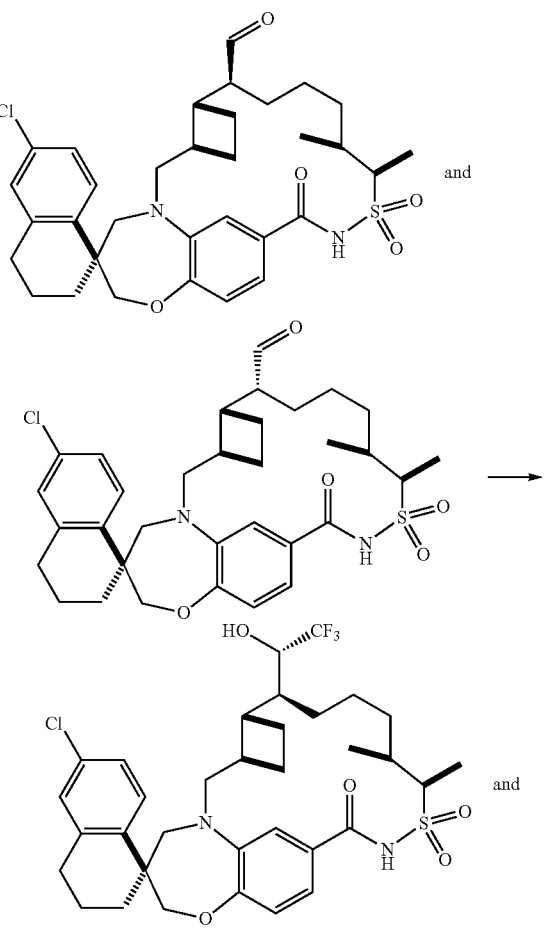

Example 47
OR
Example 66
OR
Example 86
OR
Example 87

-continued

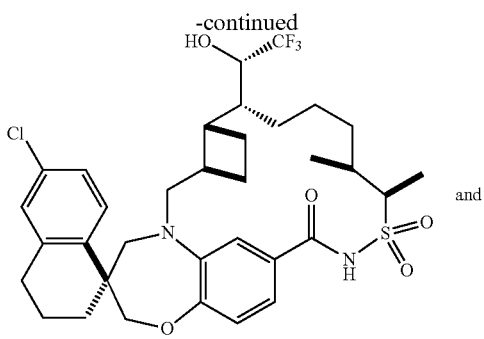

Example 47
OR
Example 66
OR
Example 86
OR
Example 87

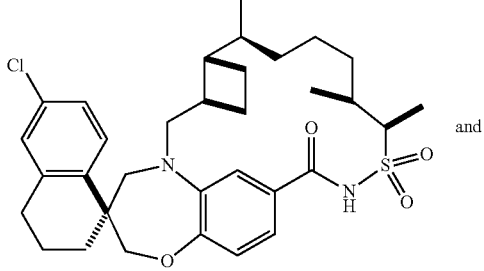

and

Example 47
OR
Example 66
OR
Example 86
OR
Example 87

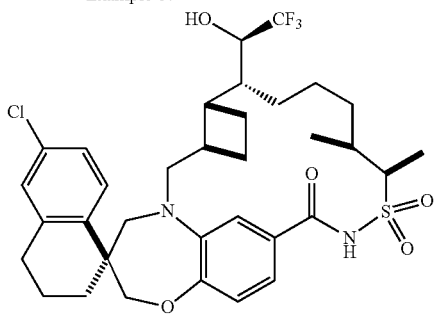

Example 47
OR
Example 66
OR
Example 86
OR
Example 87

To a solution of a mixture of (1S,3'R,6'R,7'S,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[16,18,24]triene]-7'-carbaldehyde 13',13'-dioxide and (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~.0.0~9,24~]pentacosa[16,18,24]triene]-7'-carbaldehyde 13',13'-dioxide (476 mg, 0.77 mmol) in THF (2 mL) was added dropwise (trifluoromethyl)trimethylsilane (1.1 mL, 7.7 mmol, Matrix Scientific) followed by a solution of tetrabutylammonium fluoride solution (1.0 M in THF; 0.2 mL, 0.2 mmol) under nitrogen atmosphere. The reaction mixture was heated to 60° C. for 1 h. An additional portion of tetrabutylammonium fluoride solution (1.0 M in THF; 0.2 mL, 0.2 mmol) was added. After a total reaction time of 2 hours, an additional portion of (trifluoromethyl)trimethylsilane (1.1 mL, 7.7 mmol, Matrix Scientific) and tetrabutylammonium fluoride solution (1.0 M in THF; 0.2 mL, 0.2 mmol) was added. After a total reaction time of 5 hours, the solvent was removed under reduced pressure. The residue was dissolved in THF (8 mL), treated with tetrabutylammonium fluoride solution (1.0 M in THF; 1.1 mL, 1.1 mmol), and stirred at rt for 30 min. The reaction mixture was partitioned between EtOAc and saturated sodium bicarbonate solution. The organic extract was washed with saturated NaCl solution and dried over $MgSO_4$. The crude material was absorbed onto a plug of silica gel and purified by column chromatography ($SiO_2$), eluting with a gradient of 10-100% EtOAc/heptane to obtain a mixture of four isomers, which was subjected to separation by SFC (Column: Princeton Chromatography, Mobile Phase: 65:35 (A:B) isocratic, A: Liquid $CO_2$, B: methanol (20 mM $NH_3$), Flow Rate: 70 g/min, Column/Oven temp.: 40° C., Detection: UV @ 240 nm) to give the following four products as four beige solids: (1S,3'R,6'R,7'R,11'S,12'R)-6-chloro-11',12'-dimethyl-7'-((1S)-2,2,2-trifluoro-1-hydroxyethyl)-3,4-dihydro-2H,15'H-spiro[naphthalene-1,22' [20]oxa[13]thia[1,14]diazatetracyclo[14.7.2.0~3,6~.0.0~9,24~]pentacosa[16,18,24]trien]-15'-one 13',13'-dioxide OR (1S,3'R,6'R,7'S,11'S,12'R)-6-chloro-11',12'-dimethyl-7'-((1S)-2,2,2-trifluoro-1-hydroxyethyl)-3,4-dihydro-2H,15'H-spiro[naphthalene-1,22'-[20]oxa[13]thia[1,14]diazatetracyclo[14.7.2.0~3,6~.0.0~9,24~]pentacosa[16,18,24]trien]-15'-one 13',13'-dioxide OR (1S,3'R,6'R,7'R,11'S,12'R)-6-chloro-11',12'-dimethyl-7'-((1R)-2,2,2-trifluoro-1-hydroxyethyl)-3,4-dihydro-2H,15'H-spiro[naphthalene-1,22'-[20]oxa[13]thia[1,14]diazatetracyclo[14.7.2.0~3,6~.0.0~9,24~]pentacosa[16,18,24]trien]-15'-one 13',13'-dioxide OR (1S,3'R,6'R,7'S,11'S,12'R)-6-chloro-11',12'-dimethyl-7'-((1R)-2,2,2-trifluoro-1-hydroxyethyl)-3,4-dihydro-2H,15'H-spiro[naphthalene-1,22'-[20]oxa[13]thia[1,14]diazatetracyclo[14.7.2.0~3,6~.0.0~9,24~]pentacosa[16,18,24]trien]-15'-one 13',13'-dioxide (Example 66, the first eluting isomer, $t_R$=5.08 minutes on analytical SFC; 4FBSA; 20% MeOH (+20 mM $NH_3$ in $CO_2$) with >99.5% de) (37.4 mg, 0.055 mol, 7% yield). $^1$H NMR (400 MHz, DMSO-$d_6$) δ ppm 0.91 (d, J=6.65 Hz, 3H) 1.10-1.93 (m, 19H) 2.00 (d, J=13.50 Hz, 1H) 2.39 (br. s., 2H) 2.65-2.86 (m, 2H) 3.00 (dd, J=15.16, 8.90 Hz, 1H) 3.21 (d, J=14.08 Hz, 1H) 3.60 (d, J=14.08 Hz, 1H) 3.72 (d, J=15.06 Hz, 1H) 3.83-3.96 (m, 2H) 4.03 (q, J=12.13 Hz, 2H) 6.11 (d, J=6.26 Hz, 1H) 6.84-6.93 (m, 2H) 7.05 (dd, J=8.12, 1.66 Hz, 1H) 7.18 (d, J=2.15 Hz, 1H) 7.28 (dd, J=8.51, 2.25 Hz, 1H) 7.67 (d, J=8.41 Hz, 1H) 11.91 (br. s., 1H). MS (ESI, +ve ion) m/z 683.3 (M+H)$^+$; and (1S,3'R,6'R,7'R,11'S,12'R)-6-chloro-11',12'-dimethyl-7'-((1S)-2,2,2-trifluoro-1-hydroxyethyl)-3,4-dihydro-2H,15'H-spiro[naphthalene-1,22' [20]oxa[13]thia[1,14]diazatetracyclo[14.7.2.0~3,6~.0.0~9,24~]pentacosa[16,18,24]trien]-15'-one 13',13'-dioxide OR (1S,3'R,6'R,7'S,11'S,12'R)-6-chloro-11',12'-dimethyl-7'-((1S)-2,2,2-trifluoro-1-hydroxyethyl)-3,4-dihydro-2H,15'H-spiro[naphthalene-1,22'-[20]oxa[13]thia[1,14]diazatetracyclo[14.7.2.0~3,6~.0.0~9,24~]pentacosa[16,18,24]trien]-15'-one 13',13'-dioxide OR (1S,3'R,6'R,7'R,11'S,12'R)-6-chloro-11',12'-dimethyl-7'-((1R)-2,2,2-trifluoro-1-hydroxyethyl)-3,4-dihydro-2H,15'H-spiro[naphthalene-1,22'-[20]oxa[13]thia

[1,14]diazatetracyclo[14.7.2.0~3,6~0.0~9,24~]pentacosa [16,18,24]trien]-15'-one 13',13'-dioxide OR (1S,3'R,6'R,7'S, 11'S,12'R)-6-chloro-11',12'-dimethyl-7'-((1R)-2,2,2-trifluoro-1-hydroxyethyl)-3,4-dihydro-2H,15'H-spiro [naphthalene-1,22'-[20]oxa[13]thia[1,14]diazatetracyclo [14.7.2.0~3,6~0.0~9,24~]pentacosa[16,18,24]trien]-15'-one 13',13'-dioxide (Example 47, the second eluting isomer, $t_R$=5.83 minutes on analytical SFC; 4FBSA; 20% MeOH (+20 mM NH$_3$ in CO$_2$) with >99.5% de) (90 mg, 0.132 mol, 17% yield). $^1$H NMR (400 MHz, DMSO-d$_6$) δ ppm 0.91 (d, J=6.85 Hz, 3H) 1.01-2.05 (m, 20H) 2.34-2.47 (m, 2H) 2.61-2.86 (m, 2H) 3.00 (dd, J=14.87, 9.19 Hz, 1H) 3.14-3.25 (m, 1H) 3.51-3.69 (m, 2H) 3.85 (d, J=6.85 Hz, 1H) 3.96-4.12 (m, 3H) 5.97 (d, J=6.46 Hz, 1H) 6.81-6.98 (m, 2H) 7.09 (dd, J=8.12, 1.66 Hz, 1H) 7.18 (d, J=2.15 Hz, 1H) 7.28 (dd, J=8.51, 2.25 Hz, 1H) 7.69 (d, J=8.41 Hz, 1H) 11.95 (br. s., 1H), MS (ESI, +ve ion) m/z 683.3 (M+H)$^+$;

and (1S,3'R,6'R,7'R,11'S,12'R)-6-chloro-11',12'-dimethyl-7'-((1S)-2,2,2-trifluoro-1-hydroxyethyl)-3,4-dihydro-2H, 15'H-spiro[naphthalene-1,22' [20]oxa[13]thia[1,14]diazatet-racyclo[14.7.2.0~3,6~0.0~9,24~]pentacosa[16,18,24]trien]-15'-one 13',13'-dioxide OR (1S,3'R,6'R,7'S,11'S,12'R)-6-chloro-11',12'-dimethyl-7'-((1S)-2,2,2-trifluoro-1-hydroxyethyl)-3,4-dihydro-2H,15'H-spiro[naphthalene-1, 22'-[20]oxa[13]thia[1,14]diazatetracyclo[14.7.2.0~3, 6~0.0~9,24~]pentacosa[16,18,24]trien]-15'-one 13',13'-dioxide OR (1S,3'R,6'R,7'R,1'S,12'R)-6-chloro-11',12'-dimethyl-7'-((1R)-2,2,2-trifluoro-1-hydroxyethyl)-3,4-dihydro-2H,15'H-spiro[naphthalene-1,22'-[20]oxa[13]thia [1,14]diazatetracyclo[14.7.2.0~3,6~0.0~9,24~]pentacosa [16,18,24]trien]-15'-one 13',13'-dioxide OR (1S,3'R,6'R,7'S, 11'S,12'R)-6-chloro-11',12'-dimethyl-7'-((1R)-2,2,2-trifluoro-1-hydroxyethyl)-3,4-dihydro-2H,15'H-spiro [naphthalene-1,22'-[20]oxa[13]thia[1,14]diazatetracyclo [14.7.2.0~3,6~0.0~9,24~]pentacosa[16,18,24]trien]-15'-one 13',13'-dioxide (Example 87, the third eluting isomer, $t_R$=7.80 minutes on analytical SFC; 4FBSA; 20% MeOH (+20 mM NH$_3$ in CO$_2$) with >99.5% de) (45 mg, 0.066 mol, 9% yield). $^1$H NMR (400 MHz, DMSO-d$_6$) δ ppm 0.90 (d, J=6.65 Hz, 3H) 1.06 (br. s., 2H) 1.18 (br. s., 5H) 1.33-1.45 (m, 3H) 1.49-2.12 (m, 8H) 2.42 (d, J=7.24 Hz, 1H) 2.63-2.88 (m, 2H) 3.02 (dd, J=15.16, 5.77 Hz, 1H) 3.52 (d, J=14.28 Hz, 1H) 3.64-3.86 (m, 2H) 3.95 (d, J=12.32 Hz, 1H) 4.02-4.18 (m, 2H) 6.12-6.25 (m, 1H) 6.84 (d, J=7.82 Hz, 1H) 7.10-7.23 (m, 2H) 7.26-7.39 (m, 2H) 7.65 (d, J=8.41 Hz, 1H). MS (ESI, +ve ion) m/z 683.3 (M+H)$^+$;

and (1S,3'R,6'R,7'R,11'S,12'R)-6-chloro-11',12'-dimethyl-7'-((1S)-2,2,2-trifluoro-1-hydroxyethyl)-3,4-dihydro-2H, 15'H-spiro[naphthalene-1,22' [20]oxa[13]thia[1,14]diazatet-racyclo[14.7.2.0~3,6~0.0~9,24~]pentacosa[16,18,24]trien]-15'-one 13',13'-dioxide OR (1S,3'R,6'R,7'S,11'S,12'R)-6-chloro-11',12'-dimethyl-7'-((1S)-2,2,2-trifluoro-1-hydroxyethyl)-3,4-dihydro-2H,15'H-spiro[naphthalene-1, 22'-[20]oxa[13]thia[1,14]diazatetracyclo[14.7.2.0~3, 6~0.0~9,24~]pentacosa[16,18,24]trien]-15'-one 13',13'-dioxide OR (1S,3'R,6'R,7'R,11'S,12'R)-6-chloro-11',12'-dimethyl-7'-((1R)-2,2,2-trifluoro-1-hydroxyethyl)-3,4-dihydro-2H,15'H-spiro[naphthalene-1,22'-[20]oxa[13]thia [1,14]diazatetracyclo[14.7.2.0~3,6~0.0~9,24~]pentacosa [16,18,24]trien]-15'-one 13',13'-dioxide OR (1S,3'R,6'R,7'S, 11'S,12'R)-6-chloro-11',12'-dimethyl-7'-((1R)-2,2,2-trifluoro-1-hydroxyethyl)-3,4-dihydro-2H,15'H-spiro [naphthalene-1,22'-[20]oxa[13]thia[1,14]diazatetracyclo [14.7.2.0~3,6~0.0~19,24~]pentacosa[16,18,24]trien]-15'-one 13',13'-dioxide (Example 86, the fourth eluting isomer, $t_R$=8.63 minutes on analytical SFC; 4FBSA; 20% MeOH (+20 mM NH$_3$ in CO$_2$) with >99.5% de) (65 mg, 0.124 mol, 16% yield). $^1$H NMR (400 MHz, DMSO-d$_6$) δ ppm 0.89 (d, J=6.26 Hz, 3H) 1.08-1.56 (m, 9H) 1.59-1.71 (m, 4H) 1.76-2.07 (m, 5H) 2.42 (br. s., 2H) 2.61-2.89 (m, 3H) 3.14 (d, J=13.89 Hz, 1H) 3.54 (d, J=13.89 Hz, 1H) 3.92 (br. s., 1H) 4.02 (s, 2H) 4.09-4.28 (m, 2H) 6.83 (d, J=8.02 Hz, 1H) 7.04-7.21 (m, 3H) 7.28 (dd, J=8.51, 2.25 Hz, 1H) 7.50 (br. s., 1H) 7.69 (d, J=8.41 Hz, 1H) 11.86 (br. s., 1H). MS (ESI, +ve ion) m/z 683.3 (M+H)$^+$.

Examples 41 and 44

(1s,3'r,6'r,7's,11's,12'r)-6-chloro-11',12'-dimethyl-7'-((methylsulfonyl)methyl)-3,4-dihydro-2h,15'h-spiro [naphthalene-1,22'-[20]oxa[13]thia[1,14]diazatetra-cyclo[14.7.2.0~3,6~0.0~19,24~]pent acosa[16,18, 24]trien]-15'-one 13',13'-dioxide or (1s,3'r,6'r,7'r, 11's,12'r)-6-chloro-11',12'-dimethyl-7'-((methylsulfonyl)methyl)-3,4-dihydro-2h,15'h-spiro [naphthalene-1,22'-[20]oxa[13]thia[1,14] diazatetracyclo[14.7.2.0~3,6~0.0~19,24~]pent acosa [16,18,24]trien]-15'-one

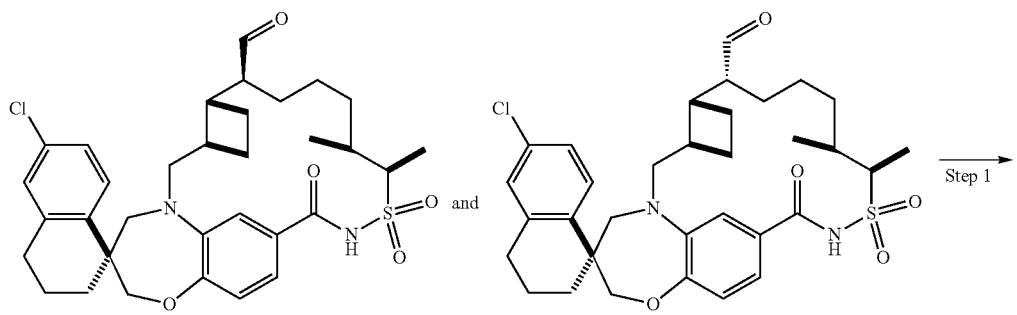

-continued
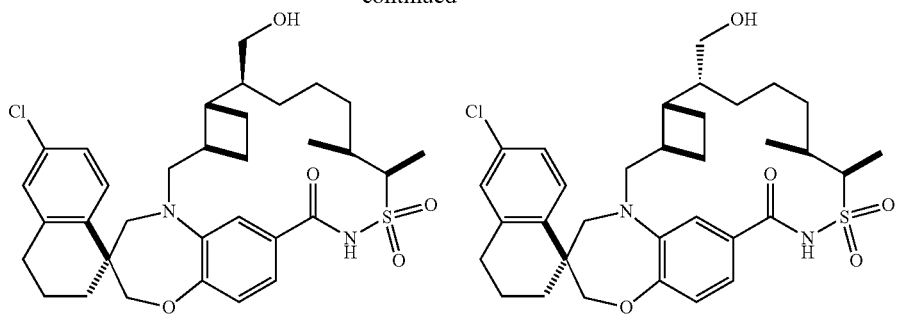
peak 2
OR
peak 1
peak 1
OR
peak 2
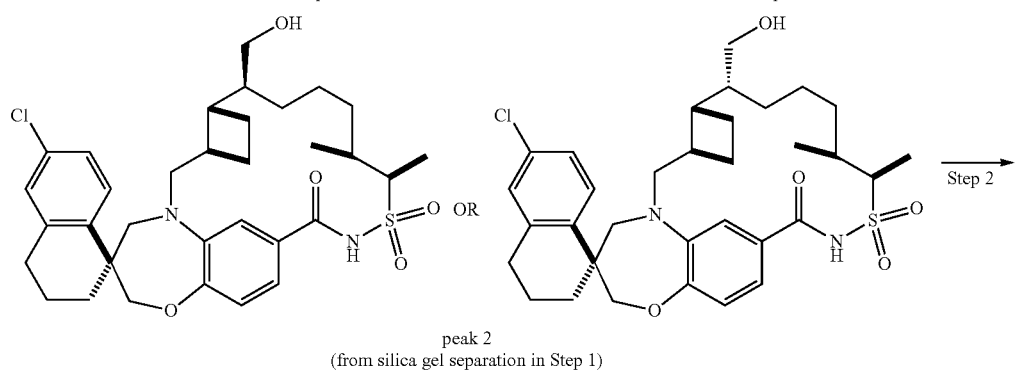
peak 2
(from silica gel separation in Step 1)
Step 2
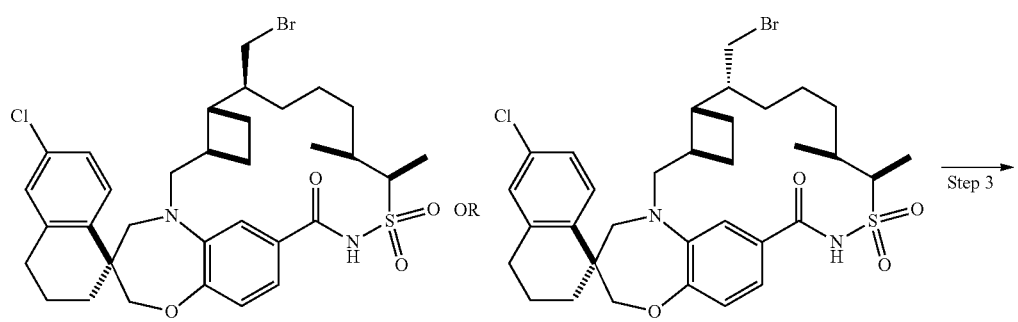
Step 3
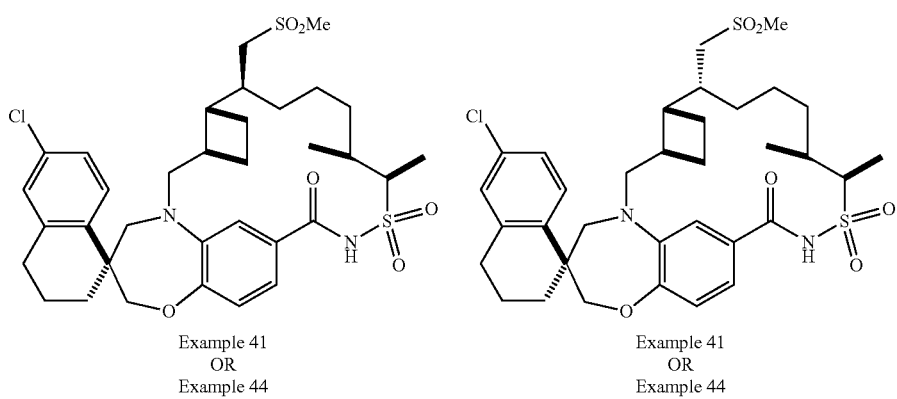
Example 41
OR
Example 44
Example 41
OR
Example 44

Step 1: (1s,3'r,6'r,7's,11's,12'r)-6-chloro-7'-(hydroxymethyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24]pent acosa[16, 18,24]trien]-15'-one 13',13'-dioxide or (1s,3'r,6'r,7'r, 11's,12'r)-6-chloro-7'-(hydroxymethyl)-1',12'-dimethyl-3,4-dihydro-2h,15'h-spiro[naphthalene-1, 22'-[20]oxa[13]thia[1,14]diazatetracyclo[14.7.2.0~3, 6~0.0~19,24~]pent acosa[16,18,24]trien]-15'-one 13',13'-dioxide (peaks 1 and 2)

To a solution of a mixture of 1S,3'R,6'R,7'S,11'S,12'R)-6-chloro-1',12'-dimethyl-15'-oxo-3,4-dihydro-2H-spiro[naphthalene-1,22'-[20]oxa[13]thia[1,14]diazatetracyclo[14.7.2.0~3,6~0.0~19,24~]pentacosa 16,18,24]triene]-7'-carbaldehyde 13',13'-dioxide and (1S,3'R,6'R,7'R,11'S,12'R)-6-chloro-11',12'-dimethyl-15'-oxo-3,4-dihydro-2H-spiro[naphthalene-1,22'-[20]oxa[13]thia[1,14]diazatetracyclo[14.7.2.0~3,6~0.0~9,24~]pentacosa[16,18,24]triene]-7'-carbaldehyde 13',13'-dioxide (160 mg, 0.26 mmol) in methanol (5 mL) was added sodium borohydride (40 mg, 1.0 mmol). The reaction mixture was stirred at room temperature for 1 h and subsequently quenched by addition of saturated NH$_4$Cl solution. Ethyl acetate was added, the organic phase was separated, washed with brine and dried over MgSO$_4$. The solvent was evaporated under reduced pressure and the residue was purified by flash chromatography on silica gel (24 g, HP silica, Teledyne Isco) eluting with a gradient of 25-75% (99.7% ethyl acetate/0.3% acetic acid) in hexanes to provide two isomeric products: (1S,3'R,6'R,7'S,11'S,12'R)-6-chloro-7'-(hydroxymethyl)-11',12'-dimethyl-3,4-dihydro-2H,15'H-spiro[naphthalene-1, 22'-[20]oxa[13]thia[1,14]diazatetracyclo[14.7.2.0~3, 6~0.0~19,24~]pentacosa[16,18,24]trien]-15'-one 13',13'-dioxide OR (1S,3'R,6R,7'R,7'R,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18, 24]trien]-15'-one 13',13'-dioxide (25 mg, 16% yield) as a white solid. It was the first eluting isomeric product. MS (ESI, +ve ion) m/z 615.2 (M+H)$^+$;
and (1S,3'R,6'R,7'R,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-dioxide OR (1S,3'R,6'R,7'S,11'S,12'R)-6-chloro-7'-(hydroxymethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18, 24]trien]-15'-one 13',13'-dioxide (65 mg, 41% yield) as a white solid. It was the second eluting isomeric product. MS (ESI, +ve ion) m/z 615.2 (M+H)$^+$.

Step 2: (1s,3'r,6'r,7's,11's,12'r)-7'-(bromomethyl)-6-chloro-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18, 24]trien]-15'-one 13',13'-dioxide or (1s,3'r,6'r,7'r, 11's,12'r)-7'-(bromomethyl)-6-chloro-11',12'-dimethyl-3,4-dihydro-2h,15h-spiro[naphthalene-1, 22'-[20]oxa[13]thia[1,14]diazatetracyclo[14.7.2.0~3, 6~0.0~19,24~]pent acosa[16,18,24]trien]-15'-one 13',13'-dioxide The second eluting peak from Step 1 (105 mg, 0.17 mmol) was dissolved in in dichloromethane (8.5 mL) and treated with triphenylphosphine (67 mg, 0.256 mmol). The reaction mixture was cooled to 0° C., followed by addition of N-bromosuccinimide (46 mg, 0.256 mmo). The reaction mixture was then warmed to room temperature and allowed to stir overnight. The reaction mixture was concentrated and the residue was purified by flash chromatography on silica gel (24 g HP column, Teledyne Isco) eluting with a gradient of 10-65% ethyl acetate in heptane to provide (1S,3'R,6'R, 7'S,11'S,12'R)-7'-(bromomethyl)-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S, 3'R,6'R,7'R,1'S,12'R)-7'-(bromomethyl)-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~9, 24~]pentacosa[16,18,24]trien]-15'-one 13',13'-dioxide as a light yellow solid (92 mg, 79% yield). $^1$H NMR (400 MHz, CHLOROFORM-d) δ ppm 0.77-0.94 (m, 3H) 0.78-0.92 (m, 3H) 0.98 (d, J=6.65 Hz, 3H) 0.94-1.06 (m, 3H) 1.08-1.46 (m, 6H) 1.11-1.31 (m, 9H) 1.65 (br. s., 9H) 1.47-1.64 (m, 4H) 1.67-1.86 (m, 3H) 1.67-1.78 (m, 2H) 1.78-1.92 (m, 2H) 1.89-2.09 (m, 5H) 1.92-2.05 (m, 5H) 2.32-2.57 (m, 2H) 2.35-2.53 (m, 2H) 2.70 (d, J=5.09 Hz, 2H) 2.69-2.83 (m, 2H) 2.91-3.05 (m, 1H) 2.97 (dd, J=15.16, 9.10 Hz, 1H) 3.13-3.46 (m, 3H) 3.20 (d, J=14.28 Hz, 1H) 3.25-3.34 (m, 1H) 3.35-3.43 (m, 1H) 3.61-3.73 (m, 1H) 3.68 (d, J=14.08 Hz, 1H) 3.75-3.87 (m, 1H) 3.81 (d, J=15.06 Hz, 1H) 4.00-4.25 (m, 3H) 4.03-4.19 (m, 3H) 6.88-7.12 (m, 4H) 6.92-7.12 (m, 4H) 7.17 (d, J=8.41 Hz, 1H) 7.14-7.23 (m, 1H) 7.65-7.78 (m, 1H) 7.71 (d, J=8.61 Hz, 1H) 8.58-8.74 (m, 1H) 8.64 (s, 1H). MS (ESI, +ve ion) m/z 679.1 (M+H)$^+$.

Step 3: (1s,3'r,6'r,7's,11's,12'r)-6-chloro-11',12'-dimethyl-7'-((methylsulfonyl)methyl)-3,4-dihydro-2h, 15'h-spiro[naphthalene-1,22'-[20]oxa[13]thia[1,14] diazatetracyclo[14.7.2.0~3,6~0.0~19,24~]pent acosa [16,18,24]trien]-15'-one 13',13'-dioxide or (1s,3'r,6'r, 7r,11's,12'r)-6-chloro-11',12'-dimethyl-7'-((methylsulfonyl)methyl)-3,4-dihydro-2h,15'h-spiro[naphthalene-1,22'-[20]oxa[13]thia[1,14] diazatetracyclo[14.7.2.0~3,6~0.0~19,24~]pent acosa [16,18,24]trien]-15'-one (examples 41 and 44)

The product obtained in Step 2 (90 mg, 0.133 mmol) was dissolved in DMF (5 mL) and treated with sodium methanesulfinate (135 mg, 1.33 mmol). The reaction mixture was stirred at 50° C. overnight and subsequently diluted with ethyl acetate. The organic phase was separated and washed with 10% aqueous citric acid solution, 5% aqueous NaHCO$_3$ solution, water and brine. The organic phase was dried over MgSO$_4$, the solvent was evaporated under reduced pressure and the residue was purified by flash chromatography on silica gel (12 g, HP silica, Teledyne Isco) eluting with a gradient of 50-100% ethyl acetate in hexane. Further purification by SFC (Column: Pyridine, Mobile Phase: 76:24 (A:B) isocratic, A: Liquid CO2, B: methanol (20 mM NH$_3$), Flow Rate: 70 g/min, Column/Oven temp.: 25° C., Detection: UV @ 220 nm) provided two isomeric products:
1 S,3'R,6'R,7'S,'S, 12'R)-6-chloro-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'R,11'S,12'R)-6-chloro-11', 12'-dimethyl-7'-((methylsulfonyl)methyl)-3,4-dihydro-2H, 15'H-spiro[naphthalene-1,22'-[20]oxa[13]thia[1,14]diazatetracyclo[14.7.2.0~3,6~0.0~9,24~]pentacosa[16,18,24] trien]-15'-one as a white solid (Example 41, 3.8 mg, 4% yield; the first eluting isomer, $t_R$=2.05 minutes on analytical SFC; 30% MeOH (+20 mM NH₃ in CO₂) with 97% de). ¹H NMR (400 MHz, CHLOROFORM-d) δ ppm 0.83-0.94 (m, 3H) 1.01 (d, J=7.04 Hz, 3H) 1.09-1.21 (m, 2H) 1.22-1.34 (m, 6H) 1.38-1.48 (m, 5H) 1.47-1.84 (m, 9H) 1.85-2.08 (m, 5H) 2.27-2.42 (m, 1H) 2.43-2.56 (m, 1H) 2.61 (s, 3H) 2.72-2.83 (m, 2H) 2.88-3.04 (m, 1H) 3.20 (d, J=14.28 Hz, 1H) 3.70 (d, J=14.28 Hz, 1H) 3.75-3.94 (m, 3H) 4.10 (s, 2H) 4.12-4.23 (m, 1H) 6.90-6.96 (m, 2H) 6.99 (s, 1H) 7.09 (d, J=1.96 Hz, 1H) 7.18 (dd, J=8.41, 2.15 Hz, 1H) 7.70 (d, J=8.61 Hz, 1H) 7.66-7.76 (m, 1H), MS (ESI, +ve ion) m/z 677.2 (M+H)⁺; and 1S,3'R,6'R,7'S,11'S,12'R)-6-chloro-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'R,11'S,12'R)-6-chloro-11',12'-dimethyl-7'-((methylsulfonyl)methyl)-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one as a white solid (Example 44. 59.3 mg, 66% yield; the second eluting isomer, t_R=2.67 minutes on analytical SFC; 30% MeOH (+20 mM NH3 in CO₂) with 99% de). ¹H NMR (400 MHz, CHLOROFORM-d) δ ppm 0.82-0.92 (m, 2H) 0.97-1.04 (m, 3H) 1.05-1.18 (m, 2H) 1.17-1.34 (m, 7H) 1.34-2.13 (m, 16H) 2.21 (td, J=8.22, 4.11 Hz, 1H) 2.44-2.58 (m, 1H) 2.58-2.89 (m, 5H) 2.91 (s, 3H) 3.01 (dd, J=15.55, 8.71 Hz, 1H) 3.21 (d, J=14.28 Hz, 1H) 3.70 (d, J=14.08 Hz, 1H) 3.89 (d, J=13.69 Hz, 1H) 3.97-4.21 (m, 3H) 6.95 (s, 2H) 7.09 (d, J=2.35 Hz, 2H) 7.18 (dd, J=8.51, 2.05 Hz, 1H) 7.68 (d, J=8.41 Hz, 1H) 7.64-7.73 (m, 1H) 7.64-7.73 (m, 1H). MS (ESI, +ve ion) m/z 677.2 (M+H)⁺.

Examples 49, 54, 61 and 75

(1s,3'r,6'r,7'r,8'e,11's,12'r)-6-chloro-7'-((1r)-1-hydroxypropyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[8,16,18,24]tetraen]-15'-one 13',13'-dioxide or (1s,3'r,6'r,7's,8'e,11's,12'r)-6-chloro-7'-((1r)-1-hydroxypropyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[8,16,18,24]tetraen]-15'-one 13',13'-dioxide or (1s,3'r,6'r,7's,8'e,11's,12'r)-6-chloro-7'-((1s)-1-hydroxypropyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[8,16,18,24]tetraen]-15'-one 13',13'-dioxide or (1s,3'r,6'r,7'r,8'e,11's,12'r)-6-chloro-7'-((1s)-1-hydroxypropyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[8,16,18,24]tetraen]-15'-one 13',13'-dioxide

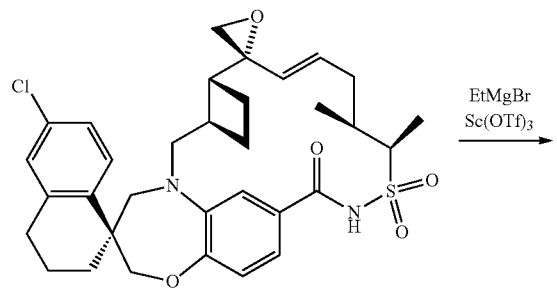

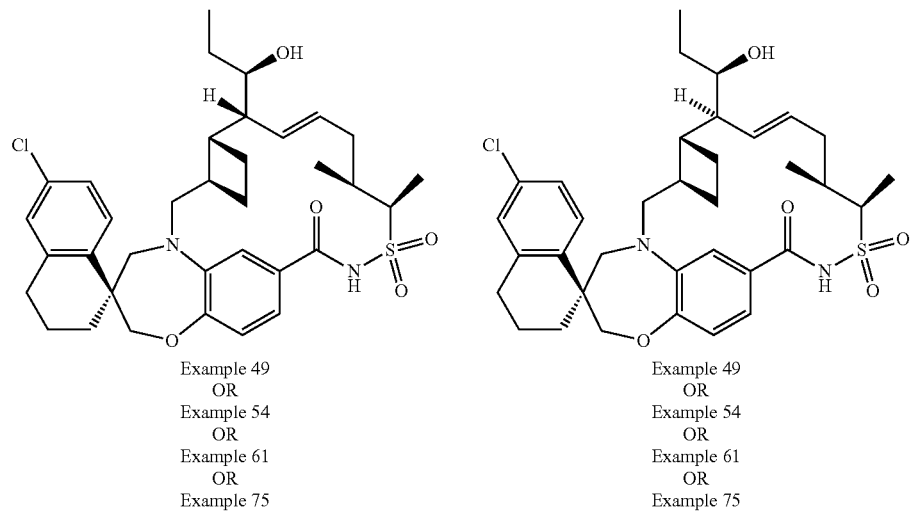

Example 49 OR Example 54 OR Example 61 OR Example 75

Example 49 OR Example 54 OR Example 61 OR Example 75

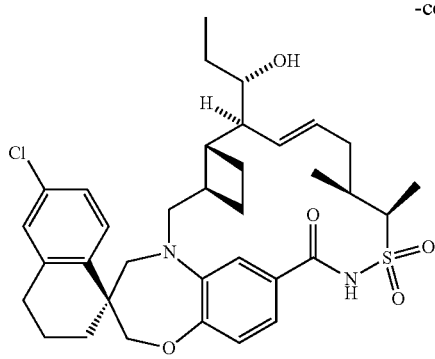

Example 49
OR
Example 54
OR
Example 61
OR
Example 75

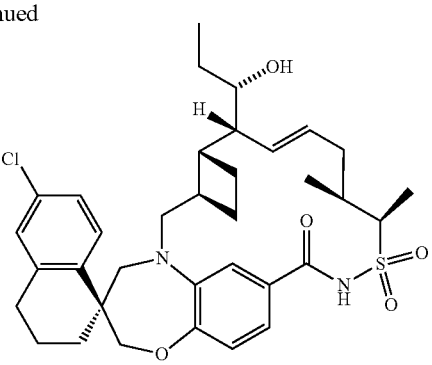

Example 49
OR
Example 54
OR
Example 61
OR
Example 75

To a mixture of scandium (III) trifluoromethanesulfonate (0.024 g, 0.046 mmol) and (1S,3'R,6'R,7'R,8'E,11'S,12'R)-6-chloro-11',12'-dimethyl-3,4-dihydro-2H,15'H-dispiro[naphthalene-1,22'-[20]oxa[13]thia[1,14]diazatetracyclo[14.7.2.0~3,6~0.0~19,24~]pentacosa[8,16,18,2 4]tetraene-7',2''-oxiran]-15'-one 13',13'-dioxide (0.283 g, 0.463 mmol) at −78° C. was added dichloromethane (2.8 mL) followed by ethylmagnesium bromide (3.0 M in diethyl ether, 0.386 mL, 1.16 mmol). The mixture was warmed to −20° C. over 1 h and additional dichloromethane (1.5 mL) was added. The reaction was quenched with saturated aqueous NH₄Cl, warmed to room temperature and diluted with EtOAc, water, and 1 M citric acid in water. The mixture was transferred to a separatory funnel and the aqueous layer (pH 4) was discarded. The organic phase was washed with saturated NaCl (1×), dried over MgSO₄, filtered through a glass frit, and concentrated. The material was purified by flash column chromatography (40 g Gold Rf silica gel column, eluted with 10% to 60% ethyl acetate (10% methanol) in heptane). Further purification by flash column chromatography (40 g Gold Rf silica gel column, eluted with 5% to 50% ethyl acetate (0.3% acetic acid) in heptane (0.3% acetic acid)) gave (1S,3'R,6'R,7'R,8'E,11'S,12'R)-6-chloro-7'-((1R)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[8,16,18,24]tetraen]-15'-one 13',13'-dioxide OR (1S,3'R,6'R,7'S,8'E,11'S,12'R)-6-chloro-7'-((1R)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[8,16,18,24]tetraen]-15'-one 13',13'-dioxide OR (1S,3'R,6'R,7'R,8'E,11'S,12'R)-6-chloro-7'-((1S)-1-hydroxypropyl)-1',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[8,16,18,24]tetraen]-15'-one 13',13'-dioxide (Example 49) (21 mg, 0.033 mmol, 7% yield), MS (ESI, +ve ion) m/z 641.2 (M+1)⁺; and (S,3'R,6'R,7'R,8'E,11'S,12'R)-6-chloro-7'-((1R)-1-hydroxypropyl)-1',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[8,16,18,24]tetraen]-15'-one 13',13'-dioxide OR (1S,3'R,6'R,7'S,8'E,11'S,12'R)-6-chloro-7'-((1R)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[8,16,18,24]tetraen]-15'-one 13',13'-dioxide OR (1S,3'R,6'R,7'S,8'E,11'S,12'R)-6-chloro-7'-((1S)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[8,16,18,24]tetraen]-15'-one 13',13'-dioxide OR (1S,3R,6'R,7'R,8'E,11'S,12'R)-6-chloro-7'-((1S)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6·0.0~19,24·]pentacosa[8,16,18,24]tetraen]-15'-one 13',13'-dioxide (Example 54) (34 mg, 0.053 mmol, 11% yield), MS (ESI, +ve ion) m/z 641.2 (M+1)⁺; and (1S,3'R,6R,7'R,8'E,11'S,12'R)-6-chloro-7'-((1R)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[8,16,18,24]tetraen]-15'-one 13',13'-dioxide OR (1S,3'R,6'R,7'S,8'E,11'S,12'R)-6-chloro-7'-((1R)-1-hydroxypropyl)-11,12-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[8,16,18,24]tetraen]-15'-one 13',13'-dioxide OR (1S,3'R,6'R,7'S,8'E,11'S,12'R)-6-chloro-7'-((1S)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[8,16,18,24]tetraen]-15'-one 13',13'-dioxide OR (1S,3'R,6'R,7'R,8'E,11'S,12'R)-6-chloro-7'-((1S)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[8,16,18,24]tetraen]-15'-one 13',13'-dioxide (Example 61) (21 mg, 0.033 mmol, 7% yield). MS (ESI, +ve ion) ml/z 641.2 (M+1)⁺; and (1S,3'R,6'R,7'R,8'E,11'S,12'R)-6-chloro-7'-((1R)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[8,16,18,24]tetraen]-15'-one 13',13'-dioxide OR (1S,3'R,6'R,7'S,8'E,11'S,12'R)-6-chloro-7'-((1R)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa

[8,16,18,24]tetraen]-15'-one 13',13'-dioxide OR (1S,3'R,6'R,7'S,8'E,11'S,12'R)-6-chloro-7'-((1S)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[8,16,18,24]tetraen]-15'-one 13',13'-dioxide OR (1S,3'R,6'R,7'R,8'E,11'S,12'R)-6-chloro-7'-((1S)-1-hydroxypropyl)-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[8,16,18,24]tetraen]-15'-one 13',13'-dioxide (Example 75) (13 mg, 0.020 mmol, 4% yield). MS (ESI, +ve ion) ml/z 641.2 (M+1)+.

Examples 70 and 79

(1s,3'r,6'r,7's,11's,12'r)-6-chloro-11,12'-dimethyl-7'-((1r)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6'r,7's,11's,12'r)-6-chloro-11',12'-dimethyl-7'-((1s)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6'r,7'r,11's,12'r)-6-chloro-11',12'-dimethyl-7'-((1r)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6'r,7'r,11's,12'r)-6-chloro-11',12'-dimethyl-7'-((15)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide (example 70) and [(1s,3'r,6'r,7's,11's,12'r)-6-chloro-11',12'-dimethyl-7'-((1r)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3'r,6'r,7's,11's,12'r)-6-chloro-11',12'-dimethyl-7'-((1s)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide] or [(1s,3'r,6'r,7'r,11's,12'r)-6-chloro-11',12'-dimethyl-7'-((1r)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3'r,6'r,7'r,11's,12'r)-6-chloro-11',12'-dimethyl-7'-((1s)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide] (example 79)

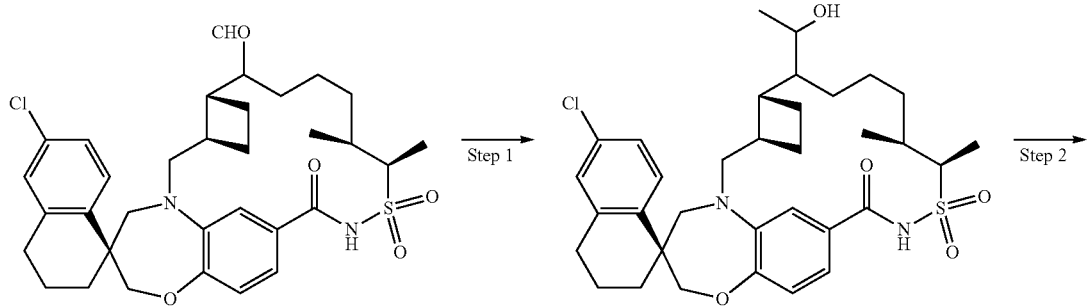

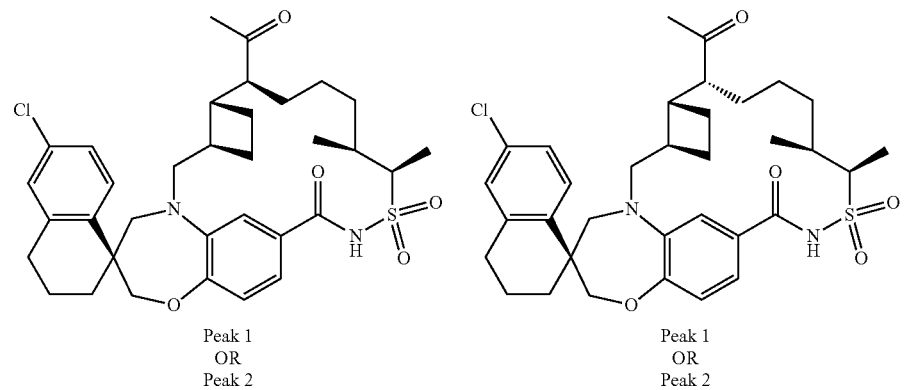

Peak 1 OR Peak 2

Peak 1 OR Peak 2

137
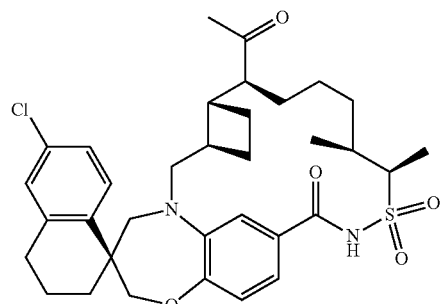
Peak 1
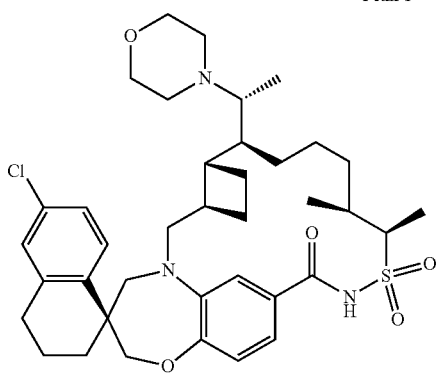
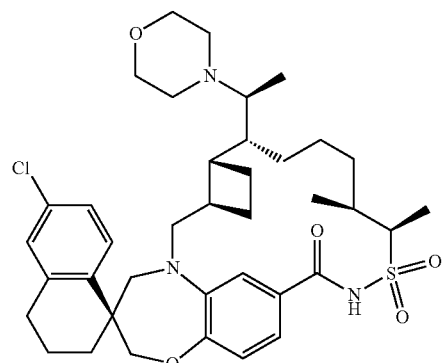
Example 70
138
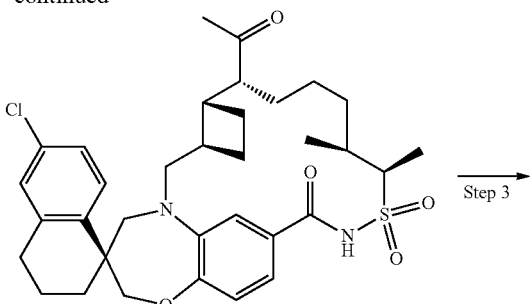
Step 3
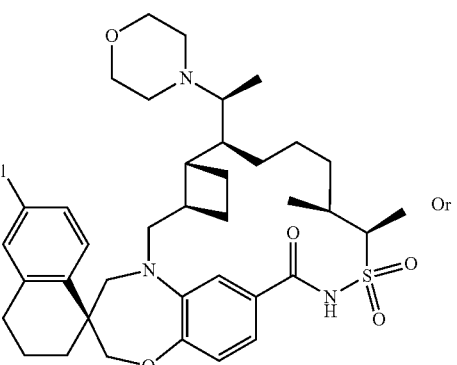
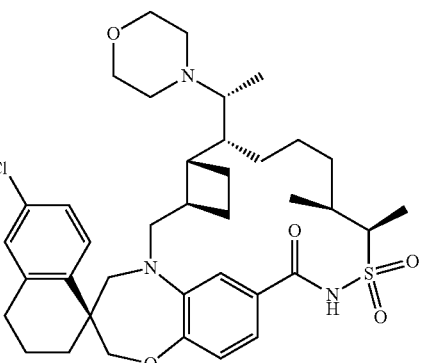
Or
and
Or

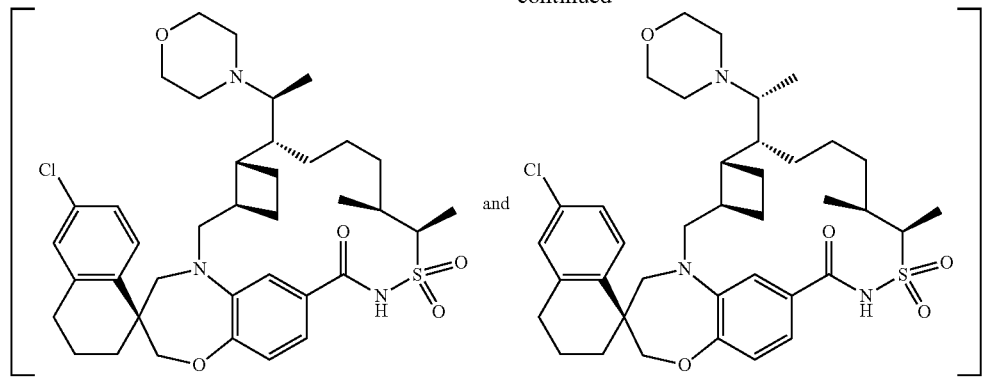

Example 79

Step 1: (1s,3'r,6'r,7's,11's,12'r)-6-chloro-7'-((1r)-1-hydroxyethyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24]pent acosa[16,18,24]trien]-15'-one 13',13'-dioxide and (1s,3'r,6'r,7'r,11's,12'r)-6-chloro-7'-((1r)-1-hydroxyethyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3'r,6'r,7's,11's,12'r)-6-chloro-7'-((1s)-1-hydroxyethyl)-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3'r,6'r,7'r,11's,12'r)-6-chloro-7'-((1s)-1-hydroxyethyl)-1',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide A solution of (1S,3'R,6'R,7'S,11'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (0.147 g, 0.24 mmol) in THF (3 mL) was cooled to −78° C. before adding methylmagnesium bromide, 3.0M in Et2O (0.959 mL, 2.88 mmol) dropwise. The reaction was stirred at −78° C. for 2.5 hours, then quenched with water and diluted with water and EtOAc. The reaction was transferred to a separatory funnel and 1M HCl was added. The phases were mixed and the organic layer was separated, washed with brine, dried over magnesium sulfate and concentrated under reduced pressure. The material was presumed to be a mixture of four stereoisomers which was used directly in step 2 without further purification assuming theoretical yield. MS (ESI, +ve) m/z 628.8 [M+H]+.

Step 2: (1s,3'r,6'r,7's,11's,12'r)-7'-acetyl-6-chloro-11',12'-dimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3'r,6'r,7'r,11's,12'r)-7'-acetyl-6-chloro-11',12'-dimethyl-3,4-dihydro-2h,15'h-spiro[naphthalene-1,22'-[20]oxa[13]thia[1,14]diazatetracyclo[14.7.2.0~3,6~0.0~19,24~] pent acosa[16,18,24]trien]-15'-one 13',13'-dioxide (peaks 1 and 2)

To a solution of (1S,3'R,6'R,11'S,12'R)-6-chloro-7'-(1-hydroxyethyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (0.151 g, 0.24 mmol) in DCM (2.4 mL) was added dess-martin periodinane (0.112 g, 0.264 mmol). The reaction was stirred for ten minutes then diluted with water and DCM. The reaction was transferred to a sepatory funnel. The phases were mixed and the organic layer was separated, washed with brine, dried over magnesium sulfate and concentrated under reduced pressure. The crude material was purified by silica gel flash chromatography using a gradient of 5-60% EtOAc with 0.3% AcOH in Heptane to afford: (1S,3'R,6'R,7'S,11'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'R,7'R,1'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-dioxide (0.062 g, 0.099 mmol, 41.2%) as the major product. It was the first peak eluting off of silica gel column. MS (ESI, +ve) m/z 627.3 [M+H]+;
and (1S,3'R,6'R,7'R,11'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide or (1S,3'R,6'R,7'S,11'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide (0.035 g, 0.056 mmol, 23.3%) as the minor product. It was the second peak eluting off of silica gel column. MS (ESI, +ve) m/z 627.3 [M+H]⁺.

Step 3: (1s,3'r,6'r,7's,11 's,12'r)-6-chloro-11',12'-dimethyl-7'-((1r)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~9,24~]pent acosa[16,18,24]trien]-15'-one 13',13'-dioxide or (1s,3'r,6'r,7's, 12'r)-6-chloro-11',12'-dimethyl-7'-((1s)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~9,24~]pent acosa[16,18,24]trien]-15'-one 13',13'-dioxide or (1s,3'r,6'r,7'r,11's,12'r)-6-chloro-11',12'-dimethyl-7'-((1r)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6'r,7'r,11's,12'r)-6-chloro-11',12'-dimethyl-7'-((1s)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide (example 70) and [(1s,3'r,6'r,7's, 11's,12'r)-6-chloro-11',12'-dimethyl-7'-((1r)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-dioxide and (1s,3'r,6'r,7's, 11's,12'r)-6-chloro-11',12'-dimethyl-7'-((1s)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide] or [(1s,3'r,6'r,7'r,11's,12'r)-6-chloro-11',12'-dimethyl-7'-((1r)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3'r,6'r,7'r,11's,12'r)-6-chloro-11',12'-dimethyl-7'-((1s)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide] (example 79)

To a solution of (1S,3'R,6'R,7'S,11'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'R,7'R,11'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (Peak 1 from the second step) (0.01 g, 0.016 mmol) in Me-THF (0.5 mL) was added morpholine (7 μL, 0.08 mmol) and tetraisopropoxytitanium (0.118 mL, 0.399 mmol). The reaction was heated to 80° C. over night. Methanol (0.05 mL, 1.244 mmol) was added followed by sodium borohydride (0.6 mg, 0.016 mmol). The reaction was stirred for 1 hour. The material was diluted with EtOAc and the reaction was added dropwise to vigorously stirring water and stirred for 15 minutes. The resulting suspension was filtered through celite. The filtrate was washed sequentially with water and brine then dried over magnesium sulfate and concentrated under reduced pressure. The material was purified by RP-HPLC using a gradient of 30-100% ACN:water with 0.1% TFA over 20 minutes to afford (1S,3'R,6'R,7'S,11'S,12'R)-6-chloro-11',12'-dimethyl-7'-((1R)-1-(4-morpholinyl)ethyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'R,7'S,11'S,12'R)-6-chloro-11',12'-dimethyl-7'-((1S)-1-(4-morpholinyl)ethyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'R,7'R,11'S,12'R)-6-chloro-11',12'-dimethyl-7'-((1R)-1-(4-morpholinyl)ethyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'R,7'R,11'S,12'R)-6-chloro-11',12'-dimethyl-7'-((1S)-1-(4-morpholinyl)ethyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide (3.9 mg, 4.8 μmol, 30%) (Example 70). MS (ESI, +ve ion) ml/z 698.3 (M+1)⁺; AND a mixture of (1S,3'R,6'R,7'S,11'S,12'R)-6-chloro-11',12'-dimethyl-7'-((1R)-1-(4-morpholinyl)ethyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide AND (1S,3'R,6'R,7'S,11'S,12'R)-6-chloro-11',12'-dimethyl-7'-((1S)-1-(4-morpholinyl)ethyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR a mixture of (1S,3'R,6'R,7'R,11'S,12'R)-6-chloro-11',12'-dimethyl-7'-((1R)-1-(4-morpholinyl)ethyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide AND (1S,3'R,6'R,7'R,11'S,12'R)-6-chloro-11',12'-dimethyl-7'-((1S)-1-(4-morpholinyl)ethyl)-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide (5.2 mg, 6.4 μmol, 40%) (Example 79). MS (ESI, +ve ion) ml/z 698.3 (M+1)+.

Example 72

[(1s,3'r,6'r,7's,11's,12'r)-6-chloro-11',12'-dimethyl-7'-((1r)-1-(4-morpholinyl)ethyl)-3,4-dihydro-2h,15'h-spiro [naphthalene-1,22'-[20]oxa[13[thia]1,14]diazatetracyclo[14.7.2.0~3,6~0.0~19,24~]pent acosa[16,18,24]trien]-15'-one 13',13'-dioxide and (1s,3'r,6'r,7's,11's,12'r)-6-chloro-11',12'-dimethyl-7'-((1s)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide] or [(1s,3'r,6'r,7'r,11's,12'r)-6-chloro-11',12'-dimethyl-7'-((1r)-1-(4-morpholinyl)ethyl)-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide and (1s,3'r,6'r,7'r,11's,12'r)-6-chloro-11',12'-dimethyl-7'-((1s)-1-(4-morpholinyl)ethyl)-3,4-dihydro-2h,15'h-spiro

[naphthalene-1,22'-[20]oxa[13]thia[1,14]diazatetra-
cyclo[14.7.2.0~3,6~.0.0~19,24~]pent acosa[16,18,
24]trien]-15'-one 13',13'-dioxide]

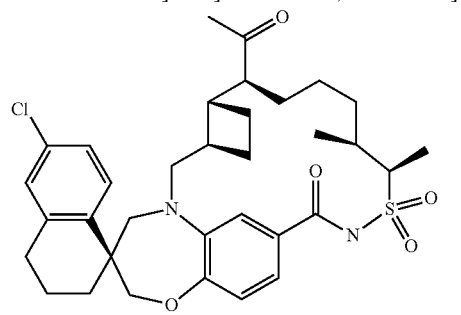

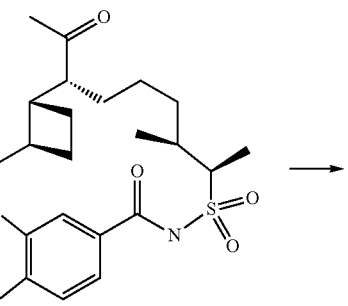

Peak 2
(from Step 2 in Examples 70 and 79)

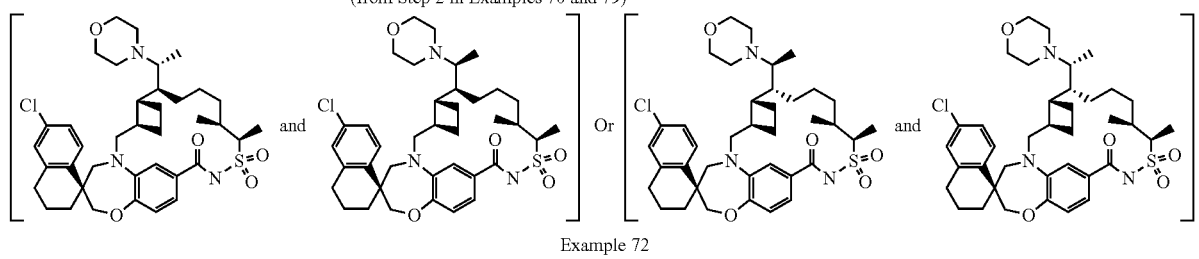

Example 72

The title compounds were prepared in a manner analogous to Example 79 but starting with the second peak off of silica gel column in the second step of the synthesis. MS (ESI, +ve ion) m/z 698.3 (M+1)+.

Examples 78 and 88

(1s,3'r,6'r,7's,11's,12'r)-6-chloro-7'-((s)-hydroxy(phenyl)methyl)-11',12'-dimethyl-3,4-dihydro-2h,15'h-spiro[naphthalene-1,22'-[20]oxa[13]thia[1,14]diaza-tetracyclo[14.7.2.0~3,6~.0.0~19,24~]pent acosa[16,18,24]trien]-15'-one 13',13'-dioxide or (1s,3'r,6'r,7's,11's,12'r)-6-chloro-7'-((r)-hydroxy(phenyl)methyl)-11',12'-dimethyl-3,4-dihydro-2h,15'h-spiro [naphthalene-1,22'-[20]oxa[13]thia[1,14] diazatetracyclo[14.7.2.0~3,6~.0.0~19,24~]pent acosa [16,18,24]trien]-15'-one 13',13'-dioxide or (1s,3'r,6'r, 7'r,11's,12'r)-6-chloro-7'-((s)-hydroxy(phenyl) methyl)-11',12'-dimethyl-3,4-dihydro-2h,15'h-spiro [naphthalene-1,22'-[20]oxa[13]thia[1,14] diazatetracyclo[14.7.2.0~3,6~.0.0~19,24~]pent acosa [16,18,24]trien]-15'-one 13',13'-dioxide or (1s,3'r,6'r, 7'r,11's,12'r)-6-chloro-7'-((r)-hydroxy(phenyl) methyl)-11',12'-dimethyl-3,4-dihydro-2h,15'h-spiro [naphthalene-1,22'-[20]oxa[13]thia[1,14] diazatetracyclo[14.7.2.0~3,6~.0.0~19,24~]pent acosa [16,18,24]trien]-15'-one 13',13'-dioxide

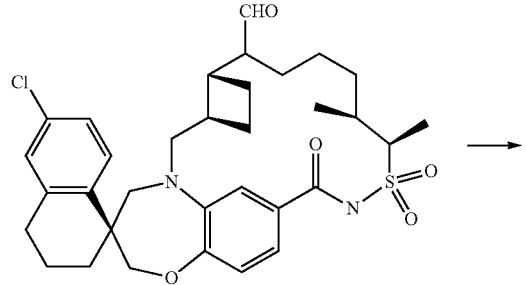

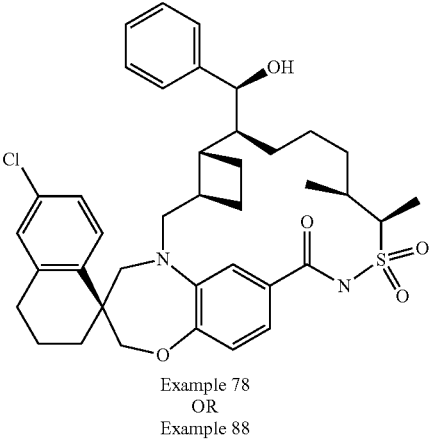

Example 78
OR
Example 88

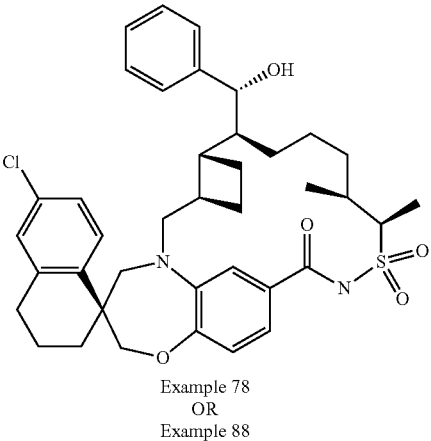

Example 78
OR
Example 88

-continued

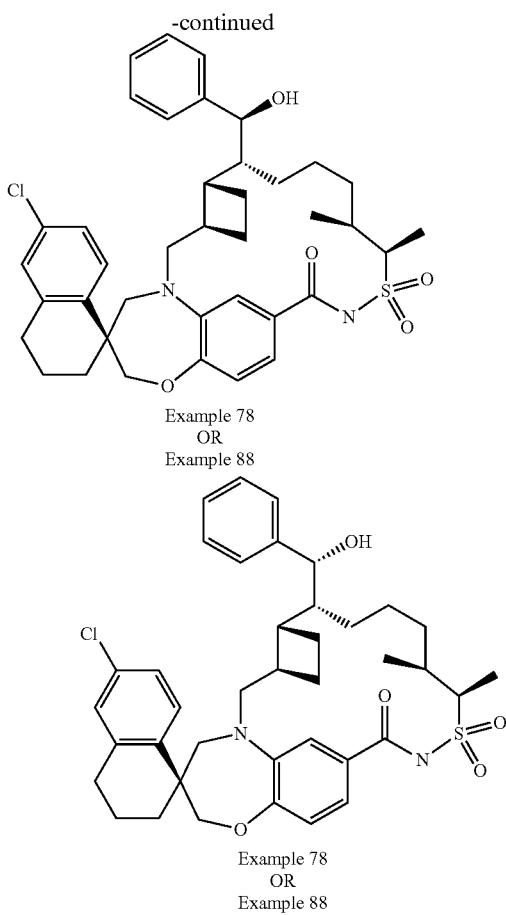

Example 78
OR
Example 88

Example 78
OR
Example 88

A solution of (1S,3'R,6'R,7'S,11'S,12'R)-7'-acetyl-6-chloro-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (0.147 g, 0.24 mmol) in THF (2.4 mL) was cooled to −78° C. before adding phenylmagnesium bromide, 1.0M in THF (2.88 mL, 2.88 mmol). The reaction was stirred at −78 for 90 minutes. The reaction was quenched with water and diluted with water and EtOAc. The reaction was transferred to a separatory funnel and 1M HCl was added. The phases were mixed and the organic layer was separated, washed with brine, dried over magnesium sulfate and concentrated under reduced pressure. The crude residue was purified by silica gel flash chromatography using a gradient of 5-50% EtOAc with 0.3% AcOH in Heptane to afford (1S,3'R,6'R,7'S,11'S,12'R)-6-chloro-7'-((S)-hydroxy(phenyl)methyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'S,11'S,12'R)-6-chloro-7'-((R)-hydroxy(phenyl)methyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'R,11'S,12'R)-6-chloro-7'-((S)-hydroxy(phenyl)methyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'R,11'S,12'R)-6-chloro-7'-((R)-hydroxy(phenyl)methyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (Example 78) (0.037 g, 0.054 mmol, 22.33%). It was the second peak off of silica gel column. MS (ESI, +ve ion) m/z 691.2 (M+1)$^+$;

and (S,3'R,6'R,7'S,11'S,12'R)-6-chloro-7'-((S)-hydroxy(phenyl)methyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'S,11'S,12'R)-6-chloro-7'-((R)-hydroxy(phenyl)methyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'R,11'S,12'R)-6-chloro-7'-((S)-hydroxy(phenyl)methyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide OR (1S,3'R,6'R,7'R,11'S, 12'R)-6-chloro-7'-((R)-hydroxy(phenyl)methyl)-11',12'-dimethyl-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (Example 88) (0.033 g, 0.048 mmol, 19.9%). It was the first peak off of silica gel column. MS (ESI, +ve ion) m/z 691.2 (M+1)+.

Examples 73 and 89

(1s,3'r,6's,7's,11's,12'r)-6-chloro-7',11',12'-trimethyl-3,4-dihydro-2h,15'h-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide or (1s,3'r,6's,7'r,11's,12'r)-6-chloro-7',11',12'-trimethyl-3,4-dihydro-2h,15'h-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide

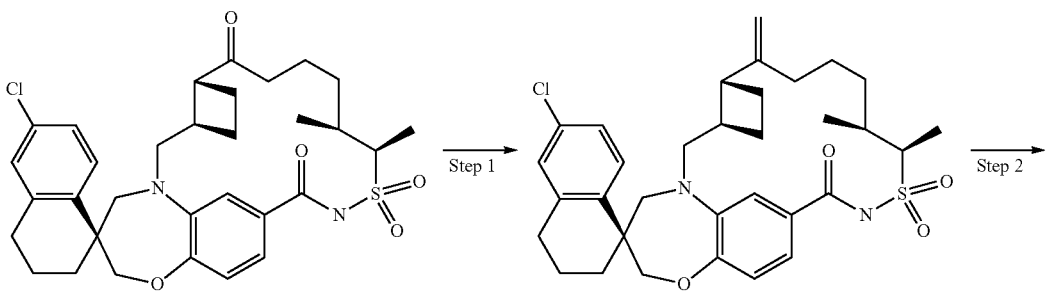

-continued

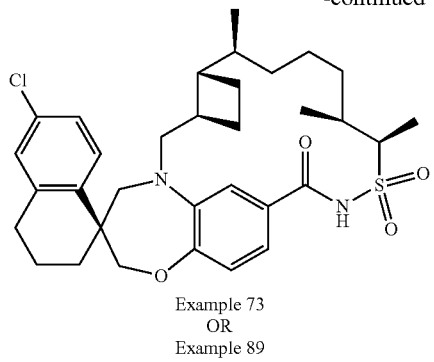

Example 73
OR
Example 89

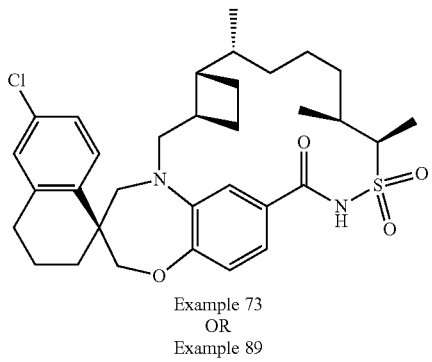

Example 73
OR
Example 89

Step 1: (1s,3'r,6'r,11's,12'r)-6-chloro-11',12'-dimethyl-7'-methylidene-3,4-dihydro-2h,159h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide To a stirred ice-cooled solution of butyllithium, 2.5 m solution in hexanes (1.923 mL, 4.81 mmol) solution of in THF (5 mL) was added bromo(methyl)triphenylphosphorane (1.908 g, 5.34 mmol) in one portion as a solid. The resulting mixture was stirred at 0° C. for 30 minutes before a solution of (1S,36'R,6'R,11'S,12'R)-6-chloro-11',12'-dimethyl-3,4-dihydro-2H,7'H, 15'H-spiro[naphthalene-1,22'-[20]oxa[13]thia[1,14]diazatetracyclo[14.7.2.0~3,6~0.0~9,24~]pentacosa[16,18,24]triene]-7',15'-dione 13',13'-dioxide (0.320 g, 0.534 mmol) in THF (15 mL) was added slowly via a syringe. The resulting mixture was stirred at 0° C. for 25 min and then poured onto ice and saturated ammonium chloride aqueous solution. The mixture was extracted with EtOAc (2×). The combined organics were dried over anhydrous sodium sulfate and concentrated in vacuo. The crude mixture was purified by silica gel flash chromatography using a gradient of 10-80% EtOAc in Hexanes to afford (1S,3'R,6'R,11'S,12'R)-6-chloro-11',12'-dimethyl-7'-methylidene-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (0.26 g, 0.435 mmol, 82% yield) as a white solid.

Step 2: (1s,3'r,6's,7's,11's,12'r)-6-chloro-7',11',12'-trimethyl-3,4-dihydro-2h,15'h-spiro[naphthalene-1,22'-[20]oxa[13]thia[1,14]diazatetracyclo[14.7.2.0~3,6~0.0~19,24~]pent acosa[16,18,24]trien]-15'-one 13',13'-dioxide or (1s,3'r,6's,7'r,11's,12'r)-6-chloro-7',11',12'-trimethyl-3,4-dihydro-2h,15'h-spiro[naphthalene-1,22'-[20]oxa[13]thia[1,14]diazatetracyclo[14.7.2.0~3,6~0.0~9,24~]pent acosa[16,18,24]trien]-15'-one 13',13'-dioxide (examples 73 and 89)

A mixture of (1S,3'R,6'R,11'S,12'R)-6-chloro-11',12'-dimethyl-7'-methylidene-3,4-dihydro-2H,15'H-spiro[naphthalene-1,22'-[20]oxa[13]thia[1,14]diazatetracyclo[14.7.2.0~3,6~0.0~9,24~]pentacosa[16,18,24]trien]-15'-one 13',13'-dioxide (14 mg, 0.023 mmol) and platinum (IV) oxide (1.065 mg, 4.69 μmol) in ethyl acetate (3 mL) was sparged with Nitrogen for 5 min. The reaction was stirred under hydrogen atmosphere (30 psi) at room temperature for 5 hours. The reaction was filtered and concentrated. The crude residue was purified by SFC chromatography using the following conditions: {250×21 mm IC column with 26.0 mL/min methanol (20 mm NH3)+39.0 g/min CO2, 40% co-solvent at 65 g/min. Temp.=28° C., Outlet pressure=100 bar, Wavelength=252 nm. Injected 0.6 mL of 14 mg sample dissolved in 3 mL of MeOH:DCM 2:1; c=4.67 mg/mL and 2.8 mg per injection. Cycle time 5.5 min, run time 12 min} to afford (1S,3'R,6'S,7'S, 11'S,12'R)-6-chloro-7',11',12'-trimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'R,11'S,12'R)-6-chloro-7',11',12'-trimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide (Example 73) (1.9 mg, 3.2 μmol, 13.5%). It was the first peak off of SFC column. MS (ESI, +ve ion) m/z 599.2 (M+1)$^+$;

And (1S,3'R,6'S,7'S,11'S,12'R)-6-chloro-7',11',12'-trimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide OR (1S,3'R,6'S,7'R,11'S,12'R)-6-chloro-7',11',12'-trimethyl-3,4-dihydro-2H,15'H-spiro[naphthalene-1,22'-[20]oxa[13]thia[1,14]diazatetracyclo[14.7.2.0~3,6~0.0~19,24~]pentacosa[16,18,24]trien]-15'-one 13',13'-dioxide (Example 79) (8.8 mg, 0.015 mmol, 63%). It was the second peak off of SFC column. MS (ESI, +ve ion) m/z 599.2 (M+1)$^+$.

TABLE 1
Examples Prepared by the General Methods
| Example Number | Starting Materials | General Method | Product Structure | Product Name | MS Data (M + 1)+ |
|---|---|---|---|---|---|
| 3 | 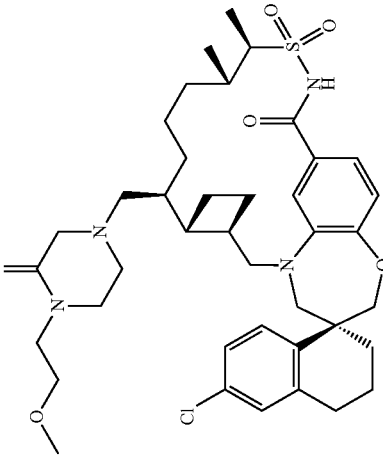 (Enamine) | 1 | 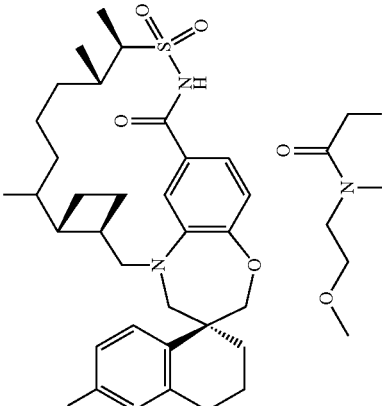 | (1'S,3'R,6'S,7'S,11'S,12'R)-6-chloro-7'-((4-(2-methoxyethyl)-3-oxo-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa 16,18,24]trien]-15'-one 13',13'-dioxide AND | 755.3 |

TABLE 1-continued

Examples Prepared by the General Methods

| Example Number | Starting Materials | General Method | Product Structure | Product Name | MS Data (M + 1)+ |
|---|---|---|---|---|---|
| 4 | (FCH Group) | 1 | [a 4 (the first eluting epimer off of reverse-phase HPLC)-to-1 epimeric mixture] | (1S,3'R,6'S,7'R,11'S,12'R)-6-chloro-7'-((4-(2-methoxyethyl)-3-oxo-1-piperazinyl)methyl)-11',12'-dimethyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide OR (1S,3'R,6'S,7'S,11'S,12'R)-7'-((9aS)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide OR | 780.5 |

TABLE 1-continued

Examples Prepared by the General Methods

| Example Number | Starting Materials | General Method | Product Structure | Product Name | MS Data (M + 1)+ |
|---|---|---|---|---|---|
| | | | 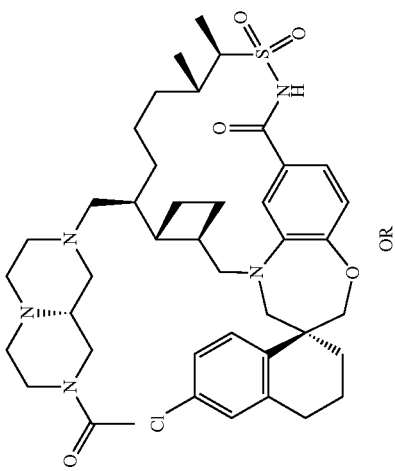 OR | (1S,3'R,6S,7S,11'S,12'R)-7'-((9aR)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | |
| | | | 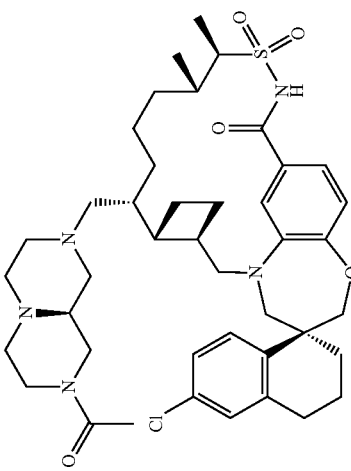 OR | (1S,3'R,6S,7R,11'S,12'R)-7'-((9aS)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3'R,6'S,7R,11'S,12'R)-7-((9aR)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 5 | (Acros Organics) | 1 | | (1S,3'R,6'S,7S,11'S,12'R)-6-chloro-11',12'-dimethyl-7'-((4-methyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 697.3 |

TABLE 1-continued

Examples Prepared by the General Methods

| Example Number | Starting Materials | General Method | Product Structure | Product Name | MS Data (M + 1)+ |
|---|---|---|---|---|---|
| 7 | (structure: aldehyde macrocycle with CHO group, and 1-(2-methoxyethyl)piperazin-2-one·HCl enamine) | 1 | (structure: macrocyclic product with 4-methylpiperazinylmethyl substituent) — the first eluting epimer off of reverse-phase HPLC; OR (structure: macrocyclic product with 4-(2-methoxyethyl)-3-oxopiperazinyl methyl substituent) | (1S,3'R,6S,7R,11'S,12'R)-6-chloro-11',12'-dimethyl-7'-((4-methyl-1-piperazinyl)methyl)-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide OR (1S,3'R,6S,7R,11'S,12'R)-6-chloro-7'-((4-(2-methoxyethyl)meraziny)methyl)-3-oxo-1-piperazinyl)methyl)-11',12'-dimethyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide | 755.3 |

TABLE 1-continued

Examples Prepared by the General Methods

| Example Number | Starting Materials | General Method | Product Structure | Product Name | MS Data (M + 1)+ |
|---|---|---|---|---|---|
| | | 4 | | (1S,3'R,6'S,7'R,11'S,12'R)-6-chloro-7'-((4-(2-methoxyethyl)-3-oxo-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | |
| 9 | | | | (1S,3'R,6'R,7'S,11'S,12'R)-7'-(1-azetidinylcarbonyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 668.5 |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3'R,6'R,7'R,11'S,12'R)-7'-(1-azetidinylcarbonyl)-6-chloro-11',12'-dimethyl-3,4-dihydro-2H,15'H-spiro[naphthalene-1,22'-[20]oxa[13]thia[1,14]diazatetracyclo[14.7.2.0~3,6~0~19,24~]pentacosa[16,18,24]trien]-15'-one 13',13'-dioxide OR | |
| 10 | | 1 | | (1S,3'R,6'S,7'S,11'S,12'R)-6-chloro-7'-((9aS)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~0~19,24~]pentacosa[16,18,24]trien]-15'-one 13',13'-dioxide OR | 739.2 |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3'R,6'S,7'R,11'S,12'R)-6-chloro-7'-((9aS)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 4 | | (1S,3'R,6'R,7'S,11'S,12'R)-6-chloro-N-(2-methoxyethyl)-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-carboxamide 13',13'-dioxide Or | 686.5 |
| 11 | | | | | |

TABLE 1-continued

Examples Prepared by the General Methods

| Example Number | Starting Materials | General Method | Product Structure | Product Name | MS Data (M + 1)+ |
|---|---|---|---|---|---|
| | 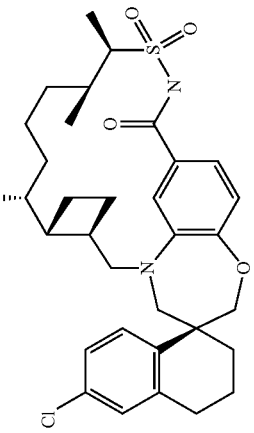 (in house) / H2N—CH2CH2—O—CH3 (Sigma-Aldrich) | | 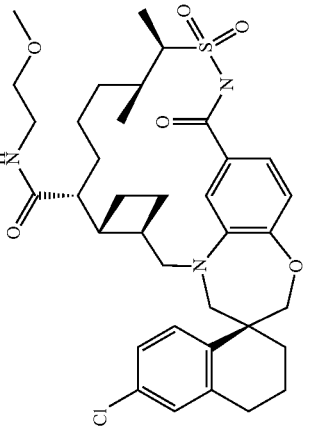 | (1S,3'R,6'R,7R,11'S,12'R)-6-chloro-N-(2-methoxyethyl)-11',12'-dimethyl-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-carboxamide 13',13'-dioxide | |
| 12 | 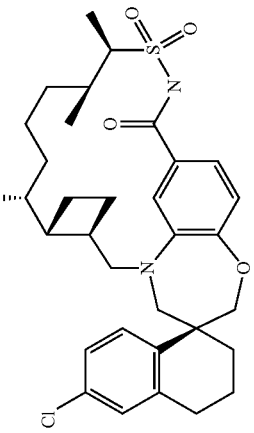 (Sigma-Aldrich) | 1 | 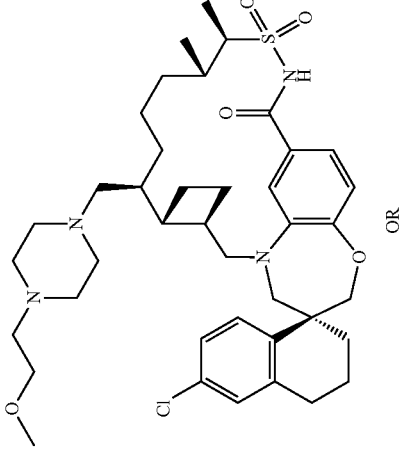 OR | (1S,3'R,6'S,7S,11'S,12'R)-6-chloro-7'-((4-(2-methoxyethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 741.2 |

TABLE 1-continued

Examples Prepared by the General Methods

| Example Number | Starting Materials | General Method | Product Structure | Product Name | MS Data (M + 1)+ |
|---|---|---|---|---|---|
| 13 | (structure with CHO group) + dimethylamino-azetidine·2HCl (Advanced ChemBlocks Inc.) | 1 | (product structure, the first eluting epimer off of reverse-phase HPLC) OR (product structure) | (1S,3'R,6'S,7R,11'S,12'R)-6-chloro-7'-((4-(2-methoxyethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR (1S,3'R,6'S,7R,11'S,12'R)-6-chloro-7'-((3-(dimethylamino)-1-azetidinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 697.2 |

TABLE 1-continued

Examples Prepared by the General Methods

| Example Number | Starting Materials | General Method | Product Structure | Product Name | MS Data (M + 1)+ |
|---|---|---|---|---|---|
| | | | 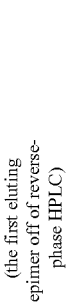 (the first eluting epimer off of reverse-phase HPLC) | (1S,3'R,6'S,7'R,11'S,12'R)-6-chloro-7'-((3-(dimethylamino)-1-azetidinyl)methyl)-11',12'-dimethyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide | |
| 14 | 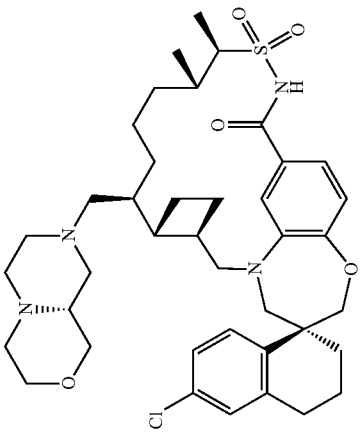 (Synthonix) | 1 | AND | (1S,3'R,6'S,7'S,11'S,12'R)-6-chloro-7'-((9aR)-hexahydropyrazino[2,1-c][1,4]oxazin-8(1H)-ylmethyl))-11',12'-dimethyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide AND | 739.2 |

TABLE 1-continued

Examples Prepared by the General Methods

| Example Number | Starting Materials | General Method | Product Structure | Product Name | MS Data (M + 1)+ |
|---|---|---|---|---|---|
| 15 | (FCH Group) | | (an approximately 85 (the first eluting epimer on reverse phase HPLC)-to-15 epimeric mixture) | (1S,3'R,6'S,7R,11'S,12'R)-6-chloro-7'-((9aR)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 1 | | (1S,3'R,6'S,7S,11'S,12'R)-7'-((9aS)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 780.5 |

TABLE 1-continued

Examples Prepared by the General Methods

| Example Number | Starting Materials | General Method | Product Structure | Product Name | MS Data (M + 1)+ |
|---|---|---|---|---|---|
| | | | OR | (1S,3'R,6S,7S,11'S,12'R)-7-(((9aR)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide OR | |
| | | | OR | (1S,3'R,6S,7R,11'S,12'R)-7-(((9aS)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide OR | |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3'R,6'S,7'R,11'S,12'R)-7'-((9aR)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 16 | | | | (1S,3'R,6'S,7'S,11'S,12'R)-6-chloro-11',12'-dimethyl-7'-((5-methyl-2,5-diazaspiro[3.4]oct-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 723.4 |

TABLE 1-continued

Examples Prepared by the General Methods

| Example Number | Starting Materials | General Method | Product Structure | Product Name | MS Data (M + 1)+ |
|---|---|---|---|---|---|
| | | | 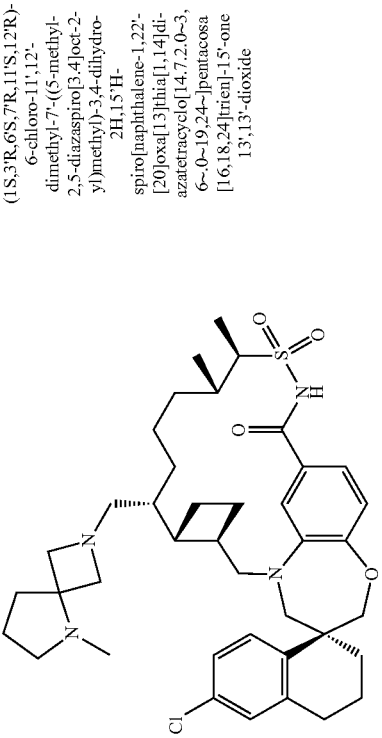 (an approximately 92 (the first eluting epimer on reverse phase HPLC)-to-8 epimeric mixture) | (1S,3'R,6'S,7'R,11'S,12'R)-6-chloro-11',12'-dimethyl-7'-((5-methyl-2,5-diazaspiro[3.4]oct-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 1 | 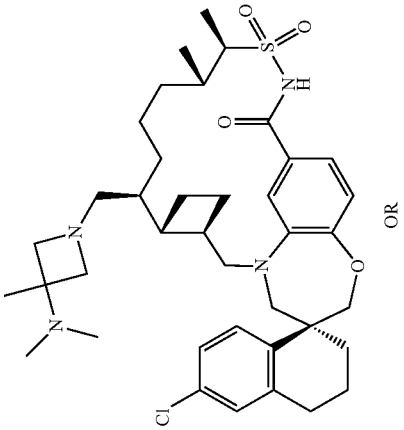 OR | (1S,3'R,6'S,7'S,11'S,12'R)-6-chloro-7'-((3-(dimethylamino)-3-methyl-1-azetidinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 711.2 |
| 17 | | | | | |

TABLE 1-continued

Examples Prepared by the General Methods

| Example Number | Starting Materials | General Method | Product Structure | Product Name | MS Data (M + 1)+ |
|---|---|---|---|---|---|
| 18 | (structure with CHO group and azetidine·2HCl from Advanced ChemBlocks Inc.) | 1 | (structure, the first eluting epimer) AND (structure) AND | (1S,3'R,6S,7R,11'S,12'R)-6-chloro-7'-((3-(dimethylamino)-1-azetidinyl)methyl)-3-methyl-1-azetidinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND (1S,3'R,6S,7S,11'S,12'R)-6-chloro-7'-((3-(dimethylamino)-1-azetidinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | 697.2 |

TABLE 1-continued

Examples Prepared by the General Methods

| Example Number | Starting Materials | General Method | Product Structure | Product Name | MS Data (M + 1)+ |
|---|---|---|---|---|---|
| | | | 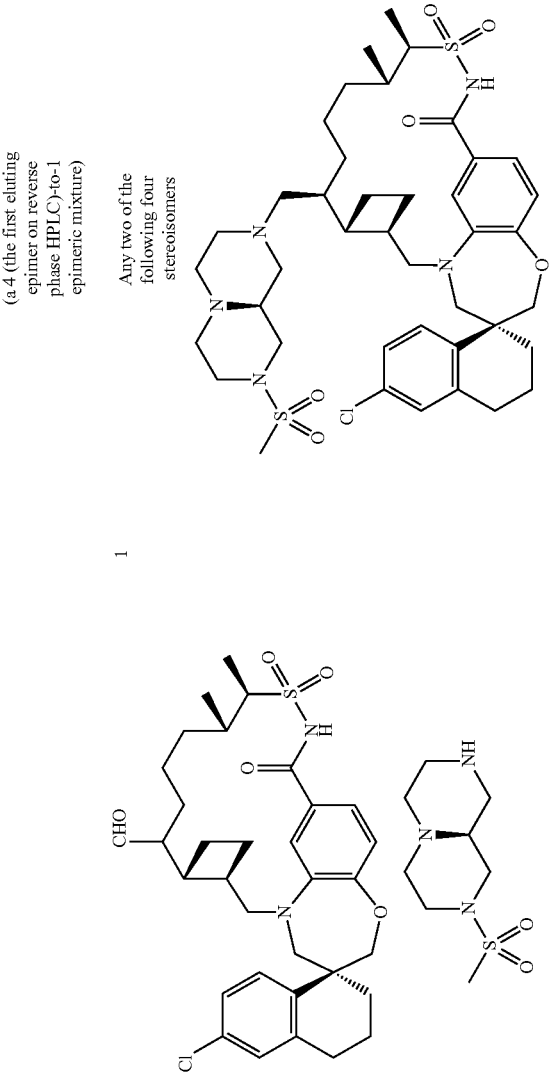 (a 4 (the first eluting epimer on reverse phase HPLC)-to-1 epimeric mixture) | (1S,3'R,6'S,7R,11'S,12'R)-6-chloro-7'-((3-(dimethylamino)-1-azetidinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 20 | 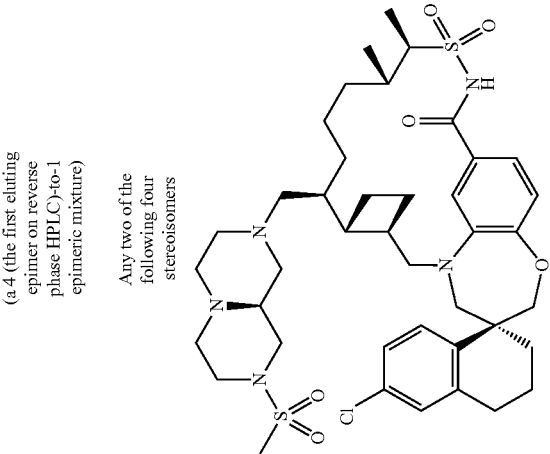 | 1 | 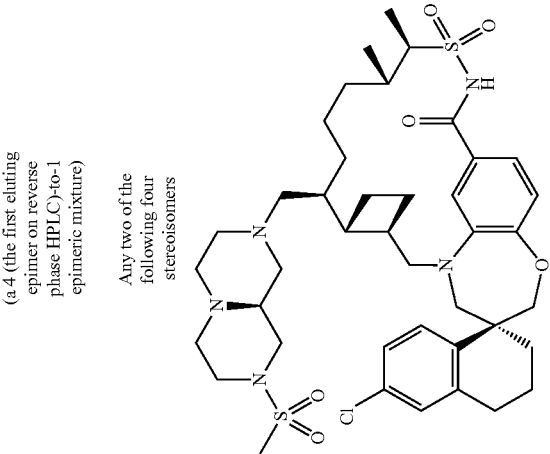 Any two of the following four stereoisomers | (1S,3'R,6'S,7R,11'S,12'R)-6-chloro-11',12'-dimethyl-7'-(((9aS)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 816.3 |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3'R,6S,7S,11'S,12'R)-6-chloro-11',12'-dimethyl-7-(((9aR)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | | | (1S,3'R,6S,7R,11'S,12'R)-6-chloro-11',12'-dimethyl-7-(((9aS)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

TABLE 1-continued

Examples Prepared by the General Methods

| Example Number | Starting Materials | General Method | Product Structure | Product Name | MS Data (M + 1)+ |
|---|---|---|---|---|---|
| 22 | 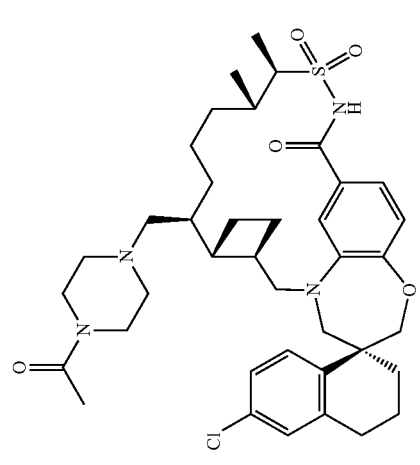<br>(Sigma-Aldrich) | 1 | 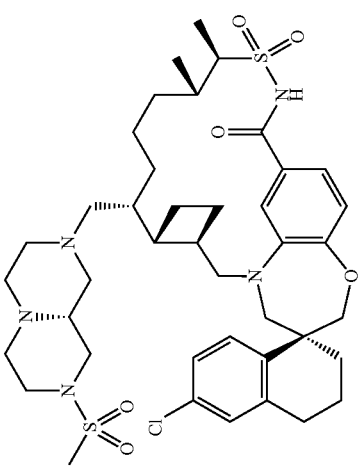(the first eluting peak off of reverse-phase HPLC, a 1-to-1 isomeric mixture) | (1S,3′R,6′S,7R,11′S,12′R)-6-chloro-11′,12′-dimethyl-7-(((9aR)-8-(methylsulfonyl)octahydro-2H-pyrazino[1,2-a]pyrazin-2-yl)methyl)-3,4-dihydro-2H,15′H-spiro[naphthalene-1,22′-[20]oxa[13]thia[1,14]diazatetracyclo[14.7.2.0∼3,6∼.0∼19,24∼]pentacosa[16,18,24]trien]-15′-one 13′,13′-dioxide<br><br>(1S,3′R,6′S,7S,11′S,12′R)-7-((4-acetyl-1-piperazinyl)methyl)-6-chloro-11′,12′-dimethyl-3,4-dihydro-2H,15′H-spiro[naphthalene-1,22′-[20]oxa[13]thia[1,14]diazatetracyclo[14.7.2.0∼3,6∼.0∼19,24∼]pentacosa[16,18,24]trien]-15′-one 13′,13′-dioxide<br>OR | 725.2 |

TABLE 1-continued

Examples Prepared by the General Methods

| Example Number | Starting Materials | General Method | Product Structure | Product Name | MS Data (M + 1)+ |
|---|---|---|---|---|---|
| | | | <br>(the first eluting epimer off of reverse-phase HPLC) | (1S,3′R,6S,7R,11′S,12′R)-7′-((4-acetyl-1-piperazinyl)methyl)-6-chloro-11′,12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide | |
| | | 1 | 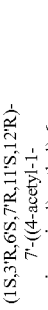 AND 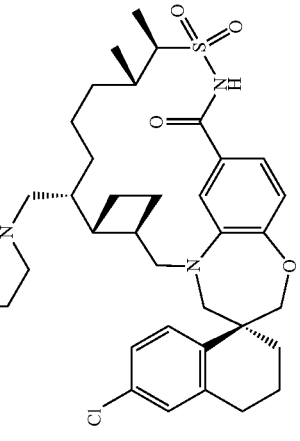 | (1S,3′R,6S,7S,11′S,12′R)-7′-((9aS)-8-acetyloctahydro-2H-pyrazino[1,2-a]pyrazin-2-yl)methyl)-6-chloro-11′,12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide AND | 780.5 |
| 25 |  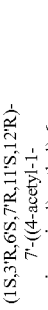<br>(FCH Group) | | | | |

TABLE 1-continued

Examples Prepared by the General Methods

| Example Number | Starting Materials | General Method | Product Structure | Product Name | MS Data (M + 1)+ |
|---|---|---|---|---|---|
| | | | AND | (1S,3'R,6'S,7'S,11'S,12'R)-7-(((9aR)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | |
| | | | AND | (1S,3'R,6'S,7'R,11'S,12'R)-7-(((9aS)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | |

TABLE 1-continued

Examples Prepared by the General Methods

| Example Number | Starting Materials | General Method | Product Structure | Product Name | MS Data (M + 1)+ |
|---|---|---|---|---|---|
| | | | 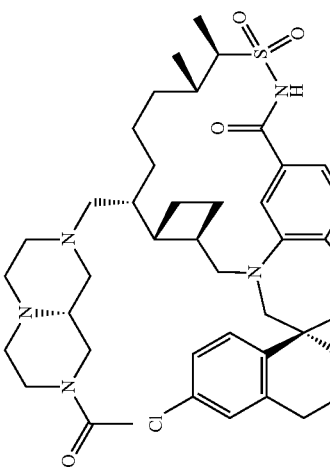<br>(an 1-to1-to-1-to-1 isomeric mixture) | (1S,3'R,6'S,7R,11'S,12'R)-7-(((9aR)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 27 | 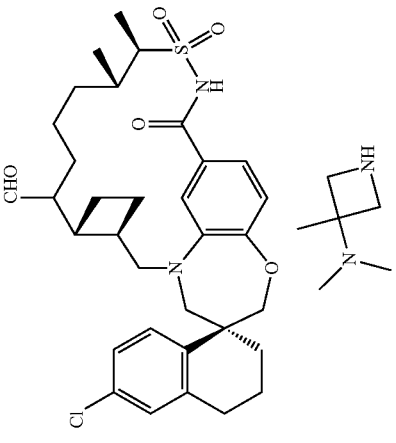<br>(Matrix Scientific) | 1 | 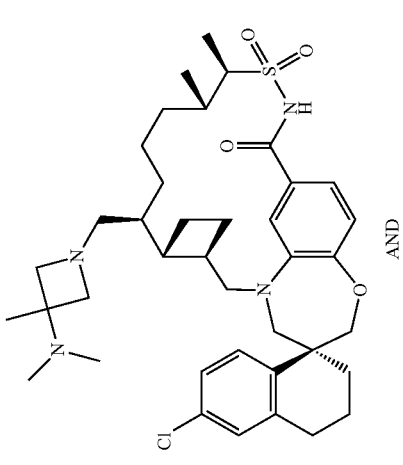<br>AND | (1S,3'R,6'S,7R,11'S,12'R)-6-chloro-7-((3-(dimethylamino)-3-methyl-1-azetidinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | 711.2 |

TABLE 1-continued

Examples Prepared by the General Methods

| Example Number | Starting Materials | General Method | Product Structure | Product Name | MS Data (M + 1)+ |
|---|---|---|---|---|---|
| 28 | (in house) HNMe₂ (Sigma-Aldrich) | 5 | | (1S,3'R,6'S,7R,11'S,12'R)-6-chloro-7'-((3-(dimethylamino)-3-methyl-1-azetidinyl)methyl)-11',12'-dimethyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide (a 6 (the first eluting epimer on reverse phase HPLC)-to-5 epimeric mixture) | |
| | | | | 2-((1S,3'R,6'S,7R,11'S,12'R)-6-chloro-11',12'-dimethyl-13',13'-dioxido-15'-oxo-3,4-dihydro-2H-spiro[naphthalene-1,22'-[20]oxa[13]thia[1,14]di-azatetracyclo[14.7.2.0~3,6~.0~19,24~]pentacosa[16,18,24]trien]-7'-yl)-N,N-dimethylacetamide AND | 670.3 |

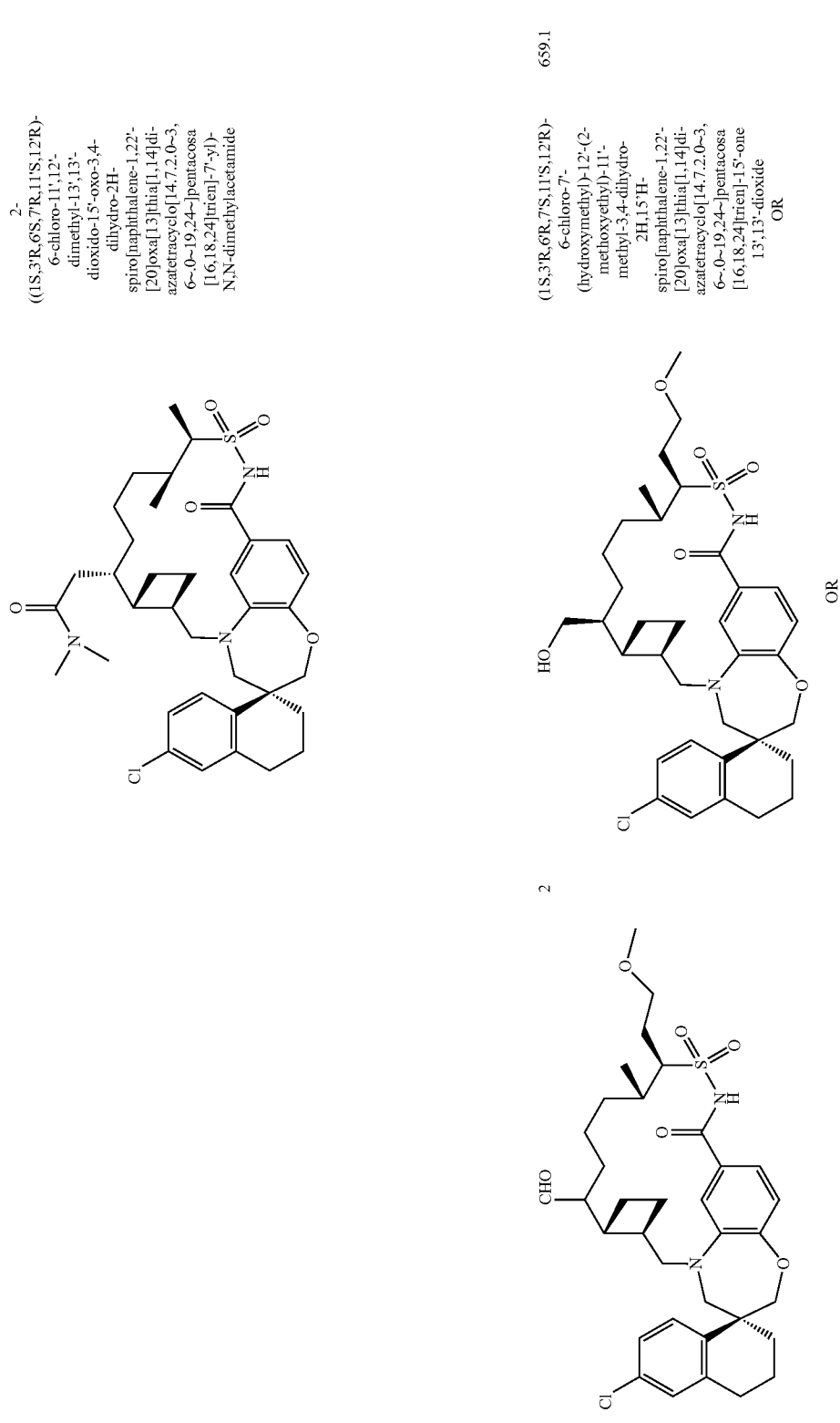

TABLE 1-continued

Examples Prepared by the General Methods

| Example Number | Starting Materials | General Method | Product Structure | Product Name | MS Data (M + 1)+ |
|---|---|---|---|---|---|
| 30 | (in house) | | | (1S,3'R,6'R,7'R,11'S,12'R)-6-chloro-7'-(hydroxymethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 1 | | (1S,3'R,6'S,7'S,11'S,12'R)-6-chloro-11',12'-dimethyl-7'-(((9aS)-8-(methylsulfonyl)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide Any two of the following four stereoisomers | 816.3 |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3′R,6S,7S,11′S,12′R)-6-chloro-11′,12′-dimethyl-7′-(((9aR)-8-(methylsulfonyl)octahydro-2H-pyrazino[1,2-a]pyrazin-2-yl)methyl)-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide | |
| | | | | (1S,3′R,6S,7R,11′S,12′R)-6-chloro-11′,12′-dimethyl-7′-(((9aS)-8-(methylsulfonyl)octahydro-2H-pyrazino[1,2-a]pyrazin-2-yl)methyl)-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide | |

TABLE 1-continued

Examples Prepared by the General Methods

| Example Number | Starting Materials | General Method | Product Structure | Product Name | MS Data (M + 1)+ |
|---|---|---|---|---|---|
| | | | (the second eluting peak off of reverse-phase HPLC, a 1-to-1 isomeric mixture) | (1S,3'R,6S,7R,11'S,12'R)-6-chloro-11',12'-dimethyl-7-(((9aR)octahydro-2H-pyrazino[1,2-a]pyrazin-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 31 | | 1 | OR | (1S,3'R,6S,7S,11'S,12'R)-6-chloro-7-(((9aR)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 739.2 |
| | (Synthonix) | | | | |

TABLE 1-continued

Examples Prepared by the General Methods

| Example Number | Starting Materials | General Method | Product Structure | Product Name | MS Data (M + 1)+ |
|---|---|---|---|---|---|
| 32 | (Synthonix) | | (the first eluting epimer on reverse phase HPLC) | (1S,3'R,6'S,7'R,11'S,12'R)-6-chloro-7'-((9aR)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | |
| | | 1 | | (1S,3'R,6'S,7'R,11'S,12'R)-6-chloro-7'-((9aS)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | 739.2 |

TABLE 1-continued

Examples Prepared by the General Methods

| Example Number | Starting Materials | General Method | Product Structure | Product Name | MS Data (M + 1)+ |
|---|---|---|---|---|---|
| 33 | | | (an approximately 85 (the first eluting epimer on reverse phase HPLC)-to-15 epimeric mixture) | (1S,3'R,6'S,7R,11'S,12'R)-6-chloro-7'-((9aS)-hexahydropyrazino[2,1-c][1,4]oxazin-8(1H)-ylmethyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 1 | AND | (1S,3'R,6'S,7R,11'S,12'R)-7'-((4-acetyl-1-piperazinyl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | 725.2 |
| | (Sigma-Aldrich) | | | | |

TABLE 1-continued

Examples Prepared by the General Methods

| Example Number | Starting Materials | General Method | Product Structure | Product Name | MS Data (M + 1)+ |
|---|---|---|---|---|---|
| | | | (a 7 (the first eluting epimer on reverse phase HPLC)-to-3 epimeric mixture) | (1S,3R,6S,7S,11'S,12'R)-7'-((4-acetyl-1-piperazinyl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 34 | (Acros Organics) | 1 | OR | (1S,3R,6S,7S,11'S,12'R)-6-chloro-11',12'-dimethyl-7'-((4-methyl-1-piperazinyl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 697.3 |

TABLE 1-continued

Examples Prepared by the General Methods

| Example Number | Starting Materials | General Method | Product Structure | Product Name | MS Data (M + 1)+ |
|---|---|---|---|---|---|
| 35 | 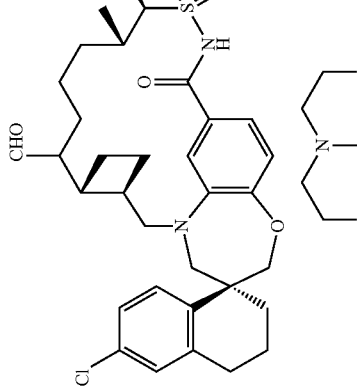<br>(FCH Group) | 1 | 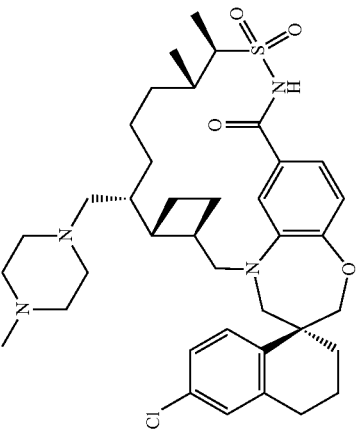<br>(the second eluting epimer off of reverse-phase HPLC)<br>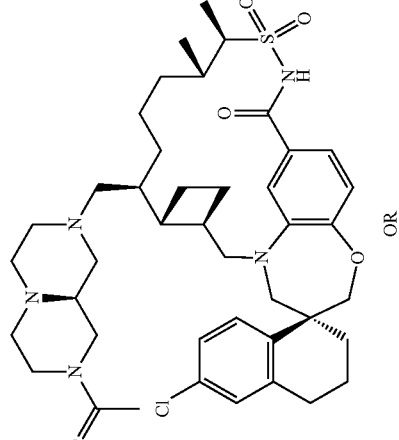OR | (1S,3'R,6S,7R,11'S,12'R)-6-chloro-11',12'-dimethyl-7'-((4-methyl-1-piperaziny)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide<br>OR<br>(1S,3'R,6S,7S,11'S,12'R)-7'-(((9aS)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 780.5 |

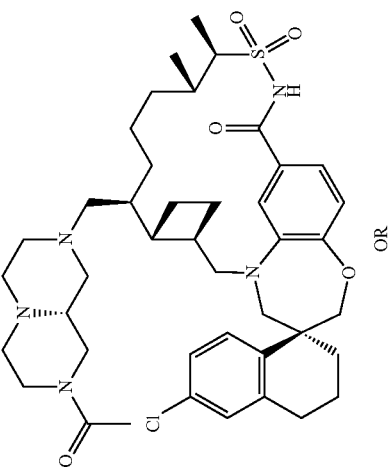

TABLE 1-continued

Examples Prepared by the General Methods

| Example Number | Starting Materials | General Method | Product Structure | Product Name | MS Data (M + 1)+ |
|---|---|---|---|---|---|
| 36 | 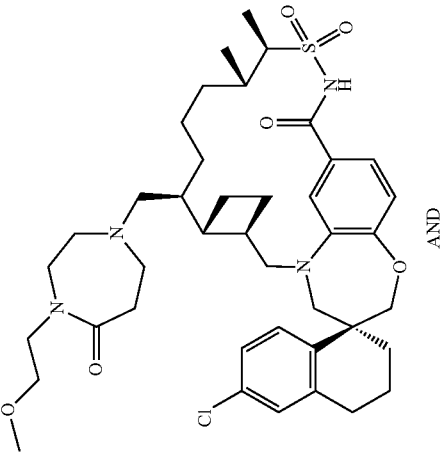 (Matrix Scientific) | 1 | 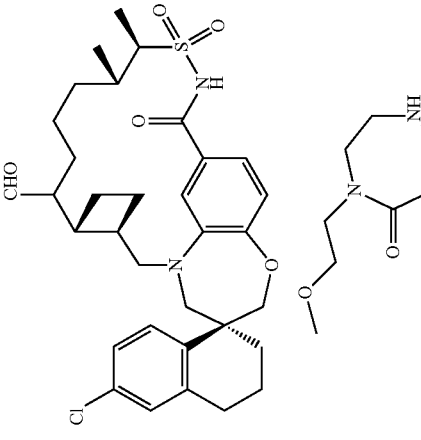 AND | (1S,3'R,6'S,7'R,11'S,12'R)-7-((9aR)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND (1S,3'R,6'S,7'R,11'S,12'R)-6-chloro-7-((4-(2-methoxyethyl)-5-oxo-1,4-diazepan-1-yl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 769.2 |

TABLE 1-continued

Examples Prepared by the General Methods

| Example Number | Starting Materials | General Method | Product Structure | Product Name | MS Data (M + 1)+ |
|---|---|---|---|---|---|
| 37 | 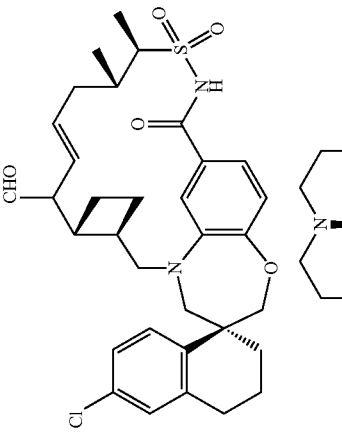 (Pharmablock) | | 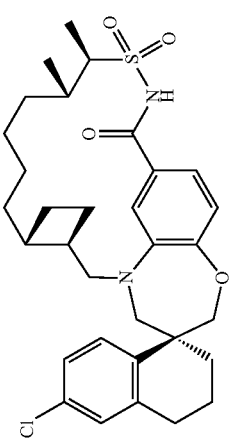 (an approximately 55 (the 1st eluting epimer on reverse phase HPLC)-to-45 epimeric mixture) 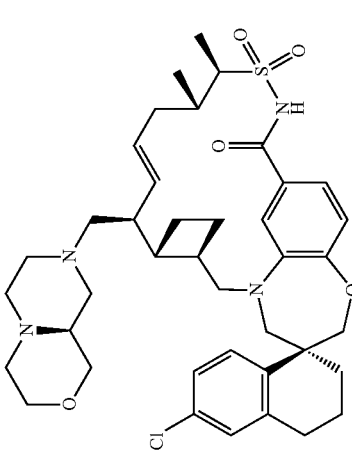 OR | (1S,3R,6S,7S,11′S,12′R)-6-chloro-7′-((4-(2-methoxyethyl)-5-oxo-1,4-diazepan-1-yl)methyl)-11′,12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide  OR  (1S,3R,6R,7S,8E,11′S,12′R)-6-chloro-7′-((9aS)-hexahydropyrazino[2,1-c][1,4]oxazin-8(1H)-yl)methyl)-11′,12′-dimethyl-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide | 737.2 |

TABLE 1-continued

Examples Prepared by the General Methods

| Example Number | General Method | Product Structure | Product Name | MS Data (M + 1)+ |
|---|---|---|---|---|
| | | | (1S,3'R,6'R,7'R,8'E,11'S,12'R)-6-chloro-7'-((9aS)-hexahydropyrazino[2,1-c][1,4]oxazin-8(1H)-yl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 38 | 4 | 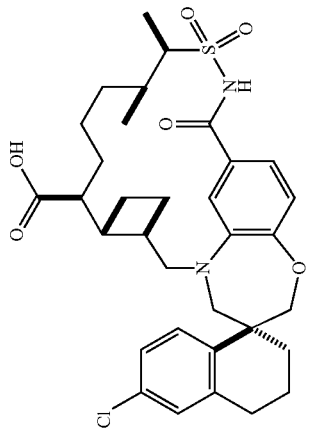 | (1S,3'R,6'R,7'S,11'S,12'R)-6-chloro-7'-((3,3-difluoro-1-azetidinyl)carbonyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 704.1 |

Starting Materials: (in house), HN⟨3,3-difluoroazetidine⟩ HCl aldrich

TABLE 1-continued

Examples Prepared by the General Methods

| Example Number | Starting Materials | General Method | Product Structure | Product Name | MS Data (M + 1)+ |
|---|---|---|---|---|---|
| 39 | | | | (1S,3R,6R,7R,11'S,12'R)-6-chloro-7'-((3,3-difluoro-1-azetidinyl)carbonyl)-11',12'-dimethyl-3,4-dihydro-2H,15'H-spiro[naphthalene-1,22'-[20]oxa[13]thia[1,14]diazatetracyclo[14.7.2.0∼3,6∼.0∼19,24∼]pentacosa[16,18,24]trien]-15'-one 13',13'-dioxide | |
| | (Sigma-Aldrich) | 1 | | (1S,3R,6R,7S,11'S,12'R)-6-chloro-7'-((4-(2-methoxyethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0∼3,6∼.0∼19,24∼]pentacosa[16,18,24]trien]-15'-one 13',13'-dioxide OR | 741.2 |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3'R,6'S,7'R,11'S,12'R)-6-chloro-7'-((4-(2-methoxyethyl)-1-piperazinyl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide (the second eluting epimer off of reverse-phase HPLC) | |
| 42 | (shown: aldehyde intermediate with CHO group AND oxo-diazepane enamine) | 1 | | (1S,3'R,6'S,7'R,11'S,12'R)-6-chloro-7'-((4-(2-methoxyethyl)-3-oxo-1,4-diazepan-1-yl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | 769.3 |

TABLE 1-continued

Examples Prepared by the General Methods

| Example Number | Starting Materials | General Method | Product Structure | Product Name | MS Data (M + 1)+ |
|---|---|---|---|---|---|
| 43 | | | (an 1-to-1 epimeric mixture) | (1S,3R,6S,7S,11S,12R)-6-chloro-7'-((4-(2-methoxyethyl))-3-oxo-1,4-diazepan-1-yl)methyl)-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 2 | OR | (1S,3R,6R,7S,10S,11'S)-6-chloro-7'-(hydroxymethyl)-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 615.1 |

TABLE 1-continued

Examples Prepared by the General Methods

| Example Number | Starting Materials | General Method | Product Structure | Product Name | MS Data (M + 1)+ |
|---|---|---|---|---|---|
| 46 | (Sigma-Aldrich) | | (the first epimer eluting off of reverse-phase HPLC) | (1S,3R,6R,7R,10S,11S)-6-chloro-7-(hydroxymethyl)-10,11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 1 | OR | (1S,3R,6S,7S,11'S,12'R)-6-chloro-11',12'-dimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 684.2 |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3'R,6'S,7'R,11'S,12'R)-6-chloro-11',12'-dimethyl-7'-(4-morpholinylmethyl)-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide | |
| 48 | (FCH Group) | 1 | | (1S,3'R,6'S,7'S,11'S,12'R)-7'-((9aS)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide OR | 780.5 |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3'R,6'S,7'S,11'S,12'R)-7'-(((9aR)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | |
| | | | | (1S,3'R,6'S,7'R,11'S,12'R)-7'-(((9aS)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3'R,6'S,7'R,11'S,12'R)-7'-(((9aR)-8-acetyloctahydro-2H-pyrazino[1,2-a]pyrazin-2-yl)methyl)-6-chloro-11',12'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 50 | (structure with CHO and spiroazetidine-pyrrolidine·HCl, Astatech) | 1 | | (1S,3'R,6'S,7'R,11'S,12'R)-6-chloro-11',12'-dimethyl-7'-((5-methyl-2,5-diazaspiro[3.4]oct-2-yl)methyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 723.5 |

TABLE 1-continued

Examples Prepared by the General Methods

| Example Number | Starting Materials | General Method | Product Structure | Product Name | MS Data (M + 1)+ |
|---|---|---|---|---|---|
| | | | 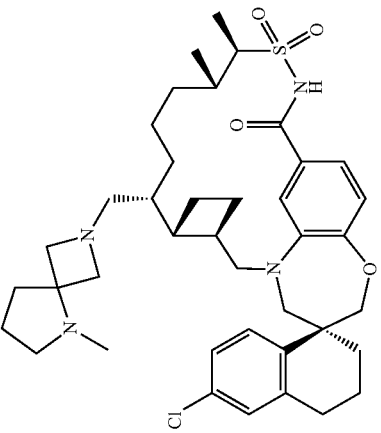 | (1S,3'R,6'S,7'R,11'S,12'R)-6-chloro-11',12'-dimethyl-7'-((5-methyl-2,5-diazaspiro[3.4]oct-2-yl)methyl)-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide | |
| 51 | | 2 | 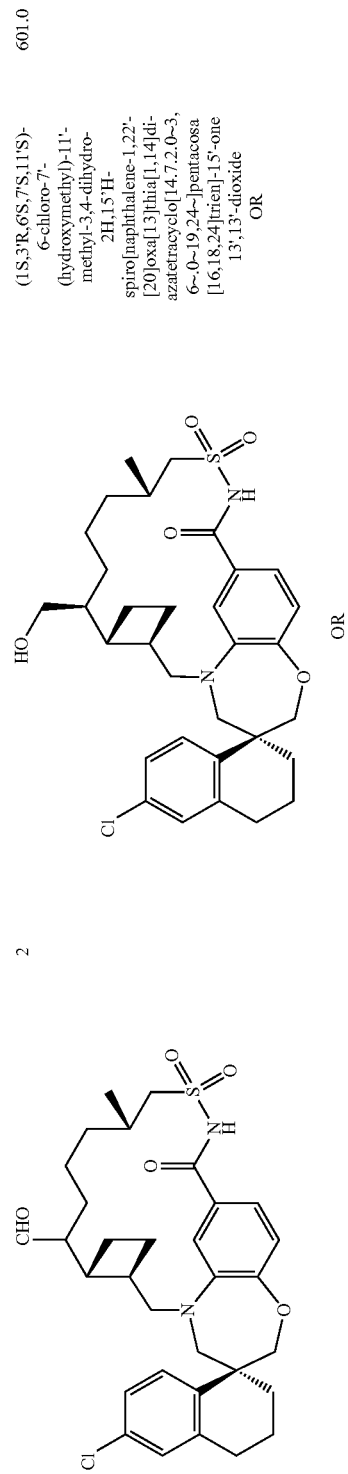 | (1S,3R,6S,7S,11S)-6-chloro-7-(hydroxymethyl)-11'-methyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide OR | 601.0 |

TABLE 1-continued

Examples Prepared by the General Methods

| Example Number | Starting Materials | General Method | Product Structure | Product Name | MS Data (M + 1)+ |
|---|---|---|---|---|---|
| 55 | | | (the first epimer eluting off of reverse-phase HPLC) | (1S,3R,6R,7R,11'S)-6-chloro-7'-(hydroxymethyl)-11'-methyl-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide | |
| | (Sigma-Aldrich) | 1 | AND | (1S,3R,6S,7S,11'S,12'R)-6-chloro-11',12'-dimethyl-7'-(4-morpholinylmethyl)-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide AND | 684.2 |

TABLE 1-continued

Examples Prepared by the General Methods

| Example Number | Starting Materials | General Method | Product Structure | Product Name | MS Data (M + 1)+ |
|---|---|---|---|---|---|
| 57 | | | 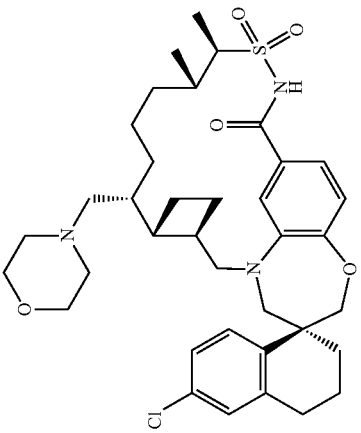 (an approximately 3 (the first eluting epimer on reverse phase HPLC)-to-2 epimeric mixture) | (1S,3'R,6S,7R,11'S,12'R)-6-chloro-11',12'-dimethyl-7'-(4-morpholinylmethyl)-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide | |
| | | 4 | 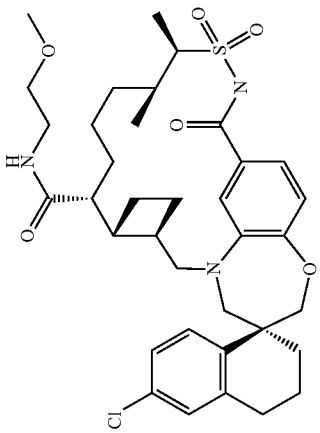 OR 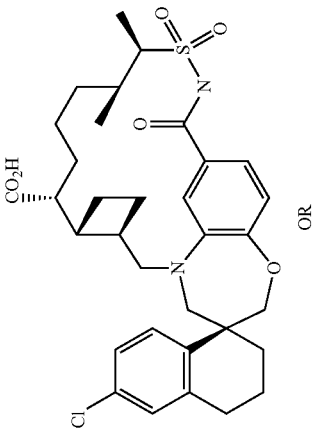 OR | (1S,3'R,6R,7R,11'S,12'R)-6-chloro-N-(2-methoxyethyl)-11',12'-dimethyl-15'-oxo-3,4-dihydro-2H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide OR | 686.5 |

TABLE 1-continued

Examples Prepared by the General Methods

| Example Number | Starting Materials | General Method | Product Structure | Product Name | MS Data (M + 1)+ |
|---|---|---|---|---|---|
| 59 | 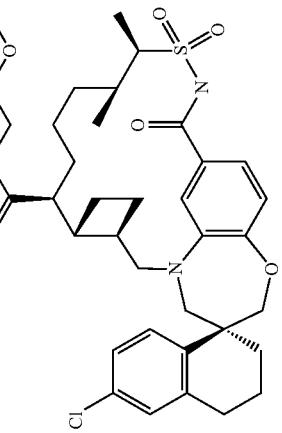 (in house) 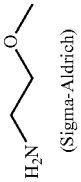 (Sigma-Aldrich) | | 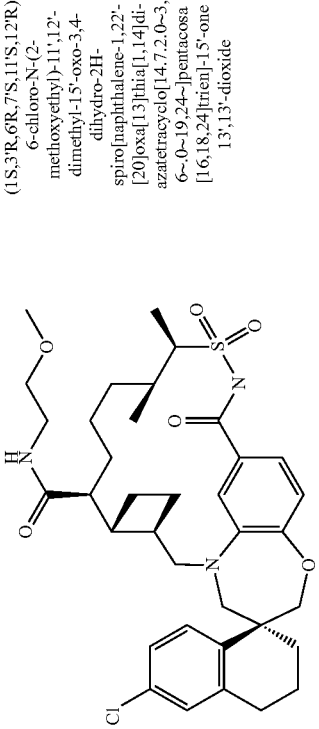 | (1S,3'R,6'R,7'S,11'S,12'R)-6-chloro-N-(2-methoxyethyl)-11',12'-dimethyl-15'-oxo-3,4-dihydro-2H-spiro[naphthalene-1,22'-[20]oxa[13]thia[1,14]di-azatetracyclo[14.7.2.0~3,6~.0~19,24~]pentacosa [16,18,24]trien]-15'-one 13',13'-dioxide | |
| | 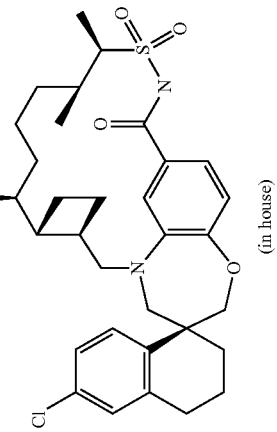 | 2 | 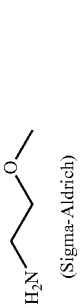 OR 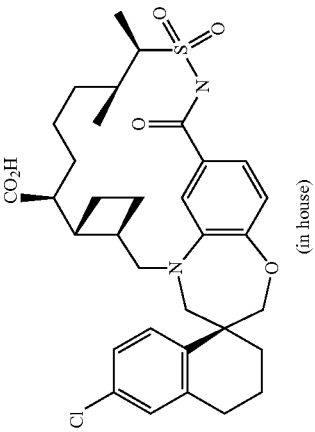 | (1S,3'R,6'R,7'S,11'S,12'R)-6-chloro-7-(hydroxymethyl)-12'-(2-methoxyethyl)-11'-methyl-3,4-dihydro-2H,15'H-spiro[naphthalene-1,22'-[20]oxa[13]thia[1,14]di-azatetracyclo[14.7.2.0~3,6~.0~19,24~]pentacosa [16,18,24]trien]-15'-one 13',13'-dioxide OR | 659.1 |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3R,6R,7R,11S,12R)-6-chloro-7'-(hydroxymethyl)-12'-(2-methoxyethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 62 | | 1 | | (1S,3R,6R,7R,8E,11S,12R)-6-chloro-11',12'-dimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | 682.5 |

TABLE 1-continued

Examples Prepared by the General Methods

| Example Number | Starting Materials | General Method | Product Structure | Product Name | MS Data (M + 1)+ |
|---|---|---|---|---|---|
| | | | (an approximately 1 (the 1st eluting epimer off of reverse-phase HPLC)-to-4 epimeric mixture) | (1S,3R,6R,7S,8E,11S,12R)-6-chloro-11,12-dimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 1 | AND | tert-butyl (9aR)-8-((((1S,3R,6S,7R,11S,12R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)methyl)octahydro-2H-pyrazino[1,2-a]pyrazine-2-carboxylate AND | 782.3 [(M + 1)-butene] |
| 64 | (Astatech) | | | | |

TABLE 1-continued

Examples Prepared by the General Methods

| Example Number | Starting Materials | General Method | Product Structure | Product Name | MS Data (M + 1)+ |
|---|---|---|---|---|---|
| | | | 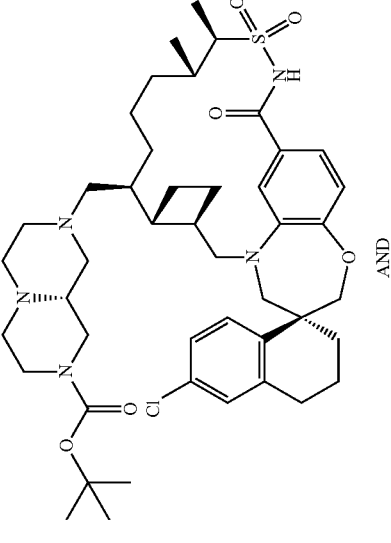 AND 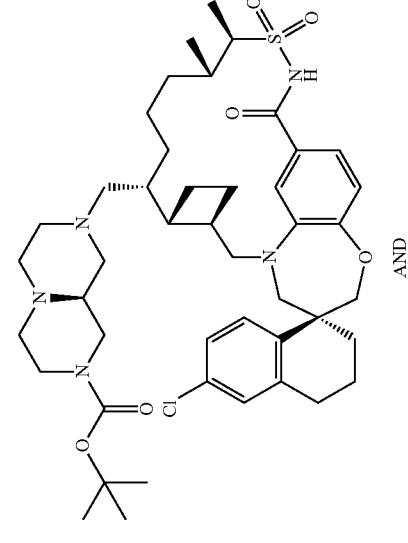 | tert-butyl (9aR)-8-((((1S,3'R,6S,7S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7-yl)methyl)octahydro-2H-pyrazino[1,2-a]pyrazine-2-carboxylate AND tert-butyl (9aS)-8-((((1S,3'R,6S,7R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7-yl)methyl)octahydro-2H-pyrazino[1,2-a]pyrazine-2-carboxylate AND | |

TABLE 1-continued

Examples Prepared by the General Methods

| Example Number | Starting Materials | General Method | Product Structure | Product Name | MS Data (M + 1)+ |
|---|---|---|---|---|---|
| | | | | tert-butyl (9aS)-8-((((1S,3'R,6S,7S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[16,18,24]trien]-7'-yl)methyl)octahydro-2H-pyrazino[1,2-a]pyrazine-2-carboxylate | |
| | | | | (1S,3'R,6S,7S,11'S,12'R)-6-chloro-11',12'-dimethyl-7'-(4-morpholinylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | 684.2 |
| | | | OR | OR | |
| 67 | (Sigma-Aldrich) | 1 | | | |

TABLE 1-continued

Examples Prepared by the General Methods

| Example Number | Starting Materials | General Method | Product Structure | Product Name | MS Data (M + 1)+ |
|---|---|---|---|---|---|
|  |  |  | 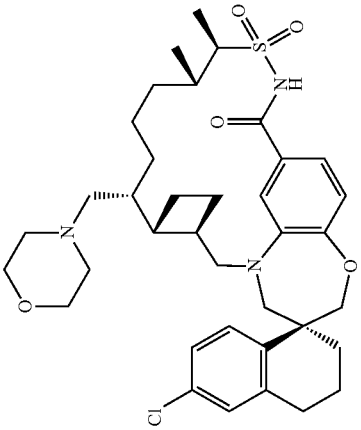 | (1S,3′R,6S,7R,11′S,12′R)-6-chloro-11′,12′-dimethyl-7′-(4-morpholinylmethyl)-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide |  |
| 68 |  | 3 | 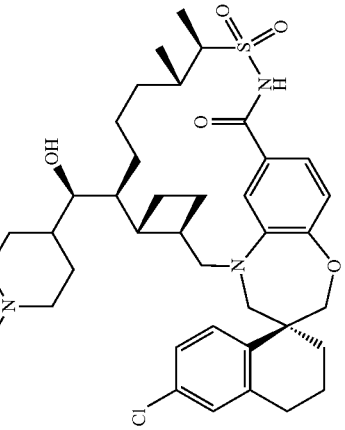 OR 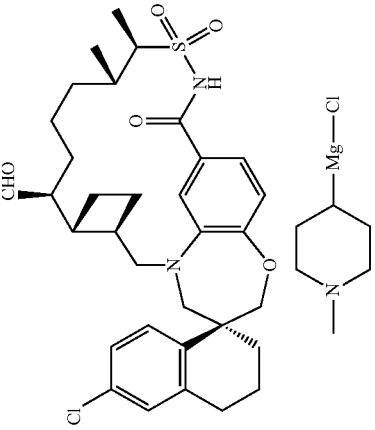 | (1S,3′R,6R,7S,11′S,12′R)-6-chloro-7′-((S)-hydroxy(1-methyl-4-piperidinyl)methyl)-11′,12′-dimethyl)-3,4-dihydro-2H,15′H-spiro[naphthalene-1,22′-[20]oxa[13]thia[1,14]diazatetracyclo[14.7.2.0~3,6~.0~19,24~]pentacosa[16,18,24]trien]-15′-one 13′,13′-dioxide OR | 712.4 |

TABLE 1-continued

Examples Prepared by the General Methods

| Example Number | Starting Materials | General Method | Product Structure | Product Name | MS Data (M + 1)+ |
|---|---|---|---|---|---|
| | | | (the first eluting peak off of reverse-phase HPLC) | (1S,3'R,6R,7S,11'S,12'R)-6-chloro-7'-((R)-hydroxy(1-methyl-4-piperidinyl)methyl)-11',12'-dimethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 71 | CHO | 2 | OR | (1S,3'R,6R,7S,12'R)-6-chloro-12'-ethyl-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 615.1 |

TABLE 1-continued

Examples Prepared by the General Methods

| Example Number | Starting Materials | General Method | Product Structure | Product Name | MS Data (M + 1)+ |
|---|---|---|---|---|---|
| 80 | | | (the first eluting epimer off of reverse-phase HPLC) | (1S,3'R,6'R,7'R,12'R)-6-chloro-12'-ethyl-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 2 | OR | (1S,3'R,6'R,7'S,11'S,12'R)-6-chloro-7'-methoxymethyl)-11',12'-dimethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 629.2 |

TABLE 1-continued

Examples Prepared by the General Methods

| Example Number | Starting Materials | General Method | Product Structure | Product Name | MS Data (M + 1)+ |
|---|---|---|---|---|---|
| | | | | (1S,3R,6R,7R,11'S,12'R)-6-chloro-7'-methoxymethyl)-11',12'-dimethyl)-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide | |
| 81 | | deprotection | | (1S,3R,6S,7R,11'S,12'R)-6-chloro-11',12'-dimethyl-7'-((9aR)-octahydro-2H-pyrazino[1,2-a]pyrazin-2-ylmethyl)-3,4-dihydro-2H,15'H-spiro[naphthalene-1,22'-[20]oxa[13]thia[1,14]di-azatetracyclo[14.7.2.0~3,6~.0~19,24~]pentacosa[16,18,24]trien]-15'-one 13',13'-dioxide AND | 738.4 |

TABLE 1-continued

Examples Prepared by the General Methods

| Example Number | Starting Materials | General Method | Product Structure | Product Name | MS Data (M + 1)+ |
|---|---|---|---|---|---|
| |  AND 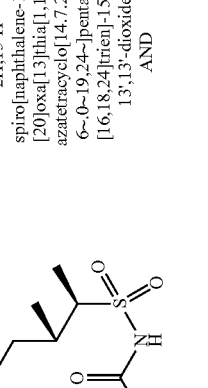 | |  AND 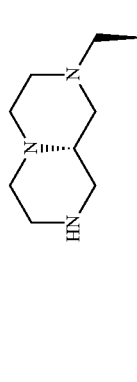 | (1S,3'R,6S,7R,11'S,12'R)-6-chloro-11',12'-dimethyl-7'-((9aS)-octahydro-2H-pyrazino[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | |
| | 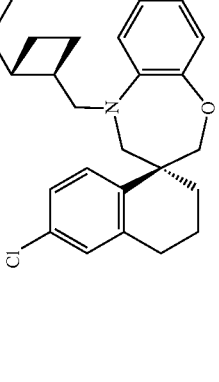 AND  | | 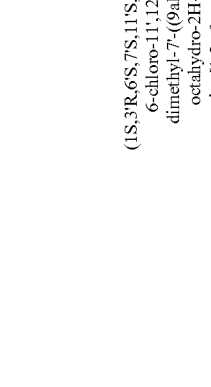 AND | (1S,3'R,6S,7R,11'S,12'R)-6-chloro-11',12'-dimethyl-7'-((9aR)-octahydro-2H-pyrazino[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide AND | |

TABLE 1-continued

Examples Prepared by the General Methods

| Example Number | Starting Materials | General Method | Product Structure | Product Name | MS Data (M + 1)+ |
|---|---|---|---|---|---|
| | 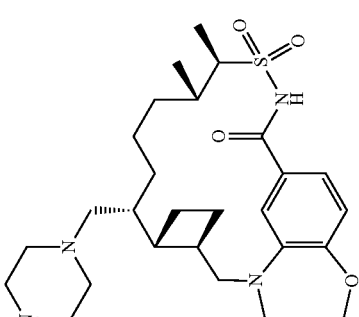(Example 64) TFA (Sigma-Aldrich) | | 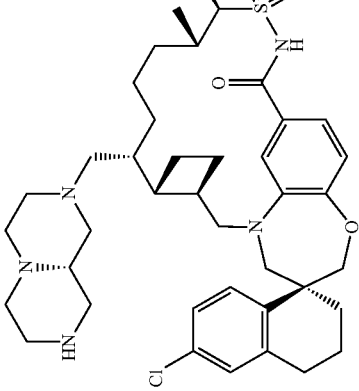 | (1S,3'R,6R,7S,11'S,12'R)-6-chloro-11',12'-dimethyl-7'-((9aS)-octahydro-2H-pyrazino[1,2-a]pyrazin-2-ylmethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 82 | 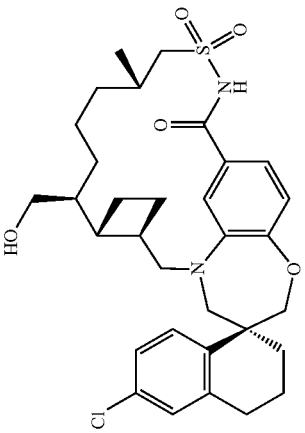 | 2 | 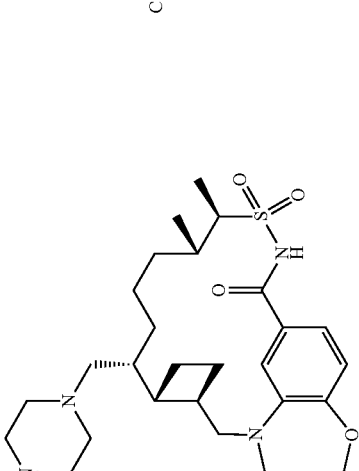 | (1S,3'R,6R,7S,11'S)-6-chloro-7'-(hydroxymethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 601.0 |

TABLE 1-continued

Examples Prepared by the General Methods

| Example Number | Starting Materials | General Method | Product Structure | Product Name | MS Data (M + 1)+ |
|---|---|---|---|---|---|
| | 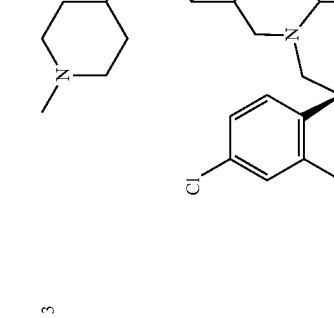 | | 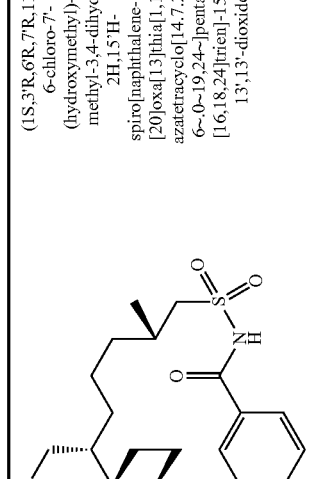  (the second eluting epimer off of reverse-phase HPLC) | (1S,3'R,6'R,7'R,11'S)-6-chloro-7'-(hydroxymethyl)-11'-methyl-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 83 | 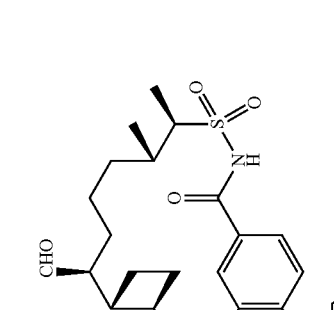  (Novel Chemical Solution) | 3 | 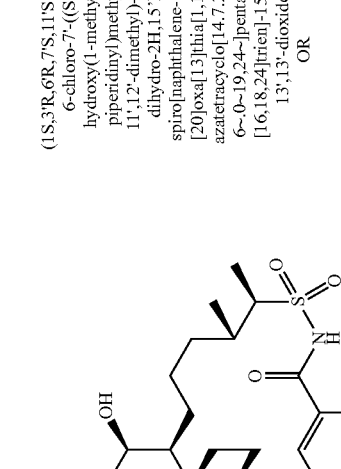  OR | (1S,3'R,6'R,7'S,11'S,12'R)-6-chloro-7'-((S)-hydroxy(1-methyl-4-piperidinyl)methyl)-11',12'-dimethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide  OR | 712.4 |

TABLE 1-continued

Examples Prepared by the General Methods

| Example Number | Starting Materials | General Method | Product Structure | Product Name | MS Data (M + 1)+ |
|---|---|---|---|---|---|
| | | | (the second eluting peak off of reverse-phase HPLC) | (1S,3'R,6'R,7'S,11'S,12'R)-6-chloro-7'-((R)-hydroxy(1-methyl-4-piperidinyl)methyl)-11',12'-dimethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| 84 | | 2 | OR | (1S,3'R,6'R,7'S,10'S,11'S)-6-chloro-7'-(hydroxymethyl)-10',11'-dimethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 615.1 |

TABLE 1-continued

Examples Prepared by the General Methods

| Example Number | Starting Materials | General Method | Product Structure | Product Name | MS Data (M + 1)+ |
|---|---|---|---|---|---|
| 85 | | | 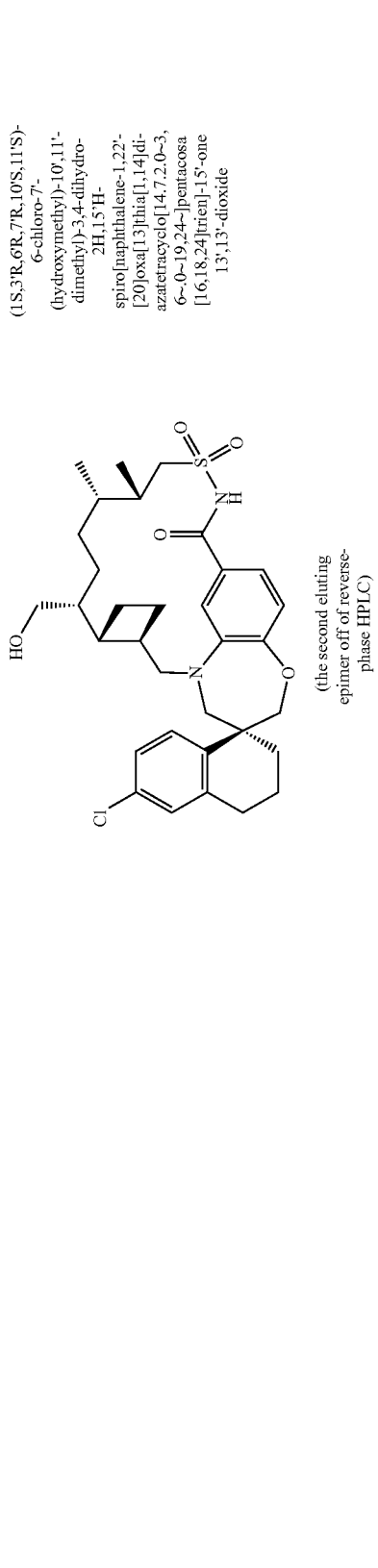 (the second eluting epimer off of reverse-phase HPLC) | (1S,3'R,6'R,7'R,10'S,11'S)-6-chloro-7'-(hydroxymethyl)-10,11'-dimethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |
| | | 2 | 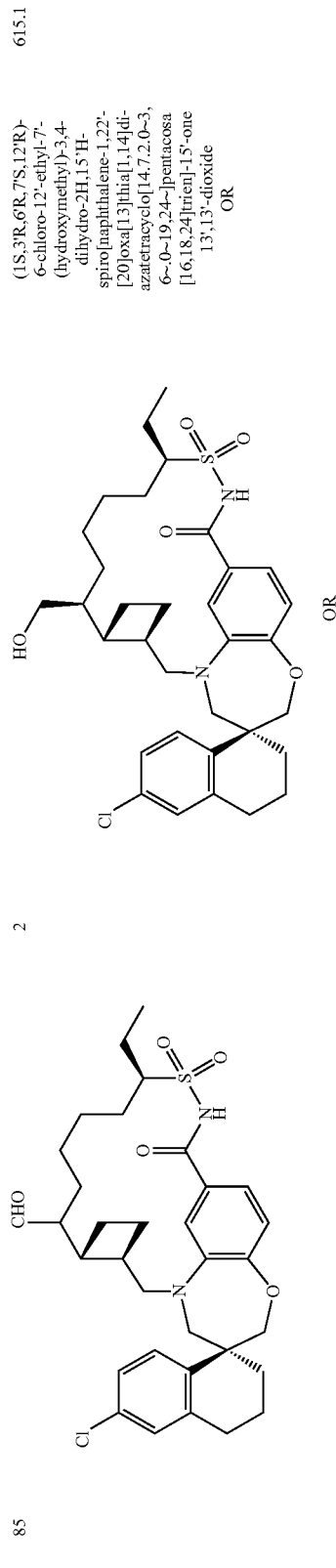 OR | (1S,3'R,6'R,7'S,12'R)-6-chloro-12'-ethyl-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide OR | 615.1 |

TABLE 1-continued
Examples Prepared by the General Methods
| Example Number | Starting Materials | General Method | Product Structure | Product Name | MS Data (M + 1)+ |
|---|---|---|---|---|---|
| | | | 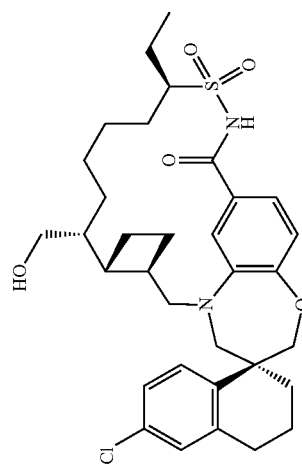<br>(the second eluting epimer off of reverse-phase HPLC) | (1S,3'R,6'R,7'R,12'R)-6-chloro-12'-ethyl-7'-(hydroxymethyl)-3,4-dihydro-2H,15'H-spiro[naphthalene-1,22'-[20]oxa[13]thia[1,14]diazatetracyclo[14.7.2.0~3,6~.0~19,24~]pentacosa[16,18,24]trien]-15'-one 13',13'-dioxide | |

BIOLOGICAL ASSAYS

Cell Free Mcl-1:Bim Affinity Assay (Mcl-1 HTRF)

The inhibition of the Mcl-1/Bim interaction was measured using a time-resolved fluorescence resonance energy transfer (TR-FRET) assay. The recombinant human Mcl-1 (C-terminally 6×His tagged Mcl-1 containing residues 171-327) was generated at Amgen Inc (Thousand Oaks, Calif.). A biotinylated peptide derived from human Bim (residues 51-76) was purchased from CPC Scientific (San Jose, Calif.). The TR-FRET assay was conducted in a 384-well white OptiPlate™ (PerkinElmer, Waltham, Mass.) in a total volume of 40 µL. The reaction mixture contained 0.1 nM Mcl-1(171-327), 0.05 nM biotin-Bim(51-76), 0.05 nM LANCES Eu-W1024 Anti-6×His (PerkinElmer), 0.072 nM Streptavidin-Xlent (Cisbio, Bedford, Mass.), and serially diluted test compounds in the binding buffer of 20 mM Hepes, pH 7.5, 150 mM NaCl, 0.016 mM Brij®35, and 1 mM dithiothreitol. Test compounds were pre-incubated with Mcl-1(171-327) and biotin-Bim (51-76) for 60 min before addition of the detection mixture (LANCE® Eu-W1024 Anti-6×His and Streptavidin-Xlent). The reaction plates were further incubated overnight and then were read on an Envision® multimode reader (PerkinElmer). Fluorescence signals were measured at 620 nm (40-nm bandwidth) and 665 nm (7.5-nm bandwidth) with a 60 µs delay after excitation at 320 nm (75-nm bandwidth). The signal ratio at 665/620 nm corresponded to the Mcl-1/Bim interaction and was used in all data analyses. The $IC_{50}$ values of test compounds were determined from duplicate data by analyzing competition curves using a four-parameter sigmoidal model in GraphPad Prism (GraphPad Software, San Diego, Calif.) or in Genedata Screener® (Genedata, Basel, Switzerland).

Cell Viability Assay (OPM-2 10 FBS)

The human multiple myeloma cell line, OPM-2, was cultured in complete growth medium containing RPMI 1640 and 10% fetal bovine serum (FBS). Cells were seeded into 384-well plates at 3000 cells/well density in complete growth medium containing 10% FBS, and incubated for 16 h with serially diluted test compounds in a 37° C. incubator with 5% $CO_2$. Cell viability was tested using CellTiter-Glo® assay (Promega, Madison, Wis.) according to the manufacturer recommendations. Luminescence was determined using an EnVision® Multilabel plate reader 25 min after the addition of detection reagent. $IC_{50}$ values were then calculated with Xlfit using a logistical 4-parameter fit model in GraphPad Prism (GraphPad Software, San Diego, Calif.) or in Genedata Screener® (Genedata, Basel, Switzerland).

Results for compounds tested in these biological assays are set forth below.

| Example Number | Mcl-1 HTRF $IC_{50}$ (µM) | OPM-2 10% FBS $IC_{50}$ IP (µM) |
|---|---|---|
| 1 | 0.000225 | 0.117 |
| 2 | 0.000123 | 0.134 |
| 3 | 0.000257 | 0.166 |
| 4 | 0.000212 | 0.172 |
| 5 | 0.000622 | 0.173 |
| 6 | 0.000353 | 0.177 |
| 7 | 0.000181 | 0.180 |
| 8 | 0.000126 | 0.221 |
| 9 | 0.000246 | 0.223 |
| 10 | 0.000291 | 0.227 |
| 11 | 0.000237 | 0.242 |
| 12 | 0.000542 | 0.254 |
| 13 | 0.000770 | 0.258 |
| 14 | 0.000291 | 0.268 |
| 15 | 0.000185 | 0.277 |
| 16 | 0.000317 | 0.283 |
| 17 | 0.000881 | 0.284 |
| 18 | 0.000840 | 0.289 |
| 19 | 0.000532 | 0.303 |
| 20 | 0.001159 | 0.304 |
| 21 | 0.000489 | 0.304 |
| 22 | 0.000375 | 0.305 |
| 23 | 0.000182 | 0.305 |
| 24 | 0.000224 | 0.322 |
| 25 | 0.000252 | 0.329 |
| 26 | 0.000336 | 0.342 |
| 27 | 0.000830 | 0.356 |
| 28 | 0.000287 | 0.364 |
| 29 | 0.000226 | 0.366 |
| 30 | 0.000516 | 0.370 |
| 31 | 0.000261 | 0.376 |
| 32 | 0.000493 | 0.380 |
| 33 | 0.000172 | 0.411 |
| 34 | 0.000602 | 0.417 |
| 35 | 0.000050 | 0.421 |
| 36 | 0.000265 | 0.443 |
| 37 | 0.000288 | 0.451 |
| 38 | 0.000517 | 0.525 |
| 39 | 0.000829 | 0.535 |
| 40 | 0.000822 | 0.564 |
| 41 | 0.000284 | 0.567 |
| 42 | 0.000408 | 0.593 |
| 43 | 0.000268 | 0.599 |
| 44 | 0.000502 | 0.617 |
| 45 | 0.000338 | 0.675 |
| 46 | 0.000743 | 0.724 |
| 47 | 0.001610 | 0.756 |
| 48 | 0.000329 | 0.768 |
| 49 | 0.000377 | 0.778 |
| 50 | 0.000923 | 0.785 |
| 51 | 0.000222 | 0.936 |
| 52 | 0.000107 | 0.939 |
| 53 | 0.001448 | 0.984 |
| 54 | 0.000624 | 0.989 |
| 55 | 0.000843 | 1.02 |
| 56 | 0.000520 | 1.03 |
| 57 | 0.000604 | 1.17 |
| 58 | 0.000995 | 1.23 |
| 59 | 0.000921 | 1.32 |
| 60 | 0.000552 | 1.33 |
| 61 | 0.000281 | 1.41 |
| 62 | 0.000388 | 1.44 |
| 63 | 0.000997 | 1.46 |
| 64 | 0.001420 | 1.50 |
| 66 | 0.007290 | 1.60 |
| 67 | 0.001049 | 1.67 |
| 68 | 0.000938 | 1.67 |
| 70 | 0.000843 | 1.86 |
| 71 | 0.000359 | 1.95 |
| 72 | 0.000849 | 1.99 |
| 73 | 0.007405 | 17.0 |
| 74 | 0.003670 | 2.04 |
| 75 | 0.000808 | 2.44 |
| 77 | 0.000442 | 20.7 |
| 78 | 0.002360 | 28.3 |
| 79 | 0.001590 | 3.00 |
| 80 | 0.001605 | 3.51 |
| 81 | 0.000831 | 3.56 |
| 82 | 0.000772 | 3.65 |
| 83 | 0.000552 | 4.23 |
| 84 | 0.003430 | 5.84 |
| 85 | 0.000676 | 7.13 |
| 86 | 0.027500 | 9.23 |
| 87 | 0.013267 | 9.89 |
| 88 | 0.011410 | >33.3 |
| 89 | 0.014250 | >33.3 |

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

The invention claimed is:

1. A compound of Formula IA:

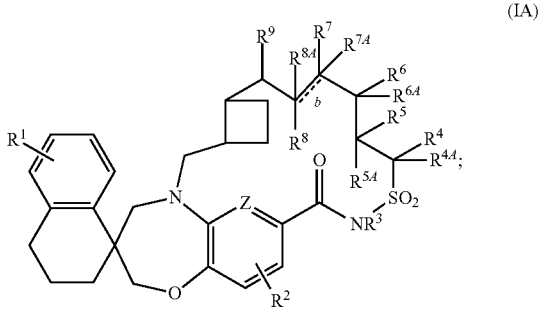

(IA)

a stereoisomer thereof, a pharmaceutically acceptable salt thereof, or a pharmaceutically acceptable salt of the stereoisomer thereof,
wherein:
Z is C or N;
b, represented by the symbol ======, is a single or double chemical bond which may be cis or trans;
$R^1$ is selected from H, halo, or $C_{1-6}$alkyl;
$R^2$ is selected from H, halo, or $C_{1-6}$alkyl;
$R^3$ is selected from H or —$C_{1-6}$alkyl;
each of $R^4$, $R^5$, $R^6$, $R^7$, and $R^8$ is independently selected from H, —$C_{1-6}$alkyl, or —$C_{1-6}$alkyl-O—$C_{1-6}$alkyl;
each of $R^{4A}$, $R^{5A}$, $R^{6A}$, $R^{7A}$, and $R^{8A}$ is independently selected from H, or —$C_{1-6}$alkyl;
$R^{7A}$ and $R^{8A}$ are absent when b is a double chemical bond;
$R^9$ is —$C_{1-6}$alkyl, unsubstituted or substituted with 1, 2, 3 or 4 $R^{10}$ substituents independently selected from halo, —OH, —$NR^aR^b$; —(=O), —$OC_{1-6}$alkyl, —$SO_2R^a$, a 5- to 12-membered spirocycloalkyl or spiroheterocycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S,
wherein the aryl, heteroaryl, cycloalkyl, heterocycloalkyl, spirocycloalkyl and spiroheterocycloalkyl groups of any of the $R^{10}$ substituents can be unsubstituted or substituted with 1, 2, 3 or 4 $R^2$ substituents independently selected from halo, —$NR^aR^b$, —$C_{1-6}$alkyl, —(=O), —$C_{1-6}$alkyl-O—$C_{1-6}$alkyl, —$SO_2R^a$, —C(=O)$R^a$, and —C(=O)$OR^a$;
wherein $R^a$ and $R^b$ are each independently H, —$C_{1-6}$alkyl, or —(CH$_2$CH$_2$O)$_n$CH$_3$, and
wherein n is 1.

2. The compound of claim 1, wherein the compound has the Formula IIa:

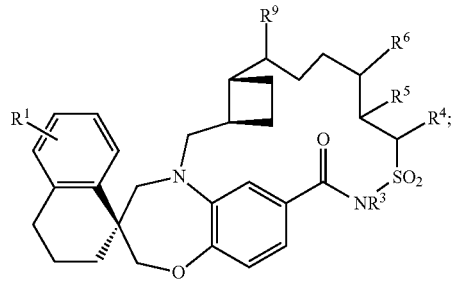

(IIa)

a stereoisomer thereof, a pharmaceutically acceptable salt thereof, or a pharmaceutically acceptable salt of the stereoisomer thereof.

3. The compound of claim 1, wherein $R^1$ is halo.

4. The compound of claim 1, wherein $R^3$ is H.

5. The compound of claim 1, wherein $R^4$ is independently selected from H, —$C_{1-6}$alkyl, or —$C_{1-6}$alkyl-O—$C_{1-6}$alkyl.

6. The compound of claim 1, wherein $R^5$ is selected from H or —$C_{1-6}$alkyl.

7. The compound of claim 1, wherein $R^6$ is selected from H or —$C_{1-6}$haloalkyl.

8. The compound of claim 1, wherein $R^9$ is —$C_{1-6}$haloalkyl unsubstituted or substituted with 1, 2, or 3 $R^{10}$ substituents.

9. The compound of claim 1, wherein $R^{10}$ is independently selected from halo, —OH, —$NR^aR^b$; —(=O), —$OC_{1-6}$alkyl, —$SO_2R^a$, a 5- to 12-membered spirocycloalkyl or spiroheterocycloalkyl, or a 3- to 12-membered monocyclic or bicyclic heterocycloalkyl group, wherein the heteroaryl, spiroheterocycloalkyl and heterocycloalkyl groups have 1, 2, 3 or 4 heteroatoms independently selected from O, N or S.

10. The compound of claim 9, wherein $R^{10}$ is a 3- to 12-membered monocyclic or bicyclic heterocycloalkyl group, wherein the heterocycloalkyl group has 1, 2, 3 or 4 heteroatoms independently selected from O, S, or N.

11. The compound of claim 1, wherein $R^9$ is independently selected from —CH$_3$, —CH$_2$OH, CH(OH)CF$_3$, —C(=O), —C(=O)OH, —CHCH$_2$(OH), —CH(OH)CH$_3$, —CH$_2$(O)CH$_3$, —C(=O)CH$_3$, —CH$_2$S(O)$_2$CH$_3$, —C(=O)NH(CH$_2$)$_2$OCH$_3$,

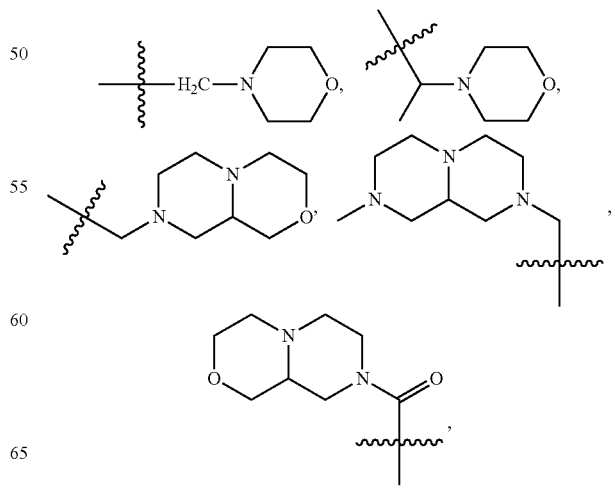

275

-continued

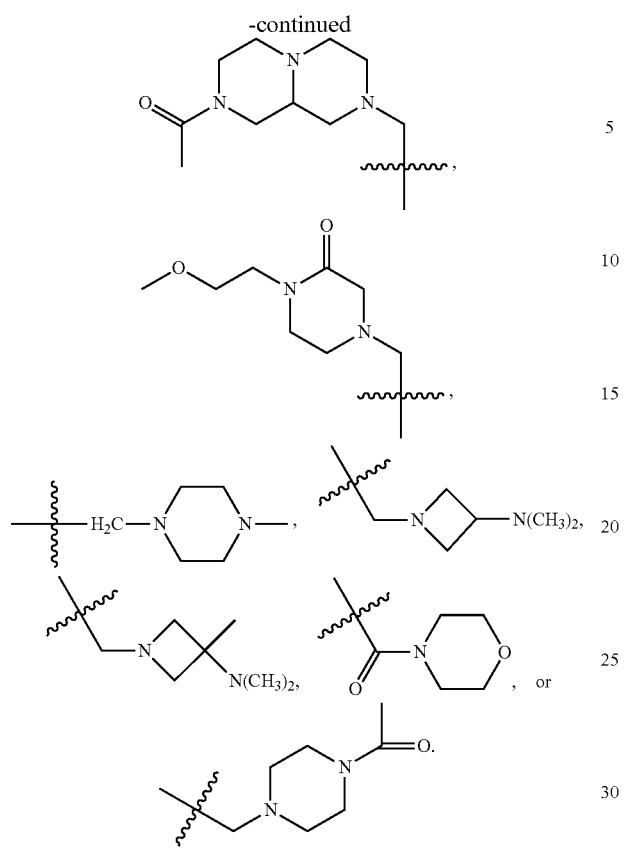

12. The compound of claim 1, wherein the compound has the Formula IIIa:

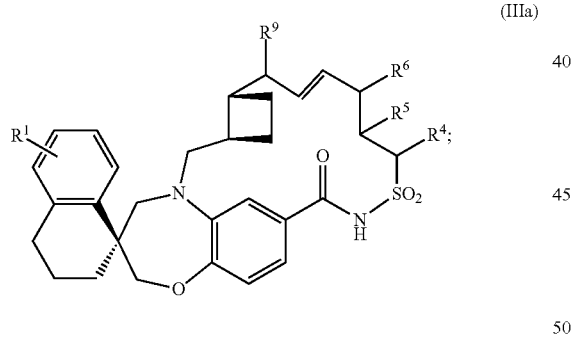

(IIIa)

or a stereoisomer thereof, a pharmaceutically acceptable salt thereof, or a pharmaceutically acceptable salt of the stereoisomer thereof.

13. The compound of claim 12, wherein $R^1$ is halo.
14. The compound of claim 12, wherein $R^4$ is —$C_{1-6}$alkyl.
15. The compound of claim 12, wherein $R^5$ is —$C_{1-6}$alkyl.
16. The compound of claim 12, wherein $R^6$ is H.
17. The compound of claim 12, wherein $R^9$ is —$CH_2OH$, —$CH(OH)CH_2CH_3$,

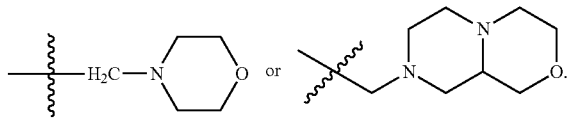

276

18. A compound, wherein the compound has a structure selected from:

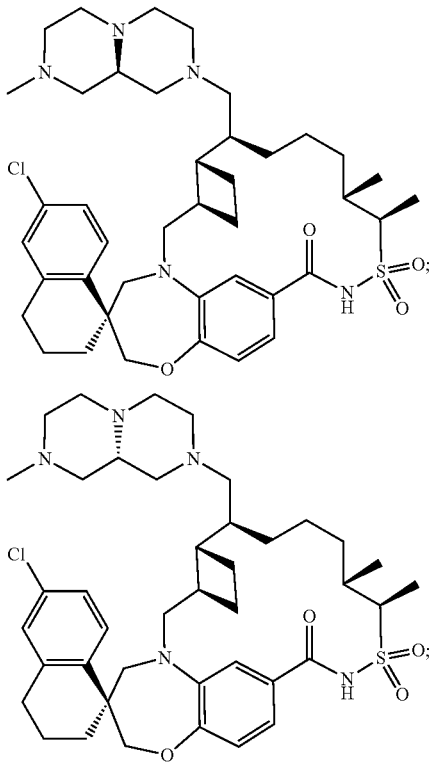

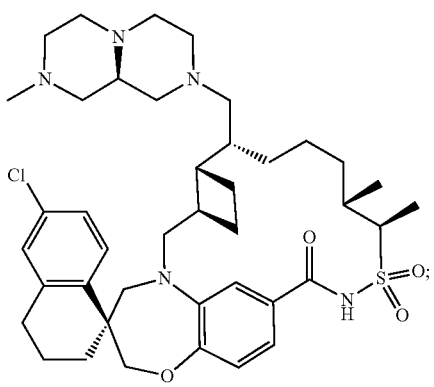

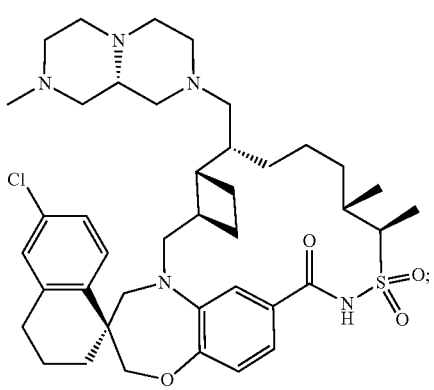

277
-continued
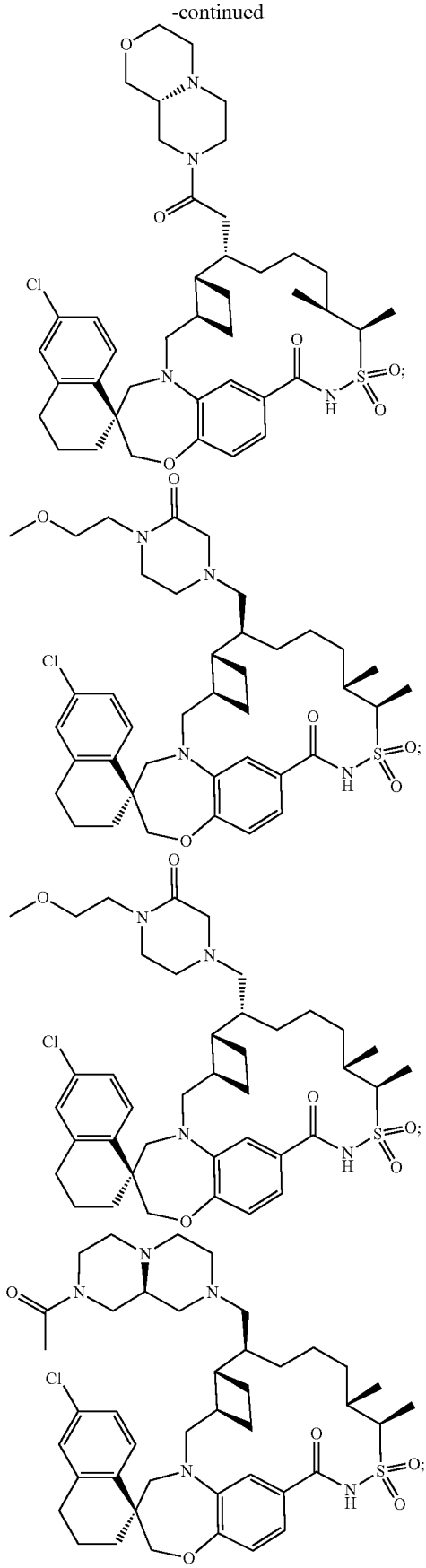
278
-continued
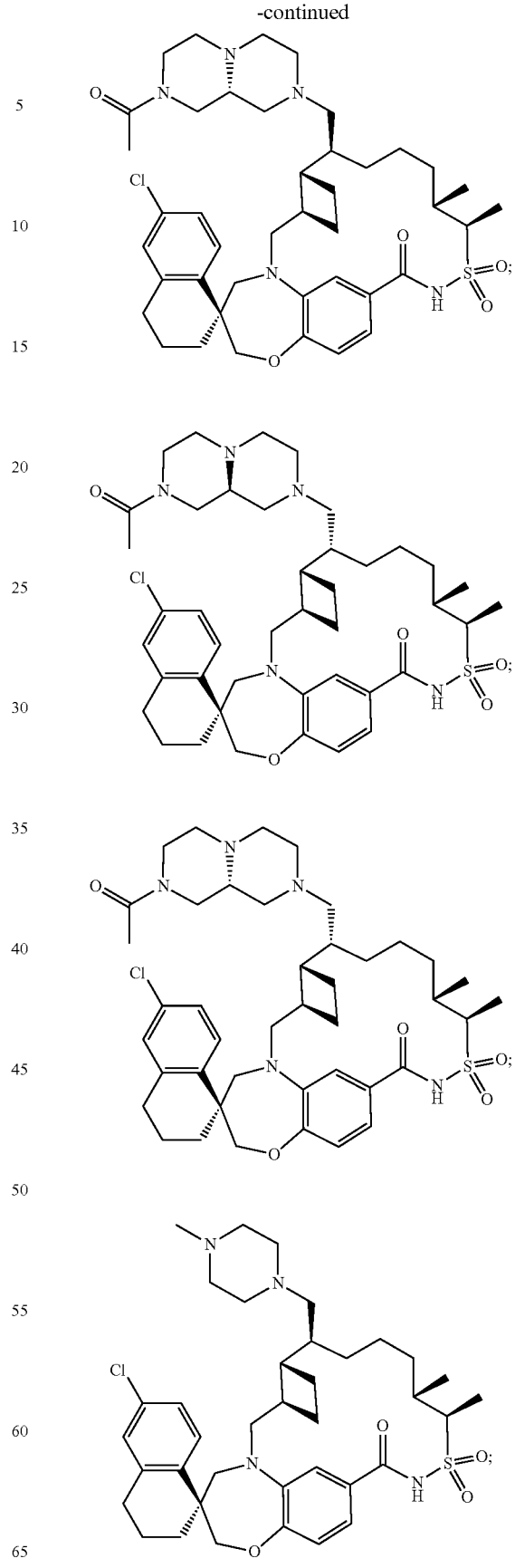

279
-continued
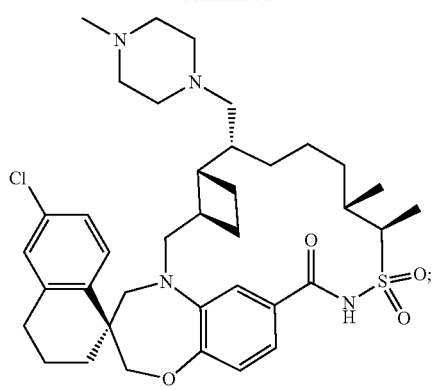
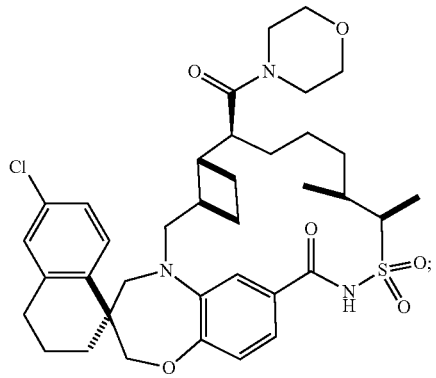
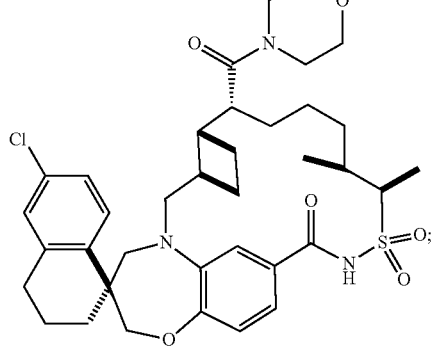
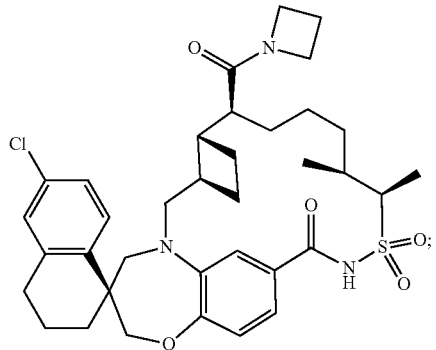
280
-continued
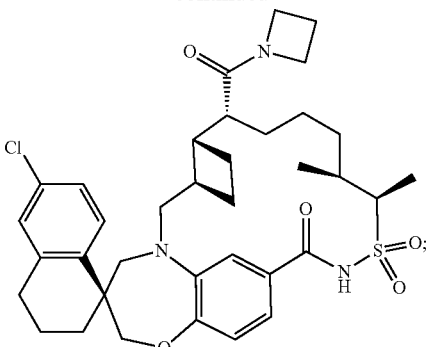
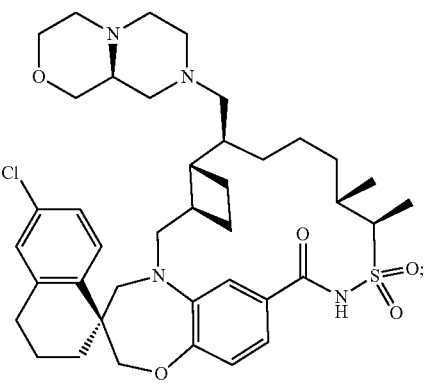
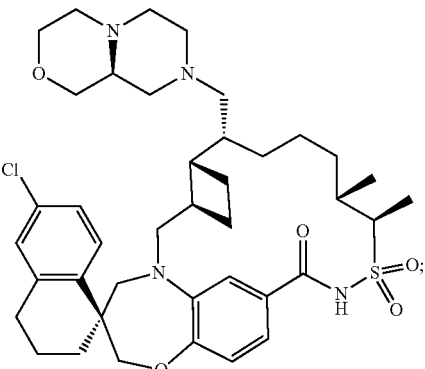
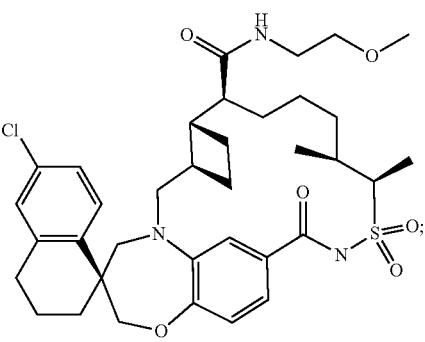

281
-continued
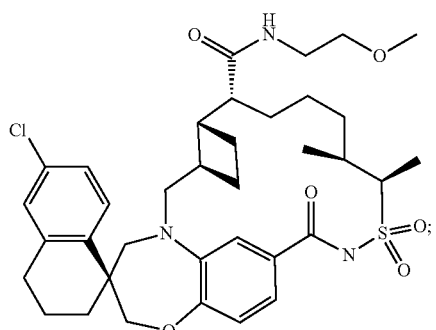
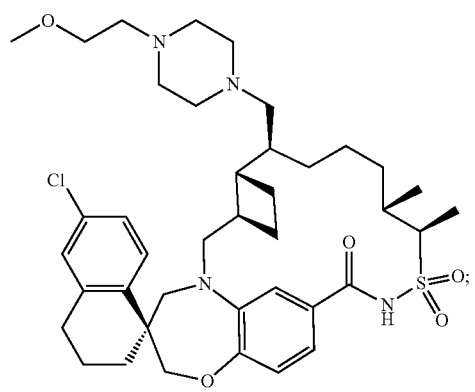
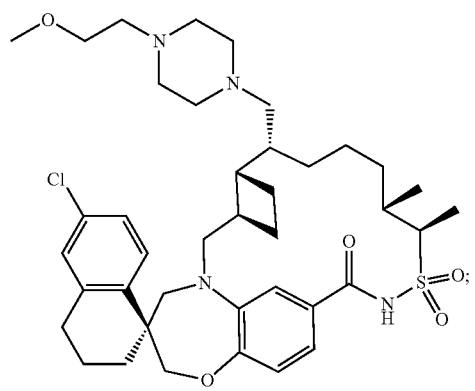
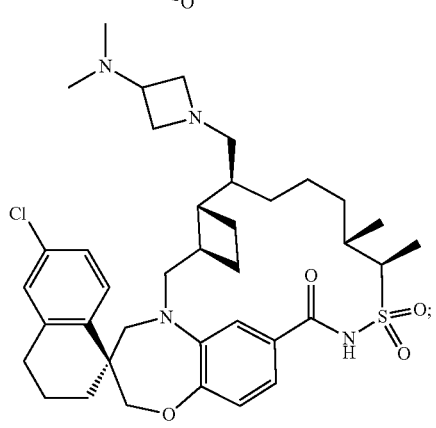
282
-continued
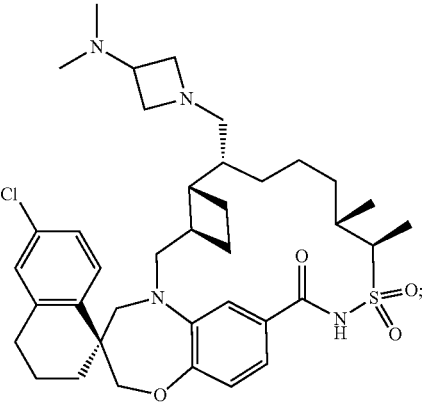
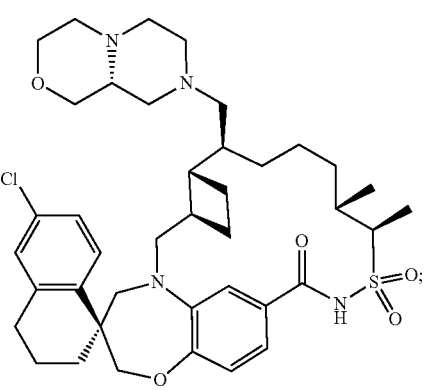
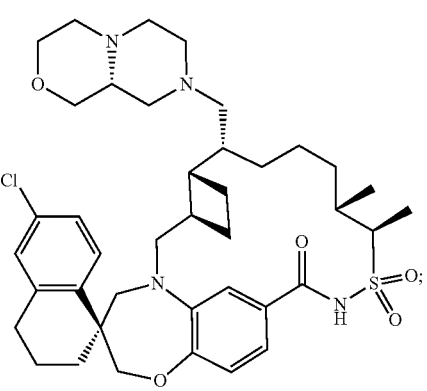
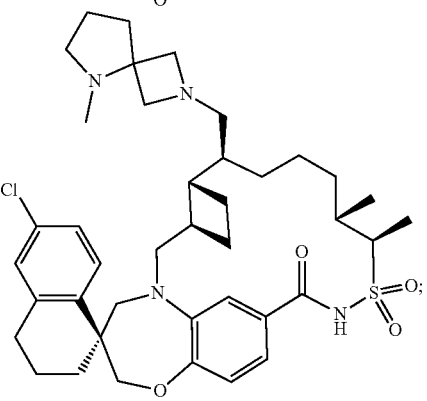

283
-continued
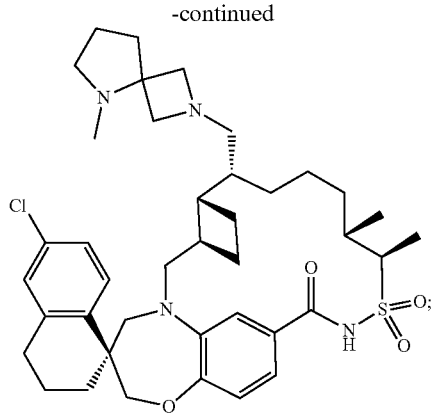
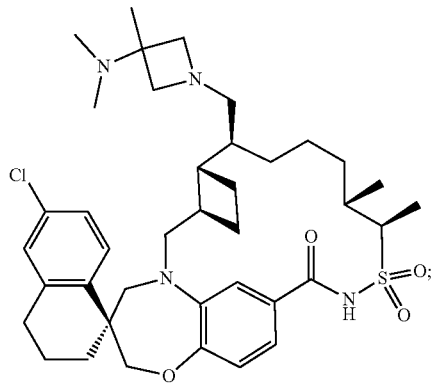
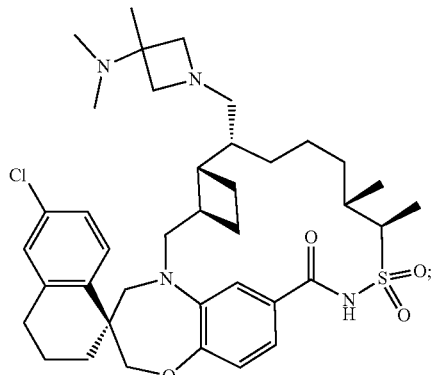
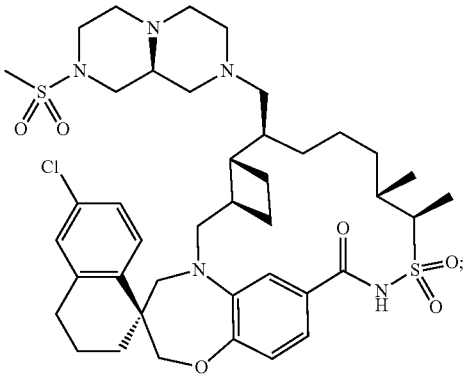
284
-continued
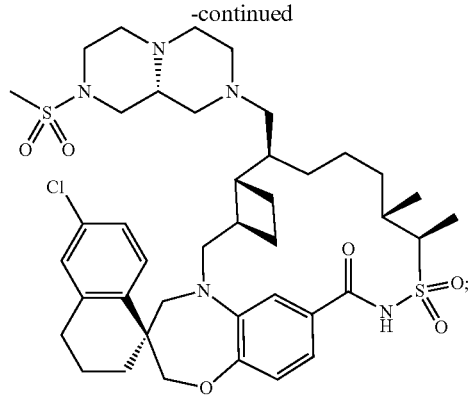
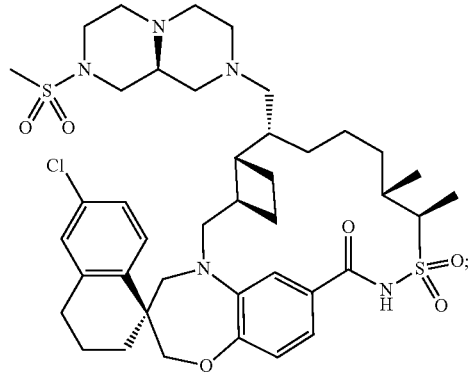
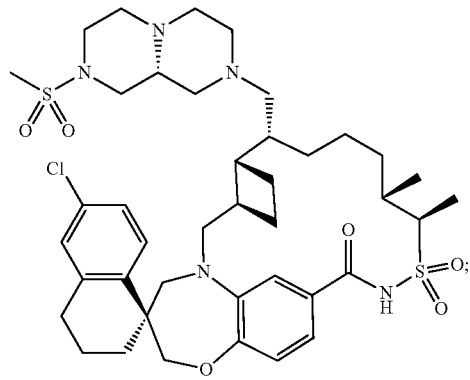
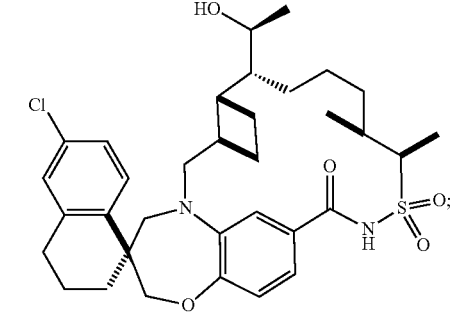

285
-continued
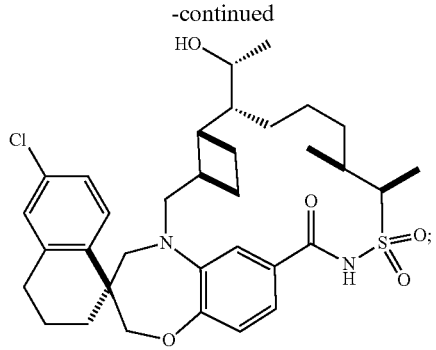
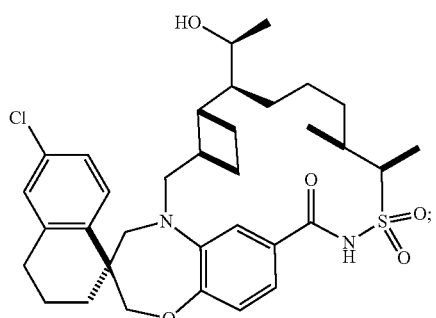
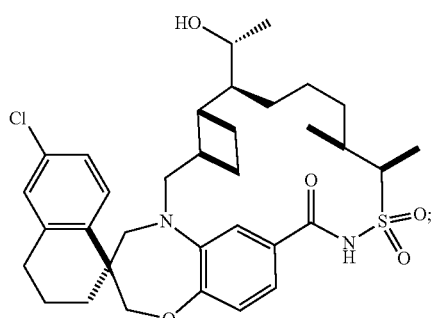
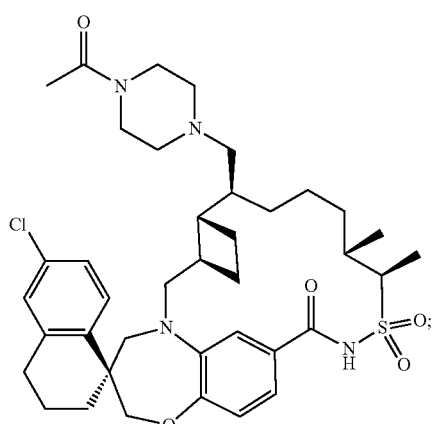
286
-continued
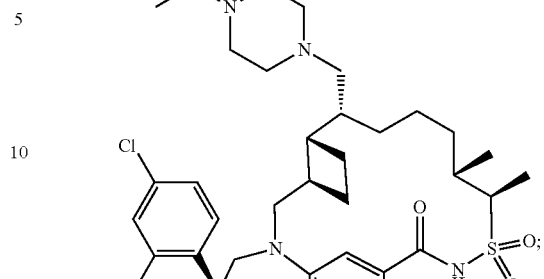
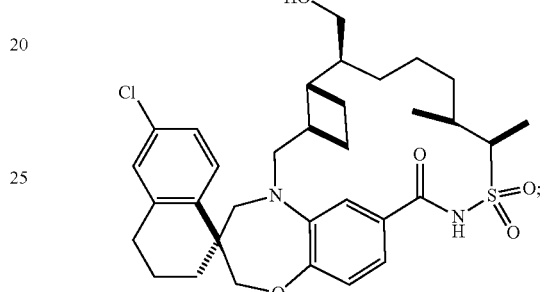
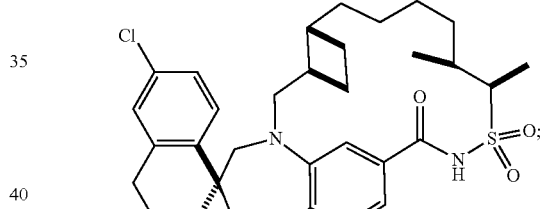
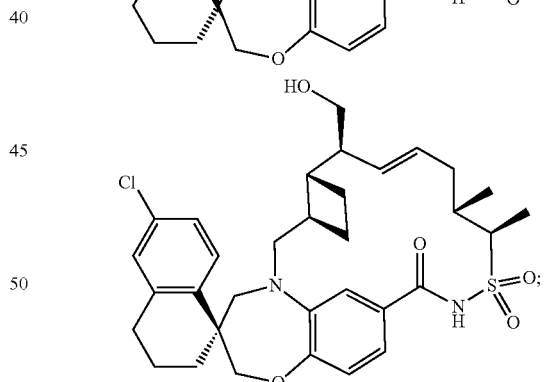

287
-continued
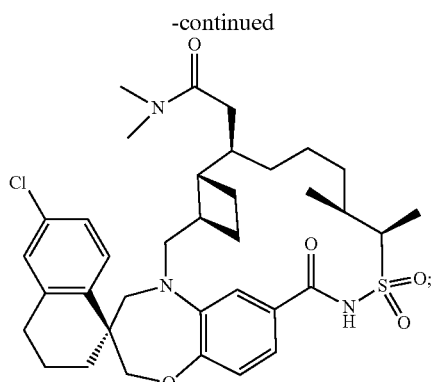
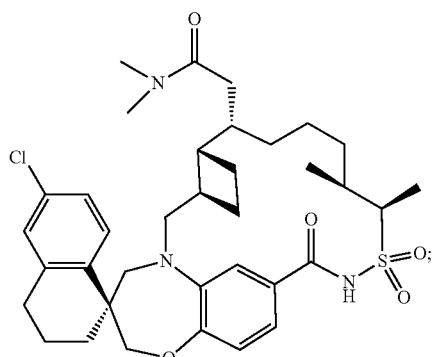
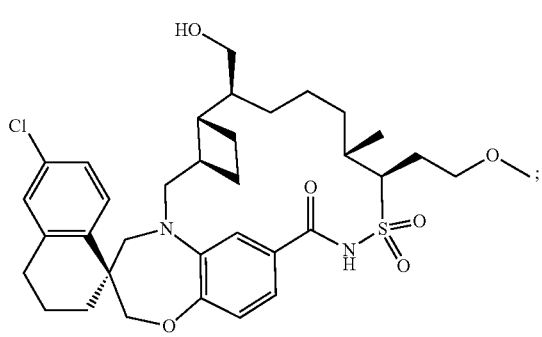
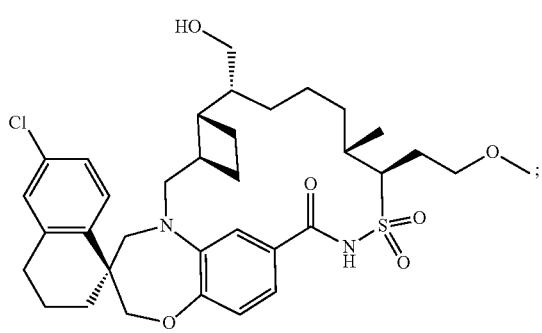
288
-continued
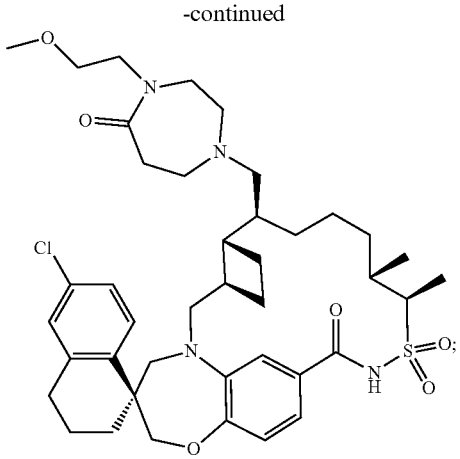
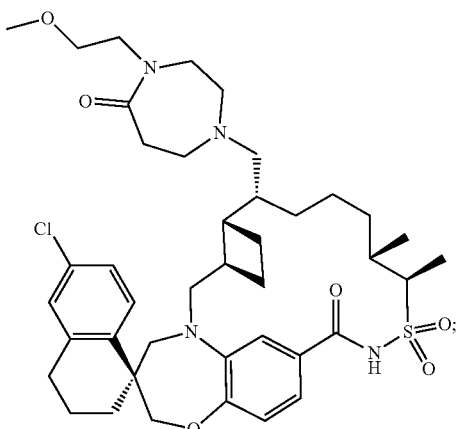
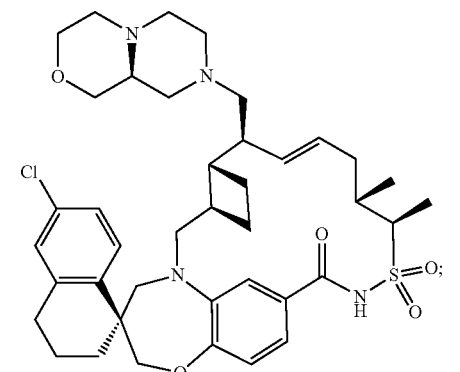
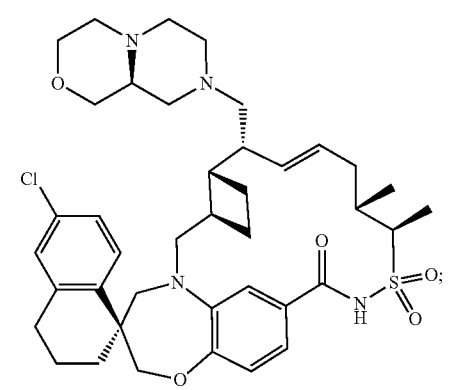

289
-continued
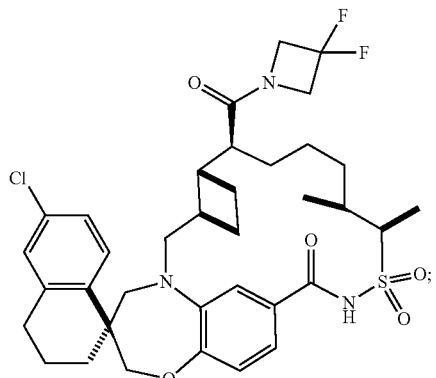
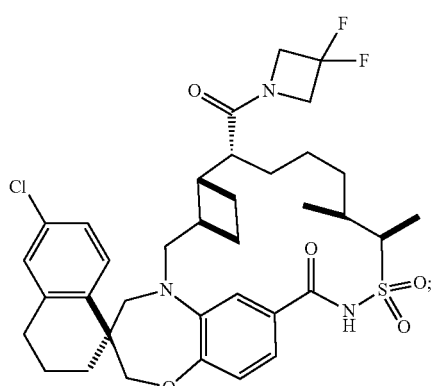
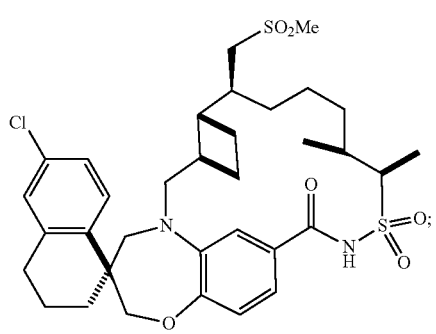
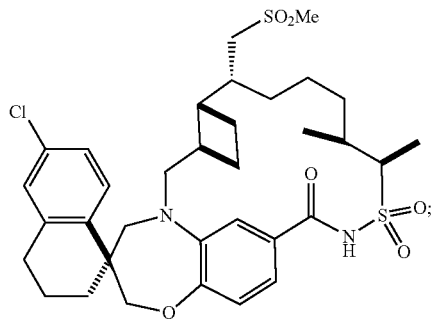
290
-continued
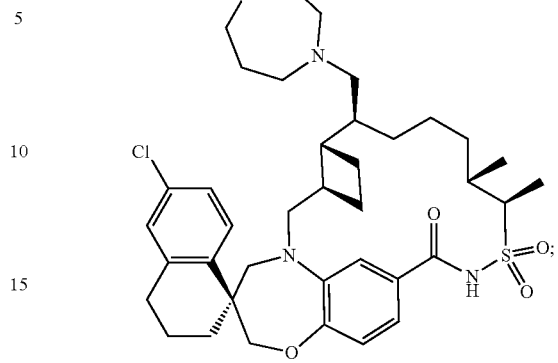
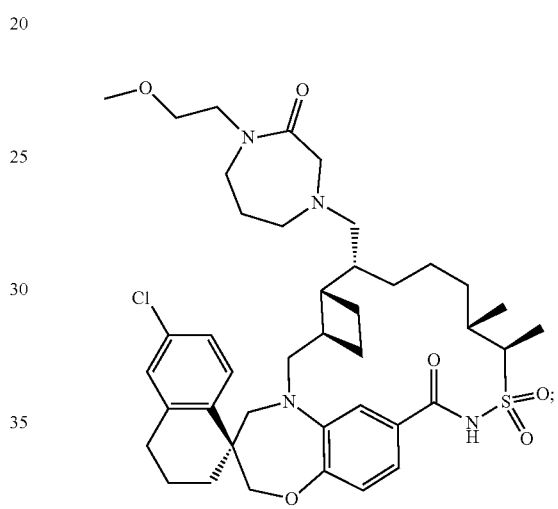
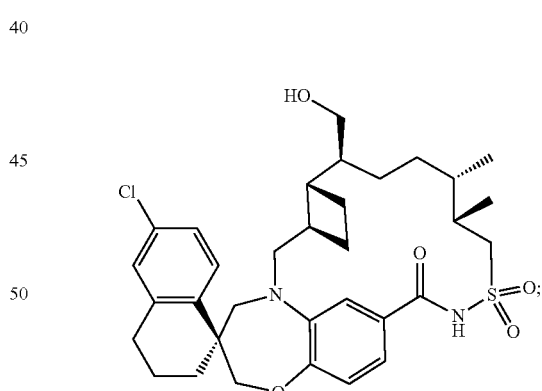
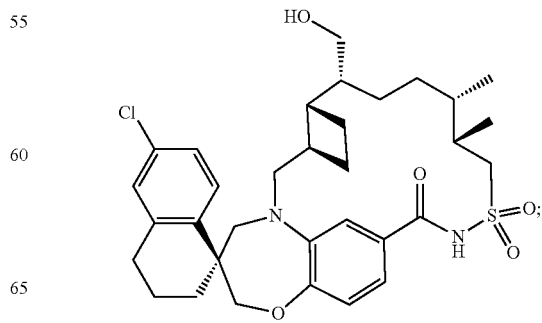

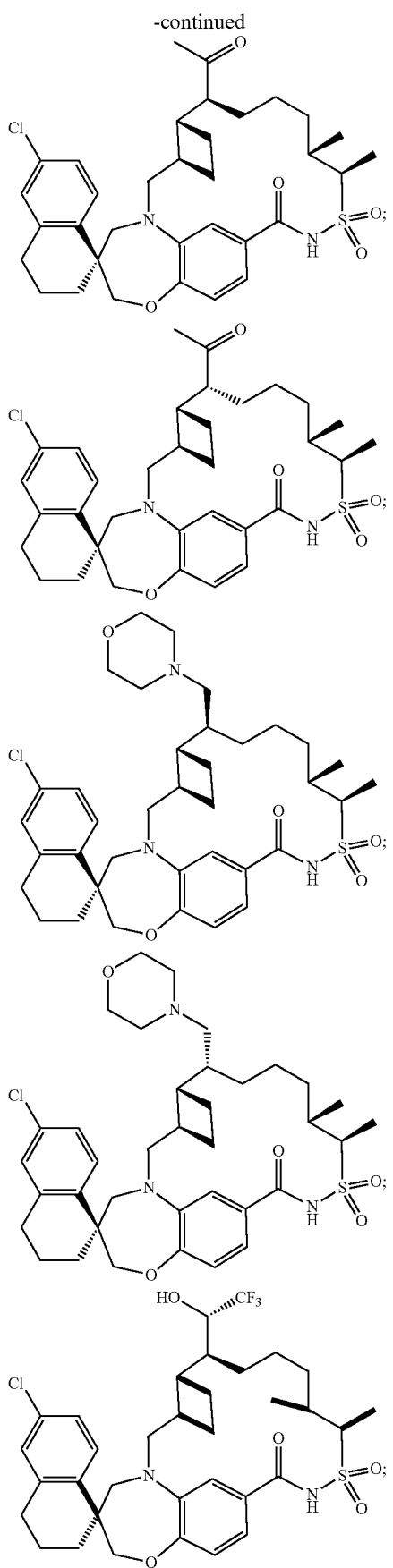
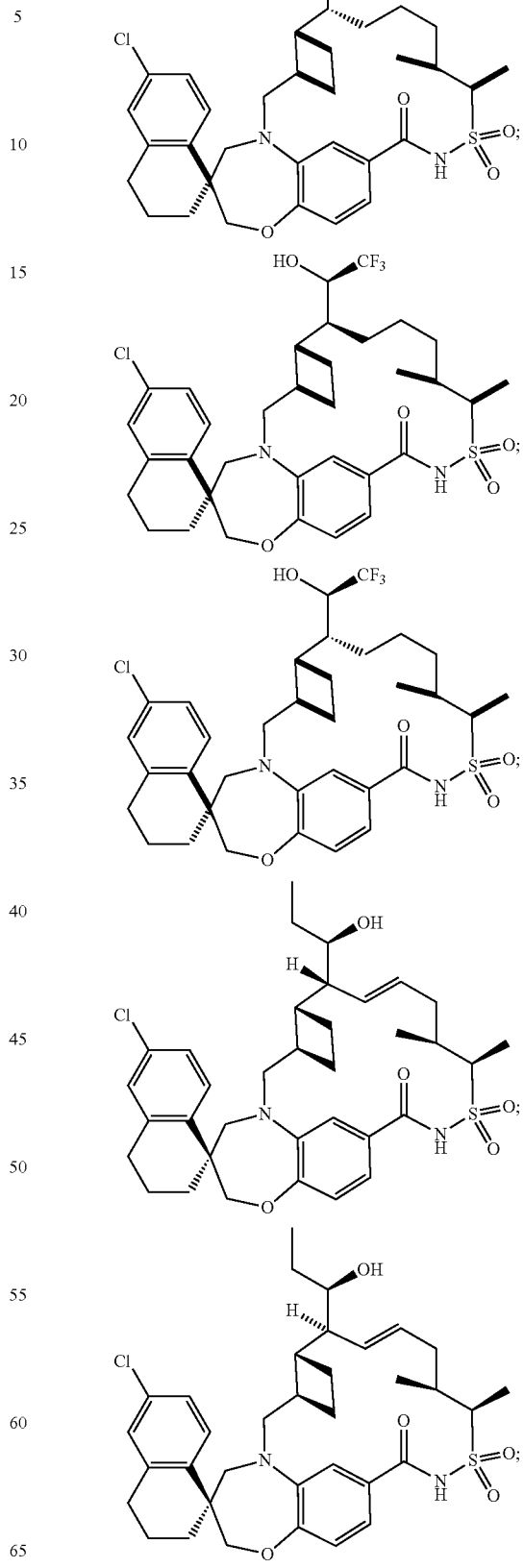

293
-continued
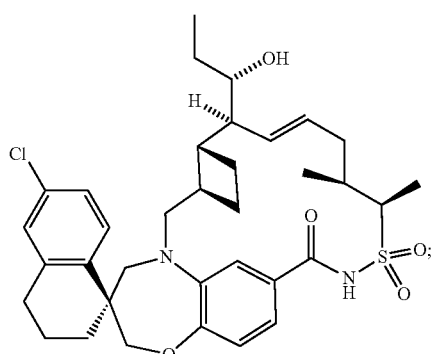
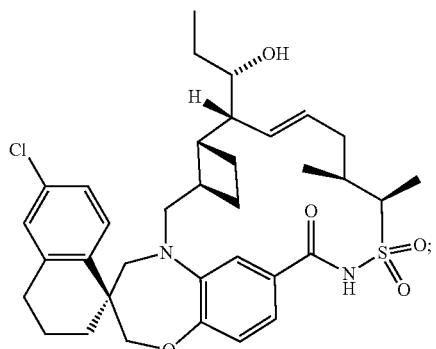
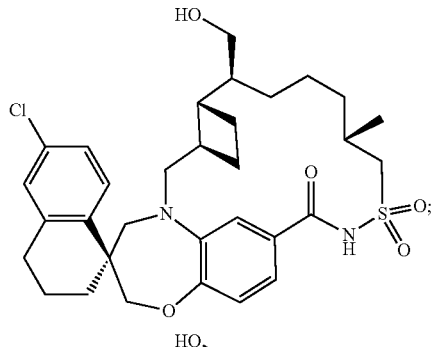
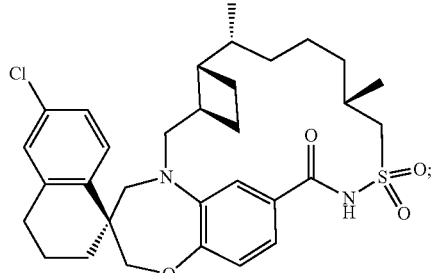
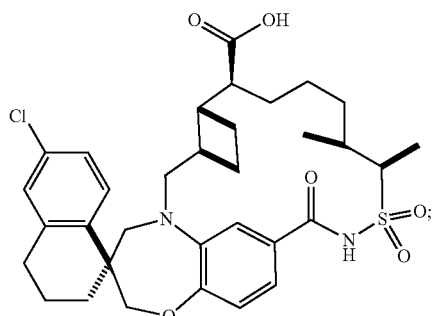
294
-continued
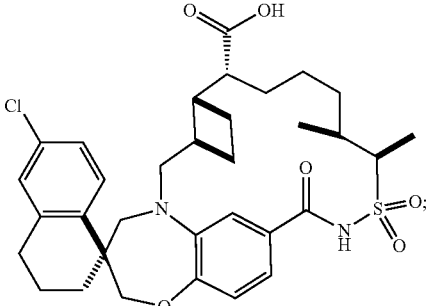
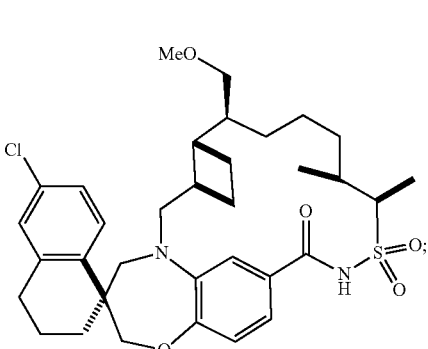
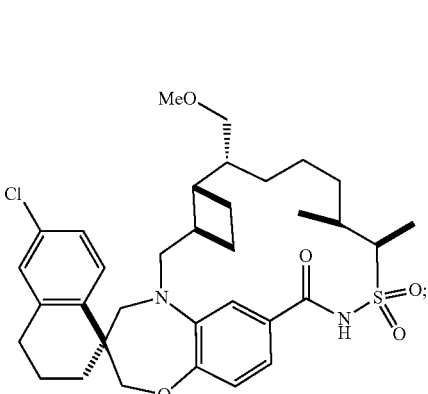
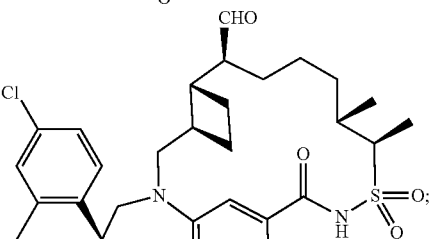
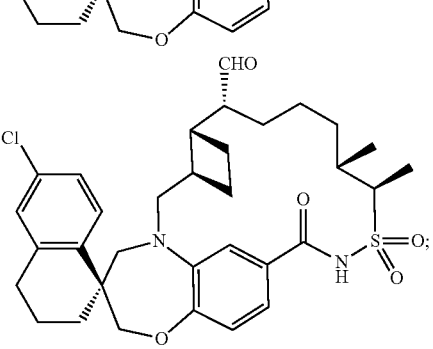

295
-continued
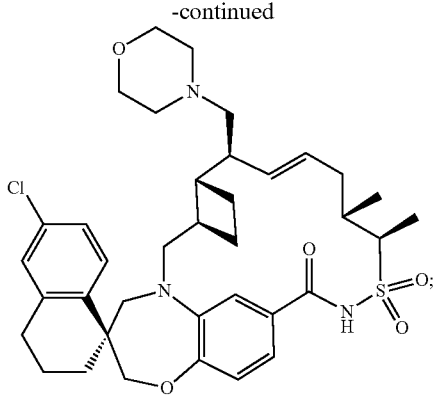
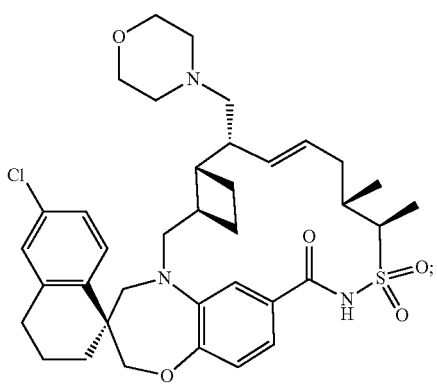
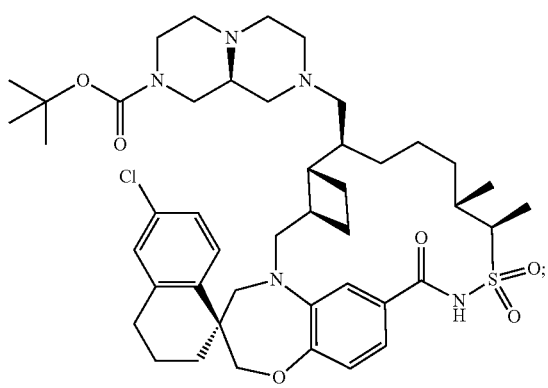
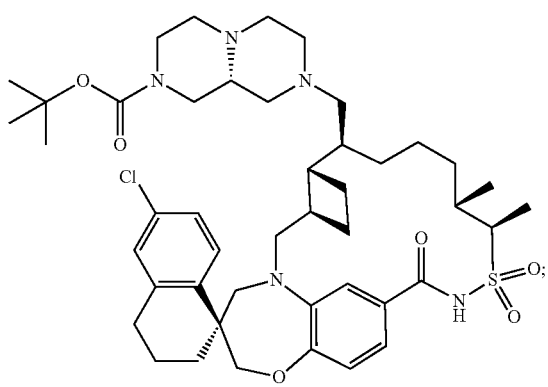
296
-continued
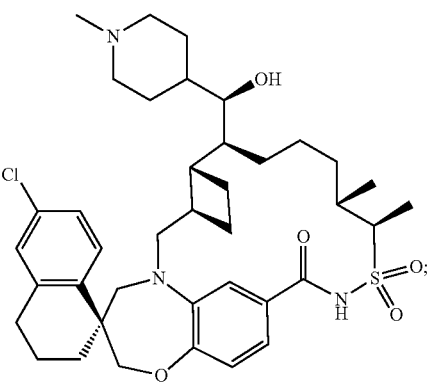
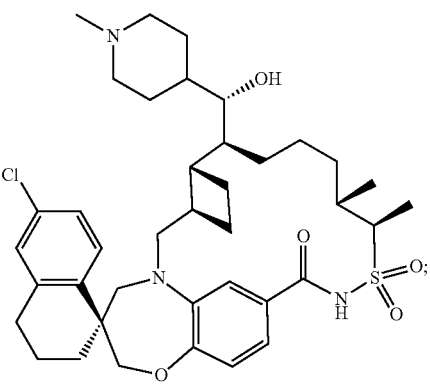

297
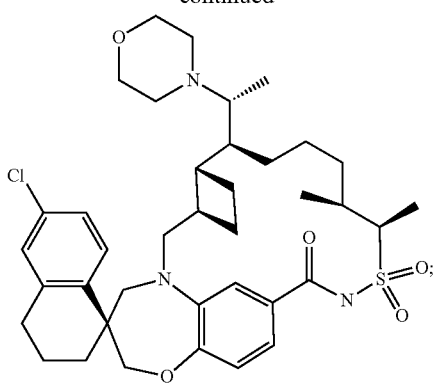
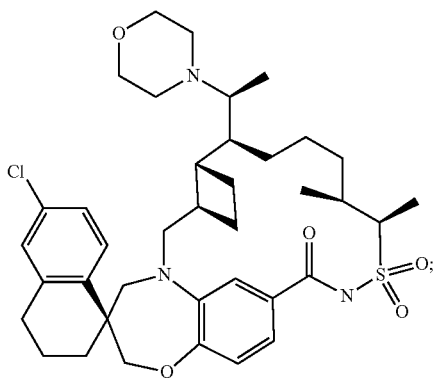
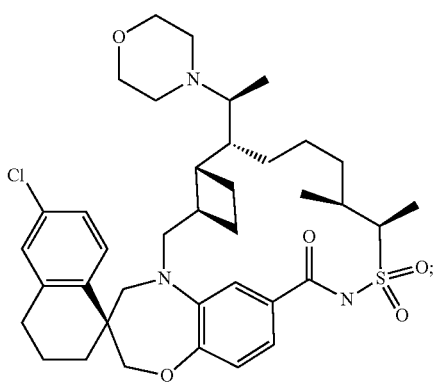
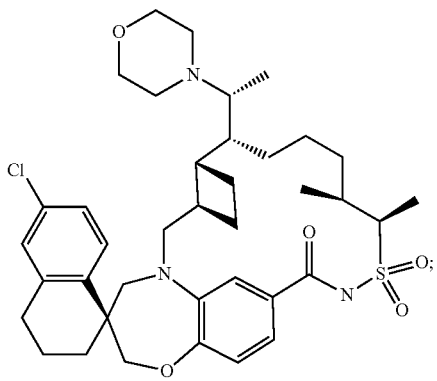
298
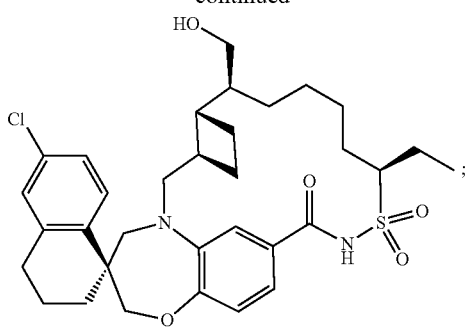
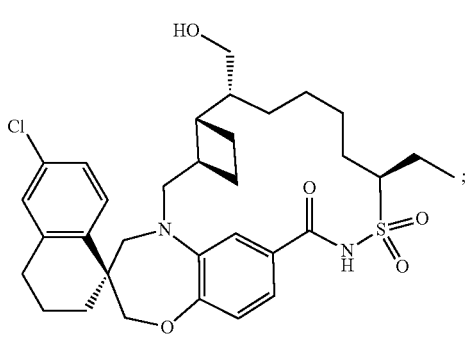
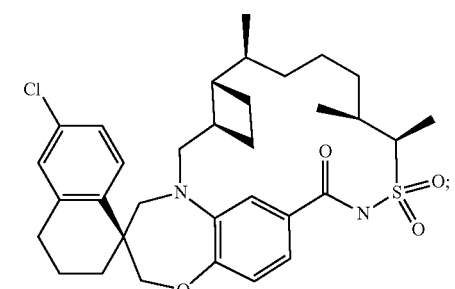
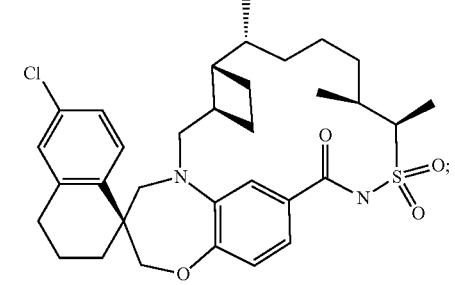
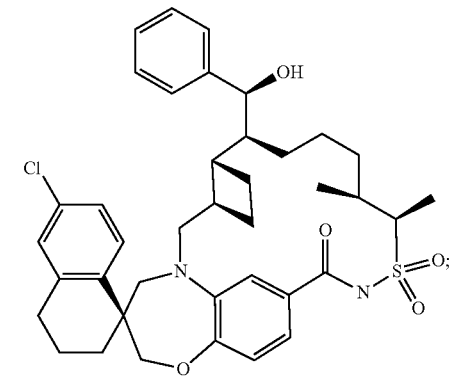

299
-continued
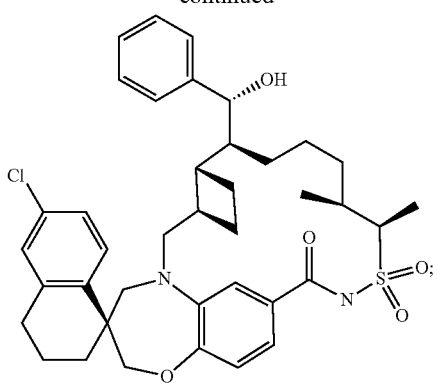
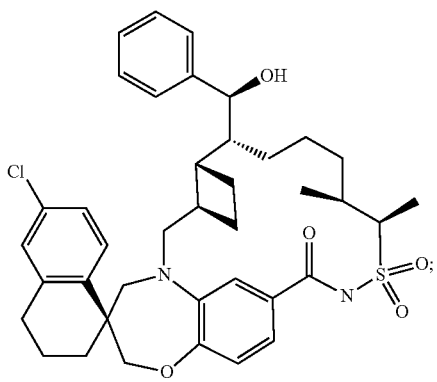
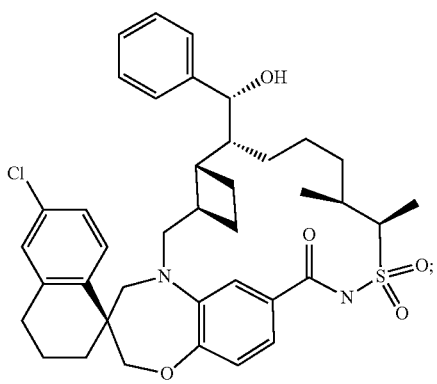
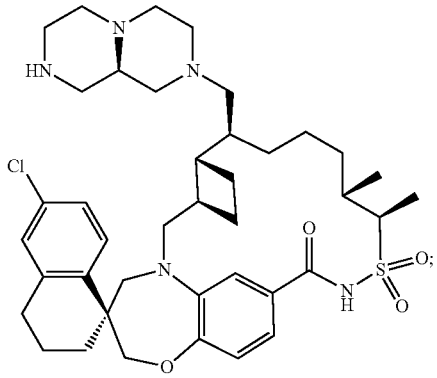
300
-continued
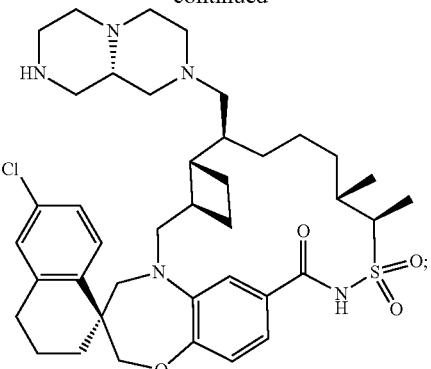
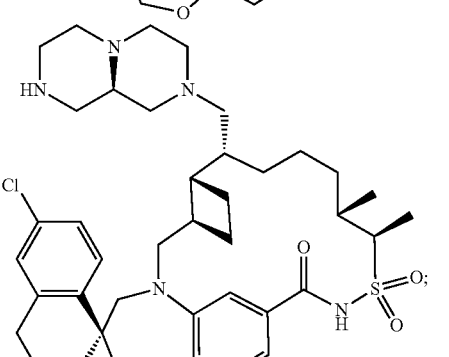
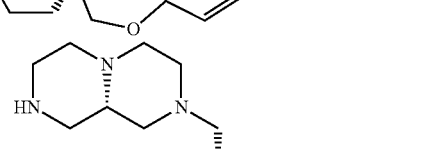
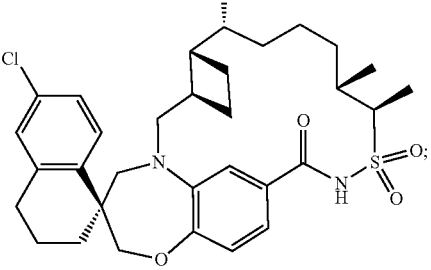 or
or a stereoisomer thereof; a pharmaceutically acceptable salt thereof, or a pharmaceutically acceptable salt of the stereoisomer thereof.
19. A compound, wherein the compound has a structure selected from:
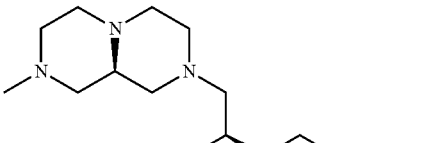
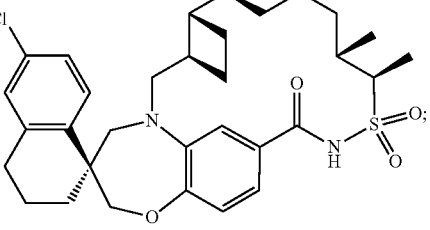

301
-continued
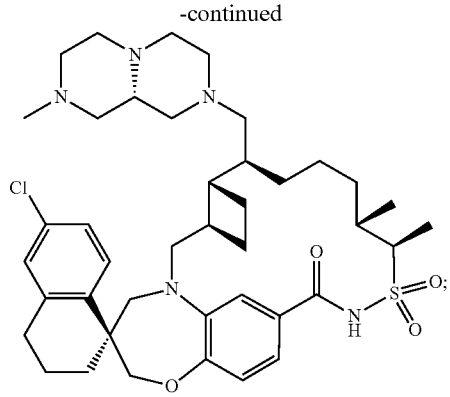
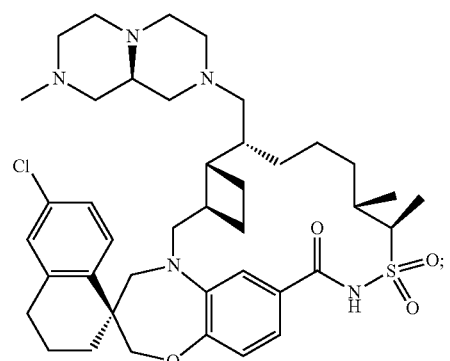
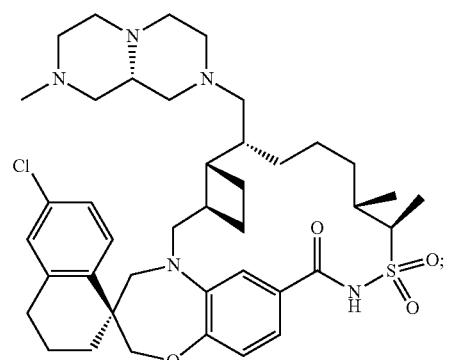
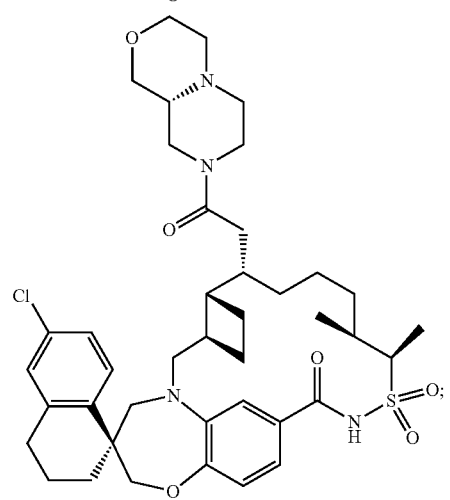
302
-continued
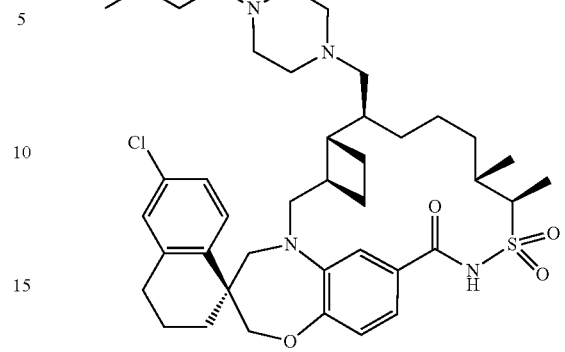
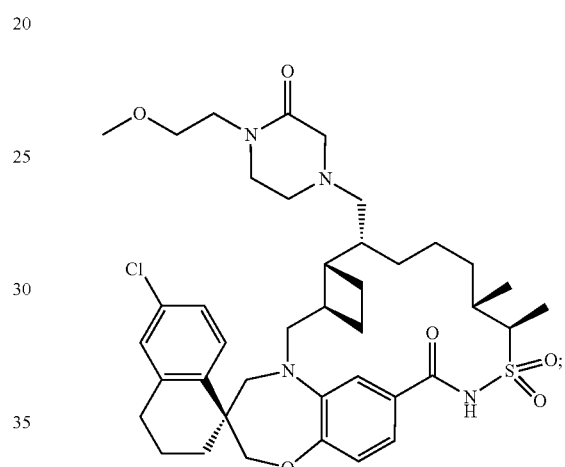
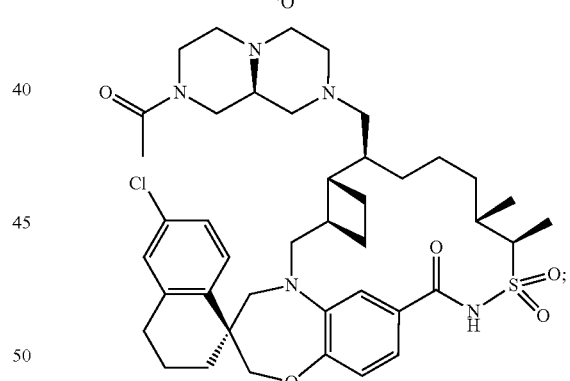
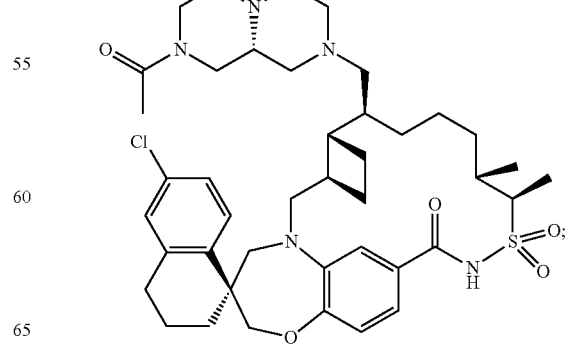

| 303 -continued | 304 -continued |
|---|---|
| 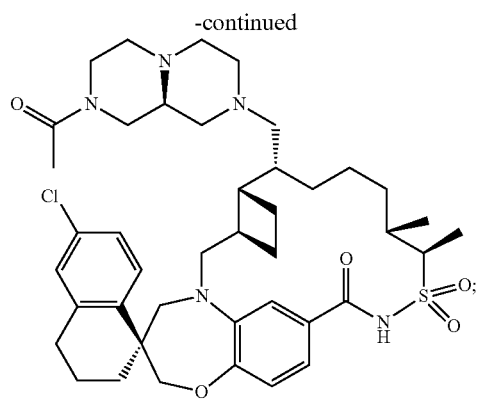 | 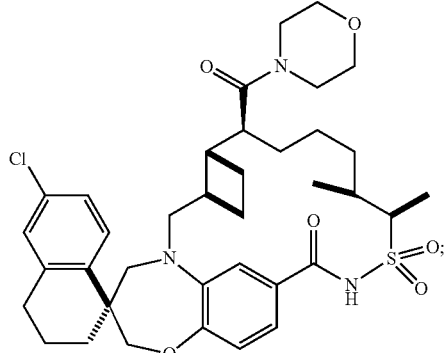 |
| 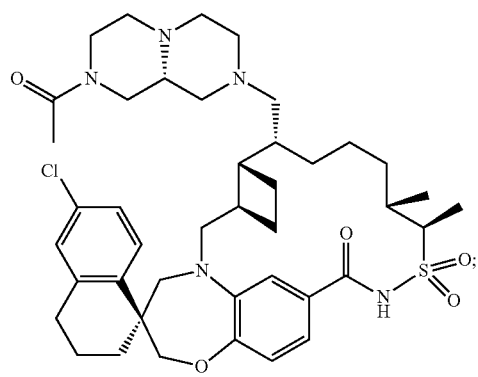 | 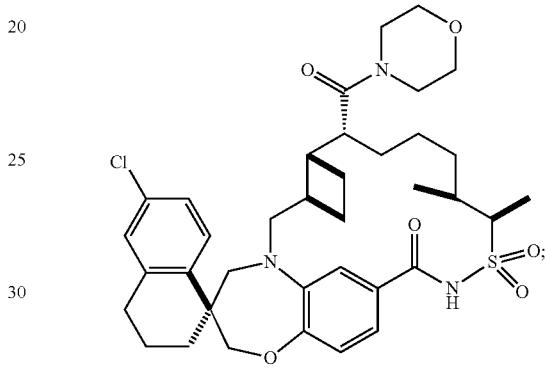 |
| 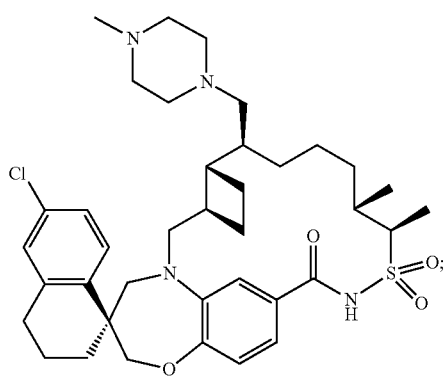 | 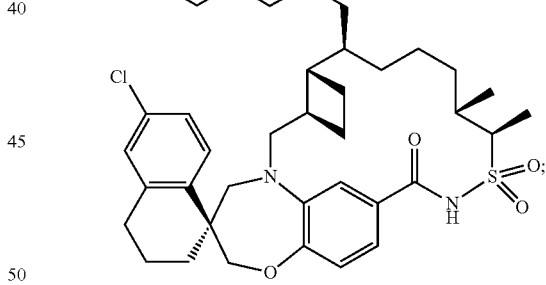 |
| 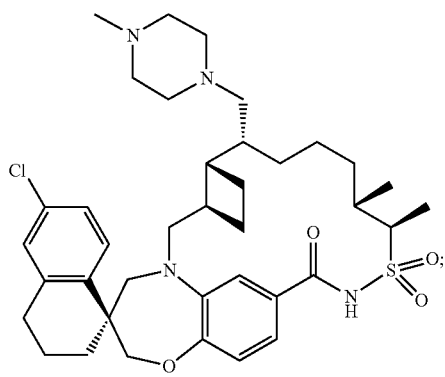 | 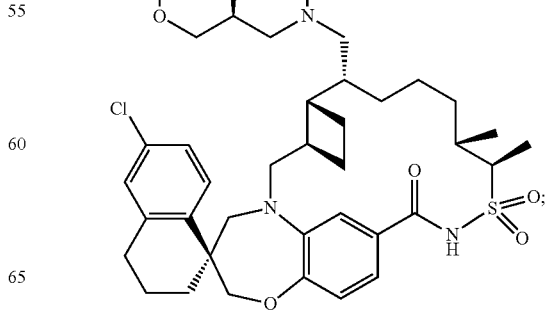 |

305
-continued
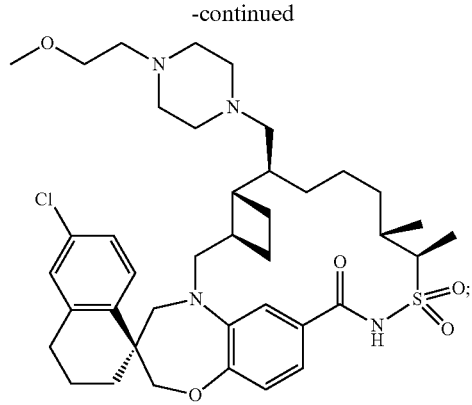
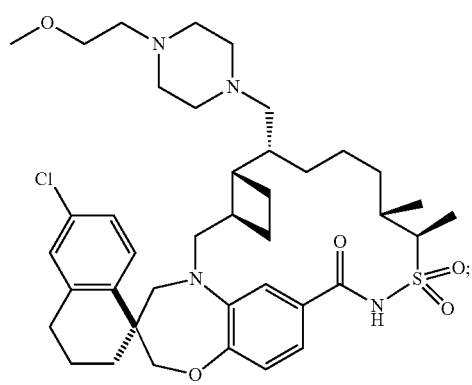
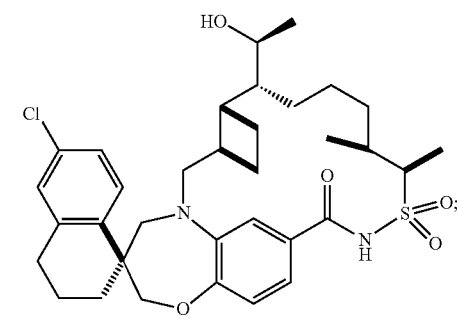
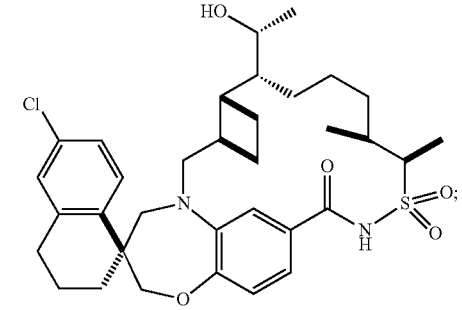
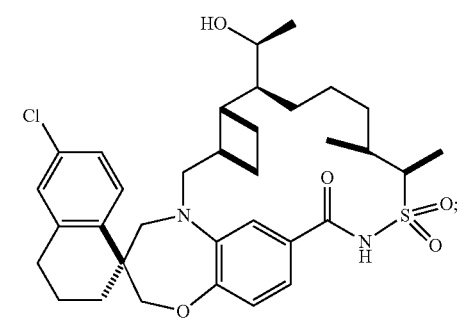
306
-continued
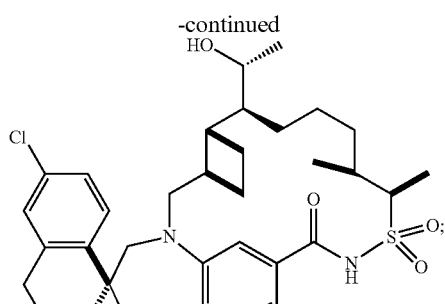
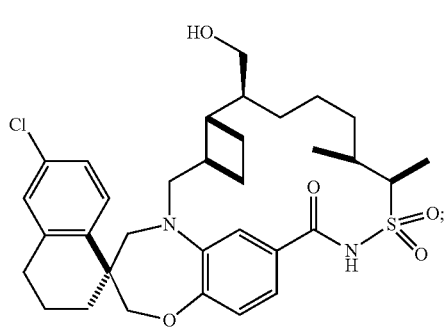
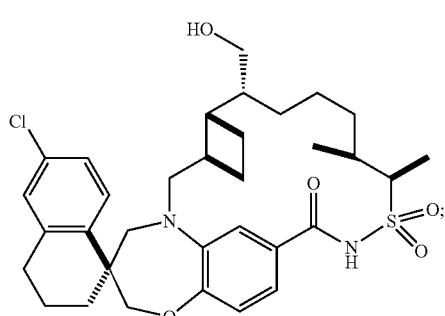
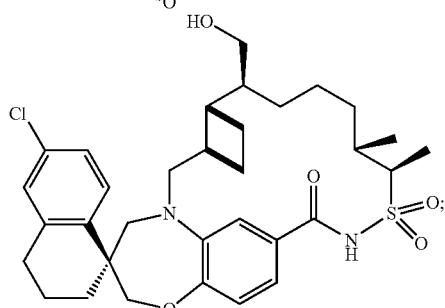
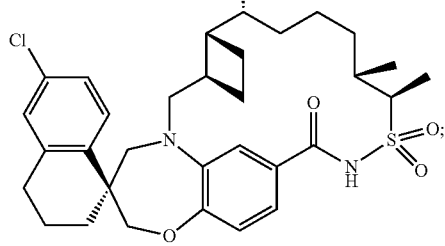

-continued

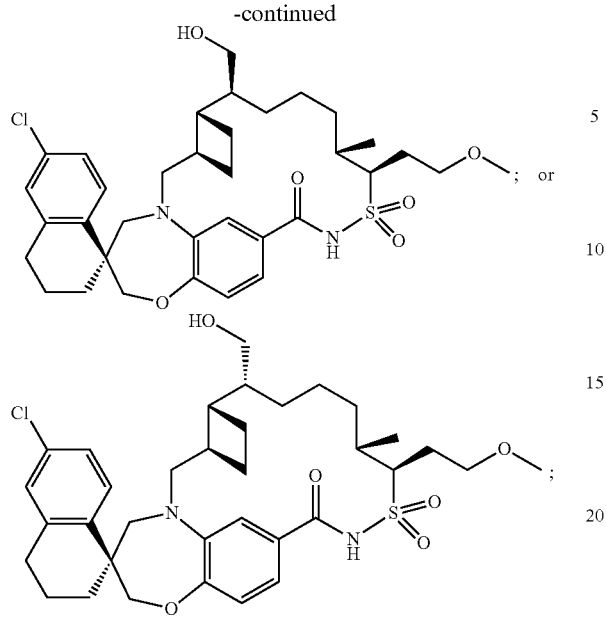

or a pharmaceutically acceptable salt thereof.

20. A pharmaceutical composition comprising the compound of claim 19 or the pharmaceutically acceptable salt thereof, and a pharmaceutically acceptable carrier or diluent.

21. A pharmaceutical composition comprising the compound of claim 1 or the pharmaceutically acceptable salt thereof, and a pharmaceutically acceptable carrier or diluent.

* * * * *